(12) United States Patent
Levin et al.

(10) Patent No.: US 11,154,354 B2
(45) Date of Patent: Oct. 26, 2021

(54) DEVICES, SYSTEMS, AND METHODS FOR TREATMENT OF HEART FAILURE BY SPLANCHNIC NERVE ABLATION

(71) Applicant: AXON THERAPIES, INC., New York, NY (US)

(72) Inventors: Howard Levin, Teaneck, NJ (US); Mark Gelfand, New York, NY (US); Zoar Jacob Engelman, Salt Lake City, UT (US); Dorin Panescu, San Jose, CA (US); Mark S. Leung, Duncan (CA)

(73) Assignee: Axon Therapies, Inc., New York, NY (US)

( * ) Notice: Subject to any disclaimer, the term of this patent is extended or adjusted under 35 U.S.C. 154(b) by 336 days.

(21) Appl. No.: 16/318,447

(22) PCT Filed: Jul. 31, 2017

(86) PCT No.: PCT/US2017/044747
§ 371 (c)(1),
(2) Date: Jan. 17, 2019

(87) PCT Pub. No.: WO2018/023132
PCT Pub. Date: Feb. 1, 2018

(65) Prior Publication Data
US 2020/0179045 A1 Jun. 11, 2020

Related U.S. Application Data

(60) Provisional application No. 62/368,912, filed on Jul. 29, 2016, provisional application No. 62/411,492, (Continued)

(51) Int. Cl.
*A61B 18/14* (2006.01)
*A61B 18/00* (2006.01)
*A61N 1/36* (2006.01)

(52) U.S. Cl.
CPC .............. *A61B 18/1492* (2013.01); *A61B 2018/00285* (2013.01); *A61B 2018/00434* (2013.01);
(Continued)

(58) Field of Classification Search
CPC ...... A61B 18/1492; A61B 2018/00285; A61B 2018/1475; A61B 2018/0022;
(Continued)

(56) References Cited

U.S. PATENT DOCUMENTS

| 3,301,258 A | 1/1967 | Werner |
| 4,403,985 A | 9/1983 | Boretos |

(Continued)

FOREIGN PATENT DOCUMENTS

| CN | 1219855 A | 6/1999 |
| CN | 102670264 A | 9/2012 |

(Continued)

OTHER PUBLICATIONS

Triposkiadis et al, The Sympathetic Nervous System in Heart Failure, 2009, Elsevier, vol. 54, No. 19, pp. 1747-1762 (Year: 2009).*

(Continued)

*Primary Examiner* — Linda C Dvorak
*Assistant Examiner* — Lindsay Regan Lancaster
(74) *Attorney, Agent, or Firm* — Shay Glenn LLP; Thomas M. Zlogar

(57) ABSTRACT

Apparatuses and methods for treating a heart failure patient by ablating a nerve of the thoracic splanchnic sympathetic nervous system to increase venous capacitance and reduce pulmonary blood pressure. A method comprising: inserting a catheter into a vein adjacent the nerve, applying stimulation energy and observing hemodynamic effects, applying ablation energy and observing hemodynamic effects, applying stimulation energy after the ablation and observing
(Continued)

hemodynamic effects and monitoring for presence of the lung in the ablation zone. An alternative method comprising: inserting a catheter into a vein adjacent the nerve, detecting that lung tissue is a safe distance from an ablation zone, and delivering ablation energy to the target nerve when lung tissue is a safe distance from the ablation zone.

20 Claims, 68 Drawing Sheets

Related U.S. Application Data filed on Oct. 21, 2016, provisional application No. 62/482,142, filed on Apr. 5, 2017.

(52) U.S. Cl.
CPC ............... *A61B 2018/00577* (2013.01); *A61B 2018/00648* (2013.01); *A61B 2018/00702* (2013.01); *A61B 2018/00791* (2013.01); *A61B 2018/00875* (2013.01); *A61B 2018/1467* (2013.01); *A61N 1/36017* (2013.01)

(58) Field of Classification Search
CPC .......... A61B 2018/00577; A61B 2018/00648; A61B 2018/00702; A61B 2018/1467; A61B 5/08; A61B 18/18; A61B 2018/00434; A61N 1/36017; A61N 1/0551

See application file for complete search history.

(56) References Cited

U.S. PATENT DOCUMENTS

| | | |
|---|---|---|
| 5,447,529 A | 9/1995 | Marchlinski et al. |
| 5,454,840 A | 10/1995 | Krakovsky et al. |
| 5,458,626 A | 10/1995 | Krause |
| 5,569,198 A | 10/1996 | Racchini |
| 5,649,974 A | 7/1997 | Nelson et al. |
| 5,658,282 A | 8/1997 | Daw et al. |
| 5,704,908 A | 1/1998 | Hofmann et al. |
| 5,722,403 A | 3/1998 | McGee et al. |
| 5,740,808 A | 4/1998 | Panescu et al. |
| 5,797,903 A | 8/1998 | Swanson et al. |
| 5,830,213 A | 11/1998 | Panescu et al. |
| 5,836,874 A | 11/1998 | Swanson et al. |
| 5,840,076 A | 11/1998 | Swanson et al. |
| 5,846,239 A | 12/1998 | Swanson et al. |
| 5,860,974 A | 1/1999 | Abele |
| 5,868,736 A | 2/1999 | Swanson et al. |
| 5,871,483 A | 2/1999 | Jackson et al. |
| 5,891,136 A | 4/1999 | McGee et al. |
| 5,925,038 A | 7/1999 | Panescu et al. |
| 5,961,513 A | 10/1999 | Swanson et al. |
| 6,044,846 A | 4/2000 | Edwards |
| 6,058,331 A | 5/2000 | King |
| 6,071,278 A | 6/2000 | Panescu et al. |
| 6,099,526 A | 8/2000 | Whayne et al. |
| 6,123,718 A | 9/2000 | Tu et al. |
| 6,165,172 A | 12/2000 | Farley et al. |
| 6,236,886 B1 | 5/2001 | Cherepenin et al. |
| 6,395,325 B1 | 5/2002 | Hedge et al. |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,569,160 B1 | 5/2003 | Goldin et al. |
| 6,656,174 B1 | 12/2003 | Hegde et al. |
| 6,658,279 B2 | 12/2003 | Swanson et al. |
| 6,658,929 B2 | 12/2003 | Atkinson |
| 6,668,198 B2 | 12/2003 | Swanson et al. |
| 6,743,197 B1 | 6/2004 | Edwards |
| 6,760,616 B2 | 7/2004 | Hoey et al. |
| 6,832,114 B1 | 12/2004 | Whitehurst et al. |
| 6,849,073 B2 | 2/2005 | Hoey et al. |
| 6,885,888 B2 | 4/2005 | Rezai |
| 6,890,315 B1 | 5/2005 | Levin et al. |
| 6,954,977 B2 | 10/2005 | Maguire et al. |
| 6,984,232 B2 | 1/2006 | Vanney et al. |
| 7,054,689 B1 | 5/2006 | Whitehurst et al. |
| 7,104,989 B2 | 9/2006 | Skarda |
| 7,149,574 B2 | 12/2006 | Yun et al. |
| 7,153,301 B2 | 12/2006 | Swartz et al. |
| 7,236,822 B2 | 6/2007 | Dobak, III |
| 7,239,912 B2 | 7/2007 | Dobak, III |
| 7,282,050 B2 | 10/2007 | Starkebaum et al. |
| 7,282,051 B2 | 10/2007 | Rioux et al. |
| 7,285,199 B2 | 10/2007 | Mitsuhashi et al. |
| 7,326,208 B2 | 2/2008 | Vanney et al. |
| 7,330,762 B2 | 2/2008 | Boveja et al. |
| 7,335,377 B2 | 2/2008 | Stern et al. |
| 7,367,972 B2 | 5/2008 | Francischelli et al. |
| 7,418,292 B2 | 8/2008 | Shafer |
| 7,427,280 B2 | 9/2008 | Gerber |
| 7,449,018 B2 | 11/2008 | Kramer |
| 7,529,582 B1 | 5/2009 | DiLorenzo |
| 7,532,938 B2 | 5/2009 | Machado et al. |
| 7,551,964 B2 | 6/2009 | Dobak, III |
| 7,599,736 B2 | 10/2009 | DiLorenzo |
| 7,623,924 B2 | 11/2009 | Narciso, Jr. |
| 7,689,276 B2 | 3/2010 | Dobak |
| 7,689,277 B2 | 3/2010 | Dobak, III |
| 7,702,386 B2 | 4/2010 | Dobak et al. |
| 7,736,362 B2 | 6/2010 | Eberl et al. |
| 7,769,442 B2 | 8/2010 | Shafer |
| 7,778,703 B2 | 8/2010 | Gross et al. |
| 7,860,570 B2 | 12/2010 | Whitehurst et al. |
| 7,865,237 B2 | 1/2011 | Machado et al. |
| 7,877,146 B2 | 1/2011 | Rezai et al. |
| 7,921,657 B2 | 4/2011 | Littrup et al. |
| 7,937,145 B2 | 5/2011 | Dobak |
| 8,007,496 B2 | 8/2011 | Rioux et al. |
| 8,155,744 B2 | 4/2012 | Rezai |
| 8,241,273 B2 | 8/2012 | Whayne et al. |
| 8,270,568 B2 | 9/2012 | Pitt |
| 8,295,926 B2 | 10/2012 | Dobak, III |
| 8,321,030 B2 | 11/2012 | Maniak et al. |
| 8,399,443 B2 | 3/2013 | Seward |
| 8,401,667 B2 | 3/2013 | Gustus et al. |
| 8,414,508 B2 | 4/2013 | Thapliyal et al. |
| 8,433,412 B1 | 4/2013 | Westlund et al. |
| 8,473,051 B1 | 6/2013 | Wessels et al. |
| 8,483,835 B2 | 7/2013 | Errico et al. |
| 8,611,496 B2 | 12/2013 | Terunuma et al. |
| 8,676,326 B1 | 3/2014 | Farazi |
| 8,676,362 B2 | 3/2014 | Gabel et al. |
| 8,798,738 B2 | 8/2014 | Machado et al. |
| 8,814,793 B2 | 8/2014 | Brabrand |
| 8,911,439 B2 | 12/2014 | Mayse et al. |
| 8,994,536 B2 | 3/2015 | Margon |
| 8,998,894 B2 | 4/2015 | Mauch et al. |
| 9,005,100 B2 | 4/2015 | Gnanashanmugam et al. |
| 9,022,948 B2 | 5/2015 | Wang |
| 9,028,472 B2 | 5/2015 | Mathur et al. |
| 9,033,969 B2 | 5/2015 | Azamian et al. |
| 9,037,259 B2 | 5/2015 | Mathur |
| 9,072,902 B2 | 7/2015 | Mathur et al. |
| 9,125,661 B2 | 9/2015 | Deem |
| 9,125,668 B2 | 9/2015 | Subramaniam et al. |
| 9,162,075 B2 | 10/2015 | Sluijter et al. |
| 9,174,050 B2 | 11/2015 | Mathur et al. |
| 9,199,091 B2 | 12/2015 | Danek et al. |
| 9,245,182 B2 | 1/2016 | Jania et al. |
| 9,278,196 B2 | 3/2016 | Fischell et al. |
| 9,345,530 B2 | 5/2016 | Ballakur et al. |
| 9,345,900 B2 | 5/2016 | Wu et al. |
| 9,370,657 B2 | 6/2016 | Tehrani et al. |
| 9,439,580 B2 | 9/2016 | Hatlestad et al. |
| 9,439,598 B2 | 9/2016 | Shimada et al. |
| 9,592,386 B2 | 3/2017 | Mathur et al. |
| 9,603,659 B2 | 3/2017 | Subramaniam et al. |
| 9,743,845 B2 | 8/2017 | Wang |

(56) References Cited

U.S. PATENT DOCUMENTS

| | | |
|---|---|---|
| 9,757,193 B2 | 9/2017 | Zarins et al. |
| 9,895,539 B1 | 2/2018 | Heit et al. |
| 10,207,110 B1 | 2/2019 | Gelfand et al. |
| 2002/0165532 A1 | 11/2002 | Hill et al. |
| 2002/0198520 A1 | 12/2002 | Coen et al. |
| 2003/0109869 A1 | 6/2003 | Shadduck |
| 2003/0216792 A1 | 11/2003 | Levin et al. |
| 2004/0247849 A1 | 12/2004 | Truckai |
| 2005/0010095 A1 | 1/2005 | Stewart et al. |
| 2005/0203462 A1 | 9/2005 | Katoh et al. |
| 2005/0245923 A1 | 11/2005 | Christopherson et al. |
| 2006/0200121 A1 | 9/2006 | Mowery |
| 2007/0167984 A1 | 7/2007 | Kieval et al. |
| 2007/0213704 A1 | 9/2007 | Truckai et al. |
| 2007/0224253 A1 | 9/2007 | Franklin |
| 2008/0200972 A1 | 8/2008 | Rittman |
| 2009/0036794 A1 | 2/2009 | Stubhaug et al. |
| 2009/0155336 A1* | 6/2009 | Rezai ............... A61F 2/82 424/423 |
| 2009/0280178 A1 | 11/2009 | Hedge et al. |
| 2010/0152731 A1 | 6/2010 | de la Rama et al. |
| 2010/0168820 A1 | 7/2010 | Maniak et al. |
| 2010/0241113 A1 | 9/2010 | Ingle |
| 2010/0249702 A1 | 9/2010 | Magana et al. |
| 2010/0305664 A1 | 12/2010 | Wingeier et al. |
| 2011/0022127 A1 | 1/2011 | Averina et al. |
| 2011/0028962 A1 | 2/2011 | Werneth et al. |
| 2011/0098761 A1 | 4/2011 | Wittenberger et al. |
| 2011/0224750 A1 | 9/2011 | Scheiner |
| 2011/0238083 A1 | 9/2011 | Moll et al. |
| 2012/0065554 A1 | 3/2012 | Pikus |
| 2012/0089047 A1 | 4/2012 | Ryba et al. |
| 2012/0143293 A1 | 6/2012 | Mauch et al. |
| 2012/0265198 A1 | 10/2012 | Crow et al. |
| 2012/0271162 A1 | 10/2012 | Liao et al. |
| 2012/0296329 A1 | 11/2012 | Ng |
| 2013/0035682 A1 | 2/2013 | Weil |
| 2013/0103026 A1 | 4/2013 | Kleshinski et al. |
| 2013/0226201 A1 | 8/2013 | Miller et al. |
| 2013/0237948 A1 | 9/2013 | Donders et al. |
| 2013/0282000 A1 | 10/2013 | Parsonage et al. |
| 2013/0289369 A1 | 10/2013 | Margolis |
| 2013/0296646 A1 | 11/2013 | Barbut et al. |
| 2013/0331813 A1 | 12/2013 | Barbut et al. |
| 2014/0025069 A1 | 1/2014 | Willard et al. |
| 2014/0031727 A1 | 1/2014 | Warnking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0180273 A1 | 6/2014 | Nair |
| 2014/0214129 A1 | 7/2014 | Waataja et al. |
| 2014/0276718 A1 | 9/2014 | Turovskiy et al. |
| 2014/0276742 A1 | 9/2014 | Nabutovsky et al. |
| 2014/0303617 A1 | 10/2014 | Shimada |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0223877 A1 | 8/2015 | Behar et al. |
| 2015/0245867 A1 | 9/2015 | Gross |
| 2015/0335286 A1 | 11/2015 | Boydell |
| 2016/0128767 A1* | 5/2016 | Azamian ............... A61B 18/1492 606/41 |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0296171 A1 | 10/2016 | Drori et al. |
| 2016/0317621 A1 | 11/2016 | Bright |
| 2016/0374754 A1 | 12/2016 | Asirvatham et al. |
| 2017/0049989 A1 | 2/2017 | Kapural |
| 2017/0202614 A1 | 7/2017 | Gross et al. |
| 2017/0216602 A1 | 8/2017 | Waataja et al. |
| 2017/0231490 A1 | 8/2017 | Toth et al. |
| 2017/0252101 A1 | 9/2017 | Hata et al. |
| 2018/0110561 A1 | 4/2018 | Levin et al. |
| 2019/0069942 A1 | 3/2019 | Azamian et al. |
| 2021/0128229 A1 | 5/2021 | Panescu et al. |

FOREIGN PATENT DOCUMENTS

| | | |
|---|---|---|
| CN | 103118619 A | 5/2013 |
| CN | 103220984 A | 7/2013 |
| CN | 103857353 A | 6/2014 |
| CN | 104257426 A | 1/2015 |
| EP | 2020943 B1 | 7/2015 |
| EP | 2755588 B1 | 5/2016 |
| EP | 2934357 B1 | 11/2017 |
| WO | WO99/12489 A2 | 3/1999 |
| WO | WO2004/039428 A2 | 5/2004 |
| WO | WO2008/049084 A2 | 4/2008 |
| WO | WO2014/150887 A1 | 9/2014 |
| WO | WO2014/197625 A1 | 12/2014 |
| WO | WO2016/084081 A2 | 6/2016 |
| WO | WO2016/090175 A1 | 6/2016 |
| WO | WO2016/132340 A1 | 8/2016 |
| WO | WO2016/176333 A1 | 11/2016 |
| WO | WO2017/074920 A1 | 5/2017 |
| WO | WO2017/096007 A1 | 6/2017 |
| WO | WO2018/125822 A2 | 7/2018 |

OTHER PUBLICATIONS

Chatterjee, Novel Interventional Therapies to Modulate the Autonomic Tone in Heart Failure, Elsevier, 2015, vol. 3, No. 10, pp. 786-802 (Year: 2015).*

Del Rio, Carotid Chemoreceptor Ablation Improves Survival in Heart Failure: Rescuing Autonomic Control of Cardiorespiratory Function, 2013, vol. 62, No. 25, pp. 2422-2430 (Year: 2013).*

Panescu et al.; U.S. Appl. No. 16/793,698 entitled "Methods and devices for endovascular ablation of a splanchnic nerve," filed Feb. 18, 2020.

Adamopoulos et al.; Comparison of different methods for assessing sympathovagal balance in chronic congestive heart failure secondary to coronary artery disease; The American Journal of Cardiology; 70(20); pp. 1576-1582; Dec. 15, 1992.

Andren-Sandberg et al.; Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The importance of mesenteric mechanoreceptors for the reflex innervation of resistance blood vessels capacity blood vessels in the splanchnic area; Pflugers Archiv fur die gesamte Physiologie des Menschen und derTiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brooksby et al.; Dynamic changes in splanchnic blood flow and blood vol. in dogs during activation of sympathetic nerves; Circulation Research; XXIX(3); pp. 227-238; Sep. 1971.

Brunner et al.; Carotid sinus baroreceptor control of splanchnic resistance and capacity. Am J Physiol.; 255; pp. H1305-H1310; Dec. 1988.

Burkhoff et al.; Why does pulmonary venous pressure rise after on of LV dysfunction: a theoretical analysis; Am. J. Physiol.; 265(5, pt. 2); pp. H1819-H1828; Nov. 1993.

Buscher et al.; Limited effect of thoracoscopic splanchnicectomy In the treatment of severe chronic pancreatitis pain: a prospective long-term analysis of 75 cases; Surgery; 143(6); pp. 715-722; Jun. 30, 2008.

(56) References Cited

OTHER PUBLICATIONS

Carneiro et al.; Change in liver blood flow and blood content in dogs during direct and reflex alteration of hepatic sympathetic nerve activity; Circulation Research; 40(2); pp. 150-158; Feb. 1, 1977.
Cody et al.; Captopril kinetics in chronic congestive heart failure; Clin pharmacol Ther.; 32(6); pp. 721-726; Dec. 1982.
Cuschieri et al.; Bilateral endoscopic splanchnicectomy through a posterior thoracoscopic approach; Journal of the Royal College of Surgeons of Edinburgh; 39(1); pp. 44-47; Feb. 1994.
Diedrich et al.; Segmental orthostatic fluid shifts; Clinical autonomic research;14(3); pp. 146-147; Jun. 2004.
Edwards Lifesciences; ClearSight System (brochure; No. AR11578); 4 pgs.; © 2014.
Edwards; The glycogenolytic response to stimulation of the splanchnic nerves in adrenalectomized calves, sheep, dogs, cats and pigs; J Physiol.; 213; pp. 741-759; Mar. 1971.
Eisenberg et al.; Neurolytic celiac plexus block for treatment of cancer pain: A meta-analysis; Anesth Analg; 80(2); pp. 290-295; Feb. 1995.
Fallick et al.; Sympathetically mediated changes in capacitance: Redistribution of the venous reservoir as a cause of decompensation; Circulation: Heart Failure; 4; pp. 669-675; Sep. 2011.
Ferrara et al.; Hemodynamics of the splanchnic and systemic circulation after hypotonic water load-comparison between normal subjects and patients with congestive heart failure; Acta Cardiologica; 38 (2); pp. 81-88; Dec. 1982.
Fiaccadori et al.; Ultrafiltration in Heart Failure; Am Heart J.; 161(3); pp. 439-449; Mar. 2011.
Folkow et al.; The Effect of Graded Vasoconstrictor Fibre Stimulation on the Intestinal Resistance and Capacitance Vessels; Acta physiologica Scandinavica; 61; pp. 445-457; Aug. 1964.
Foss et al.; Reversal of genetic salt-sensitive hypertension by targeted sympathetic ablation; Hypertension; 61(4); pp. 806-811; Apr. 1, 2013.
Francis et al.; Clinical notes, suggestions and new instrument; JAMA; 134(1); pp. 20-21; May 3, 1947.
Fujita; Splanchnic circulation following coeliac plexus block; Acta Anaesthesiol Scand.; 32(4); pp. 323-327; May 1988.
GAMBRO®; Aquadex FlexFlowTM (brochure, No. L5189 Rev. B); 4 pgs.; © Aug. 2011.
Garcea et al.; Percutaneous splanchnic nerve radiofrequency ablation for chronic abdominal pain; ANZ Journal of Surgery; 75(8); pp. 640-644; Aug. 1, 2005.
Giraudo et al.; Endoscopic palliative treatment of advanced pancreatic cancer: Thoracoscopic splanchnicectomy and laparoscopic gastrojejunostomy; Annals of Oncology; 10(4); pp. S278-S280; Jan. 1, 1999.
Goldblatt et al.; Studies on experimental hypertension II: The effect of resection of splanchnic nerves on experimental renal hypertension; The Journal of Experimental Medicine; 65(2); pp. 233-241; Feb. 1, 1937.
Goroszeniuk et al.; Permanent percutaneous splanchnic nerve neuromodulation for management of pain due to chronic pancreatitis: A case report; Neuromodulation; ;14(3); pp. 253-257; May-Jun. 2011.
Greenway et al.; Role of splanchnic venous system in overall cardiovascular homeostasis; In Federal Proceedings; 42(6); pp. 1678-1684; Apr. 1983.
Greenway; Blockade of reflex venous capacitance responses in liver and spleen by hexamethonium, atropine, and surgical section; Can. J. Physiol. Pharmacol.; 69(9); 1284-1287; Sep. 1991.
Griffith et al.; The vasomotor control of the liver circulation; American Journal of Physiology; 95(1); pp. 20-34; Oct. 1930.
Griffith et al.; Vasomotor Control of the Liver Circulation. Proceedings of the Society for Experimental Biology and Medicine; 27(7); pp. 673-674; Apr. 1930.
Herman et al.; Splenic afferents and some of their reflex responses; American Journal of Physiology-Regulatory, Integrative and Comparative Physiology; 242(3); pp. R247-R254; Mar. 1982.

Ihse et al.; Bilateral thoracoscopic splanchnicectomy: effects on pancreatic pain and function; Annals of Surgery; 230(6); pp. 785-791; Dec. 1, 1999.
Ischia et al.; A new approach to the neurolytic block of the coeliac plexus: the transaortic technique; Pain; 16(4); pp. 333-341; Aug. 31, 1983.
Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.
Kang et al.; Bilateral thoracoscopic splanchnicectomy with sympathectomy for managing abdominal pain in cancer patients; Am J Surg; 194(1); pp. 23-29; Jul. 2007.
Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.
Kaufman et al.; Effect of portal hypertension on splenic blood flow, intrasplenic extravasation and systemic blood pressure; American Journal of Physiology-Regulatory, Integrative and Comparative Physiology; 284(6); pp. R1580-R1585; Jun. 1, 2003.
Kimura et al.; Application of electrical impedance analysis for diagnosis of a pulmonary mass; Chest; 105(6); pp. 1679-1682; Jun. 1994.
King et al.; Splanchnic circulation is a critical neural target in angiotensin II salt hypertension in rats; Hypertension; 50(3); pp. 547-556; Sep. 2007.
Krishna et al.; Video-assisted thoracoscopic sympathectomy-splanchnicectomy for pancreatic cancer pain; Journal of Pain and Symptom Management; 22(1); pp. 610-616; Jul. 1, 2001.
Lang-Lazdunski et al.; Videothoracoscopic splanchnicectomy for intractable pain from adrenal metastasis; Ann Thorac Surg; 73(4); pp. 1290-1292; Apr. 2002.
Le Pimpec Barthes; Thoracoscopic splanchnicectomy for control of intractable pain in pancreatic cancer; The Annals of Thoracic Surgery; 65(3); pp. 810-813; Mar. 31, 1998.
Leksowski; Thoracoscopic splanchnicectomy for the relief of pain due to chronic pancreatitis; Surg Endosc.; 15(6); pp. 592-596; Jun. 2001.
Lica et al.; Thoracoscopic left splanchnicectomy—role in pain control in unresectable pancreatic cancer. Initial experience; Chirurgia; 109(3); pp. 313-317; May-Jun. 2014.
Lieberman et al.; Celiac plexus neurolysis with the modified transaortic approach; Radiology; 175(1); pp. 274-276; Apr. 1990.
Lillemoe et al.; Chemical splanchnicectomy in patients with unresectable pancreatic cancer. A prospective randomized trial; Annals of Surgery; 217(5); pp. 447-457; May 1, 1993.
Lin et al.; Bilateral thoracoscopic lower sympathetic-splanchnicectomy for upper abdominal cancer pain. The European journal of surgery; Supplement 572; pp. 59-62; 1994.
Lonroth et al.; Unilateral left-side thoracoscopic sympathectomy for visceral pain control: a pilot study; The European Journal of Surgery; 163(2); pp. 97-100; Feb. 1, 1997.
Maass-Moreno et al.; Carotid baroreceptor control of liver and spleen volume in cats; Am J Physiol; 260(1 Pt 2); pp. H254-H259; Jan. 1991.
Maher et al.; Thoracoscopic splanchnicectomy for chronic pancreatitis pain; Surgery; 120(4); pp. 603-610; Oct. 1996.
Myhre et al.; Monitoring of celiac plexus block in chronic pancreatitis; Pain; 38(3); pp. 269-274; Sep. 1989.
Nakazato et al.; Extrinsic innervation of the canine abdominal vena cava and the origin of cholinergic vasoconstrictor nerves; J. Physiol.; 328; pp. 191-203; Jul. 1982.
Nath et al.; Biophysics and pathology of catheter energy delivery systems; Progress in Cardiovascular Diseases; XXXVII(4); pp. 185-204; Jan./Feb. 1995.
Pan et al.; Differential responses of regional sympathetic activity and blood flow to visceral afferent stimulation; Am J Physiol Regul Integr Comp Physiol.; 280(6); pp. R1781-R1789; Jun. 2001.
Pietrabissa et al.; Thoracoscopic splanchnicectomy for pain relief in unresectable pancreatic cancer; Archives of Surgery; 135(3); pp. 332-335; Mar. 1, 2000.

(56) References Cited

OTHER PUBLICATIONS

Plancarte et al.; Management of chronic upper abdominal pain in cancer: transdiscal blockage of the splanchnic nerves; Regional Anesthesia and Pain Medicine; 35(6); pp. 500-506; Nov. 1, 2010.
Prasad et al.; Thoracoscopic splanchinicectomy as a palliative procedure for pain relief in carcinoma pancreas; Journal of Minimal Access Surgery; 5(2); pp. 37-39; (Author Manuscript); Apr. 1, 2009.
RAJ; Celiac plexus/splanchnic nerve blocks; Techniques in Regional Anesthesia and Pain Management; 5(3); pp. 102-115; Jul. 2001.
Raj et al.; Radiofrequency lesioning of splanchnic nerves; Pain Practice; 2(3); pp. 242-247; Sep. 2002.
Saenz et al.; Thoracoscopic splanchicectomy for pain control in patients with unresectable carcinoma of the pancreas; Surgical Endoscopy; 14(8); pp. 717-720; Aug. 1, 2000.
Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.
Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.
Shimada et al.; Clinical evaluation of transhiatal bilateral splanchnicotomy for patients with intractable supramesenteric pain; Surgery Today; 29(11); pp. 1136-1140; Nov. 1999.
Smigielski et al.; Assessment of quality of life in patients with non-operated pancreatic cancer after videothoracoscopio splanchnicectomy; Videosurgery and Other Miniinvasive Techniques; 6(3); pp. 132-137; Sep. 1, 2011.
Stefaniak et al.; A comparison of two invasive techniques in the management of intractable pain due to inoperable pancreatic cancer; European Journal of Surgical Oncology; 31(7); pp. 768-773; Sep. 30, 2005.
Takahashi et al.; Thoracoscopic splanchnicectomy for the relief of intractable pain; Surgical Endoscopy; 10(1); pp. 65-68; Jan. 1, 1996.
Tavassoli et al.; Thoracoscopic splanchnicectomy for pain control in urresectable pancreatic cancer; Journal of Cardio-Thoracic Medicine; 1(2); pp. 53-56; Aug. 6, 2013.
Tsybenko et al.; Central nervous control of hepatic circulation; J Aut Nerv Sys; 33(3); pp. 255-266; May 1991.
Van Vliet et al.; Time course of renal responses to greater splanchnic nerve stimulation; American Journal of Physiology Regulatory, Integrative and Comparative Physiology; 260(5); pp. R894-R905; May 1991.
Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.
Wilkins et al.; The effect of splanchnic sympathectomy In hypertensive patients upon estimated hepatic blood flow in the upright as contrasted with the horizontal position; Journal of Clinical Investigation; 30(3); pp. 312-317; Mar. 1951.
Worsey et al.; Thoracoscopic pancreatic denervation for pain control in irrsectable pancreatic cancer; British Journal of Surgery; 80(8); pp. 1051-1052; Aug. 1, 1993.
Wroclaw Medical Univ. (Poland); Removing a section of nerve visceral improved (press release; with machine translation); retrieved Oct. 10, 16 from the internet: http://www.zdrowie.abc.com.pl/aktualnoscifwrcclaw-u8uniecte-fragmentu-nerwu-trzewnego-popfawilo-u-chorej-wydolnosc-serca,25247.html; 5 pgs.; Sep. 23, 2016.

Yan et al.; Neurolytic celiac plexus block for pain control in unresectable pancreatic cancer; Am J Gastroenterol; 102(2); pp. 430-438; Feb. 2007.
Levin et al.; U.S. Appl. No. 15/017,260 entitled "Devices And Methods For Treatment Of Heart Failure By Splanchnic Nerve Ablation," filed Feb. 5, 2016.
Panescu et al.; U.S. Appl. No. 16/222,823 entitled "Methods and devices for endovascular ablation of a splanchnic nerve," filed Dec. 17, 2018.
Levin et al.; U.S. Appl. No. 16/510,503 entitled "Devices and methods for treatment of heart failure by splanchnic nerve ablation," filed Jul. 12, 2019.
Gelfand et al.; U.S. Appl. No. 16/277,824 entitled "Devices and methods for treatment of heart failure via electrical modulation of a splanchnic nerve," filed Feb. 15, 2019.
Baghdadi et al.; Systematic review of the role of thoracoscopic splanchnicectomy in palliating the pain of patients with chronic pancreatitis: Surgical endoscopy; 22(3); pp. 580-588; Dec. 28, 2007.
Buscher et al : Bilateral thoracoscopic, splanchnicectomy for pain in patients with chronic pancreatitis impairs adrenomedullary but net noradrenergic sympathetic function; Surgical Endoscopy; 26(8); p. 2183-2188; Aug. 2012.
Crespy et al.; Anatomical bases of the transhiatus approach to the greater splanchnic nerve; Anatomia Clinica; 6(4); pp. 247-254; Dec. 1, 1984.
Dayal et al.: Variations in the formation of thoracic splanchnic nerves; European Journal of Anatomy; vol. 18: pp. 141-151; (year of pub. sufficiently earlier than effective US filing date and any foreign priority date) 2014.
Gafanovich et al.; Chronic diarrhea-induced by celiac plexus block?; Journal of Clinical Gastroenterology; 26(4); pp. 300-302; Jun. 1, 1998.
Girouard et al.; Optical mapping in a new guinea pig model of ventricular tachycardia reveals mechanisms for multiple wavelengths in a single reentrant circuit; Circulation; 93(3); pp. 603-613; Feb. 1, 1996.
Loukas et al.; A review of the thoracic splanchnic nerves and celiac ganglia; Clinical Anatomy; 23(5); pp. 512-522; Jul. 2010.
Mallet-Guy et al.; Treatment of chronic pancreatitis by unilateral splanchnicectomy; Archives of Surgery; 60(2); pp. 233-241; Feb. 1, 1950.
Masuda et al.; Splanchnicectomy for pancreatic cancer pain; BioMed Research International; Jan. 1, 2014.
Naidoo et al.; Thoracic splanchnic nerves: implications for splanchnic denervation; Journal of Anatomy; 199(5); pp. 585-590; Nov. 2001.
Norman: Posterior Mediastinum; As last known Jun. 6, 2013: retrieved from the internet (https: web.archive.org/web/20130606053828/http://www.wesnorman.com/thoraxlesson5.htm); 11 pages; on Sep. 16, 2020.
Raj et al.; The development of a technique for radiofrequency lesioning of splanchnic nerves; Current Review of Pain; 3(5); pp. 377-387; Oct. 1999.
Sadar et al.; Bilateral thoracic sympathectomy-splanchnicectomy in the treatment of intractable pain due to pancreatic carcinoma: Cleveland Clinic Quarterly; 41; pp. 185-188; (year of pub. sufficiently earlier than effective US filing date and any foreign priority date)1974.
Iranitalab, U.S. Appl. No. 17/152,665 entitled "Methods and devices for endovascular ablation of a splanchnic nerve," filed Jan. 19, 2021.
Levin et al.; U.S. Appl. No. 17/171,447 entitled "Devices and methods for treatment of heart failure by splanchnic nerve ablation," filed Feb. 9, 2021.

\* cited by examiner

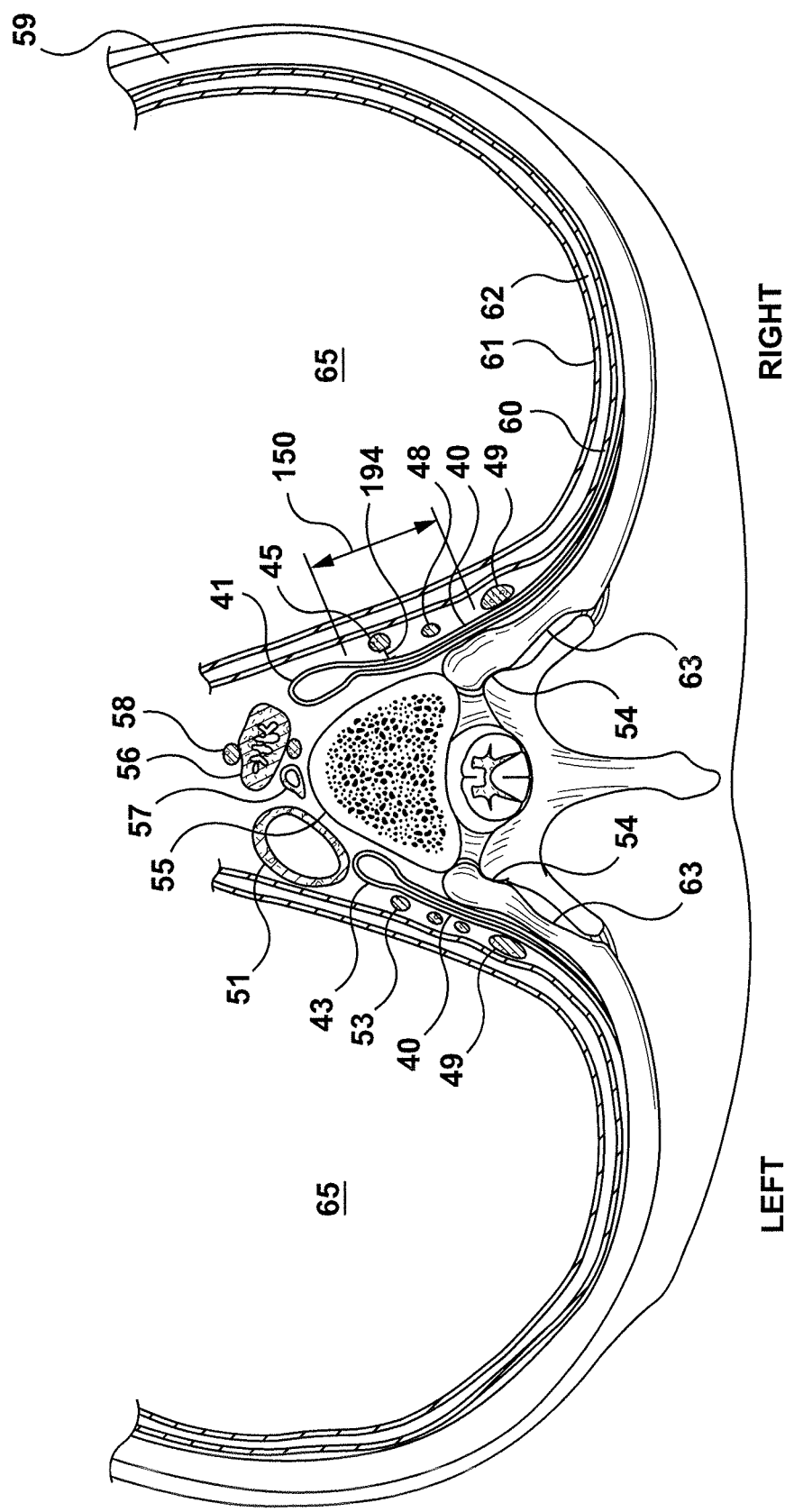

Frequency profile of $Z_{mag}$ during safe state

Frequency profile of $Z_{mag}$ during unsafe state

Frequency profile of $Z\varphi_f$ during safe state

Frequency profile of $Z\varphi_f$ during unsafe state

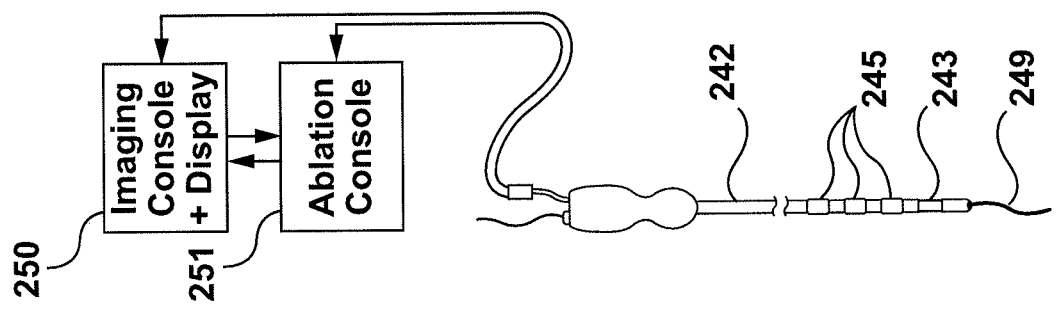
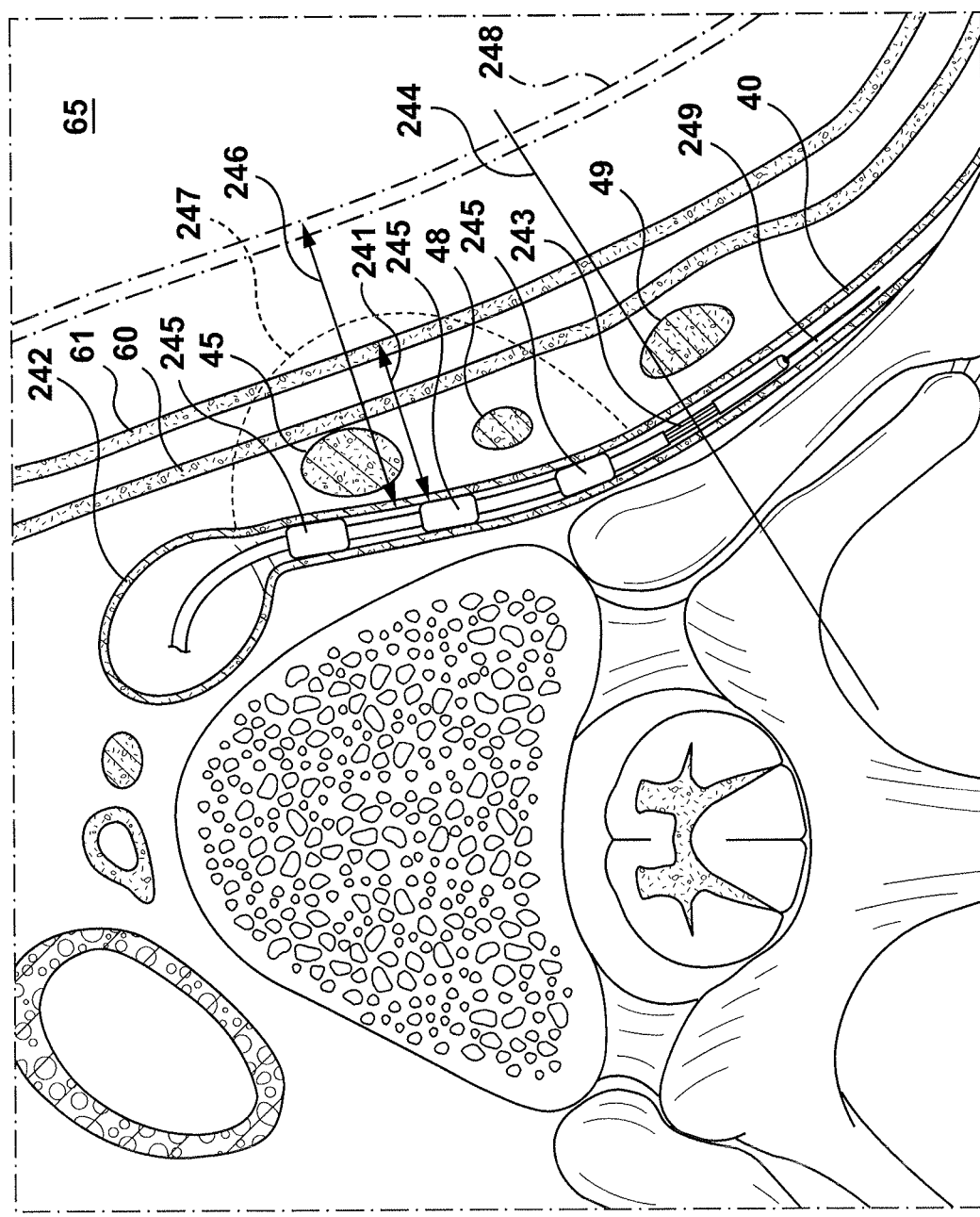
FIG. 33A
FIG. 33B

DEVICES, SYSTEMS, AND METHODS FOR TREATMENT OF HEART FAILURE BY SPLANCHNIC NERVE ABLATION

CROSS REFERENCE TO RELATED APPLICATIONS

This application claims priority to the following U.S. Provisional Applications, each of which is herein incorporated by reference in its entirety: 62/368,912 filed Jul. 29, 2016; 62/411,492 filed Oct. 21, 2016; and 62/482,142 filed Apr. 5, 2017.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Heart failure (HF) is a medical condition that occurs when the heart is unable to pump sufficiently to sustain the organs of the body. Heart failure is a serious condition and affects millions of patients in the United States and around the world.

In the United States alone, about 5.1 million people suffer from heart failure and according to the Center for Disease Control, the condition costs the nation over $30 billion in care, treatments, medications, and lost production. The normal healthy heart is a muscular pump that is, on average, slightly larger than a fist. It pumps blood continuously through the circulatory system to supply the body with oxygenated blood. Under conditions of heart failure, the weakened heart cannot supply the body with enough blood and results in cardiomyopathy (heart muscle disease) characterized by fatigue and shortness of breath, making even everyday activities such as walking very difficult.

Oftentimes, in an attempt compensate for this dysfunction, the heart and body undergo physiological changes that temporarily mask the inability of the heart to sustain the body. These changes include the enlargement of heart chamber, increased cardiac musculature, increased heart rate, raised blood pressure, poor blood flow, and imbalance of body fluids in the limbs and lungs.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

Systolic dysfunction is characterized by a decrease in myocardial contractility. A reduction in the LVEF results when myocardial contractility is decreased throughout the left ventricle. CO is maintained in two ways: left ventricular enlargement results in a higher SV and an increase in contractility as a result of the increased mechanical advantage from stretching the heart. However, these compensatory mechanisms are eventually exceeded by continued weakening of the heart and CO decreases, resulting in the physiologic manifestations of HF. The left side of the heart cannot pump with enough force to push a sufficient amount of blood into the systemic circulation. This leads to fluid backing up into the lungs and pulmonary congestion. In general terms, systolic dysfunction is defined as an LVEF less than 40% and heart failure in these patients can be broadly categorized as heart failure with reduced ejection fraction (HFrEF).

Diastolic dysfunction refers to cardiac dysfunction in which left ventricular filling is abnormal and is accompanied by elevated filling pressures. In diastole, while the heart muscle is relaxed the filling of the left ventricle is a passive process that depends on the compliance (defined by volume changes over pressure changes), or distensibility, of the myocardium or heart muscle. When the ventricles are unable to relax and fill, the myocardium may strengthen in an effort to compensate to poor SV. This subsequent muscle hypertrophy leads to even further inadequate filling. Diastolic dysfunction may lead to edema or fluid accumulation, especially in the feet, ankles, and legs. Furthermore, some patients may also have pulmonary congestion as result of fluid buildup in the lungs. For patients with HF but without systolic dysfunction, diastolic dysfunction is the presumed cause. Diastolic dysfunction is characteristic of not only hypertrophic cardiomyopathy (HCM), which is characterized by the thickening of heart muscle, but also restrictive cardiomyopathy (RCM), which is characterized by rigid heart muscle that cannot stretch to accommodate passive filling. In general terms, diastolic dysfunction is defined as a LVEF of greater than 40% and HF in these patients can be broadly categorized as heart failure with preserved ejection fraction (HFpEF).

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema, etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation.

Thus there remains a need for improved therapies for heart failure patients that is safe and effective, and devices and systems that are adapted to perform those therapies.

SUMMARY

In view of the foregoing, it would be desirable to provide apparatuses and methods to affect neurohumoral activation for the treatment of HF including heart failure with preserved ejection fraction (HFpEF) and patients with impeded circulating blood volume expansion tolerance, exercise limitations and dyspnea on exertion.

The present disclosure includes methods, devices, and systems that provide improved treatment options for patients suffering from HF by ablating a portion of the thoracic splanchnic nerves (TSN), which include the greater, lesser and least splanchnic nerves, and their contributing nerves that originate from the sympathetic chain and form at least one of the thoracic splanchnic nerves that innervate organs and vasculature of the abdominal compartment and the greater splanchnic nerve (GSN) in particular. Since the GSN, lesser splanchnic nerve, and least splanchnic nerve forms from preganglionic fibers emerging from the sympathetic trunk as roots or tributaries, which relay to the celiac ganglion, all the preganglionic fibers that form thoracic splanchnic nerves between the sympathetic trunk and celiac ganglion are called thoracic splanchnic nerves for simplicity. By selectively ablating specific nerves, the disclosure provides novel methods and devices that can affect circulating blood volume, pressure, blood flow and overall heart and circulatory system functions. In this way, the present disclosure helps to introduce novel solutions to treat HF and particularly HFpEF based on the most contemporary physiological theories regarding HF.

Tools for catheter navigation include use of extravascular landmarks such as intercostal space and/or vertebrae. Internal scans or detection methods may include fluoroscopic detection of radiographic landmarks, CT scans, MRI and/or ultrasound. These scans would be used for direct nerve visualization, or visualization of adjacent vascular (e.g., azygos) and non-vascular structures (diaphragm, vertebrae, ribs). The use of radiocontrast and a guide wire can aid in the placement of the ablation element of the device.

At the targeted site, some proposed methods of target modulation, specifically to ablate a target nerve include cryo or high temperature based ablation, local drug delivery (e.g., local injection and infiltration by neurolitics, sympatholytics, neurotoxins), local anesthetics, or energy delivery that could include radio frequency (RF) ablation, ultrasound energy delivery, or mechanical compression.

The present disclosure may provide treatments that are used in the cardiac catheterization laboratory to ablate a splanchnic nerve such as a greater splanchnic nerve unilaterally on the right or left side of the body or bilaterally on both sides to mobilize blood out of the effective circulation (stressed volume) and shift it into splanchnic organs or vasculature, and splanchnic vascular bed (venous reservoir), increase venous compliance, in order to decrease and normalize cardiac preload, reduce venous congestion, relieve pulmonary congestion, reduce pulmonary blood pressures and thus sensation of dyspnea, especially in response to exercise, and to increase or relatively maintain stroke volume, enhance blood circulation and improve overall heart function while maintaining a sufficiently normal response to orthostatic posture changes. As such, the disclosed methods of therapy, devices, and systems can grant patients suffering from heart disease a return to a higher quality of living and may prevent hospital admissions with ADHF.

Further, the present disclosure can be used in the therapy of acute as well as chronic HF decompensation. Acute HF decompensation would be prevented or its progression halted by an offloading of the stressed volume and relieving venous congestion, which is the main component of the renal dysfunction in HF. The disclosed devices and methods of therapy can be used in support of traditional medical therapy like diuretics as they can interrupt or delay progression of cardiac decompensation. The offloading of the stressed volume and relieving venous congestion can be expected to increase diuretic responsiveness of the patients.

In a chronic CHF state, the disclosed devices and methods of therapy can be used to improve fluid distribution, increase venous compliance and capacitance, relieve venous congestion, reduce pulmonary artery and left atrial pressure during exercise, improve relaxation of ventricles and thus improve symptoms of congestion like shortness of breath and improve exercise capacity.

Compared to prior methods of nerve ablation, the disclosed devices and methods of therapy aim to reliably and consistently target selective TSN ablation in a safe manner that causes no or minimal adverse effects such as pain, orthostatic and gastric side effects observed in the past surgical procedures, serious long term damage to gastric function, damage to lung and visceral pleura, or other unintended, untargeted nerve damage.

Additionally, the disclosed devices and methods of treatment fulfill a long desired need to provide a treatment for HF, especially for patients of diastolic or HFpEF and particularly a need to reduce pulmonary artery blood pressure and relieve dyspnea (shortness of breath) in response to exercise and in some cases at rest. Resulting measurable improvements in health may comprise increasing exercise capacity by reducing an increase of pulmonary capillary wedge pressure and pulmonary artery pressure in response to exertion.

Additional Embodiments of Summary

1. A device for nerve ablation, in particular for treatment of heart failure by nerve ablation, comprising;
   a. an endovascular catheter having at least one ablation element;
   b. an energy source capable of transmitting energy to the ablation element; and
   c. a controller active on the energy source and configured to control the energy source and to execute a command procedure comprising energizing the ablation element.
2. The device of embodiment 1, wherein the endovascular catheter has:
   i. a proximal region,
   ii. a flexible shaft, and
   iii. a distal region,
      wherein the flexible shaft connects the proximal and distal regions and is configured to access a vasculature of a patient,
      wherein the proximal region is configured to remain external to the patient, and
      wherein the distal region is configured to be advanced through the patient vasculature and comprises the at least one ablation element.
3. The device of any one of the preceding embodiments wherein the catheter comprises at least one stimulation element and/or at least one detection element.
4. The device of embodiment 3 wherein the distal region of the catheter comprises the at least one ablation element, the at least one stimulation element and the at least one detection element
5. The device of any one of the preceding embodiments 3 or 4, wherein the energy source is capable of transmitting energy to the ablation element, to the stimulation element and/or to the detection element.
6. The device of any one of the preceding embodiments 3 or 4 or 5, wherein the controller active on the energy source is configured to control the energy source to execute the command procedure, which comprises at least two of the following steps:

a. energizing the ablation element,
b. energizing the stimulation element, and
c. energizing the detection element.
7. The device of any one of the preceding embodiments 3 or 4 or 5 or 6, wherein the controller active on the energy source is configured to control the energy source to execute the command procedure, which comprises the following steps:
a. energizing the ablation element,
b. energizing the stimulation element, and
c. energizing the detection element.
8. The device of any one of the preceding embodiments, wherein the energy source is part of the catheter proximal region.
9. The device of any one of the preceding embodiments, wherein the controller comprises a digital control unit and an embedded software program which when executed by the digital control unit configures the controller to execute the control procedure, or an analog circuit configured to execute the control procedure.
10. The device of any one of the preceding embodiments, further comprising a user interface, optionally part of the catheter proximal region, communicatively coupled with the controller and configured to receive inputs from a user and transmit said inputs to the controller.
11. The device of any one of the preceding embodiments comprising a plurality of ablation elements, and wherein each ablation element is associated with at least one stimulation element.
12. The device of any one of the preceding embodiments, wherein the ablation element is one chosen from the list consisting of: an electrode, a cryo console, a drug delivery device, injector of neurolytic blocking agent, an ultrasound device, an radio frequency device, a thermal ablation device, a laser emitter and any combination thereof, and/or wherein the stimulation element is one chosen from the list consisting of: an electrode, a cryo console, a drug delivery device, injector of neurolytic blocking agent, an ultrasound device, an radio frequency device, a thermal ablation device, a laser emitter and any combination thereof.
13. The device of any one of the preceding embodiments from 3 to 12, wherein the stimulation element comprises at least one electrode or an electrode pair or electrode pairs, optionally wherein the controller is configured to command the energy source to supply the stimulation element with a current having voltage waveform comprised between 10 and 500 Hz. The waveform may be tuned to optimize TSN response to stimulation of a TSN and minimize response of pain receptors. For example, a nerve stimulation waveform with fast slew rates and low amplitudes may be used to generate a physiological response such as increased blood pressure or heart rate from a TSN but not cause pain to the patient. In one embodiment, the current to stimulate the TSN would have a short duration, in a range about the respective chronaxie, and generate an electric field of a minimum intensity equal to 12.3 V/m. To generate such field, a 3 F to 8 F catheter carrying electrodes configured in a monopolar or bipolar stimulation configuration may be used. The electrodes may have a length of 0.5 to 4 mm. If configured for bipolar stimulation, the electrodes may be separated by a 0.5 to 20 mm distance. For a typical stimulating impedance of 200 to 1000Ω, the resulting stimulating currents may be in the 0.1-5 mA range, or stimulating voltages in the 0.05-5 V range. Electric field intensities in the range of 30 to 500 V/m, at pulse durations of 0.12 ms, can be safely used to capture a TSN without causing pain to patients.
14. The device of any one of the preceding embodiments, wherein the ablation element comprises a radio frequency device and wherein the radio frequency device is configured to output an electrical current having a frequency in a range of 300 kHz to 3 MHz and a power in a range of 5 to 50 W.
15. The device of any one of the preceding embodiments from 3 to 14, wherein the detection element is chosen from the group comprising:
a. systemic venous pressure transducers,
b. pulmonary venous pressure transducers,
c. pulmonary arterial pressure transducers,
d. at least one cardiac output detector,
e. at least one blood flow monitor,
f. or combinations thereof.
16. The device of any one of the preceding embodiments from 3 to 15, wherein the distal region further comprises two distinct detection elements each configured to be positioned at a respective and different part of the patient vasculature.
17. The device of any one of the preceding embodiments from 3 to 16, wherein the detection element comprises one or more blood pressure transducers.
18. The device of any one of the preceding embodiments from 3 to 17, wherein the detection element comprises one or more tissue temperature sensors.
19. The device of any one of the preceding embodiments from 3 to 18, wherein the detection element comprises one or more hemodynamic sensors.
20. The device of any one of the preceding embodiments from 3 to 19, wherein the detection element comprises one or more environmental temperature sensors.
21. The device of any one of the preceding embodiments from 3 to 20, wherein the detection element comprises one or more tissue impedance sensors.
22. The device of any one of the preceding embodiments, wherein the distal region comprises a deployable structure chosen from the list consisting of a balloon, a cage, a basket, a preformed shape, lasso and loop and any combination thereof.
23. The device of any one of the preceding embodiments, comprising a guidewire—optionally equipped with an atraumatic tip—to facilitate advancement of the catheter through patient vasculature.
24. The device according to embodiment 23, wherein the catheter comprises a guidewire lumen for delivery of the catheter over the guidewire.
25. The device of any one of the preceding embodiment from 3 to 24, wherein the ablation element and the stimulation element are positioned on the catheter relative to one another so that an area, in which the stimulation signal is delivered by the stimulation element, correlates with an ablation zone in which ablation energy delivered by the ablation element is sufficient to cause irreversible ablation of nerve tissue.
26. The device of any one of the preceding embodiments, wherein the catheter is one or more of sterile, elongated, flexible, irrigated, sheathed, deflectable, radio florescent, radio opaque, or any combination thereof.
27. The device of any one of the preceding embodiments, wherein the command procedure, which the controller is configured to execute, comprises executing a mapping algorithm for identifying proper positioning in the patient vasculature of one or both of the ablation element and the stimulation element.

28. The device of embodiment 27, wherein the controller is configured to execute said mapping algorithm before commanding the energy source to energize one or both the ablation element and the stimulation element.

29. The device of embodiment 27 or 28, wherein the mapping algorithm includes:
    a) commanding the energy source to energize the at least one ablation element or the at least one stimulation element for applying a stimulation through an inner wall of a vein and stimulate an adjacent nerve,
    b) detecting changes in a patient's hemodynamic or physiological parameter,
    c) determining that the at least one ablation element, or that the at least one stimulation element, be in a proper position based on the detected changes.

30. The device of embodiment 29, wherein the step of determining that the at least one ablation element, or that the at least one stimulation element, be in a proper position based on the detected changes comprises the following sub-steps:
    1. comparing the detected changes in the patient's hemodynamic or physiological parameter with a predetermined acceptable value or set of values,
    2. establishing that the at least one ablation element, or that the at least one stimulation element, be in a proper position if the detected changes in the patient's hemodynamic or physiological parameter conform to the acceptable value or set of values.

31. The device of embodiment 29 or 30, wherein the mapping algorithm includes a step d) of generating a signal indicative of proper placement of the at least one ablation element or of the at least one stimulation element if—following said step c) of determining—it has been concluded that the detected changes in the patient's hemodynamic or physiological parameter conform to the acceptable value or set of values.

32. The device of embodiment 31, wherein generating said signal comprises commanding a user interface associated with the controller to issue a first audible and/or visible information.

33. The device of any one of embodiments from 29 to 32, wherein the mapping algorithm comprises a step e) of generating a further signal indicative of wrong placement of the at least one ablation element or of the at least one stimulation element if—following said step c) of determining—it has been concluded that the detected changes do not conform to said acceptable value or set of values.

34. The device of embodiment 33, wherein generating said further signal comprises commanding a user interface associated with the controller to issue a second audible and/or visible information different from the first audible and/or visible information.

35. The device of any one of embodiments from 29 to 34, wherein the mapping algorithm includes detecting a re-positioning of the distal region of the catheter, and repeating the steps a) to c) or a) to d) or a) to e) until when—following the step of determining—it has been concluded that the detected changes in the patient's hemodynamic or physiological parameter conform to said acceptable value or set of values.

36. The device of any one of the preceding embodiments from 25 to 35, wherein the ablation element comprises one or more ablation electrodes or electrode pairs, and/or wherein the stimulation element comprises one or more stimulation electrodes or electrode pairs.

37. The device of embodiment 36, wherein the step of commanding the energy source to energize the at least one ablation element or the at least one stimulation element comprises commanding the energy source to apply electrical energy to the at least one ablation electrode or the at least one stimulation electrode.

38. The device of embodiment 36 or 37, wherein the step of determining that the at least one ablation element, or that the at least one stimulation element, be in a proper position comprises determining when an ablation electrode or a stimulation electrode is proximate a target nerve in the patient by detecting the change in at least one selected hemodynamic parameter or physiological parameter of the patient while respectively the ablation electrode or stimulation electrode applies electrical energy.

39. The device of embodiment 36 or 37 or 38, wherein the catheter comprises a plurality of ablation electrodes, optionally located on the distal region of the catheter, and wherein commanding the energy source to apply electrical energy to the ablation electrode comprises commanding the energy source to:
    1. sequentially apply electrical energy from each of the ablation electrodes and
    2. select at least one of the ablation electrodes which, when applying the electrical energy, causes a change to the at least one selected hemodynamic parameter or physiological parameter.

40. The device of embodiment 36 or 37 or 38 or 39, wherein the catheter comprises a plurality of stimulation electrodes, optionally located on the distal region of the catheter, and wherein commanding the energy source to apply electrical energy to the stimulation electrode comprises commanding the energy source to:
    1. sequentially apply electrical energy from each of the stimulation electrodes and
    2. select at least one of the stimulation electrodes which, when applying the electrical energy, causes a change to the at least one selected hemodynamic parameter or physiological parameter.

41. The device of any one of embodiments from 36 to 40, wherein commanding the energy source to apply electrical energy to the stimulation electrodes comprises commanding the energy source for delivering at least one stimulation pulse sequentially to each of the stimulation electrodes, and wherein the mapping algorithm includes:
    1. recording a baseline of the selected hemodynamic or physiological parameter while the stimulation electrodes do not apply electrical energy to the vein, and
    2. recording values of the selected hemodynamic or physiological parameter in response to each stimulation pulse.

42. The device of any one of embodiments from 36 to 41, wherein commanding the energy source to apply electrical energy to the ablation electrodes comprises commanding the energy source for delivering at least one stimulation pulse sequentially to each of the ablation electrodes, and wherein the mapping algorithm includes:
    1. recording a baseline of the selected hemodynamic or physiological parameter while the ablation electrodes do not apply electrical energy to the vein, and 2. recording values of the selected hemodynamic or physiological parameter in response to each stimulation pulse.
43. The device of embodiment 41 or 42, wherein the mapping algorithm includes a step of correlating the recorded value to the ablation electrode, or stimulation electrode, applying the electrical energy while the value was recorded.
44. The device of embodiment 41 or 42 or 43, wherein the stimulation pulse has a current (I) of 0 to 10 mA, a pulse width (pw) of 100 to 1000 us, a frequency (F) of 20 to 40 Hertz and a duty cycle (D) of 20 to 60 seconds.
45. The device of embodiment 41 or 42 or 43 or 44, further comprising, for each sequential application:
   1. determining if the value for selected hemodynamic or physiological parameter is greater than a threshold from the baseline, optionally >20% from baseline,
   2. allowing the selected hemodynamic or physiological parameter to return to or near the baseline and repeat for at least three measurement, recording average measurements for at least 3 stimulations, and
   3. if standard error is within +/−10%, confirming the change in the selected parameter.
46. The device of any one of embodiments from 29 to 45, wherein the hemodynamic or physiological parameter is selected from the group of responses consisting of pupil dilation, increased sweating, increased heart rate, increased blood pressure, increased mean arterial pressure and any combination thereof.
47. The device of any one of the preceding embodiments, wherein the catheter is configured for ablation of a greater splanchnic nerve or greater splanchnic nerve roots or the sympathetic chain trunk.
48. The device of any one of embodiments from 36 to 47, wherein the ablation element comprises at least two RF electrodes positioned on the distal region of the catheter.
49. The device according to any one of the preceding embodiments comprising an imaging device communicatively connected to the controller.
50. The device of the preceding embodiment, wherein the imaging device comprises one of: an X-Ray imaging device, a computerized tomography (CT) imaging device, a magnetic resonance imaging (MRI) device, an ultrasound imaging transducer.
51. The device of any one of the preceding embodiments from 27 to 48, in combination with embodiment 49 or with embodiment 50, wherein the mapping algorithm comprises receiving images from the imaging device, and determining correct positioning of the ablation element based on said images.
52. The device of embodiment 51, wherein the mapping algorithm further comprises causing the energy source to deliver ablative energy to ablation element to ablate tissue surrounding the vasculature where the distal region is inserted, for example the intercostal vein, within a radius of 5 mm.
53. The device of any one of embodiments 51 or 52, wherein the controller is configured to allow the energy source to deliver ablative energy to the ablation element only if correct positioning of the ablation element has been determined.
54. The device of embodiment 51 or 52 or 53, wherein the ablation element comprises at least two RF electrodes and wherein determining the correct positioning of the ablation element comprises determining the correct positioning of the at least two RF electrodes based on said images.
55. The device of embodiment 54, further wherein causing the energy source to deliver ablative energy to the ablation element comprises causing the energy source to deliver RF energy to the at least two RF electrodes to thermally ablate tissue surrounding the vasculature where the distal region is inserted, for example the intercostal vein, within a radius of 5 mm.
56. The device of any one of the preceding embodiments wherein the catheter—and in particular a distal region of the catheter—is configured to be inserted into a patient's intercostal vein and is configured to place the ablation elements or the stimulation elements into the intercostal vein a distance from where it branches off the azygos vein, in particular from within 5 cm (e.g. within 3 cm, within 2 cm, within 1 cm) from the ostium. The device of embodiment 56 wherein the catheter—and in particular the distal region of the catheter—is configured to place the ablation elements or the stimulation elements such that the most distal ablation or stimulation element, optionally an RF electrode, be placed within the intercostal vein and within 5 mm of a costovertebral joint.
57. The device of any one of the preceding two embodiments wherein the catheter—and in particular a distal region of the catheter—comprises at least two RF electrodes, said two RF electrodes being either ablation elements or stimulation elements, and wherein the catheter—and in particular said catheter distal region—is configured such that when the most distal electrode is placed within the intercostal vein and within 5 mm of a costovertebral joint the at least two RF electrodes are configured on the catheter to be positioned between the costovertebral joint and the ostium of the intercostal vein joining an azygos vein.
58. The device of any one of the preceding three embodiments, wherein the catheter comprises one or more markers positioned on the catheter distal region to identify catheter insertion depth into a vessel, in particular into an intercostal vein.
59. The device of embodiment 59, wherein said markers comprise radio-opaque markers or mechanical markers, optionally radio opaque bands or annular protrusions or annular indents, positioned on the catheter distal region and identifiable by an imaging device.
60. The device of any one of the preceding embodiments from 49 to 59, wherein—with the catheter distal region inserted in an intercostal vein—the imaging device is configured for generating an image related to a position of the patient's lung relative to said intercostal vein receiving the catheter distal region, and wherein the controller is configured to:
   1. receive the generated image,
   2. determine from the generated image whether the position of the patient's lung relative to said intercostal vein is within a predetermined distance,
   3. allow the energy source to deliver ablative energy only if the position of the patient's lung is beyond said predetermined distance.
61. The device of any one of the preceding embodiments from 49 to 60, wherein the imaging device comprises an ultrasound imaging transducer communicatively connected to the controller and positioned on a distal region of the catheter.

62. The device of the preceding embodiment, wherein the ultrasound imaging transducer is configured for generating a sonogram to image a position of the patient's lung relative to an intercostal vein, and wherein the controller is configured to:
   1. receive the generated sonogram,
   2. determine from the generated sonogram whether the position of the patient's lung relative to the intercostal vein is within a predetermined distance,
   3. allow the energy source to deliver ablative energy only if the position of the patient's lung is beyond said predetermined distance.
63. The device of embodiment 60 or 61 or 62, wherein the predetermined distance is at least 6 mm, wherein the controller is configured to cause the energy source to deliver ablative energy when the position of the patient's lung is at least 6 mm away from a wall of said intercostal vein, and to cause the energy source not to deliver ablative energy when the position of the patient's lung is within 6 mm of the wall of the intercostal vein.
64. The device of embodiment any one of the preceding embodiments, wherein the controller is configured to cause the energy source to deliver ablative energy suitable to create a thermal lesion of tissue within 5 mm of the ablation element while not ablating tissue beyond 5 mm of the ablation element.
65. The device of any one of the preceding embodiments, wherein the controller is configured to execute a lung presence detection procedure comprising the following further steps:
   receive or determine at least one measured value of a physical parameter of tissue present in an ablation zone proximate the ablation element,
   compare said value of the measured physical parameter with at least one reference value,
   and—based on said comparison—detect presence of lung tissue in the ablation zone.
66. The device of embodiment 65, wherein the physical parameter is an electrical parameter of tissue.
67. The device of embodiment 66, wherein the physical parameter is electrical impedance of tissue.
68. The device of embodiment 65 or 66, wherein the controller is configured to receive the measured value of the physical parameter of tissue present between a catheter electrode and a dispersive electrode or between two catheter electrodes.
69. The device of embodiment 65 or 66 or 67 or 68, comprising an electric parameter sensor communicatively connected to the controller, and wherein the controller is configured to:
   command the energy source to cause an electric current to flow between a catheter electrode connected to the energy source and a dispersive electrode connected to the energy source or between two catheter electrodes connected to the energy source,
   receive the at least one measured value of the physical parameter from the electric parameter sensor.
70. The device of embodiment 65, wherein the physical parameter is an acoustic parameter of tissue.
71. The device of embodiment 66, wherein the physical parameter is acoustic conductance of tissue.
72. The device of embodiment 70 or 71, wherein the controller is configured to receive the measured value of the physical parameter of tissue present between a catheter acoustic emitter and an acoustic receiver separate from the catheter or between a catheter acoustic emitter and a catheter acoustic receiver, said acoustic transmitter and acoustic receiver being communicatively connected with the controller.
73. The device of embodiment 72, wherein the controller is configured to:
   command the energy source to cause emission of an emitted acoustic signal from said acoustic emitter,
   receive from the acoustic receiver a detection signal related to an acoustic signal detected by the acoustic receiver as a consequence of the emitted acoustic signal,
   determine a value of the physical parameter based on said emitted signal and said detected signal.
74. The device of embodiment 67 or 68 or 69, wherein electrical frequency used for measuring tissue impedance is 5 kHz to 5 MHz.
75. The device of any one of embodiments from 65 to 74, wherein the controller is configured to allow the energy source to energize the ablation energy—optionally to deliver ablative energy—only if the presence of the lung in the ablation zone is not detected.
76. The device of any one of the preceding embodiments, wherein the controller is configured to command the energy source to titrate ablative energy to create a lesion that reduces injury to the lung.
77. The device of the preceding embodiment, wherein the ablation element comprises an ablation electrode and wherein the titration involves changes in the magnitude or energy, ramp, and time.
78. The device of embodiment 77, wherein the ablation element is configured for focused or unfocused high frequency or low frequency ultrasound, and the titration involves changes in magnitude of energy, time, focal depth, or frequency.
79. The device according to any one of the preceding embodiments, wherein the controller is configured to command the energy source to apply ablation energy continuously or intermittently.
80. The device of any one of the preceding embodiments from 65 to 79, wherein the controller is configured to repeat the lung presence detection procedure either continuously or at time intervals.
81. The device of embodiment 80, wherein the controller is configured to prevent the energy source to energize the ablation element when presence of the lung in the ablation zone is detected and to cause the energy source to energize the ablation element as soon as no presence of the lung in the ablation zone detected.
82. The device according to any one of the preceding embodiments, comprising a catheter withdrawal unit configured for totally or partially retracting the catheter from the vasculature.
83. The device of embodiment 82, wherein the catheter withdrawal unit comprises an automated mechanism communicatively connected with the controller and active on the catheter, the controller being configured to command automated mechanism for retracting the catheter from the vasculature.
84. The device of embodiment 84, wherein the automated mechanism comprises one of a linear actuator, a motorized unit, a ratchet wheel, a ratchet rack, a screw mechanism.
85. The device according to embodiment 83 or 84, wherein the controller is configured to command the automated mechanism for retracting the catheter from the vasculature either at a constant rate or at rate dependent on a predetermined feedback signal.

86. The device according to the preceding embodiment, wherein the feedback signal comprises one of said tissue temperature change or impedance change, and wherein the controller is configured to induce automatic pull back of the catheter from the vasculature acting on the automated mechanism based on said feedback signal.
87. The device according to any one of the preceding embodiments from 83 to 86, wherein the controller is configured to command automated mechanism for retracting the catheter from the vasculature whilst energy is applied to the ablation electrode and thus along the walls of the vasculature.
88. The device according to any one of the preceding embodiments from 83 to 87, wherein the controller is configured to command automated mechanism for retracting the catheter from the vasculature according to a spiral pattern.
89. The device according to any one of the preceding embodiments from 83 to 88, wherein the controller is configured to command automated mechanism for retracting the catheter from the vasculature according at a constant rate, for example about 1 mm per second, while delivering ablation energy to create an elongated lesion.
90. The device according to any one of the preceding embodiments from 83 to 89, wherein the controller is configured to command automated mechanism for retracting the catheter from the vasculature according at a constant rate, for example about 1 mm per second, while making multiple stationary lesions by delivering ablation energy in short increments, for example making multiple 5 mm lesions that overlap.
91. The device of any one of the preceding embodiments comprising deployable splines and ablation elements positioned on the deployable splines.
92. The device of embodiment 91, wherein the splines are made of superelastic material such as Nitinol and have the ability to conform to the contours of the vessel wall.
93. The device of embodiment 91 or 92 comprising splines of different lengths in order for them to be packed into smaller device when collected into a sheath.
94. The device of any one of the preceding embodiments comprising electrodes mounted on a resilient spring in the shape of the helix.
95. The device according to any one of the preceding embodiments, wherein the command procedure includes a monitoring sequence comprising monitoring a physiological reaction to confirm successful ablation of the target nerve and repeating delivery of ablation energy if the physiological reaction does not change compared to the physiological state prior to delivering ablation energy.
96. The device according to any one of the preceding embodiments comprising a respiratory monitor communicatively connected with the controller.
97. The device of the preceding embodiment, wherein the respiratory monitor comprises one or more respiratory sensors—optionally including a respiratory belt, an accelerometer, an oxygen saturation meter, a tissue impedance meter—configured to generate electric signals related to patient's ventilation.
98. The device of the preceding embodiment wherein the controller is configured to:
receive from the respiratory monitor signals related to patient's ventilation,
determine from said signals coming from the respiratory monitor one or more of the following patient's ventilation parameters:
ventilation rate (breaths per unit of time),
ventilation rate (total volume inspired or expired per unit time),
exhalation start time in each breath,
inhalation start time in each breath,
exhalation duration per breath,
inhalation duration per breath,
control said source to deliver ablation energy based on one or more of said ventilation parameters.
99. The device of embodiment 96 or 97, wherein respiratory monitor is configured to generate signals related to patient's ventilation, and includes a own computing unit configured to determine from said signals one or more of the following patient's ventilation parameters:
ventilation rate (breaths per unit of time),
ventilation rate (total volume inspired or expired per unit time),
exhalation start time in each breath,
inhalation start time in each breath,
exhalation duration per breath,
inhalation duration per breath,
wherein the controller is to receive one or more of said ventilation parameters and control said source to deliver ablation energy based on one or more of said ventilation parameters.
100. The device according to any one of embodiments 98 or 99, wherein the controller is configured to synchronized delivery of ablation energy to one of said ventilation parameters.
101. The device of any one of the preceding embodiments from 96 to 100, wherein the controller is configured to control the energy source such that delivery of ablation energy only occurs during exhalation.
102. The device of any one of the preceding embodiments from 96 to 101, wherein the controller is configured to detect when the patient's breath inspiration starts and to consequently command the energy source to interrupt delivery of ablation energy when the patient begins to inspire.
103. The device of any one of the preceding embodiments from 96 to 102, wherein the controller is configured to detect when patient's breath inspiration is taking place and to command the energy source to prevent delivery of ablation energy during patient's breath inspiration.
104. The device of any one of the preceding embodiments from 96 to 103, wherein the controller is configured to detect when patient's breath inspiration ends and to command the energy source to resume delivery of ablation energy.
105. The device of any one of the preceding embodiments, wherein the controller is configured—during or immediately before delivery of ablation energy—to issue a signal to the user interface for instructing the patient to preform maximal forced expiration.
106. The device of any one of the preceding embodiments, wherein the controller is configured to adjust power or ablation time based on breath rate in order to maintain total ablation energy delivery over a prefixed time interval.
107. The device according to any one of the preceding embodiments, wherein the controller is configured to control said energy source to deliver ablation energy at an amplitude capable of generating a thermal lesion during patient's exhalation interval.

108. A method for improving heart function in a human patient with heart failure or with symptoms associated with heart failure, comprising:

positioning an endovascular catheter comprising a proximal region, a flexible shaft, and a distal region, wherein the flexible shaft connects the proximal and distal regions and is a length sufficient to access the abdominal vasculature of the patient relative to an access location, wherein the proximal region is configured to remain external to the patient, and wherein the distal region is configured to be advanced through the patient vasculature and dimensioned to terminate in the abdominal vasculature in contact with the inner wall of a blood vessel and comprises at least one ablation element, at least one stimulation element, and at least one detection element;

advancing the distal region through patient vasculature;

application of at least one ablation element; and removing the endovascular catheter from the patient.

109. The method of embodiment 108, wherein the advancing step further comprises confirming positioning success.

110. The method of embodiment 108, wherein the application step further comprises confirmation of an ablation of a nerve.

111. The method of embodiment 108, wherein the proximal region comprises an energy source and a controller with embedded logic and software.

112. The method of embodiment 108, wherein the proximal region comprises an energy source and a controller with embedded logic and software, and further comprises a user interface.

113. The method of embodiment 108, wherein every ablation element is associated with at least one stimulation element.

114. The method of embodiment 108, wherein the distal region further comprises a detection element chosen from the group comprising of systemic, pulmonary arterial and venous pressure transducers, at least one cardiac output detector, at least one blood flow monitor, or combinations thereof.

115. The method of embodiment 108, wherein the distal region further comprises a detection element and at least one other detection element positioned in a different part of the circulation system.

116. The method of embodiment 108, wherein the ablation element is chosen from the list consisting of an electrode, cryo console, drug delivery device, injection of neurolytic blocking agent, ultrasound device, radio frequency device, thermal ablation device, laser emitter and any combination thereof.

117. The method of embodiment 116, wherein the radio frequency device outputs an electrical current having a frequency in a range of 350 to 500 kHz and a power in a range of 5 to 50 W.

118. The method of embodiment 108, wherein the detection element is a blood pressure transducers.

119. The method of embodiment 108, wherein the detection element is a tissue temperature sensor.

120. The method of embodiment 108, wherein the detection element is a hemodynamic sensor.

121. The method of embodiment 108, wherein the detection element is an environmental temperature sensor.

122. The method of embodiment 108, wherein the detection element is a tissue impedance sensor.

123. The method of embodiment 108, wherein the distal region comprises a deployable structure chosen from the list consisting of a balloon, a cage, a basket, a preformed shape, lasso and loop and any combination thereof.

124. The method of embodiment 108, wherein the access location is a radial, brachial, subclavian, jugular or femoral veins.

125. The method of embodiment 108, wherein the positioning step is preceded by the introduction and advancement of a guidewire to facilitate advancement of a catheter through patient vasculature.

126. The method of embodiment 108, wherein the abdominal vasculature are small veins.

127. The method of embodiment 108, wherein the abdominal vasculature are small intrathoracic veins.

128. The method of embodiment 108, wherein the abdominal vasculature is an azygos vein.

129. The method of embodiment 108, wherein the abdominal vasculature is a hemiazygos vein.

130. The method of embodiment 108, wherein the abdominal vasculature is an intercoastal vein.

131. The method of embodiment 108, wherein the ablation element and stimulation element are positioned on the catheter relative to one another so that the area in which the stimulation signal delivered by the stimulation element correlates with an ablation zone in which ablation energy delivered by the ablation element is sufficient to cause irreversible ablation of nerve tissue.

132. The method of embodiment 108, wherein the catheter may be configured to sterile, elongated, flexible, irrigated, sheathed, deflectable, radio florescent, radio opaque, or any combination thereof.

133. The method of embodiment 108, wherein the confirming the positioning the distal region is performed by an automated algorithmic process to confirm a change in at least one selected hemodynamic or physiological parameter.

134. The method of embodiment 133, comprising selecting electrode or electrode pair, recording a baseline of the hemodynamic parameter, delivering stimulation pulse with a current (I), a pulse width (pw), a frequency (F) and a duty cycle (D) in about I=0 to 10 mA, pw=100 to 1000 us, F=20 to 40 Hz, D=50% pulsing between 20 to 60 s, recording the selected hemodynamic parameter.

135. The method of embodiment 134, further comprising determining if the selected hemodynamic parameter is >20% from baseline, allowing parameter to return to baseline and repeating for at least three measurement, recording average measurements for at least 3 stimulations, and if standard error is within +/−10%, confirming the change in the selected parameter.

136. The method of embodiment 135, wherein the hemodynamic or physiological parameter is selected from the group of responses consisting of pupil dilation, increased sweating, increased heart rate, increased blood pressure, increased mean arterial pressure and any combination thereof.

137. A method for improving heart function in a human patient with heart failure or with symptoms associated with heart failure, comprising:

positioning an endovascular catheter comprising a proximal region, a flexible shaft, and a distal region, wherein the flexible shaft connects the proximal and distal regions and is a length sufficient to access the abdominal vasculature of the patient relative to an access location, wherein the proximal region is configured to remain external to the patient, and wherein the distal region is configured to be advanced through the patient vasculature and dimensioned to terminate in the abdominal vasculature in contact with the inner wall of a vein adjacent a target nerve and comprises at least one ablation element, at least one stimulation element, and at least one detection element;

advancing the distal region through patient vasculature, applying electrical stimulation to the inner wall of a vein sufficient to stimulate the adjacent nerve, detecting physiological changes to confirm positioning success application of at least one ablation element;

reapplying electrical stimulation to the inner wall of a vein previously sufficient to stimulate the adjacent nerve to confirm irreversible ablation of target nerve; and removing the endovascular catheter from the patient.

138. The method of embodiment 137 further comprising repositioning the distal region and repeating electrical stimulation until positioning is confirmed.

139. A method comprising determining that an electrode on a catheter in an intercostal vein of a live mammalian patient is proximate a target nerve in the patient by detecting a change in at least one hemodynamic parameter or physiological parameter of the patient while the electrode applies electrical energy to the intercostal vein.

140. The method of embodiment 139, wherein the electrode is one of a plurality of electrodes on the catheter and the method further comprises applying electrical energy to the intercostal vein sequentially from each of the electrodes and selecting at least one of the electrodes which, when applying the electrical energy, causes a change to the at least one selected hemodynamic parameter or physiological parameter.

141. The method of embodiment 140 further comprising recording a baseline of the selected hemodynamic or physiological parameter while the electrodes do not apply electrical energy to the intercostal vein, delivering at least one stimulation pulse sequentially to each of the electrodes, wherein the stimulation pulse has a current (I) of 0 to 10 mA, a pulse width (pw) of 100 to 1000 us, a frequency (F) of 20 to 40 Hertz and a duty cycle (D) of 20 to 60 seconds, recording a values of the selected hemodynamic or physiological parameter in response to each stimulation pulse, and correlating the recorded value to the electrode applying the electrical energy while the value was recorded.

142. The method of embodiment 141, further comprising, for each sequential application, determining if the value for selected hemodynamic or physiological parameter is greater than a threshold from the baseline, allowing the selected hemodynamic or physiological parameter to return to or near the baseline and repeat for at least three measurement, recording average measurements for at least 3 stimulations, and if standard error is within +/−10%, confirming the change in the selected parameter.

143. The method of embodiment 139, wherein the hemodynamic or physiological parameter is selected from the group of responses consisting of pupil dilation, increased sweating, increased heart rate, increased blood pressure, increased mean arterial pressure and any combination thereof.

144. A catheter configured for ablation of a greater splanchnic nerve or greater splanchnic nerve roots comprising at least two RF electrodes positioned on a distal region of the catheter, a lumen for delivery over a guidewire and configured to create multiple overlapping lesions.

145. A method of using the catheter of embodiment 144 comprising steps of: a.) delivering the distal region of the catheter through a patient's venous system to an intercostal vein, wherein the most distal RF electrode is placed within the intercostal vein and within 5 mm of a costovertebral joint, and wherein the at least two RF electrodes are configured on the catheter to be positioned between the costovertebral joint and the ostium of the intercostal vein joining an azygos vein, b) imaging the distal region of the catheter within the intercostal vein using a medical imaging modality to confirm desired placement of the at least two RF electrodes, c) delivering ablative RF energy to the at least two RF electrodes to thermally ablate tissue surrounding the intercostal vein within a radius of 5 mm, and d) removing the catheter from the patient.

146. The method of embodiment 145 further comprising monitoring a physiological reaction to confirm successful ablation of the target nerve and repeating delivery of ablation energy if the physiological reaction does not change compared to the physiological state prior to delivering ablation energy.

147. A system for endovascular ablation of a greater splanchnic nerve or a greater splanchnic nerve root comprising an ablation catheter configured for endovascular ablation of a greater splanchnic nerve or a greater splanchnic nerve root, a respiratory monitor, a computerized controller, and an ablation energy console, wherein signals from the respiratory monitor are used by the computerized controller to control delivery of ablation energy at an amplitude capable of generating a thermal lesion during the patient's exhalation and period of rest coinciding with the patient's inhalation.

148. A catheter configured for endovascular ablation of a greater splanchnic nerve or a greater splanchnic nerve root from within an intercostal vein comprising an ablation energy element and an ultrasound imaging transducer positioned on a distal region of the catheter, and a guidewire lumen.

149. A method of using the catheter of embodiment 148 comprising generating a sonogram from the ultrasound imaging transducer to image a position of the patient's lung relative to the intercostal vein, delivering ablative energy when the position of the patient's lung is at least 6 mm away from a wall of the intercostal vein, and not delivering ablative energy when the position of the patient's lung is within 6 mm of the wall of the intercostal vein, wherein the ablative energy is configured to create a thermal lesion of tissue within 5 mm of the ablation element while not ablating tissue beyond 5 mm of the ablation element.

150. A method of improving a subject's heart function or symptoms related to heart failure, comprising:
ablating at least a portion of a thoracic splanchnic nerve to block a nerve signal along the at least one thoracic splanchnic nerve, whereby blocking the nerve signal increases vascular compliance of the splanchnic reservoir.

151. The method of embodiment 150 further comprising intravascularly advancing an ablation element carried by an ablation catheter into an intercostal vein of the subject, and wherein the ablating step comprises delivering ablative energy from the ablation element to the at least a portion of a thoracic splanchnic nerve.

152. The method of embodiment 151 wherein the method further comprises advancing the ablation catheter into the intercostal vein from an azygos vein, hemiazygos vein or accessory hemiazygos vein.

153. The method of embodiment 152, wherein advancing the ablation catheter into the intercostal vein comprises advancing the ablation catheter into a T5-T11 intercostal vein, and optionally a T8-T11 intercostal vein.

154. The method of embodiment 152, wherein advancing the ablation catheter into the intercostal vein comprises advancing the ablation catheter into an intercostal vein at a level that is within three levels superior to the subject's diaphragm.

155. The method of embodiment 151, wherein delivering the ablative energy comprises delivering the ablative energy when the ablation element is positioned between 0 and 50 mm from an ostium where the intercostal vein branches from an azygos vein.

156. The method of embodiment 151 wherein delivering ablative energy from the ablation element to the at least one of the splanchnic nerve, a splanchnic nerve root, and a sympathetic chain trunk comprises creating an ablation zone that extends no more than about 5 mm radially outward from the ablation element.

157. The method of 151, wherein the ablating step comprises retracting the ablation element within the intercostal vein while delivering ablative energy from the ablation element to create an axially extending ablation zone, optionally axially extending and non-linear (e.g., helical).

158. The method of embodiment 151 wherein delivering the ablative energy comprises delivering ablative RF energy.

159. The method of embodiment 151 wherein delivering the ablative energy comprises delivering ablative ultrasound energy.

160. The method of embodiment 159 wherein the ablation element comprises an ultrasound transducer, further comprising filling a balloon with fluid, the ultrasound transducer disposed within the balloon.

161. The method of embodiment 151 further comprising confirming a desired position of the ablation element within the intercostal vein.

162. The method of embodiment 161 wherein the ablation catheter further carries a temporary modulation element, wherein advancing the ablation element into an intercostal vein of the subject also advances the temporary modulation element into the intercostal vein.

163. The method of embodiment 162 further comprises delivering a temporary modulation signal other than an ablation signal from the temporary modulation element, optionally inhibiting or stimulating, and measuring a physiological response (e.g., hemodynamic changes) to the temporary modulation signal, and determining if the response indicates that the ablation element is in a desired position to deliver the ablative energy to ablate the at least one of a splanchnic nerve, a splanchnic nerve root, and a sympathetic chain trunk.

164. The method of embodiment 163 wherein measuring a physiological response comprises measuring at least one of blood pressure and heart rate.

165. The method of embodiment 163 wherein the determining step comprises determining if at least one non-target nerve is not in an ablation zone that is created as a result of the ablating step.

166. The method of embodiment 150 wherein the method causes a measureable improvement in the subject's capacity for exercise.

167. A transvascular ablation catheter comprising a deployable balloon mounted to a first shaft through which a lumen passes, an energy delivery element positioned on a second shaft that is slidably engaged in the lumen of the first shaft.

168. The catheter of embodiment 167 wherein the energy delivery element has a diameter larger than the lumen and is positioned distal to the deployable balloon.

169. The catheter of embodiments 167 or 168 further configured to allow the energy delivery element to slide within a range of 0 to 3 cm distal to the deployable balloon.

170. The catheter of embodiments 167 to 169 further comprising a guidewire lumen passing through the second shaft.

171. The catheter of embodiments 167 to 170 further comprising a second deployable balloon positioned distal to the energy delivery element and wherein the catheter is configured to allow the energy delivery element to slide in a range between the first and second balloons.

172. A method of improving heart function while reducing the risk of damage to lung tissue of a subject, comprising: sensing at least one characteristic of the subject's lung; and delivering ablative energy to ablate at least one of a splanchnic nerve, a splanchnic nerve root, and a sympathetic chain trunk to block a nerve signal along the at least one of the splanchnic nerve, a splanchnic nerve root, and a sympathetic chain trunk, whereby blocking the nerve signal increases vascular compliance of the splanchnic reservoir, and wherein at least one delivery parameter of the ablative energy is based on the at least one characteristic of the subject's lung.

173. The method of embodiment 172 wherein sensing at least one characteristic of the patient's lung comprises sensing at least one aspect of the patient's ventilation cycle.

174. The method of embodiment 172 wherein sensing at least one aspect of the patient's ventilation cycle comprises sensing when the patient is in inspiration and when the patient is in expiration, and the at least one delivery parameter of the ablative energy is the time during which the ablating energy is delivered relative to when the patient is in expiration and when the patient is in inspiration.

175. The method of embodiment 174 wherein delivering the ablative energy does not occur during inspiration.

176. The method of embodiment 175 wherein delivering the ablative energy occurs while the patient is holding their breath after expiration.

177. The method of embodiment 176 wherein the method further comprises instructing the patient to hold their breath after expiration.

178. The method of embodiment 175 wherein delivering the ablative energy occurs at least partially during expiration.

179. The method of embodiment 173, further comprising pausing the delivery of ablative energy when it is determined that the lung is within an ablation zone, and restarting the delivery of ablative energy when it is determined that the lung is outside of the ablation zone.

180. The method of embodiment 173, further comprising pausing the delivery of ablative energy when the patient enters into a first portion of the ventilation cycle, and restating the delivery of ablative energy when it is determined that the subject has entered a second part of the ventilation cycle different than the first part.

181. The method of embodiment 172 wherein sensing at least one characteristic of the patient's lung comprises sensing tissue impedance or conductance near the target nerve to estimate a position of the lung relative to an ablation element or an ablation zone.

182. The method of embodiment 181 wherein delivering ablative energy comprises delivering ablative energy after determining the position of the lung is further than a stored distance.

183. The method of embodiment 181 wherein sensing tissue impedance or conductance near the target tissue comprises sensing impedance or conductance during a ventilation cycle and mapping changes in impedance or conductance near the target nerve during the patient's ventilation cycle.

184. The method of embodiment 183 wherein delivering ablative energy comprises delivering ablative energy after determining the position of the lung is further than a stored distance.

185. The method of embodiment 183 wherein sensing tissue impedance or conductance near the target tissue comprises sensing impedance or conductance during a ventilation cycle and mapping changes in impedance or conductance near the target nerve during the patient's ventilation cycle.

186. The method of embodiment 185 further comprises determining, based on the sensed impedance or conductance, when the patient is at the end of an expiration phase.

187. The method of embodiment 184 wherein estimating a position of the lung relative to an ablation element or ablation zone occurs while the patient is in expiration or at the end of the expiration phase.

188. The method of embodiment 183 further comprising monitoring the patient's ventilation cycle, and relating the ventilation cycle to the sensed impedance or conductance during the ventilation cycle.

189. The method of embodiment 181 wherein estimating a position of the lung relative to an ablation element comprises estimating a distance between lung tissue and an ablation element or an ablation zone.

190. The method of embodiment 189 wherein estimating a distance between lung tissue and an ablation element or ablation zone comprises estimating a distance between lung tissue and an ablation element or ablation zone while the patient is in expiration or at the end of the expiration phase.

191. The method of embodiment 189 wherein delivering ablative energy occurs after determining the lung is far enough away from the ablation element or the ablation zone.

192. The method of embodiment 181 wherein sensing tissue impedance or conductance comprises sensing tissue impedance or conductance using a sensing device positioned in an intercostal vein.

193. The method of embodiment 172 wherein sensing at least one characteristic of the patient's lung comprises imaging tissue from within the vessel in which an imaging element is placed to determine a distance from the vessel to lung tissue.

194. The method of embodiment 193 wherein determining a distance from the vessel to lung tissue comprises determining when the lung tissue is sufficiently far enough from the vessel or an ablation zone to safely ablate the at least one of the splanchnic nerve, a splanchnic nerve root, and a sympathetic chain trunk, and wherein delivering the ablative energy occurs when the lung is far enough away from the vessel or the ablation zone.

195. The method of embodiment 172 further comprising directing the ablative energy toward the target nerve tissue and away from non-target tissue.

196. The method of embodiment 172 further comprising positioning a distal region of an ablation catheter in an intercostal vein, optionally via the azygos vein.

197. The method of embodiment 196, wherein the intercostal vein is a T5-T11 intercostal vein, optionally a T8-T11 intercostal vein.

198. The method of embodiment 196, wherein the intercostal vein is an intercostal vein within three levels superior to the patient's diaphragm.

199. The method of embodiment 172 wherein delivering the ablative energy comprises delivering ablative energy at a location where a recess in the lung is formed and does not include lung tissue.

200. The method of embodiment 172, further comprising instructing the patient to at least one of perform expiration and hold their breath after expiration, and wherein delivering the ablative energy does not occur during inspiration, but does occur during at least one of when the patient is expiring and holding their breath after expiration.

201. The method of embodiment 172 wherein the method causes a measureable improvement in the subject's capacity for exercise.

202. The method of embodiment 201 wherein the improvement in the subject's capacity for exercise comprises reducing an increase of pulmonary capillary wedge pressure (PCWP) and pulmonary artery pressure (PAP) in response to exertion.

203. The method of embodiment 172 wherein the method causes a measureable improvement in vascular compliance (an index of dP/dV).

204. The method of embodiment 172 wherein the method reduces pulmonary vascular pressure and PCWP that is index of pulmonary artery pressure (LVEDP).

205. A method of improving heart function in a human patient with heart failure or with symptoms associated with heart failure, comprising: delivering an ablation catheter to a vessel adjacent a thoracic splanchnic nerve, the ablation catheter including an ablation element and a lung monitoring element axially spaced from the ablation element; activating the lung monitoring element; determining if the patient's lung is outside of an ablation zone associated with the ablation element; activating the ablation element to deliver ablative energy towards a splanchnic nerve only when the patient's lung is determined to be outside of the ablation zone, and thereby block a nerve signal along the thoracic splanchnic nerve.

206. A method of improving heart function in a human patient with heart failure or with symptoms associated with heart failure, comprising: intravascularly delivering an ablation catheter to an intercostal vein, the ablation catheter including an ablation element and a lung monitoring electrode axially spaced from the ablation element; activating the lung monitoring electrode; monitoring bioimpedance within a sensitivity zone adjacent the lung monitoring electrode; determining if the patient's lung is at a safe distance from an ablation zone associated with the ablation element; and activating the ablation element to deliver ablative energy towards a greater splanchnic nerve only when the patient's lung is determined to be at a safe distance from the ablation zone, and thereby block a nerve signal along the greater splanchnic nerve.

207. A method of improving heart function in a human patient with heart failure or with symptoms associated with heart failure, comprising: delivering an ablation catheter to a vessel adjacent a splanchnic nerve, the ablation catheter including an ablation element; determining if the patient's lung is outside of an ablation zone associated with the ablation element, or is far enough away from the ablation element to avoid significant injury; activating the ablation element to deliver ablative energy towards a splanchnic nerve only when the patient's lung is determined to be outside of the ablation zone or far enough away, and thereby block a nerve signal along the greater splanchnic nerve.

208. A system for endovascular ablation of thoracic splanchnic nerves comprising of a catheter comprising a distal region configured for delivery through a patient's vasculature to an azygos vein, hemiazygos vein, accessory hemiazygos vein or posterior intercostal vein, the distal region comprising: an ablation energy delivery element configured to ablate tissue within an ablation zone; an impedance measurement electrode configured to measure tissue bioimpedance within a bioimpedance sensitivity zone; and a controller in communication with the ablation energy delivery element and impedance measurement electrode; wherein the controller is configured to: increase delivery of ablation energy when the measured tissue impedance indicates absence of lung tissue in the bioimpedance sensitivity zone; and decrease delivery of ablation energy when the measured tissue impedance indicates a presence of lung tissue in the bioimpedance sensitivity zone.

209. A system of embodiment 208 wherein the bioimpedance measurement electrode is within 30 mm of the ablation energy delivery element.

210. A system of embodiment 208 or 209 wherein the bioimpedance measurement electrode is positioned at least 10 mm from the ablation energy delivery element.

211. A system of embodiment 208 wherein the measured tissue impedance that indicates presence of lung tissue in the bioimpedance sensitivity zone comprises impedance in a range of 500 to 2000 ohms, and the measured tissue impedance that indicates absence of lung tissue in the bioimpedance sensitivity zone is in a range of 100 to 500 Ohms.

212. A system of embodiment 209 configured to create the ablation zone having a radius of no more than 5 mm from the surface of the ablation energy delivery element and configured to create the bioimpedance sensitivity zone having a radius greater than the radius of the ablation zone and no more than 20 mm from the impedance measurement electrode.

213. A system of embodiment 208 further comprising an impedance reference circuit.

214. A system of embodiment 208 further comprising a second impedance measurement electrode positioned on the catheter proximal to the first impedance measurement electrode.

215. A system of embodiment 214 wherein the catheter is configured to position the first impedance measurement electrode in a first intercostal vein and the second impedance measurement electrode is positioned in one of an azygos vein, a second intercostal vein, a hemiazygos vein, or an accessory hemiazygos vein.

216. A system of embodiment 214 wherein the catheter is configured to position the first and second impedance electrodes such that an electrical current pathway between the first and second impedance electrodes passes through a region of the patient wherein lung tissue moves in and out with respiration.

217. A system of embodiment 208 wherein the at least on ablation energy delivery element is an RF electrode in electrical communication with a dispersive ground pad.

218. A system of embodiment 100 wherein the at least on ablation energy delivery element is two RF electrodes in bipolar configuration positioned on the distal region of the catheter.

219. A method of using the catheter of embodiment 218 comprising positioning the two RF electrodes in an intercostal vein in a range where a thoracic splanchnic nerve is expected to cross the intercostal vein between the ostium of the azygos vein and an adjacent costovertebral joint.

220. A method of transvascular ablation of a nerve, comprising: advancing an elongate shaft carrying an ablation element into a blood vessel proximate to a target nerve, the blood vessel having a lumen; decreasing the size of the lumen at a location along the blood vessel; after the decreasing step, delivering ablation energy from the ablation element towards the target nerve; and ablating at least a portion of the target nerve with the ablation energy.

221. A method of transvascular ablation of a nerve, comprising: advancing an elongate shaft carrying an ablation element into a blood vessel proximate to a target nerve, the blood vessel having a lumen; decreasing the rate of blood flow at a location along the blood vessel; after the decreasing step, delivering ablation energy from the ablation element towards the target nerve; and ablating at least a portion of the target nerve with the ablation energy.

222. An apparatus for transvascular ablation of a target nerve, comprising: a delivery device configured to connect to an elongated shaft configured to be inserted into a blood vessel lumen, wherein the delivery device is configured for: causing a decrease of at least one of the size of the lumen at a location along the blood vessel or the blood flow at a location along the blood vessel, and delivering ablation energy adapted for the ablation of said target nerve.

223. An apparatus according to embodiment 223, wherein the delivery device is configured to operate at least in a lumen reducing energy mode and an ablation energy mode, wherein in lumen reducing energy mode the delivery device is adapted to cause a first energy to be generated and delivered from an energy delivery element, and wherein in the ablation energy mode, the delivery device is adapted to cause a second energy, different from the first energy, to be generated and delivered from said or a further energy delivery element.

224. An apparatus according to embodiment 224, wherein the elongated shaft comprises: a number of electrodes carried by a portion of the elongated shaft; and the delivery device comprises: a power supply configured to supply energy to said number of electrodes; a controller connected to the power supply, wherein the controller is configured to execute the following controller steps: when the delivery device is in the lumen reducing energy mode, control the power supply to deliver to one of said number of electrodes the first energy configured to cause a reduction in the size of the vessel lumen, and when the delivery device is in the ablation energy mode, control the power supply to deliver to one or more of said number of electrodes the second energy configured to cause ablation of said target nerve.

225. An apparatus according to embodiment 224, wherein the elongated shaft comprises: a number of electrodes carried by a portion of the elongated shaft; and a further elongated shaft with a further number of electrodes carried by a portion of the further elongated shaft; and the delivery device comprises: a power supply configured to supply energy to said number of electrodes and to said further number of electrodes; a controller connected to the power supply, wherein the controller is configured to execute the following controller steps: when the delivery device is in the lumen reducing energy mode, control the power supply to deliver to one of said number of electrodes the first energy configured to cause a reduction in the size of the vessel lumen, and when the delivery device is in the ablation energy mode, control the power supply to deliver to one or more of said further number of electrodes the second energy configured to cause ablation of said target nerve.

226. An apparatus according to embodiment 225 or 226, wherein controlling the power supply to deliver to one of said number of electrodes the first energy configured to cause a reduction in the size of the vessel lumen comprises delivering an electric signal to said number of electrodes causing one or more of: heating of the electrode surface to a predetermined temperature and causing emission from the electrode of a stimulating signal causing contraction of the blood vessel.

227. An apparatus according to embodiment 225, 226 or 227, wherein controlling the power supply to deliver to one of said number of electrodes the first energy configured to cause a reduction in the size of the vessel lumen comprises delivering radiofrequency electrical current.

228. An apparatus according to embodiment 225 in combination with any one of embodiments 227 to 228, wherein controlling the power supply to deliver to one or more of said number of electrodes the second energy configured to cause ablation of said target nerve comprises delivering ablative radiofrequency electrical current.

229. An apparatus according to embodiment 226 in combination with any one of embodiments 227 to 228, wherein controlling the power supply to deliver to one or more of said further number of electrodes the second energy configured to cause ablation of said target nerve comprises delivering ablative radiofrequency electrical current.

230. An apparatus according to embodiment 229 or 230, wherein the ablative radiofrequency electrical current of the second energy is delivered at a lower power and for a longer duration than the radiofrequency electrical current of the first energy.

231. An apparatus according to embodiment 231, wherein the first energy is RF energy with a power in a range of 10 to 20 W for a duration in a range of 5 to 15 seconds, and the second energy is RF energy with a power in a range of 2 to 10 W for a duration in a range of 1 to 2 minutes.

232. An apparatus according to any one of embodiments 227-231, 231, 232, when combined with embodiment 225, wherein the power supply is configured to deliver sequentially the first energy and the second energy to the same electrodes, or wherein the number of electrodes comprises at least one vessel restriction element and at least one ablation element, further wherein the power supply is configured to deliver the first energy to the vessel restriction element and the second energy to the ablation element.

233. An apparatus according to any one of embodiments 227-231, 231, 232, when combined with embodiment 226, wherein the elongated shaft and the further elongated shaft are coupled the one with the other, with the elongated shaft being slidable relative the further elongated shaft, optionally with the elongated shaft being slidable inside the further elongated shaft, for the further number of electrodes carried by the further elongated shaft to be positionable at a distance from the number of electrodes carried by the elongated shaft.

234. An apparatus according to any one of embodiments 225-234, wherein said controller is configured to sequentially deliver said first energy and then said second energy to first cause occlusion or partial occlusion of said vessel lumen and then cause ablation of said target nerve.

235. An apparatus according to embodiment 224, wherein the elongate shaft comprises: a number of electrodes carried by a portion of the elongated shaft such that, with the elongate shaft inserted into the vessel lumen, the number of electrodes may be positioned proximate to the target nerve; and the delivery device comprises: a power supply configured to supply energy to said number of electrodes; a conduit fluidly connectable to a source including at least one of: a vacuum source or a vasoconstrictor drug source, or a source of balloon inflation fluid; wherein the conduit has an aperture located in proximity of the number of electrodes or the conduit supplies a balloon located in proximity of the number of electrodes; a controller connected to the power supply and connectable to the source, said controller being configured to execute the following controller steps: when the delivery device is in the lumen reducing energy mode, control the source to respectively cause one of: suction of fluid through said aperture to cause a reduction in size of the vessel lumen, or delivery of said vasoconstrictor drug through said aperture to cause a reduction in size of the vessel lumen, or supply of the balloon inflation fluid to inflate the balloon and occlude the vessel lumen; when the delivery device is in the ablation energy mode, control the power supply to deliver to one or more of said number of electrodes an energy configured to cause ablation of said target nerve.

236. An apparatus according to embodiment 236, wherein said controller is configured to sequentially control said source and then the power supply to first cause one of said suction of fluid or delivery of said vasoconstrictor drug or supply of balloon inflation fluid and, then, delivery of said energy to the number of electrodes, thereby first causing occlusion or partial occlusion of said vessel lumen and then determining ablation of said target nerve.

237. An apparatus according to embodiment 236 or 237, wherein controlling the power supply to deliver to one or more of said number of electrodes the energy configured to cause ablation of said target nerve comprises delivering ablative radiofrequency electrical current.

238. An apparatus according to any one of embodiments 236-238, wherein the elongated shaft presents a distal end which in use is positionable inside the vessel lumen, the number of electrodes comprising at least one ablation element connectable to the power supply, and wherein the apparatus either presents: said aperture allowing suction of fluid using the vacuum source or allowing delivery of said vasoconstrictor drug using the vasoconstrictor drug source, the aperture being located or being positionable at a portion of the elongated shaft closer to the distal end of the elongated shaft than the ablation element; or said balloon which is located or positionable at a portion of the elongated shaft closer to the distal end of the elongated shaft than the ablation element.

239. An apparatus according to any one of embodiments 236-239, wherein the conduit is fluidly connectable with said source of balloon inflation fluid and supplies a balloon located in proximity of the number of electrodes; further wherein the conduit distally carries said balloon, with the elongate shaft slidably housing said conduit or with the elongate shaft and the conduit being both slidably housed within a common guide sheath such that the balloon is positionable at a distance from said number of electrodes carried by the elongate shaft, optionally wherein the balloon is positionable more distally compared to said number of electrodes.

240. An apparatus according to any one of the embodiments 225-240, wherein the controller is further configured to execute the following controller steps: control the power supply to deliver to one of said number of electrodes or to said further number of electrodes a nerve stimulation signal towards the thoracic splanchnic nerve, and receive a measure of a physiological response to the stimulation signal, wherein the measure of the physiological response to the stimulation signal is detected by one of the number of electrodes or by one of said further number of electrodes by a dedicated sensor of the apparatus.

241. An apparatus according to any one of embodiments 225-241, wherein the controller is further configured to execute the following controller step: control the power supply to deliver to one of said number of electrodes, a plurality of times at separate time intervals, said energy configured to cause ablation of said target nerve.

242. An apparatus according to any one of embodiments 225-242, comprising a temperature sensor, associated to the elongate shaft in a position proximate to said number of electrodes, or associated to the further elongate shaft in a position proximate to the further number of electrodes, wherein the temperature sensor is connected to the controller, and wherein the controller is configured to execute the following controller steps: receive a temperature detection signal from the temperature sensor, determine from said temperature signal an actual temperature of tissue in contact with or proximity of the temperature sensor, compare the actual temperature with a target temperature, control the power supply—when the delivery device is in the ablation energy mode—to supply energy to the number of electrodes or to the further number of electrodes, in particular RF ablation energy with power in a range of 5 W to 15 W, until the actual temperature reaches the target temperature.

243. An apparatus according to any one of embodiments 225-243, wherein the elongate shaft comprises an impedance sensor, associated to the elongate shaft in a position proximate to said number of electrodes, or associated to the further elongate shaft in a position proximate to the further number of electrodes, wherein the impedance sensor is connectable to said controller, and wherein the controller is configured to execute the following controller steps: receive an impedance detection signal from the impedance sensor, determine from the impedance detection signal an actual impedance of tissue in contact with or proximity of the impedance sensor, compare the actual impedance with a target impedance, control the power supply or the source to interrupt the lumen reducing mode in response to a rise in tissue actual impedance to above the target impedance, the target impedance being optionally in a range between 250-300 ohms.

244. An apparatus according to any one of embodiments 223-244 wherein said elongate shaft portion presents cross-section having maximum radial size not greater than 5 mm, preferably not greater than 3 mm.

245. An apparatus according to any one of embodiments 223-245 wherein the elongated shaft is slidably guided inside a delivery sheath.

246. An apparatus according to any one embodiments 223-246 wherein the elongated shaft is guided over a guidewire.

247. An apparatus according to any one of embodiments 223-247, wherein the controller is a digital control unit capable of executing an executable computer program stored on a memory connected with the control unit.

248. An apparatus according to any one of embodiments 223-248 comprising said elongate shaft.

249. An apparatus according to any one of embodiments 236-249 comprising said source.

250. A computer executable program stored on a memory, wherein the computer executable program when executed by the controller of the apparatus of embodiment 246 configures said controller to execute the controller steps of anyone of embodiments 223-250.

251. A computer executable method for transvascular ablation of a nerve from a blood vessel, comprising: a computer executable method stored on a memory and executable by a processor, the computer executable method comprising a lumen reducing energy mode and an ablation energy mode, wherein the lumen reducing energy mode is, when initiated, adapted to cause a first type of energy to be generated and delivered from an energy delivery element on a medical device, and wherein the ablation energy mode is, when initiated, adapted to cause a second type of energy to be generated and delivered from a second energy delivery element on the medical device, the second type different than the first type, and wherein the energy delivery element and the second energy delivery element can be the same element or different elements on the medical device.

252. The method of embodiment 252, further comprising a console that includes the memory.

253. The method of embodiment 253, further comprising a medical device carrying an energy delivery element, the computer executable method adapted to cause energy delivery to the energy delivery element.

254. The method of embodiment 252, wherein the ablation energy mode comprises a lower power energy and is for a longer duration than the lumen reducing energy mode.

255. The method of embodiment 255, wherein the lumen reducing mode delivers RF energy with a power in a range of 10 to 20 W for a duration in a range of 5 to 15 seconds, and the ablation energy mode delivers RF energy with a power in a range of 2 to 10 W for a duration in a range of 1 to 2 minutes.

256. A system of embodiment 255, wherein the ablation energy mode further comprises an initial delivery of RF energy with power in a range of 5 W to 15 W until a target temperature is reached.

257. The method of embodiment 252, wherein the lumen reducing energy mode is adapted to stop or initiate a stop in energy delivery in response to a rise in tissue impedance, optionally from about 150 ohms to 250-300 ohms.

258. The method of embodiment 252, wherein the computer executable method is adapted to, upon receiving an input, initiate the ablation energy mode.

259. The method of embodiment 252, wherein the computer executable method is further adapted to, upon receipt of the input, stop the lumen reducing energy mode, and optionally automatically initiate the ablation energy mode.

260. A system for endovascular ablation of a thoracic splanchnic nerve or a thoracic splanchnic nerve root comprising: an ablation catheter carrying at least one electrode; an ablation energy console configured to operatively couple to the at least one electrode; a physiologic monitor which outputs first set of output signals sensing the patient's breathing cycle; a computerized controller configured to receive first set of signals as inputs and to generate a second set of signals; and wherein the second set of signals synchronize the delivery of ablation energy by the ablation energy console to the ablation catheter electrodes.

261. A system for endovascular ablation of a thoracic splanchnic nerve or a thoracic splanchnic nerve root comprising: an ablation energy console configured to operatively couple to electrodes carried by an ablation catheter introduced endovascularly in proximity to the thoracic splanchnic nerve or the thoracic splanchnic nerve root; a physiologic monitor which outputs first set of signals sensing the patient's breathing cycle; a computerized controller configured to receive first set of signals as inputs and to generate a second set of signals; and wherein the second set of signals synchronize the delivery of ablation energy by the ablation energy console to the ablation catheter electrodes.

262. An ablation system including: a signal generator connectable to an ablation catheter, the signal generator comprising: an adapter configured to allow electrical communication between the signal generator and the ablation catheter; and a memory storing a computer executable method; a controller connectable to the memory, the controller being configured to execute the computer executable method, wherein the computer executable method comprises the following steps: in response to a received impedance measurement signal received by the signal generator, determining if the received impedance measurement signal is indicative of a lung being absent from a sensitivity zone or is at a safe distance from an ablation element carried by the catheter, causing the generation of an ablation signal at an ablation level in response to a determination that the lung is absent from a sensitivity zone or is at a safe distance from an ablation element, repeating the determining step, pausing the ablation signal at the ablation level in response to a determination that the lung is not absent from a sensitivity zone or is not at a safe distance from an ablation element, repeating the determining step, at a time subsequent to the pausing step, again causing the generation of an ablation signal at an ablation level in response to a determination that the lung is absent from a sensitivity zone or is at a safe distance from an ablation element.

263. The ablation system of embodiment 263 wherein the controller is active on a power supply connected to an ablation element of the ablation catheter, wherein generation or pausing said ablation signals cause the power supply to respectively send or to stop sending to the ablation element corresponding ablation energies.

264. The ablation system of 263 to 265 further comprising an ablation catheter.

BRIEF DESCRIPTION OF THE DRAWINGS

FIGS. 6A and 6B are schematic illustrations of anatomical relationships of some blood vessels, splanchnic nerves and other anatomy.

FIGS. 33A and 33B are schematic illustrations of a transverse view of a patient showing an ablation catheter delivered to an intercostal vein for ablation of a target nerve comprising an ultrasound imaging transducer.

DETAILED DESCRIPTION

Figure 1:
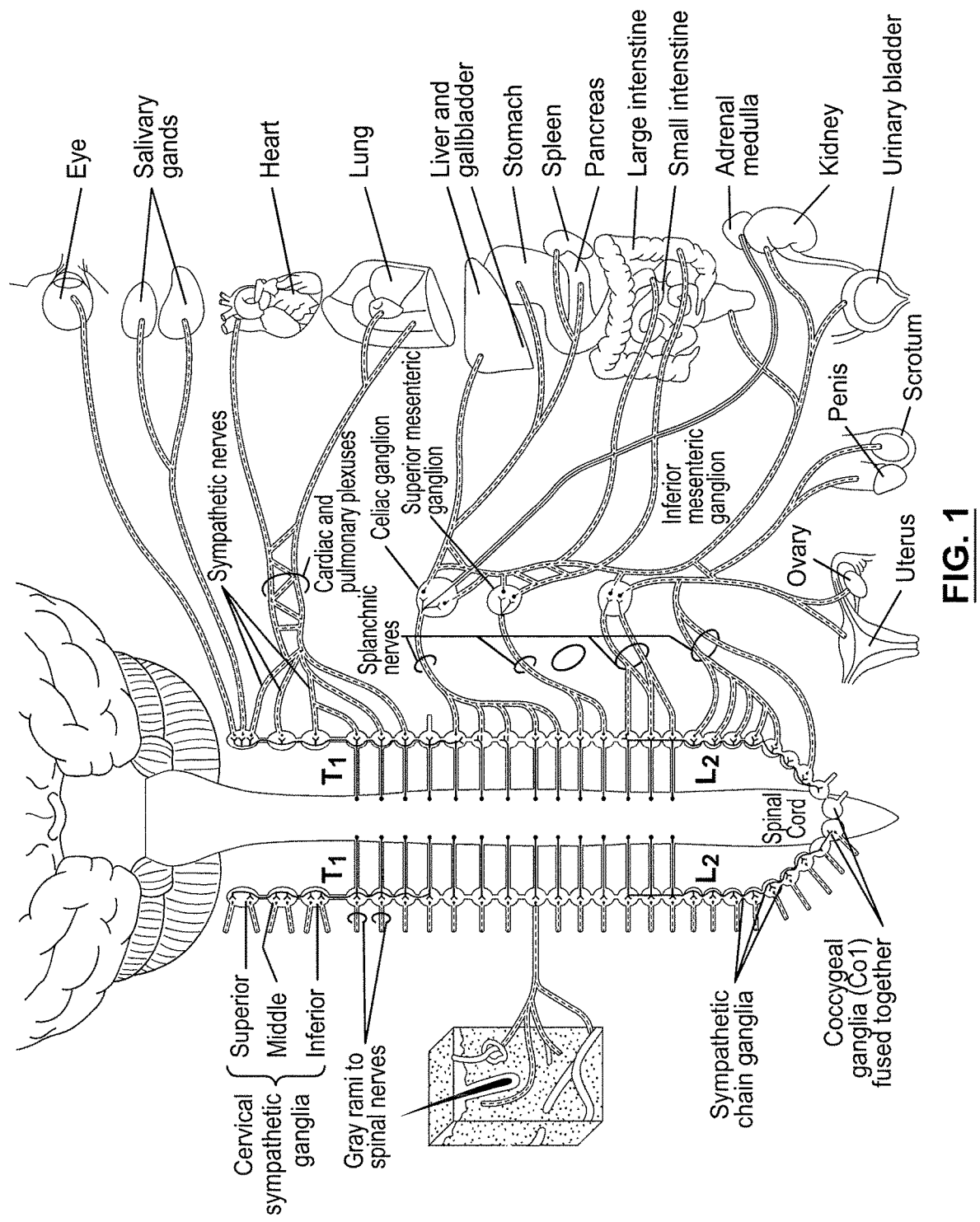
FIG. 1 is an anatomical representation of the supply of sympathetic nerve fibers to organs of the human body.

The present disclosure relates to medical devices, methods, and systems that provide treatment of heart disease, dysfunction and heart failure, particularly HFpEF or measurable symptoms of heart disease such as dyspnea through the mechanism of increased venous capacitance and relief of pulmonary congestion and increased diuretic responsiveness. This treatment may also be beneficial in treating other diseases associated with redistribution of blood volume such as hypertension, cardio-renal syndrome, portal hypertension, and tricuspid regurgitation, or other conditions associated with the thoracic splanchnic nerve such as intractable abdominal pain (e.g., with cancer patients), or diuretic resistance. This treatment is provided through ablation of at least a portion of a target nerve comprising thoracic splanchnic nerves (e.g., greater splanchnic nerve, lesser splanchnic nerve, least splanchnic nerve, splanchnic nerve roots, splanchnic nerves) with a medical device delivered to a vessel (e.g., azygos vein system, intercostal vein, or several selected intercostal veins) used to impede or stop communication of a nerve signal along the ablated nerve or nerves, which can affect physiological responses that are directly or indirectly involved in the numerous factors of cardiovascular health.

One embodiment comprises a catheter or other elongate medical device delivered through a patient's vascular system to a vessel of the azygos vein system for ablating a portion of a right or left thoracic splanchnic nerve. The catheter may comprise an ablation element (e.g., RF electrodes, cryogenic applicator, chemical agent delivery needle, ultrasound transducer, laser emitter), and can also be configured to confirm proximity to a target nerve, such as a thoracic splanchnic nerve or TSN roots, or non-target neural structures (e.g., electrical stimulation electrodes, cryogenic applicator, chemical agent delivery needle, visual aids such as radiopaque or echogenic markers). The catheter may be used as part of a system comprising other components that contribute to the function of the catheter. For example, the system may comprise an ablation energy source (e.g., RF signal generator, cryo console, ultrasound signal generator, chemical agent source or pump, laser generator), a controller with signal inputs and amplifiers and embedded software logic, or a computerized user interface. To ablate a portion of a target nerve, the ablation energy source delivers ablation energy from an ablation element positioned in a patient's blood vessel (e.g., azygos, intercostal or hemiazygos vein) proximate the target nerve. The ablation energy passes from the ablation element to the target nerve. To confirm proximity to a target or non-target neural structures a stimulating agent, such as an electric field or a drug known to activate sympathetic nerves, may be delivered to temporarily activate or block nerve activity, and a physiological response may be observed or monitored for correlation to the nerve stimulation or block. Similarly, success of ablation may be confirmed by electric stimulation of the target nerve and observing a physiologic response, including changes in the physiologic response compared to pre-ablation or absence of physiologic response where one is expected. In some embodiments, presence of anatomic structures that are not targeted for ablation, such as lungs, can be detected, optionally automatically, using signals such as electric or acoustic impedance of tissue.

Anatomy

Figure 6A:
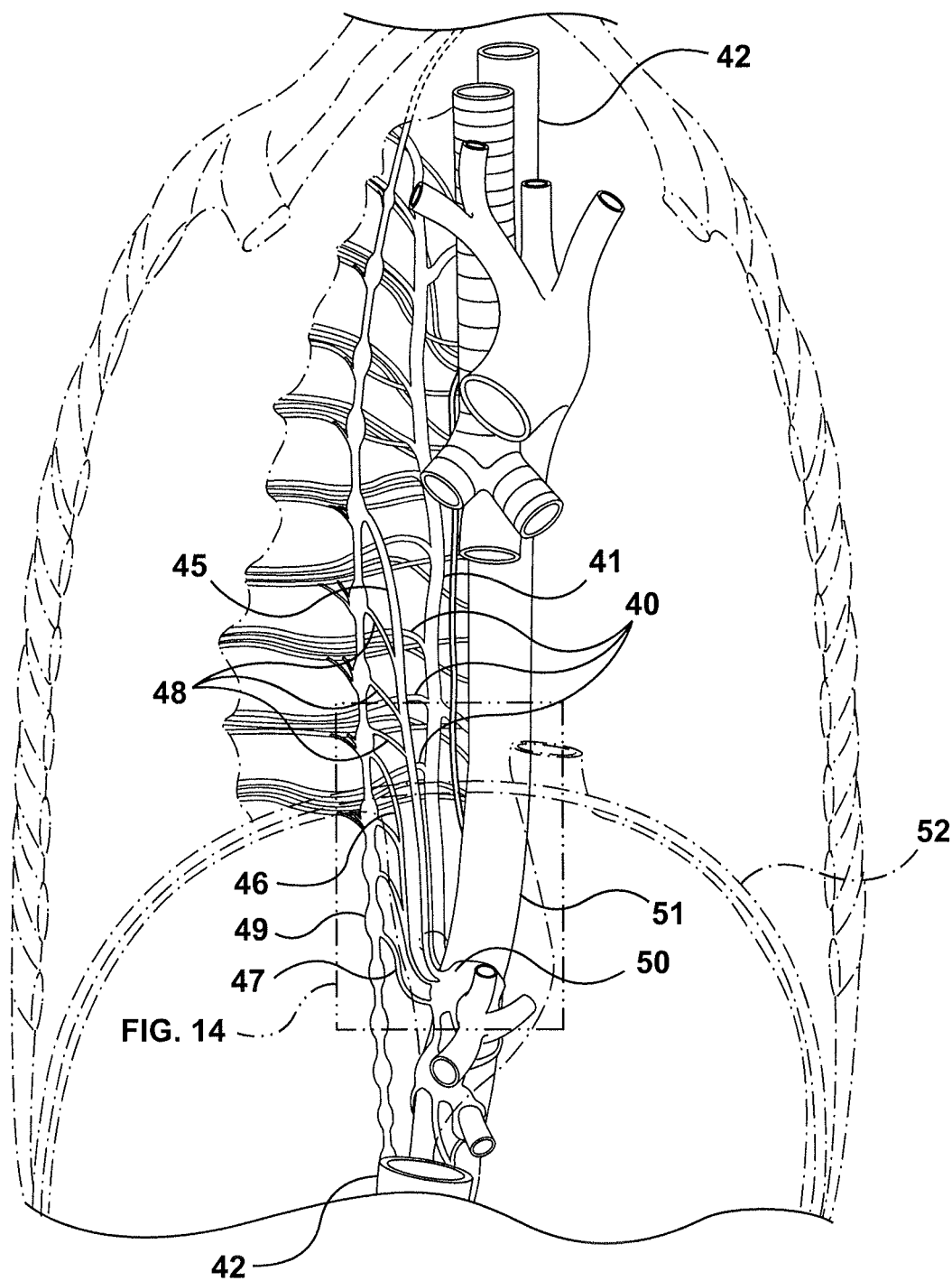

FIGS. 6A (a sagittal sectional view) and 6B (a transverse view at a level above the diaphragm within two or three vertebral levels, e.g., at the T10 level) are schematic illustrations of anatomical relationships of some blood vessels and splanchnic nerves. The azygos vein 41 runs up the side of the thoracic vertebral column (comprising thoracic vertebrae 55 labeled T1 to T12 on FIG. 7) draining towards the superior vena cava 42 and inferior vena cava. The azygos venous system comprises the azygos vein 41, hemiazygos vein 43, and the accessory hemiazygos 44 vein (see FIG. 7). Tributaries of the azygos vein comprise the posterior intercostal veins (herein also referred to as intercostal veins 40), which drain the intercostal spaces. Tributaries of the hemiazygos and accessory hemiazygos veins comprise the left posterior intercostal veins (herein also referred to as intercostal veins 40). These veins, in particular the intercostal veins 40 pass quite closely across at least a portion of target nerves of the splanchnic nerve bundle (e.g., greater splanchnic nerve 45, lesser splanchnic nerve 46, least splanchnic nerve 47, greater splanchnic nerve roots 48). Since the GSN 45 forms from preganglionic fibers emerging from the sympathetic trunk 49 as GSN roots 48, which relay to the celiac ganglion 50, all the preganglionic fibers that form the GSN 45 between the sympathetic trunk 49 and celiac ganglion 50 are referred to herein as the GSN for simplicity. Similarly, all the preganglionic fibers that form the thoracic splanchnic nerves, including the greater, lesser, and least splanchnic nerves between the sympathetic trunk 49 and celiac ganglion 50 are referred to herein as the thoracic splanchnic nerves. A region 150 shown in FIG. 6B of an intercostal vein 40 between the azygos vein 41 and costovertebral joint 54 is proximate to the GSN 45 and GSN roots 48 (e.g., typically a distance 194 of about 1 to 5 mm). The sympathetic trunk is near by the costovertebral joint 54 or neck of the rib 63. Also shown in FIG. 6A are the aorta 51 and diaphragm 52. Also shown in FIG. 6B are the esophagus 56, thoracic duct 57, vagus nerves 58, rib 59, parietal pleura 60, visceral pleura 61, and pulmonary pleural cavity 62, and lungs 65.

In the context of this disclosure the TSN can mean right or left thoracic splanchnic nerve and their contributing nerves and transvenous ablation or stimulation can be performed from the azygos vein or one or more intercostal veins to access the right thoracic splanchnic nerve, or from the hemiazygos vein or intercostal veins to access the left thoracic splanchnic nerve, or from their respective tributaries or a bilateral treatment can be performed from both the azygos and hemiazygos veins and their tributaries to access both right and left thoracic splanchnic nerves.

Ablation of a TSN (excluding the roots) as well as one or more TSN roots may result in greater efficacy compared to ablation of only a TSN or only a TSN root. People may have 2 to 7 GSN roots. Most commonly the highest root is at the level of the T5 or T6 vertebra but it can be as high as T3 in rare cases.

Physiology

About 5% of the total body water is located within the vasculature in the form of blood. The venous system contains approximately 70% of total blood volume and is roughly 30 times more compliant than the arterial system. Venous compliance is a measure of the ability of a hollow organ or vessel to distend and increase in volume with increasing internal pressure (e.g., dP/dV). A number of mechanisms are involved in regulation of volume, most importantly the neurohormonal system. On the arterial side, flow and resistance are regulated by resistance vessels. The sympathetic nervous system plays a major role in determining systemic vascular resistance (SVR) predominantly through activation and deactivation of cardiopulmonary and arterial baroreflexes, as well as through changes in circulating norepinephrine.

Capacitance is a determinant of the venous vascular function and higher vascular capacitance allows more blood to be stored in the respective vasculature. The autonomic nervous system is the main regulatory mechanism of vascular capacitance.

Circulating blood is distributed into two physiologically but not anatomically separate compartments: the "venous reservoir" and "effective circulatory volume". The term "venous reservoir" (or "unstressed volume") refers to the blood volume that resides mainly in the splanchnic vascular bed and does not contribute to the effective circulating volume. The venous reservoir that is also referred to as "unstressed volume" or "vascular capacitance" can be recruited through a number of mechanisms like activation of the sympathetic nervous system, drugs, or hormones.

The term "effective circulatory volume" (or "stressed volume") refers to blood that is present mainly in the arterial system and in non-splanchnic venous vessels and is one of the main determinants of preload of the heart. The stressed blood volume and systemic blood pressure are regulated by the autonomic nervous system of which the sympathetic nervous system is a part.

The unstressed volume of blood is mostly contained in the splanchnic reservoir or "splanchnic vascular bed". The splanchnic reservoir consists of vasculature of the visceral organs including the liver, spleen, small and large bowel, stomach, as well as the pancreas. Due to the low vascular resistance and high capacitance the splanchnic vascular bed receives about 25% of the CO and the splanchnic veins contain anywhere from 20% to 50% of the total blood volume.

Consequently, the splanchnic vascular bed serves as the major blood reservoir, which can take up or release, actively and passively, as the major part of any change in circulating blood volume.

While experimenting with human patients with HF, cadavers and animals, the authors were able to: (a) artificially manipulate and modify the venous reservoir by selectively ablating or stimulating the GSN, and (b) access the GSN very closely from superficial veins through the venous system, for example, the azygos vein system including intercostal veins in humans and some animals, even though it is hidden deep in the body.

Splanchnic veins are considerably more compliant than veins of the extremities. Animal and human studies demonstrate that the splanchnic reservoir can not only store considerable amounts of blood, but blood can also be actively or passively recruited from it into the systemic circulation in response to variations of the venous return of blood to the heart and physiologic need for heart preload. One of the main determinants of active recruitment is sympathetic nerve activity (SNA), which through hormones and a neurotransmitters epinephrine and norepinephrine causes venoconstriction, thereby reducing splanchnic capacitance and increasing effective circulatory volume. This can be explained by a large numbers of adrenergic receptors in the splanchnic vasculature that are sensitive to changes to the sympathetic nervous system. Compared with arteries, splanchnic veins contain more than five (5) times the density of adrenergic terminals. The consequence is a more pronounced venous vasomotor response in the splanchnic system compared to other vascular regions.

The splanchnic vascular bed is well suited to accommodate and store large amounts of blood as well as shift blood back into active circulation, naturally acting in a temporary blood volume storage capacity. The high vascular capacitance allows the splanchnic vascular bed to maintain preload of the heart and consequently arterial blood pressure and CO over a wide range of total body volume changes. Once the storage capacity of the splanchnic vascular bed is reached, increases in total body fluid express themselves as increased cardiac preload beyond physiologic need and eventually extravascular edema and particularly fluid accumulation in the lungs that is a symptom common in HF.

Increased activation of the sympathetic nervous system (SNS) and the neurohormonal activation along with increases in body fluids and salts have long been debated as causes versus effects of HF. It has been previously suggested that in HF redistribution of the splanchnic reservoir, driven by increased SNA to the splanchnic vascular bed leading to decreased venous compliance and capacitance, is responsible for increased intra-cardiac filling pressure (preload) in the absence of increases in total body salt and water. HF is marked by chronic over-activity of the SNS and the neurohormonal axis. It is now suggested that SNA and neurohormonal activation result in an increased vascular tone and consequently in decreased vascular capacitance of the splanchnic vascular bed. While peripheral vascular capacitance is mostly unchanged in HFpEF and HFrEF compared to healthy controls, the vascular capacitance of the splanchnic vascular can be significantly decreased.

So-called "acute HF" is initiated by a combination of two pathways: cardiac and vascular. The "cardiac pathway" is generally initiated by a low cardiac contractility reserve, while the "vascular pathway" is common to acute HF (AHF) that exhibits mild to moderate decrease in cardiac contractility reserve.

In acute decompensated heart failure (ADHF), which is characterized by worsening of the symptoms: typically shortness of breath (dyspnea), edema, and fatigue, in a patient with existing heart disease, the cardiac filling pressures generally start to increase more than 5 days preceding an admission. While this could reflect a state of effective venous congestion following a build-up of total fluid volume, nearly 50% of patients gain only an insignificant amount of weight (<1 kg) during the week before admission. This means that in about 50% of cases, decompensated HF is not caused by externally added fluid, but rather symptoms and signs of congestion can be entirely explained by redistribution of the existing intravascular volume.

Acute increases in sympathetic nervous tone due to a variety of known triggers like cardiac ischemia, arrhythmias, inflammatory activity and psychogenic stress and other unknown triggers can disrupt the body's balance and lead to a fluid shift from the splanchnic venous reservoir into the effective circulation. This results ultimately in an increase in preload and venous congestion. This explains the finding that in ADHF in both HFrEF and HFpEF was preceded by a significant increase in diastolic blood pressures.

In many patients with HFpEF relatively small increases in diastolic pressures/preload can result in decompensation due to impaired relaxation of the ventricles. Thus patients with HFpEF are more sensitive to intrinsic or extrinsic fluid shifts.

Chronic CHF is characterized by longstanding venous congestion and increased neurohumoral activation. Like in acute heart failure, the splanchnic vascular bed has been identified as a major contributor to HF pathophysiology. Chronic decrease in vascular compliance and capacitance makes the human body more susceptible to recurrent acute decompensations, making significant the consequences of chronic congestion of the splanchnic compartment. While the splanchnic vascular compartment is well suited to accommodate acute fluid shifts (e.g., change of posture and orthostasis, exercise and dietary intake of water), the regulation of the splanchnic vascular bed becomes maladaptive in chronic disease states associated with increased total body volume and increased splanchnic vascular pressure.

Clinically observed effects of HF drug regimens like nitroglycerin and ACE inhibitors exhibit their positive effects in the treatment of HF in part through an increase in splanchnic capacitance subsequently shifting blood into the venous reservoir thereby lowering left ventricular diastolic pressure. Where left ventricular diastolic pressure is mentioned it is understood that it may mean left ventricular end diastolic pressure (LVEDP) and since LVEDP is hard to measure may also mean pulmonary capillary wedge pressure (PCWP) which is a common clinical index of LVEDP.

An orthostatic stress test (tilt test) or simpler "legs up" test can help to distinguish low vascular capacitance from normal. Orthostatic stress causes blood shifts from the stressed volume into the unstressed volume. Veins of the extremities are less compliant than splanchnic veins, and therefore, their role as blood volume reservoir is relatively minimal. Less known is that during body tilt or standing up blood goes mostly into the splanchnic compartment, which results in a decreased preload to the right and left heart. Stimulation of the atrial and carotid baroreceptors results in an increased sympathetic tone causing splanchnic vasoconstriction. This compensatory mechanism is important, as it can rapidly shift volume from the unstressed compartment into active circulation. The hemodynamic response to tilt in chronic HF is atypical, as there is no significant peripheral pooling in the upright posture. It is assumed that the reduced capacitance of the splanchnic compartment serves as a marker of sympathetic tone to the splanchnic vasculature.

Acute oral or intravenous fluid challenge can also serve as a test of splanchnic vascular capacitance. The vascular capacitance determines how "full" the unstressed volume reservoir (venous reservoir) is and how much more fluid can be taken up to it in order to buffer the increase in effective circulation (stressed volume). A fluid challenge could test the capacitance by measuring the effects of a fluid bolus given via an I.V. infusion on cardiac filling pressures.

Patients with a "full tank", (low capacitance of venous reservoir), will not be able to buffer the hemodynamic effects of the fluid bolus as well as patients with a high capacitance in the venous reservoir. This will manifest in a bigger blood pressure increase for the same added volume. Thus patients with HF, HFpEF and patients with increased SNA will be more likely to respond to the fluid challenge with a disproportional rise in cardiac filling pressures. This could serve as a patient selection tool as well as measure of therapeutic success.

Similarly, patients with HFpEF have abnormally high magnitude of increases in pulmonary pressure and PWCP in response to mild exercise such as hand-grip or pedaling a stationary bicycle. This response is caused by their inability to compensate for the release of fluid from unstressed volume into the circulating volume that is mediated by sympathetic splanchnic nerves. Hemodynamic response to exercise may be another way of selecting suitable patients and testing the effect of ablation.

FIG. 1 is an anatomical representation of the supply of sympathetic nerve fibers to organs of the human body. The SNS is part of the autonomic nervous system, which also includes the parasympathetic nervous system.

The SNS activates what is often termed the fight or flight response. Like other parts of the nervous system, the sympathetic nervous system operates through a series of interconnected neurons. Sympathetic neurons are frequently considered part of the peripheral nervous system, although there are many that lie within the central nervous system.

Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through chemical synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, noradrenaline and adrenaline bind adrenergic receptors on peripheral tissues. Binding to adrenergic receptors causes the effects seen during the fight-or-flight response. These include pupil dilation, increased sweating, increased heart rate, and increased blood pressure.

Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Thoracic splanchnic nerves (e.g., greater, lesser, or least splanchnic nerves), which synapse in the prevertebral ganglia are of particular interest for this therapy.

Increasing evidence suggests that fluid homeostasis and control of intravascular fluid distribution is disrupted in patients with HF. Dysregulation of this key cardiovascular regulatory component could not only explain findings in chronic HF but also in ADHF. Consequently, blocking of the autonomic nervous system to alter fluid distribution in the human body could be used as a therapeutic intervention. Additionally, the classical understanding of HF pathophysiology emphasizes the mechanism of poor forward flow (i.e., low CO), resulting in neurohumoral, or sympathetic nervous system (SNS) up-regulation. However, new evidence emphasizes the concurrent role of backward failure (i.e., systemic congestion) in the pathophysiology and disease progression of HF. Coexisting renal dysfunction with diuretic resistance often complicates the treatment of HF and occurs more frequently in patients with increased cardiac filling pressures. Chronic congestive heart failure (CHF) is characterized by longstanding venous congestion and increased neurohumoral activation. Critically important has been the identification of the splanchnic vascular bed as a major contributor to blood pooling and cardiac physiology. Newly evolving methods and devices involving sympathetic nervous system blocking and manipulation of systems including the splanchnic vascular bed have opened novel avenues to approach the treatment of heart disease. In particular, the role of sympathetic nerves that innervate smooth muscle in the walls of splanchnic veins have become better known. In the case of hyperactivity of these nerves they became a novel target in the treatment of CHF.

Figure 2:
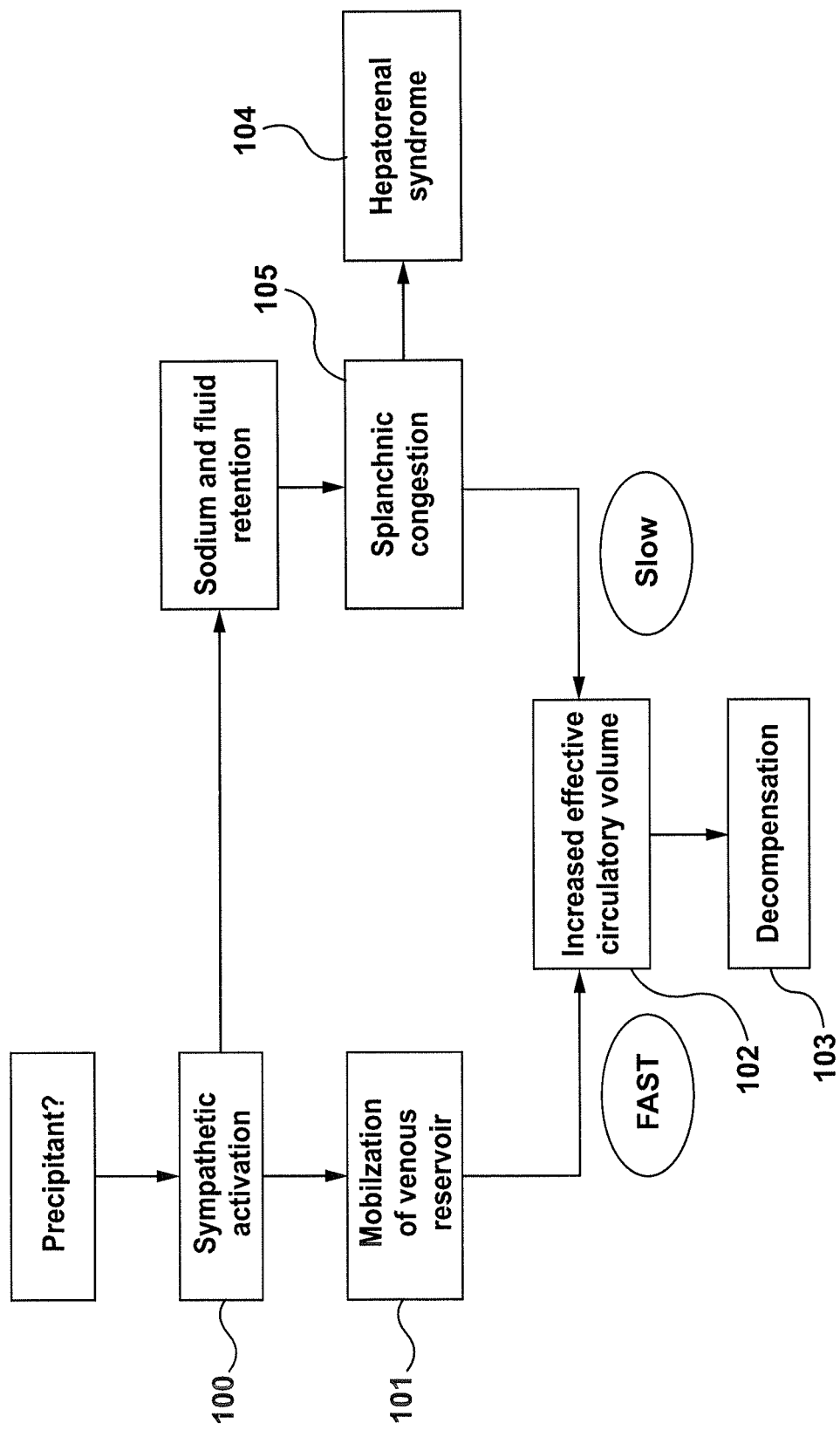
FIG. 2 is a flow diagram showing the mechanisms of decompensated heart failure

FIG. 2 is a flow diagram showing the mechanisms of decompensated heart failure. It illustrates the role of sympathetic nerve activation 100 in the mobilization of venous reservoir 101 into the effective circulatory volume 102 leading to decompensation 103. Reversing, at least partially, by ablation of a greater splanchnic nerve, the sympathetic activation of splanchnic nerves is expected to relieve HF symptoms, improve exercise capacity and reduce load on the failing heart.

A particular area of interest in the body is the splanchnic compartment, splanchnic vascular bed, or splanchnic reservoir, which include the vasculature of the visceral organs including the liver, spleen, small and large bowel, stomach as well as the pancreas. The splanchnic venous vascular bed serves as the major blood reservoir and can be affected by activation (e.g., stimulation) or deactivation (e.g., blocking or ablation) of thoracic splanchnic nerves and particularly of the greater splanchnic nerve (GSN) causing relaxation of veins, mobilization, release or uptake of venous blood from or to splanchnic vascular beds, respectively, and important changes in circulating blood volume.

The TSN, particularly the GSN, may at least partially control splanchnic venous compliance and capacitance. Capacitance is reduced in CHF patients and particularly in some very hard to treat HFpEF patients as a part of overall elevated sympathetic state. The sympathetic fibers in the greater splanchnic nerve bundle that control contraction of splanchnic veins are a target of the proposed ablation therapy.

The splanchnic congestion 105 and high venous pressure is believed to adversely affect renal function and as illustrated by hepatorenal syndrome 104 that causes diuretic resistance. It is believed by the authors that the proposed ablation may reverse this phenomenon, improve renal function and enable diuretics to work (e.g., restore diuretic responsiveness).

Figure 3:
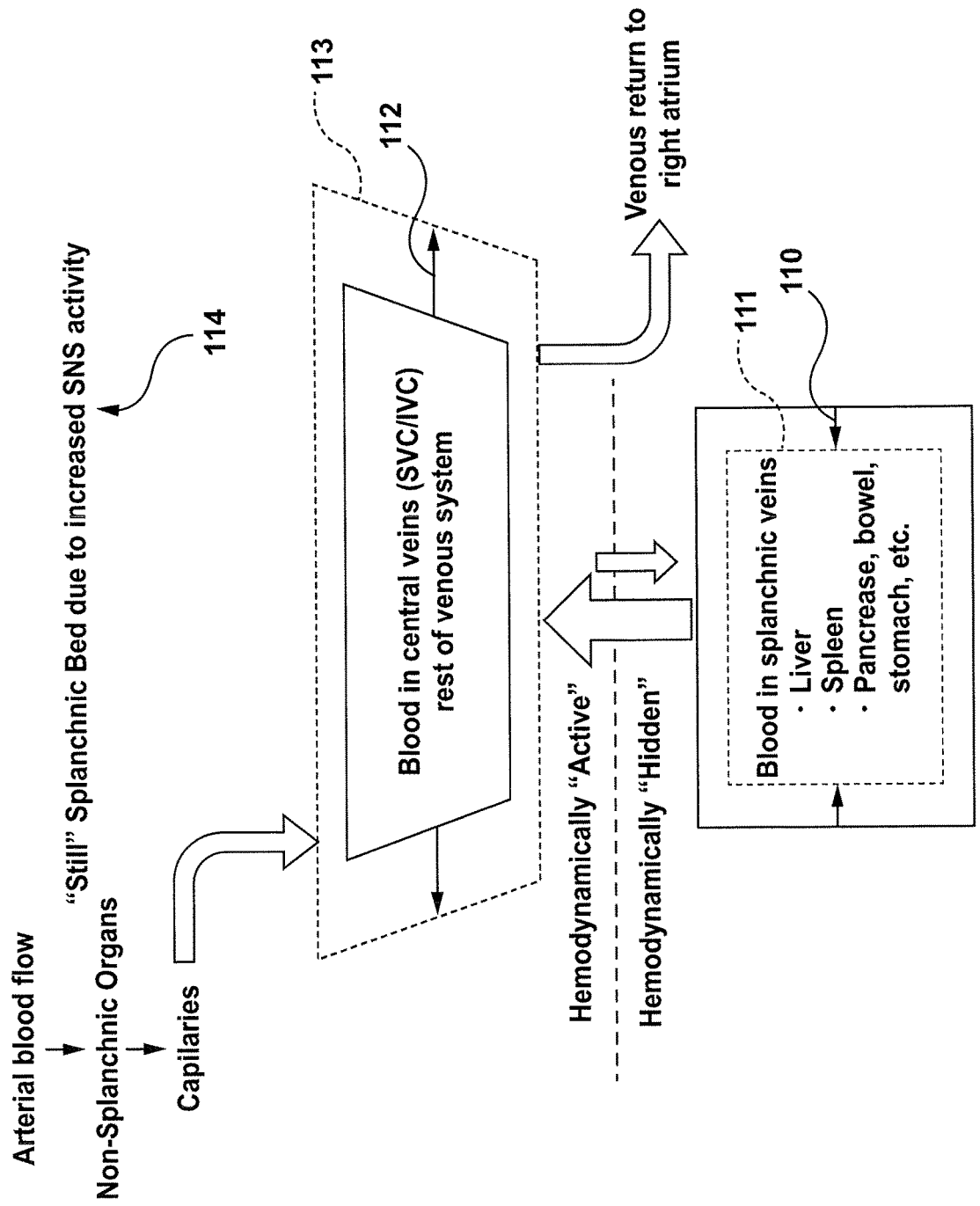
FIG. 3 is a partial flow diagram showing the role of splanchnic compartment in blood volume distribution in heart failure.
Figure 4:
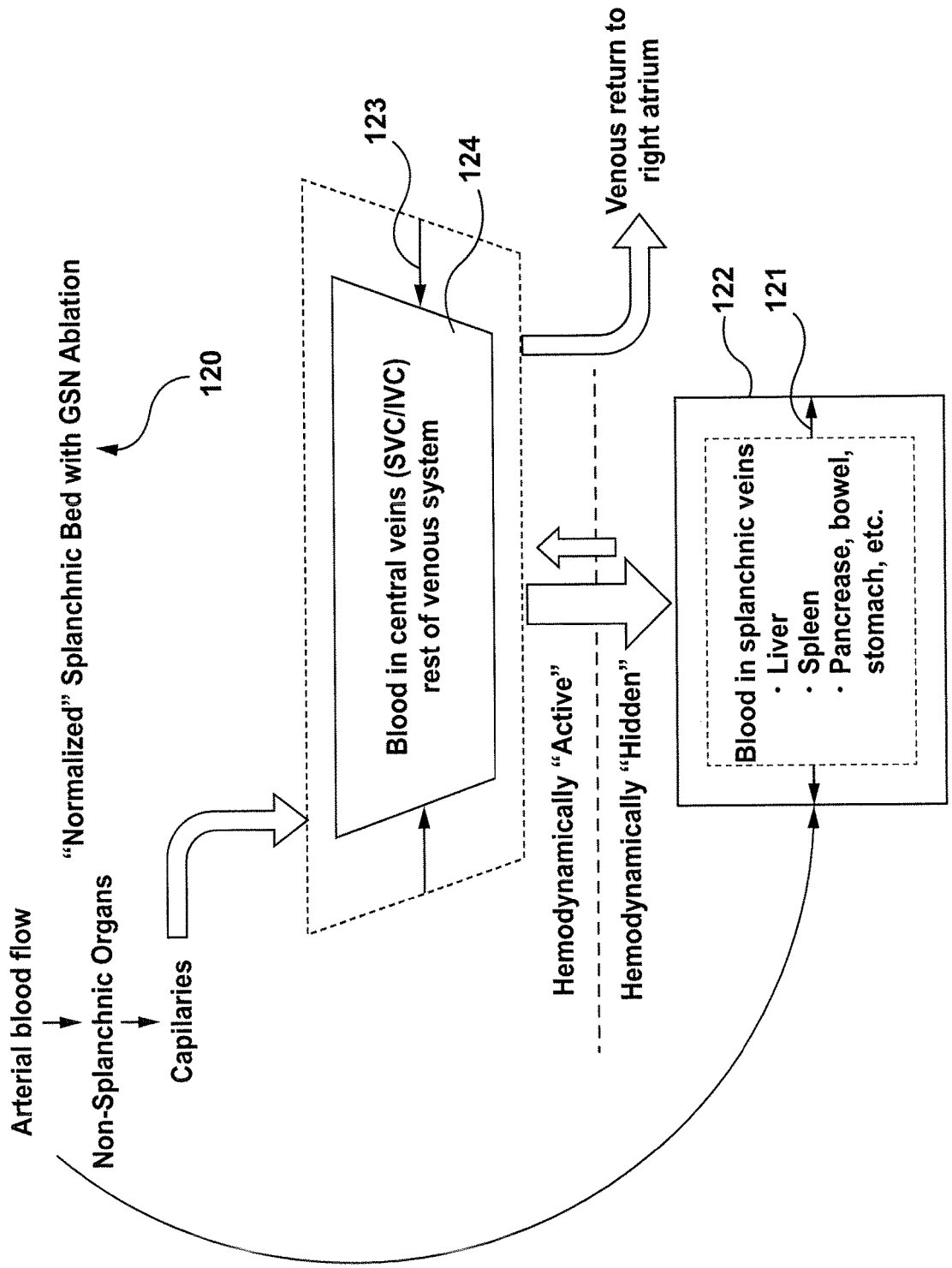
FIG. 4 is a partial flow diagram showing a role of therapeutic effects of the disclosed therapies to heart failure.

FIG. 3 and FIG. 4 show some of the interactions between increases in sympathetic nervous system activity, including natural activity (e.g., rate of firing and number of efferent sympathetic fibers engaged in firing) of the GSN, and the storage of blood in the splanchnic bed. As illustrated by FIG. 3, increased central SNA 114, can manifest, at least partially, in the elevated activity of the GSN in all types of HF, resulting in a lower splanchnic capacitance and possibly stiffened, less-compliant splanchnic bed and regional effects including a decrease in the amount of blood stored in the splanchnic veins perfusing and surrounding the splanchnic organs (e.g., liver, spleen, pancreas, stomach, bowels) 110 and an increase in the amount of blood in central (and pulmonary) veins 112. The volume of blood in splanchnic veins or the splanchnic vascular bed 111 can be described as a "venous reservoir", or "unstressed volume" and refers to the blood volume that does not contribute to the effective circulating volume and is therefore hidden from circulation or the hemodynamically hidden blood volume. The volume of blood in central veins 113 can be termed "effective circulatory volume" or "stressed volume" and refers to blood that is present mainly in the non-splanchnic veins and is one of the main determinants of preload to the heart and in CHF can contribute to venous congestion, high pulmonary circulation pressures and sensation of dyspnea.

Conversely, as illustrated by FIG. 4, decreased sympathetic nervous system activity or a splanchnic bed normalized with TSN ablation 120 may result in the compliance of the splanchnic bed, which may be relaxed or normalized from the "stiff" or contracted state and less responsive to the volume redistribution in response to exercise. Ablating a target splanchnic nerve can result in a decrease of efferent sympathetic tone to smooth muscle in the walls of veins in the splanchnic vascular bed referred to as splanchnic "venodilation" resulting in an increase 121 in the volume of blood stored in the splanchnic bed 122 and a decrease 123 of volume of blood in the central veins 124, reduced release mobilization of blood from unstressed volume into systemic circulation in response to exercise or in the overall decrease in sympathetic nervous system activity. Other effects of TSN ablation may comprise reduction of pulmonary vascular pressure and pulmonary capillary wedge pressure that is index of left ventricular end-diastolic pressure, which are important measurable improvements in the treatment of HF. Understanding and utilizing these interactions are some of the primary aims of several embodiments disclosed herein. Specifically, the compliance and capacitance of splanchnic vasculature is desired to be increased.

Figure 5:
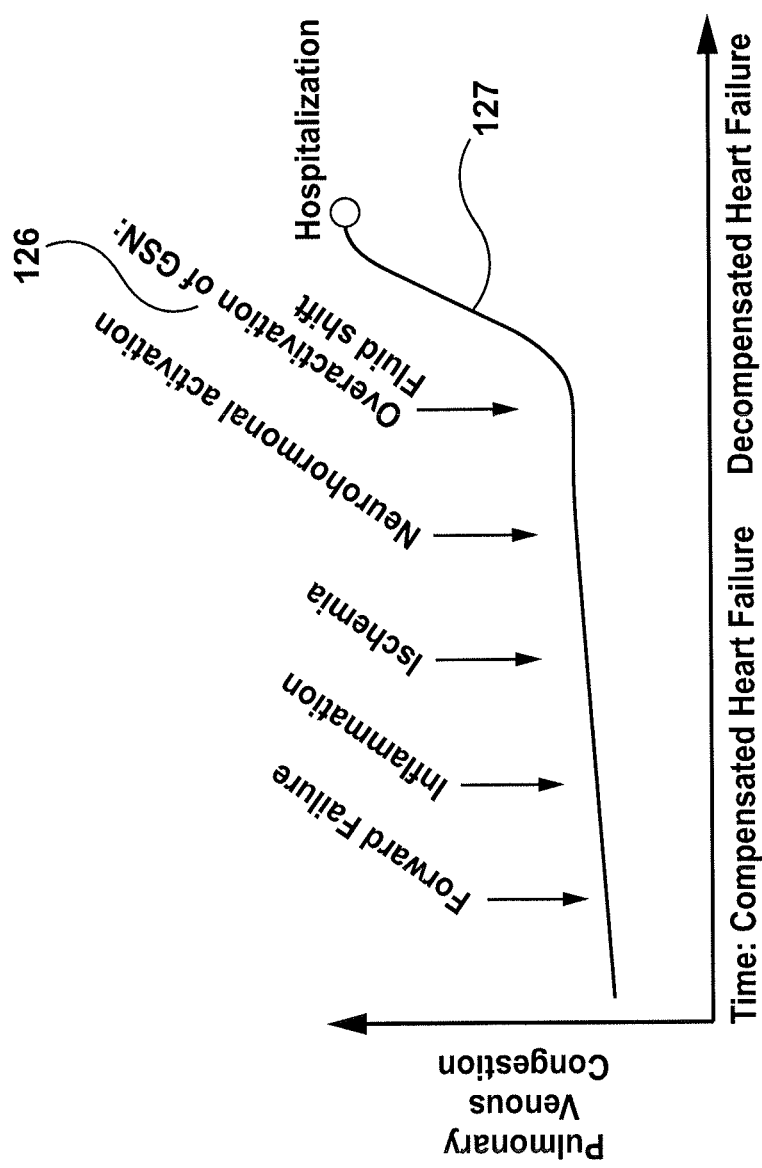
FIG. 5 is a graphical representation of pathophysiology of acute decompensated heart failure.

FIG. 5 shows one possible clinical scenario in which the sympathetic hyperactivity of the greater splanchnic 126 nerve leads to the acceleration of fluid overload 127 and pulmonary venous congestion in a HFpEF patient. Preventable hospital admission of the HF patient is precipitated by the increase of pulmonary blood pressures in response to exercise that causes "dyspnea upon exertion". This sensation can be partially explained by the patient's inability to buffer the sudden increase of venous blood volume and pressure caused by exercise that is transmitted to the pulmonary circulation and left atrium of the heart.

Endovascular Ablation

Endovascular nerve ablation, or ablation of neural structures using a catheter or other elongate medical device delivered through a blood vessel, particularly ablation of deep visceral nerves that are near the blood vessel (e.g., often less than about 5 mm from an internal vessel wall, but as far as 10 to 20 mm away), may be more advantageous than surgical resection or surgical ablation. For example, endovascular ablation may be less invasive, be faster procedurally, and have faster patient recovery. The terms 'ablation' or "ablating" (or other derivatives thereof) is defined herein as causing irreversible tissue necrosis. It may be beneficial to use a patient's venous system to deliver ablation energy since interventions in veins are considered safer than in arteries. Blood pressure in a vein is lower and limits risk of bleeding and debris or clot from ablation is safer since veins terminate in the lungs, which act as a natural blood filter. It is also advantageous that veins are more elastic and can be occluded and stretched in order to achieve better fixation and apposition of an ablating device in relation to the target nerve. Specifically, in the case of an azygos or hemiazygos vein or even more so in the case of intercostal veins, there is large redundancy in the venous system and occlusion of these veins is not dangerous to the patient. This is in contrast to some arteries, where occlusion does present dangers and risks to the patient, and is avoided or minimized as much as possible.

There are several accepted methods of ablating a nerve through a wall of a blood vessel, such as RF ablation using resistive heating, microwave ablation, cryo-ablation using cold, ultrasound heating ablation, optical or laser-based ablation, direct thermal conduction, and injection of neurolytic blocking agent (e.g., form of nerve block involving the deliberate injury of a nerve by the application of chemicals, in which case the procedure is called "neurolysis") in which chemicals such as alcohol or more specifically acting sympatholytic agents like guanethidine, botox (i.e., botulinum toxin A) and others can be applicable. A large majority of previously disclosed transvascular nerve ablation methods and devices focus on ablating nerve structures that are in the target vessel adventitia and from within a target vessel that is relatively large with significant blood flow (e.g., renal, pulmonary, carotid, hepatic, or jugular blood vessels). In the currently disclosed procedures and apparatuses, the target nerve(s) are located at a distance from the target blood vessel in a range of 0 to 5 mm or in some patient's up to about 8 mm. Also, the target blood vessel may be a vein of the azygos vein system or more particularly and intercostal vein, which is relatively small and has very low blood flow. This situation requires unique apparatus or procedural features.

Methods and devices for ablating a greater splanchnic nerve using an ablation catheter positioned in an azygos or intercostal vein can be configured and/or positioned to safely avoid important non-target nerves and structures. For example, the celiac ganglion is near the greater splanchnic nerve. Placement of an ablation element that creates, for example, a 5 mm diameter lesion that permanently destroys the TSN where it is in close proximity of the azygos vein or intercostal vein at or slightly above the diaphragm (e.g., at or above the T11 or T12 vertebral body) will protect the celiac ganglion from ablation. Celiac ganglia are located in the abdominal cavity just below the diaphragm. Thus a targeted selective ablation of nerves is possible to meet needs of different groups of patients with HF.

Figure 7:
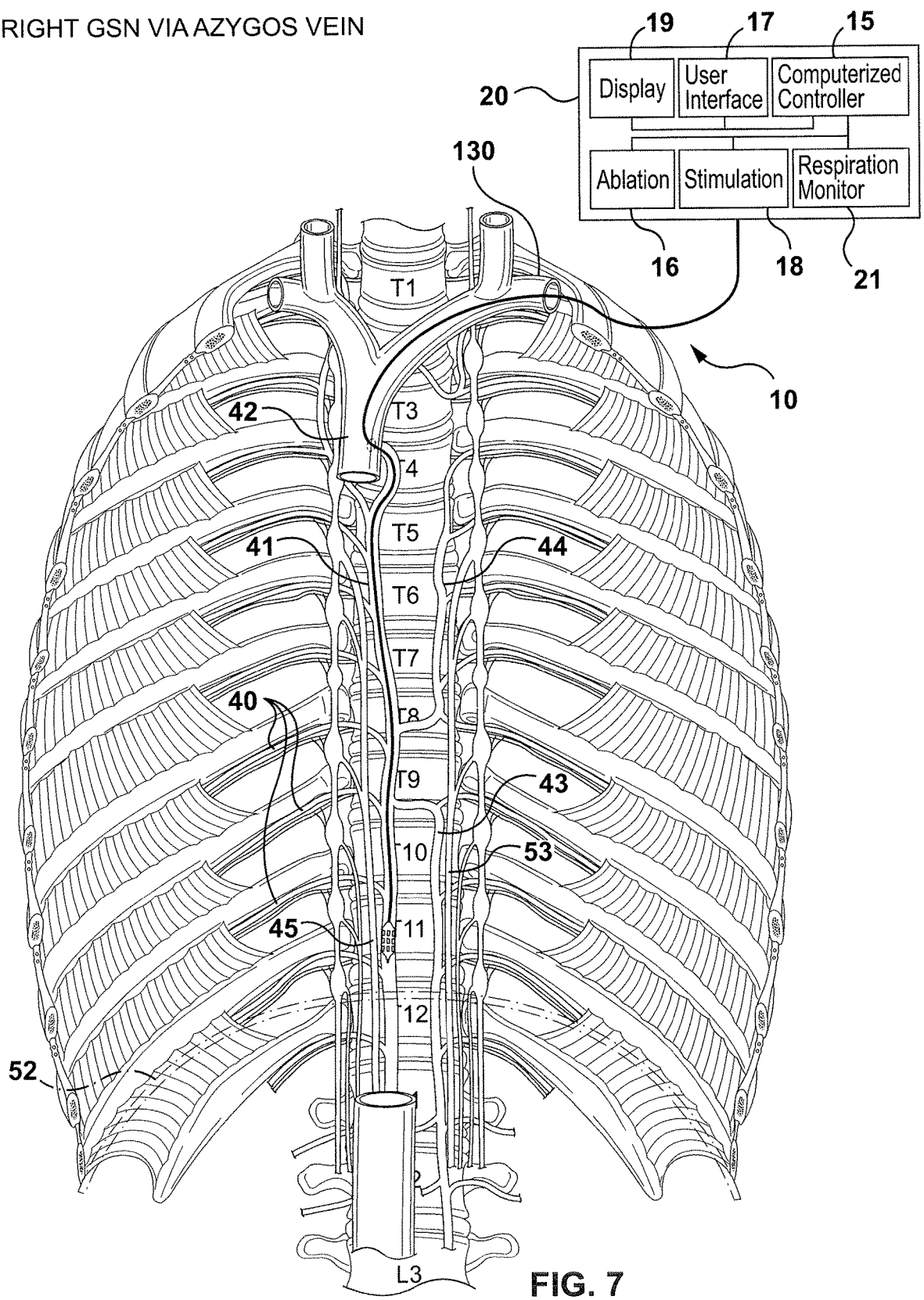
FIG. 7 is an anatomical representation showing azygos vein catheterization for right TSN ablation with an intravenous catheter suitable for stimulation and ablation.
Figure 8:
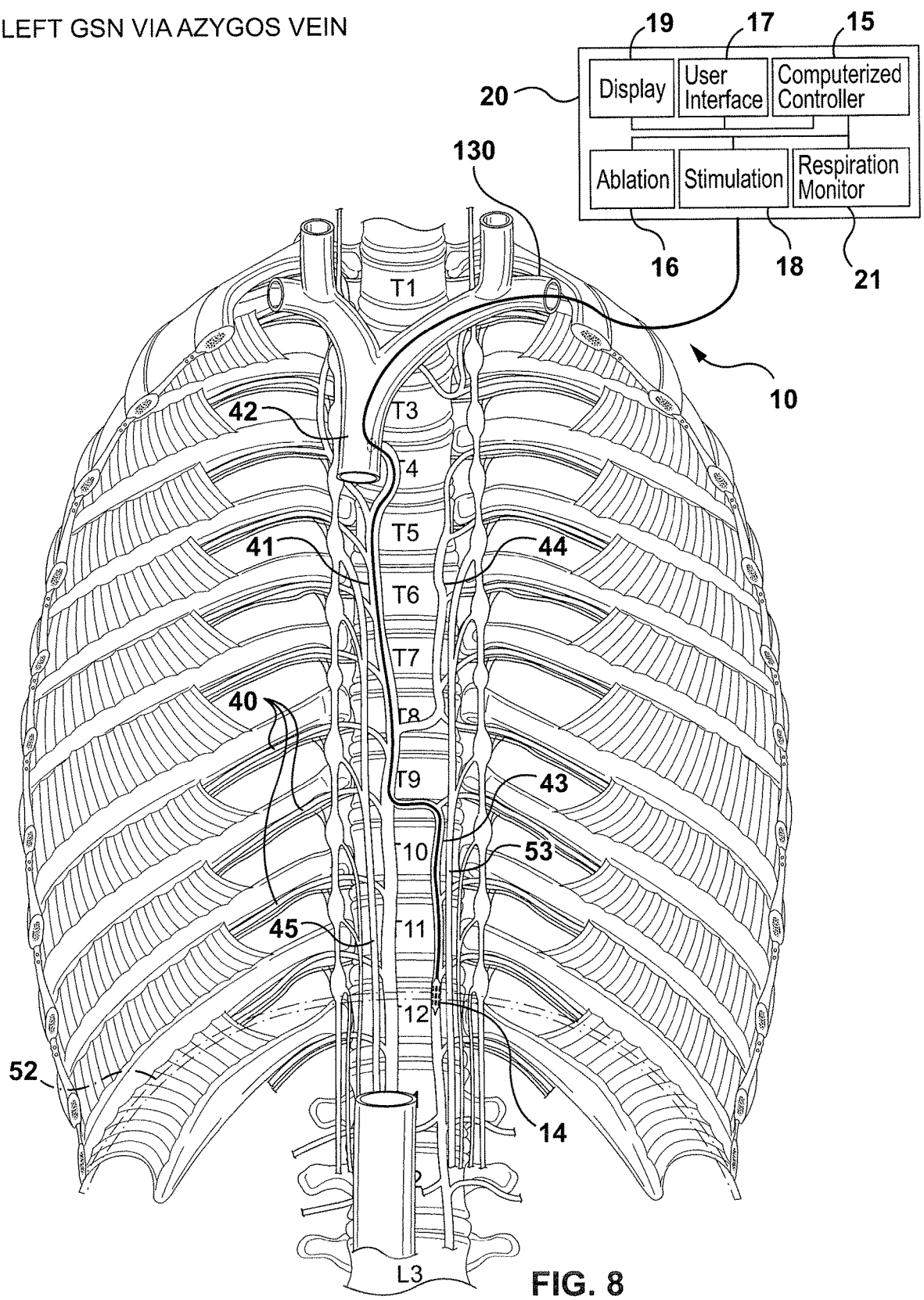
FIG. 8 is an anatomical representation showing azygos vein catheterization for left TSN ablation with an intravenous catheter suitable for stimulation and ablation.
Figure 9:
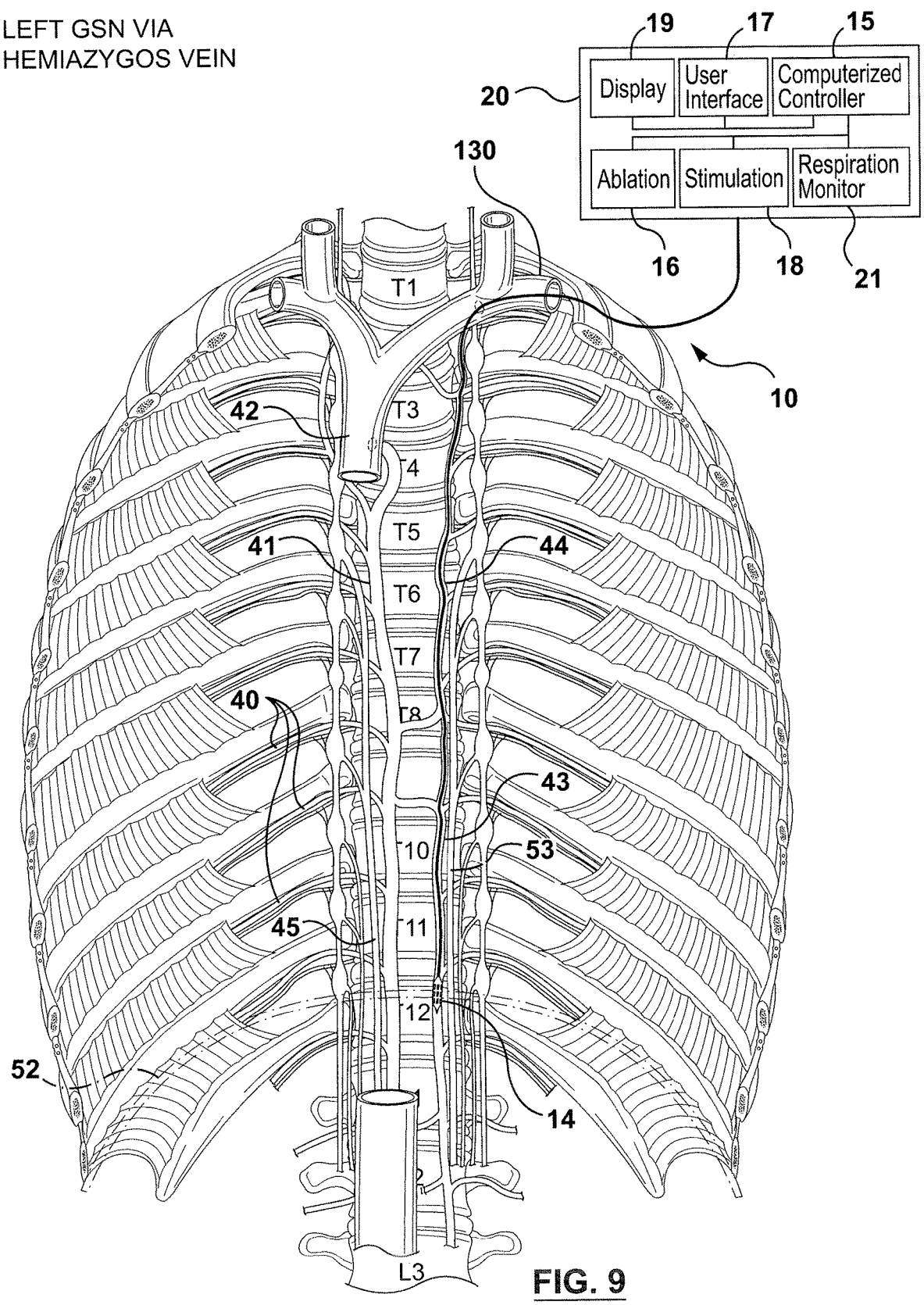
FIG. 9 is an anatomical representation showing hemiazygos vein catheterization for left TSN ablation with an intravenous catheter suitable for stimulation and ablation.
Figure 10:
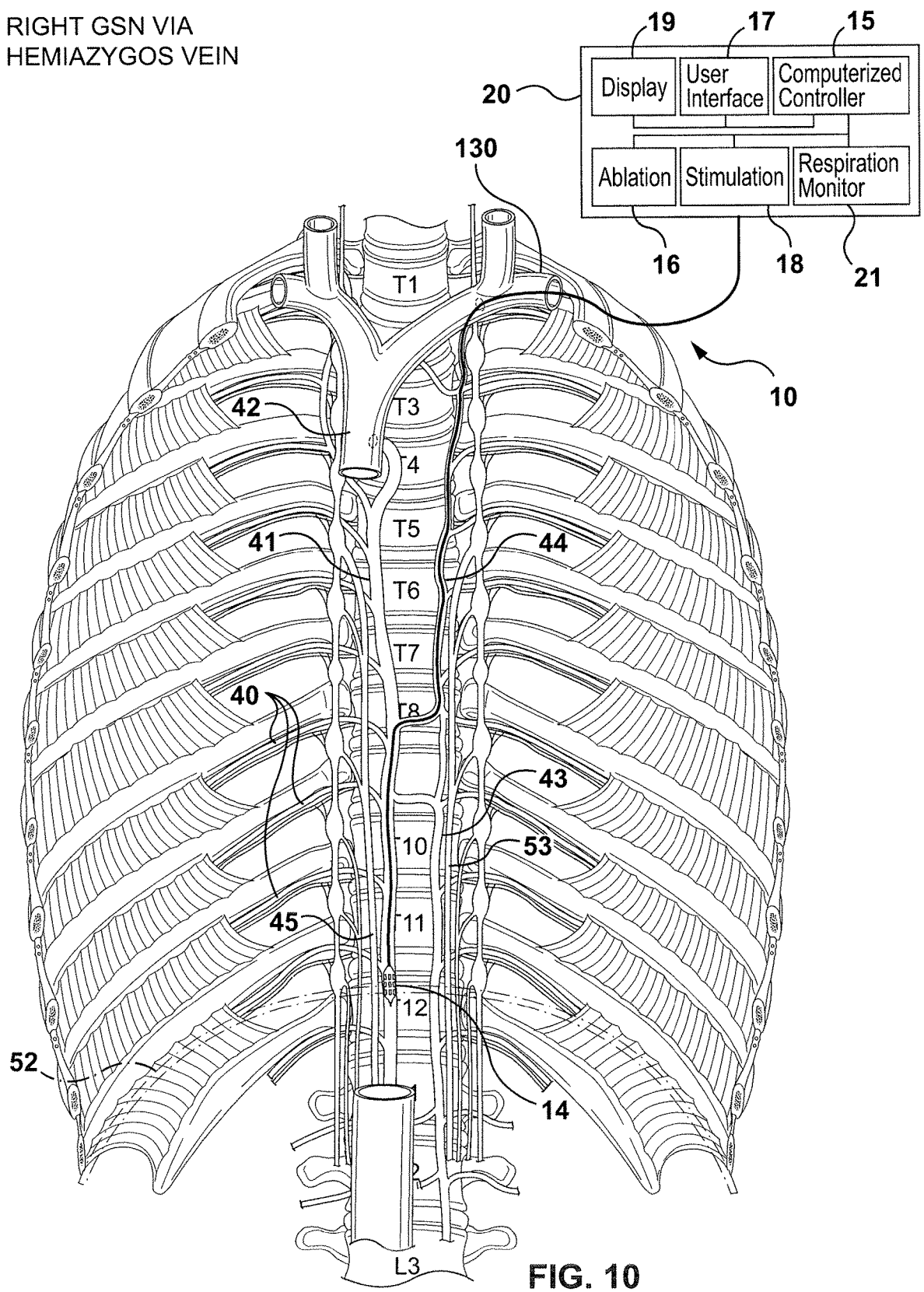
FIG. 10 is an anatomical representation showing hemiazygos vein catheterization for right TSN ablation with an intravenous catheter suitable for stimulation and ablation.

FIG. 7 shows an example of a catheterization approach from a left subclavian vein 130 (or left radial vein not shown that leads to the subclavian vein) to a suitable position in an azygos vein 41 for right TSN 45 ablation. As shown, a working end of the medical device has been positioned in azygos vein 41. FIG. 8 shows an example of a catheterization approach from the left subclavian vein 130 to a suitable position in a hemiazygos vein 43 for left TSN 53 ablation by crossing over from azygos vein 41 to hemiazygos vein 43. As shown, a working end of the medical device has been positioned in hemiazygos vein 43. FIG. 9 shows an example of a catheterization approach to a hemiazygos vein 43 from an accessory hemiazygos vein 44 in patients having a connecting vein between the accessory hemiazygos vein to the hemiazygos vein, for left-sided TSN ablation. As shown, a working end of the medical device has been positioned in hemiazygos vein 43. FIG. 10 shows an example of a catheterization approach to an azygos vein 40 via an accessory hemiazygos vein 44. As shown, a working end of the medical device has been positioned in azygos vein 41. Endovascular approaches to the azygos vein system may comprise introduction into the vascular system, for example, at the radial, brachial, subclavian, jugular or femoral veins.

A guidewire may facilitate advancement of a catheter 10 through tortuous vessel pathways. The catheter may include an extended tubular member or shaft including lumens, such as for a guidewire, or injection of drugs or radiocontrast. Bilateral or unilateral TSN ablation (both left and right, or left or right) is possible and may be desired based on the patient's anatomy, responses to diagnostic stimulation or response to therapy.

The catheters 10 or 132 in FIGS. 7 to 11B may each comprise at least one ablation element 14 or 22 adapted to deliver ablation therapy, as well as at least one electrical stimulation element 23 or 32 to confirm proximity to a target nerve, such as a GSN, or non-target neural structures. The catheter 10 in each of FIGS. 7 to 10B may be used as part of a system comprising other components that contribute to the function of the catheter. The system may comprise an ablation energy source 16 (e.g., RF signal generator, cryo console, ultrasound signal generator, chemical agent source or pump, laser energy generator, microwave signal generator), an electrical stimulation energy source 18, a computer controller 15 with embedded logic and software, a ventilation monitor 21 linked to the computer console to synchronize ablation with a expiration to avoid iatrogenic injury of the lung or pleurae, and a user interface 17 with manual controls and displays 19. A console 20 may house the ablation energy source 16, the electrical stimulation energy source 18, the computer controller 15, user interface 17, an optional lung detection system or ventilation monitor 21, or displays. Optional respiration monitor 21 can be a lung detection monitor adapted to detect presence of the lung close to the ablation zone. Respiration monitors and lung detection procedures and devices are optional in any of the embodiments herein, even if not specifically identified as such.

Figure 11A:
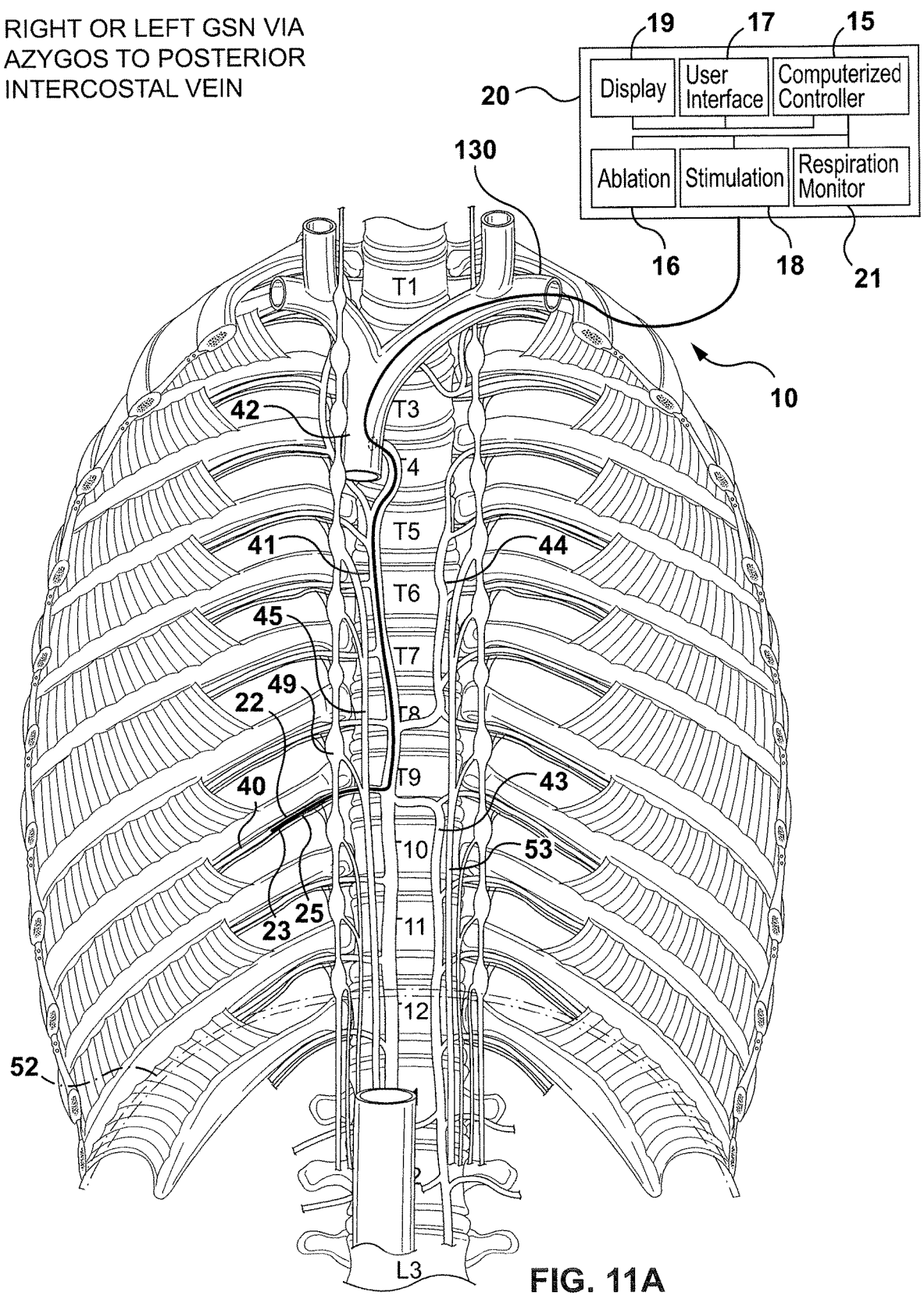
FIGS. 11A and 11B are anatomical representations showing right TSN catheterization via the azygos vein to a posterior intercostal vein.
Figure 11B:
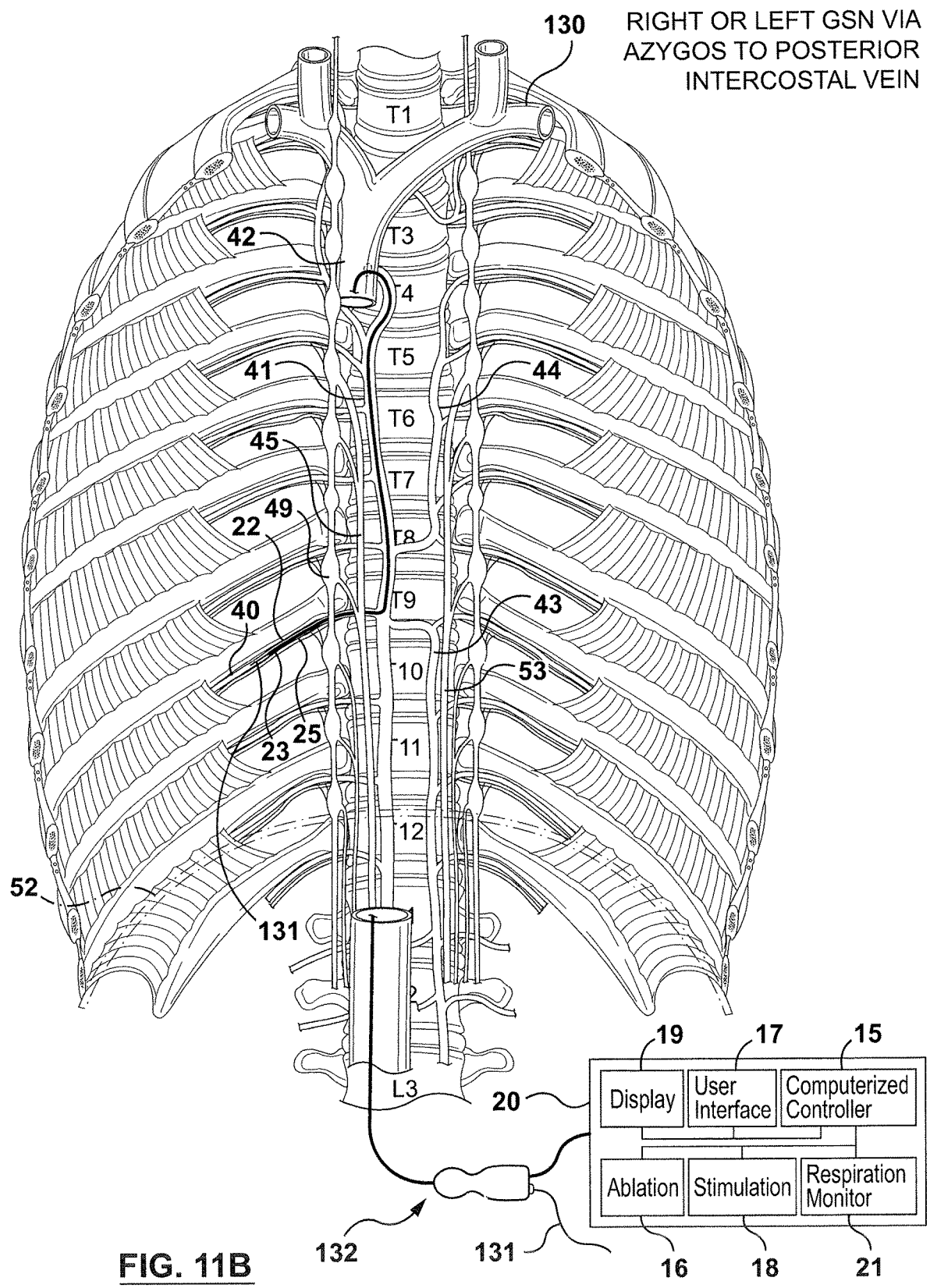

In an embodiment, as shown in FIG. 11A, at least one ablation element 22, and optionally at least one stimulation element 23 or optional ventilation monitoring or lung detection element 25, on a distal region of a catheter 10 are positioned in an intercostal vein 40 near a GSN 45 and sympathetic chain 49. The ablation element 22 and stimulation element 23 may be electrodes suitable for stimulation of nerves and measurement of impedance. The catheterization approach shown in this example is introduced into a left subclavian vein 130, or left radial vein (not shown), traverses via the azygos vein 41 into a posterior intercostal vein 40 at a T9 level. Other approaches are possible through suitable veins. Other posterior intercostal veins on the right or left sides and at other levels (e.g., above the diaphragm, or at levels T9, T10, or T11) or ablations in multiple intercostal veins simultaneously or consecutively may be involved in a catheterization method of a proposed therapy. A femoral vein approach from the groin, as shown in FIG. 11B, and a radial vein approach from the arm are important and have advantages and increase comfort for the patient. In these approaches a catheter may be delivered over a guide wire 131 (see FIG. 11B). A catheter may comprise any combination of at least one ablation element to deliver ablation therapy, at least one electrical stimulation element to confirm proximity to a target nerve, such as a GSN, or non-target neural structures, and a lung detection element (e.g., impedance monitoring element, ultrasound transducer). A catheter 10 or 132 may be used as part of a system comprising other components that contribute to the function of the catheter. The system may comprise a computerized controller having a computerized algorithm, stored thereon in a memory and executable by a processor, that is in communication with an ablation energy source 16, an electrical stimulation controller 18, an interface with sensors such as impedance, temperature, ultrasonic sensing of living tissues, an optional lung detection or ventilation monitor 21, and a user interface 17. Additional elements such as monitoring of temperature and impedance of tissue at the ablation site may be added to improve performance and safety of the ablation system.

Figure 12:
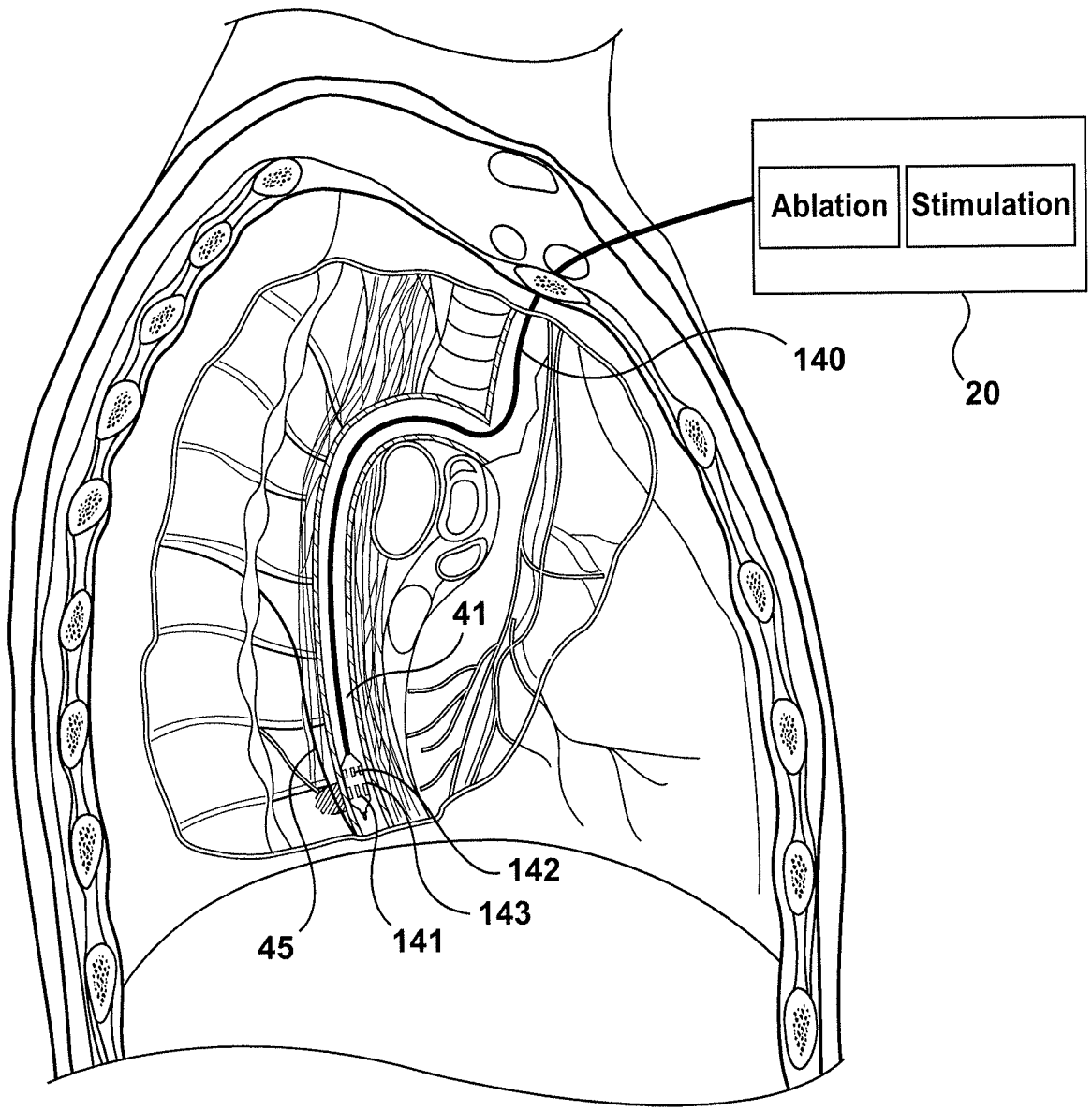
FIG. 12 is an anatomical representation showing the azygos vein and greater splanchnic nerve and their proximity, which allows for a transvenous approach with an intravenous catheter deployable structure suitable for stimulation and ablation.

In an embodiment, as illustrated in FIG. 12, an ablation element 141 on a catheter 140 is positioned in an azygos vein 41 near a greater splanchnic nerve 45. The catheter 140 may comprise a deployable structure 143 positioned at its distal region of the catheter. The deployable structure 143 comprises at least one ablation element 141 (e.g., RF electrode, microwave antenna, ultrasound transducer, electrothermal element, cryogenic element, optical element) that is placed in apposition with the azygos vein 41 as shown or a hemiazygos vein or an intercostal vein (not shown) wall when the deployable structure 143 is deployed, optionally expanded. The deployable structure 143 may be, for example without limitation, a balloon, a cage or cage-like device, a basket, two or more expandable splines, or a preformed shape such as a lasso or loop. The deployable structure 143 may further comprise at least one of at least one stimulation element 142 (e.g., electrical stimulation cathode and optionally anode), a visualization aid (e.g., radiopaque marker, contrast delivery lumen), and a lung detection monitor (e.g., impedance monitor, ultrasound transducer). Intravenous access via an azygos vein 41 or hemiazygos vein to a posterior intercostal vein allows for a catheter to access an area in proximity to the thoracic splanchnic nerves, in particular, the greater splanchnic nerve (GSN).

Experiments in animals and human cadavers were performed by the authors in which the GSN was successfully accessed with a catheter advanced to an azygos vein at the level of the diaphragm wherein an electrode was positioned close enough to electrically stimulate and ablate the greater splanchnic nerve. In animal experiments GSN access was performed on the right side. Physiology was confirmed by observing hemodynamic effects of greater splanchnic nerve stimulation with electric pulses applied from the azygos vein. The authors also performed experiments where the GSN was surgically accessed, visualized, stimulated and later resected and ablated using video-assisted thoracoscopic surgery (VATS). Consistent and similar hemodynamic effects that suggested therapeutic possibilities and benefits were observed.

Stimulation Confirmation Embodiments

Regardless of the modality of ablation, embodiments of devices, systems, and methods may further be configured to assist the ablation procedure with a confirmation of safety and efficacy prior to and/or following an ablation step. Confirmation of safety may comprise detection of a non-target nerve, organ or anatomic structure or absence thereof within a range of ablation energy delivery. Confirmation of technical efficacy may comprise detection of a target nerve within range of ablation energy delivery before an ablation step and absence of a target nerve signal transmission following the ablation step. Confirmation of procedural efficacy may comprise temporarily blocking a target nerve to assess if a resulting physiologic response is representative of a desired clinical effect of the procedure.

To facilitate a technically effective procedure, an embodiment may involve confirming that the ablation lesion will be created in a desired location and that a targeted nerve is sufficiently within range of ablation energy delivery before ablation energy is delivered to cause irreversible damage to the target nerve or potentially to an untargeted area. This may be achieved by delivering an electrical stimulating signal from at least one, for example, stimulating electrode to excite nerves in proximity to the stimulating electrode and observing a physiologic effect such as hemodynamic changes or a patient's sensory response such as sensation within the epigastric region, which may indicate that a target thoracic splanchnic nerve is within an ablation zone of the stimulating electrode. The stimulating electrodes may be a pair of electrodes constituting an anode and cathode, a single monopolar electrode communicating with a dispersive electrode, the same component that is used to deliver an electrical ablation energy such as radiofrequency or electroporation, or a distinct electrode or pair of electrodes positioned appropriately relative to an ablation element (e.g., within 4 mm). Stimulating electrodes can also be disposed on a device that is different than the device carrying an element to deliver ablation energy.

Figure 13:
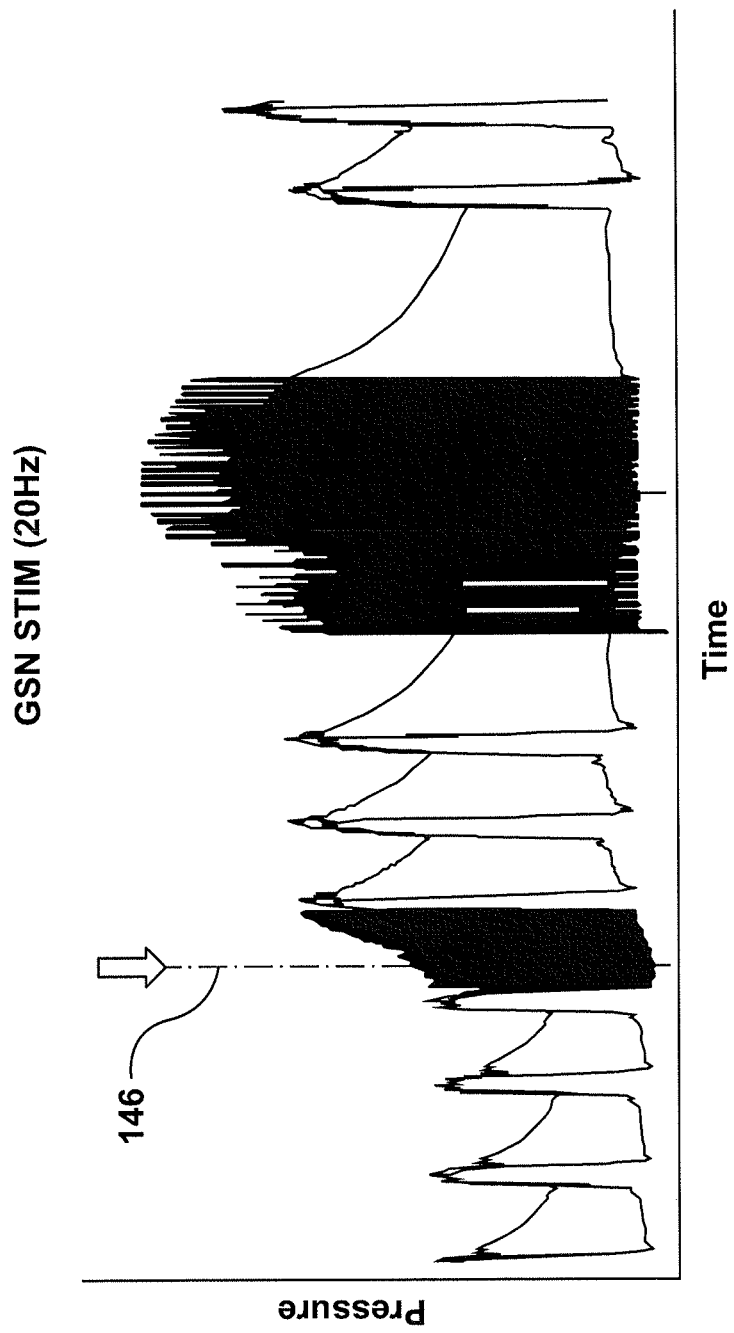
FIG. 13 is a plot of aortic and ventricular pressure in response to electrical stimulation of a GSN in an animal study.

FIG. 13 illustrates a response to stimulation 146 of a GSN at a level just above the diaphragm in an animal experiment performed by the authors. The recognizable waveforms of increased aortic and left ventricular pressure reflect the physiologic response to electrical stimulation of the GSN. Similar increases were observed in central venous pressure, right atrial pressure and pulmonary artery pressure that can be measured and monitored in real time in any well-equipped modern catheterization laboratory by a trained cardiologist.

In an embodiment wherein a stimulation electrode or pair of electrodes is distinct from an ablation element they may be positioned on a catheter relative to one another so that the stimulation zone (e.g., region in which the stimulation signal delivered by the stimulation electrode is strong enough to elicit an action potential in a nerve) correlates with an ablation zone (e.g., region in which ablation energy delivered by the ablation element is sufficient to cause irreversible or long lasting damage to nerve tissue).

A stimulation signal may be controlled by a computerized console 20 (see FIGS. 7 to 10B) or any other console described herein and may comprise a signal profile that facilitates confirmation of technically efficacious positioning. The computerized console 20 may include processors accessing non-transitory memory storing instructions that cause the console to generate a stimulation signal. For example, the size of a stimulation zone (zone where applied current excites the target nerve) may be a function of amplitude and a signal profile. The console may achieve the stimulation zone by delivering signal energy by varying amplitude (e.g., linear ramp, stepwise ramp, alternating levels) or frequency of stimulation. An observed response corresponding to a given amplitude may indicate distance of a target nerve to an ablation element, and delivery of ablation energy may be adjusted (e.g., manually or automatically) to create an efficacious ablation zone corresponding to the stimulation zone.

For example a different energy delivery electrode can be selected or the catheter can be repositioned. In another example, a signal profile comprises periods of on and off (e.g., stimulating amplitude(s) and non-stimulating energy levels) in which a physiologic response may follow the signal profile to eliminate false positive or negative assessments.

In an embodiment, a transvenous application of electrical stimulation of a nerve delivering currents of 0.5 to 15 mA, frequency of 1 to 50 Hz and pulse duration of 50 to 500 microseconds may be suitable to test if proximity to the nerve is within the target distance, for example, without limitation, within about 5 mm. Sedation may be used in order to prevent painful sensation by the patient. If a physiologic response is elicited, the cathode electrode is very likely to be within 1 to 5 mm distance from the target nerve and ablation in that area is likely to destroy the nerve permanently while sparing nerves outside of the ablation zone in embodiments configured to create an ablation zone of a targeted size, for example about 5 mm. It is estimated that a region 33 closest to the target nerve 45 and the corresponding electrode 34 (see FIG. 14) will elicit a response at the lowest energy (example of nerve mapping). For example, the ablation element(s) may be an RF electrode(s) (e.g., having an exposed surface area of about 5 to 15 $mm^2$) in monopolar configuration with a dispersive grounding pad on the patient's skin to complete the electrical circuit.

Ablation energy may be radiofrequency electrical current having a frequency in a range of about 200 to 3000 kHz and a power in a range of about 1 to 100 W (e.g., preferably within 5 to 50 W).

The delivery of RF energy may be controlled by an energy delivery console 16 associated with the computer console 20 (see FIG. 10) that uses temperature feedback from a temperature sensor associated with the RF electrode. Temperature feedback may comprise a temperature sensor, such as a T-type thermocouple, thermistor or temperature-sensitive resistive bridge, associated with each ablation element. The sensor may be encapsulated inside the electrode and covered by electrically-isolating epoxies to minimize electrical interferences from the ablation circuit into the temperature measurement circuit. Alternatively, the temperature sensor may be exposed to external medium (e.g., placed in a groove or opening) so that it reads values closer to tissue temperatures. In such case, the temperature sensor may be encapsulated with a thermally-insulating epoxy to minimizes thermal interferences from the electrode metal or from other construction elements located inside the electrode (e.g., steering wires). Observation of a physiologic response may involve equipment for measuring the response (e.g., equipment known in the art for measuring or monitoring hemodynamic parameters such as blood pressure and heart rate, or with sensors associated with the catheter or the system) that provides an indication of the parameter. Physiologic monitoring equipment is typically available in catheterization labs and may optionally be in communication with the computerized console 20 or the stimulation energy source 18 or the computerized controller. Alternatively, monitoring equipment can be integrated with the controller to save space and increase responsiveness and reliability.

Confirmation of efficacious positioning may be accomplished manually by a practitioner by observing the parameter measurements in real time. Alternatively, confirmation may be performed automatically by the computerized system console 20 that takes input from the physiologic monitoring equipment and compares it to a stimulation signal profile (automated mapping). The automated mapping or confirmation assessment may further select or assist in selecting an appropriate ablation energy delivery profile.

In an embodiment a catheter or other medical device may be configured to monitor a physiologic response to nerve stimulation and comprises a blood pressure transducer on the catheter that may be positioned in a blood vessel in addition to an ablation element and a stimulation element. The device or system may further comprise a second blood pressure transducer that may be positioned in a different part of the circulation system (e.g., arterial system such as femoral or radial artery, pulmonary circulation such as pulmonary artery, central venous system such as vena cava or right atrium of the heart or splanchnic circulation or pulmonary circulation system such as in a pulmonary artery) to compare blood pressure measured in different locations and assess changes in response to nerve (e.g., splanchnic or target or nearby non-target nerve) stimulation.

To facilitate a safe procedure, an embodiment may involve confirming that the ablation lesion will not do irreversible damage to important non-target nerves, such as celiac ganglia, if that is the selected therapy modality, before ablation energy is delivered. This may be achieved by electrically stimulating the adjacent nerves with the same or different electrodes and observing the physiologic effects (e.g., heart rate or hemodynamic such as blood pressure or flow). An embodiment may utilize the same principles and components as described above wherein a stimulation zone is correlated to an ablation zone however an observed physiologic response may be indicative that an important non-target nerve is stimulated. An undesired response may occur instead of or as well as a physiologic response from stimulating a target nerve. In either case, a response from an important non-target nerve may indicate that it is unsafe to ablate as positioned. For example, an increase of central venous pressure (CVP) or pulmonary artery pressure (PAP) can indicate the desired response in combination with the reduction of Heart Rate (HR); however, a concomitant increase in HR may indicate that an important non-target nerve is within the stimulation zone and associated ablation zone (e.g., nerve stimulating an adrenal gland) and the ablation element and the associated stimulation element may be repositioned and confirmation of safety and efficacy may be reapplied. If both a target nerve and important non-target nerve are stimulated by the same stimulation signal then the nerves may be quite close together and delivering ablation energy may be unsafe. To avoid risk of injuring the non-target nerve the ablation element and stimulation element may be moved and stimulation repeated until a position is found that is both safe and effective. For example, the catheter can be advanced or different electrodes selected on the catheter placed along the azygos, hemiazygos or intercostal vein traveling along, crossing or traversing the GSN and sympathetic chain (See FIG. 14). Alternatively, a catheter may comprise multiple ablation elements and corresponding stimulation elements positioned along a length (e.g., about 1 to 5 cm) of a distal segment of the catheter and stimulation regimens may be delivered to select a position among the multiple positions that is optimal.

Alternatively, a stimulation signal profile may narrow the stimulation zone to identify an appropriate ablation setting that would ablate the target nerve and not the non-target nerve. In another embodiment a catheter may comprise a stimulation element (e.g., at least one electrode or an electrode pair or pairs) having a stimulation zone that spatially corresponds with an ablation zone, and additionally have at least a second stimulation element that is far enough away from the ablation element(s) that the second stimulation zone corresponds to a region that is beyond the ablation zone. In this embodiment a physiologic response elicited by the second stimulation element and not the stimulation element associated with the ablation element may indicate safe positioning. In an embodiment wherein the ablation element is a cryo-ablation element, a cryo-mapping technique may be applied to cool the area and temporarily impede nerve conduction without permanently destroying the nerves. For example, the cryo-mapping technique may comprise delivering cryogenic energy from the cryo-ablation element but with a duration or temperature that only temporarily impedes nerve conduction. A physiologic response of a target nerve or non-target nerve to temporarily impeded nerve conduction may be different than a stimulated nerve. A temporarily impeded target nerve may have a similar response as an ablated target nerve but with a short duration.

Figure 14:
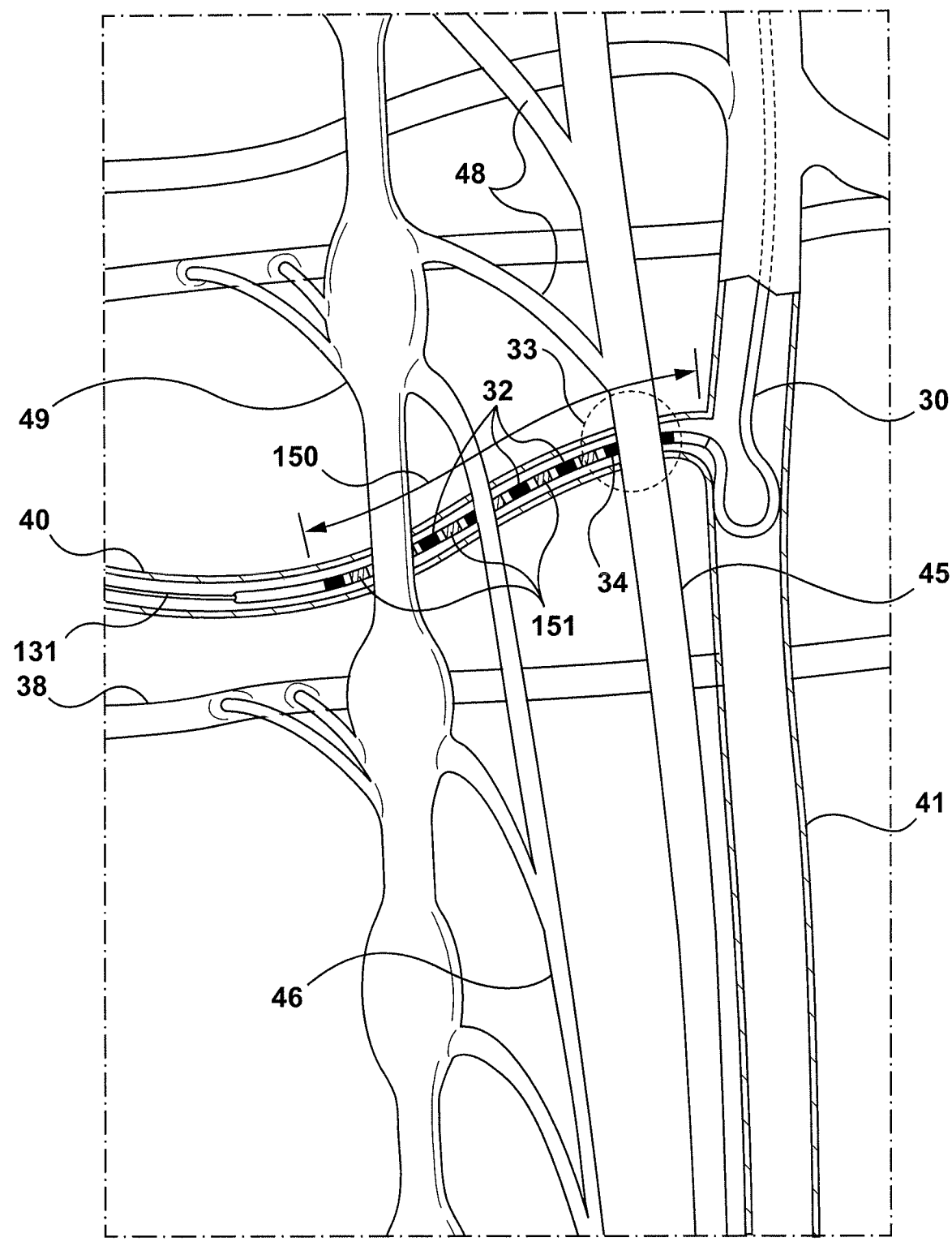
FIG. 14 shows a catheter suitable for stimulation and ablation deployed in an intercostal vein in close proximity to a TSN and sympathetic chain.

FIG. 14 is a schematic illustration of an endovascular catheter 30 including multiple ablation elements 151 and a plurality of stimulation elements 32, axially alternating and spaced along the length of a portion of catheter 30. Alternatively, the stimulation elements 32 may also function as ablation elements such as RF electrodes. The catheter is positioned in an intercostal vein 40 via an azygos vein 41. The catheter may enter the azygos vein 41 from a femoral or radial vein and may be introduced over a guidewire. The ablation 151 and stimulation elements 32 may be on the surface of the catheter and positioned at regular increments along the length of a distal end region of the catheter 30.

The distal segment of the catheter 132 can be navigated into the azygos and intercostal vein space at a level of a thoracic vertebrae just above the diaphragm (e.g., within 2 or 3 levels above the diaphragm which may be T9, T10 or T11) as illustrated by FIG. 11B. The distal region of the catheter 132 is in close proximity to both the GSN 45 and the sympathetic chain 49. The diameter of the catheter where electrodes are located may be 2 to 6 mm and almost occluding and even possibly distending the intercostal vein 40. A catheter can be intentionally deformed or comprise resilient elements to achieve apposition to the venous walls. The targeted nerve can be identified by using electrical stimulation of the nerves along the distal region of the catheter using selected electrodes as cathodes and anodes and monitoring the physiological responses. Alternatively, all or any number of nerves crossing the targeted segment of the intercostal vein or veins can be ablated.

Figure 15A:
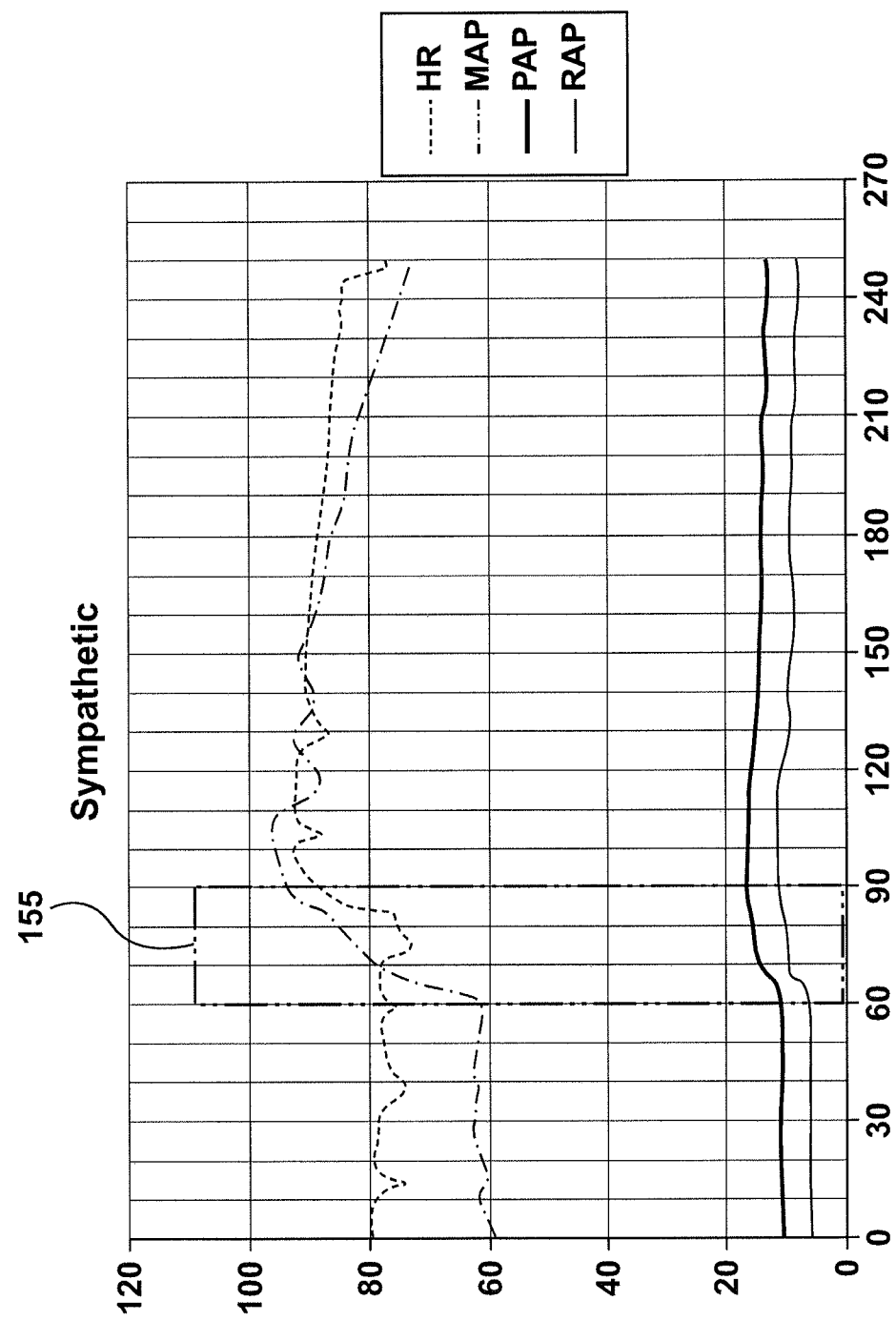
FIGS. 15A and 15B illustrate the different physiological responses between stimulation of the sympathetic chain (FIG. 15A) versus stimulation of the GSN (FIG. 15B).
Figure 15B:
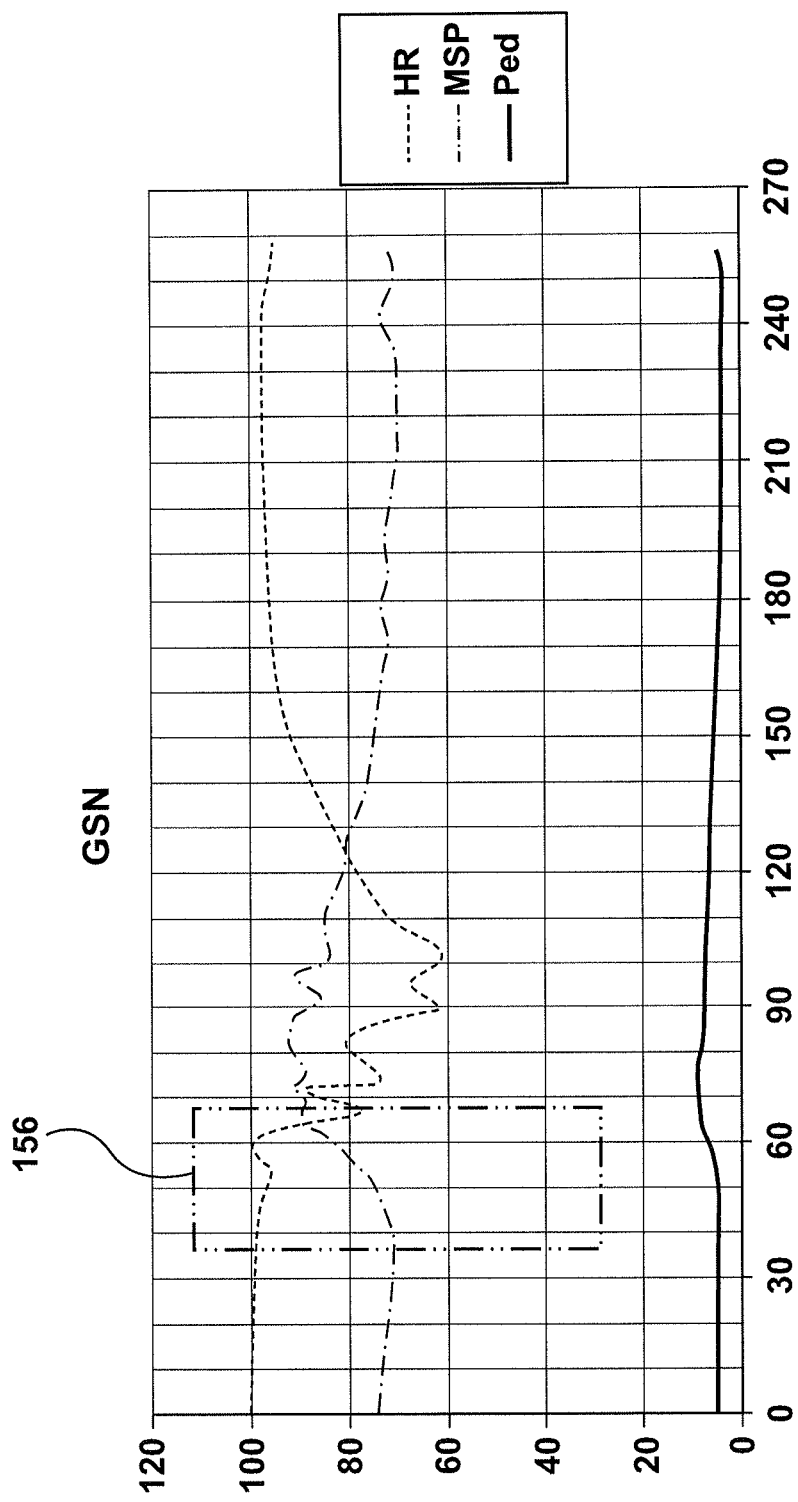

FIGS. 15A and 15B are plots of the different physiological responses observed during stimulation of the sympathetic chain 49 and GSN 45 in animals, respectively. In an animal study, the left sympathetic chain was stimulated via a catheter positioned in an intercostal vein. The heart rate (HR) and mean arterial pressure (MAP) increased during stimulation of the sympathetic chain 49 as shown on FIG. 15A. The box 155 illustrates time of application of stimulation energy between 60 and 90 seconds on X-axis.

Changes in pulmonary artery pressure (PAP) and right atrial pressure (RAP) confirm that the preload of the heart increased in response to stimulation.

In a separate experiment the right GSN 45 was selectively stimulated using a cuff electrode placed on a thoracic section of the GSN 45. Results are illustrated by FIG. 15B. During the GSN stimulation period shown as a box 156, mean systolic pressure (MSP) measured in the femoral artery increased while heart rate HR decreased. The reduction of HR was likely caused by the normal compensatory response of the arterial baroreflex when the sudden upregulation of heart stroke volume is detected. The authors confirmed that while blood flow in the inferior vena cava increased, cardiac output remained relatively constant. The Ped trace on FIG. 15B illustrates the increase of left ventricular end diastolic pressure (LVEDP) in response to the mobilization of fluid from the venous reserve.

To facilitate a clinically effective procedure, an embodiment may involve confirming that a patient will experience the desired physiologic effect of ablation before delivering ablation energy. This may be achieved by electrically, pharmacologically or cryogenically blocking the nerve temporarily and observing the physiologic response (e.g., hemodynamic effect). Optionally, vascular nerve mapping or confirmation of technically efficacious positioning as described herein to indicate that a target nerve is within an ablation zone or confirmation of safe positioning to indicate that an important non-target nerve is not within the ablation zone may first be done, then a temporary nerve block may be performed to assess potential clinical success. If potential clinical success is assessed to have a physiologic response as desired then ablation energy may be delivered to produce a permanent or more long lasting clinical effect, which may be analogous to the temporary clinical effect. Conversely, if the physiologic response to temporary blocking is not as desired, a physician may decide to not proceed with ablation. A different set of stimulation and ablation elements may be chosen to apply confirmation steps a different position may be found or the procedure may be aborted.

To facilitate a technically and clinically effective procedure, an embodiment may involve confirming that an ablation was successful and that the target nerve no longer conducts signals following delivery of ablation energy. This may be achieved by delivering stimulation signals with the same or different stimulation elements and observing the physiologic (e.g., hemodynamic) effect.

Since the greater splanchnic nerve often tracks along the azygos vein for a considerable length, (e.g., up to about 3 to 5 cm) in close proximity, it may be possible to stimulate the greater splanchnic nerve distal to the ablation site and observe the absence of the hemodynamic effect. A device configured to stimulate distal to an ablation site may comprise a stimulation element having a stimulation zone associated with an ablation zone and additionally, a stimulation element positioned distal to the ablation element a sufficient distance to be beyond the ablation zone.

An embodiment of a method for confirming that the relative position of an ablation element to the target nerve (in this case a thoracic splanchnic nerve) is safe and technically effective before delivering ablation energy or selecting the appropriate ablation element and corresponding stimulation elements from a group of ablation and stimulation elements on a device may include the use of a mapping algorithm.

Figure 16:
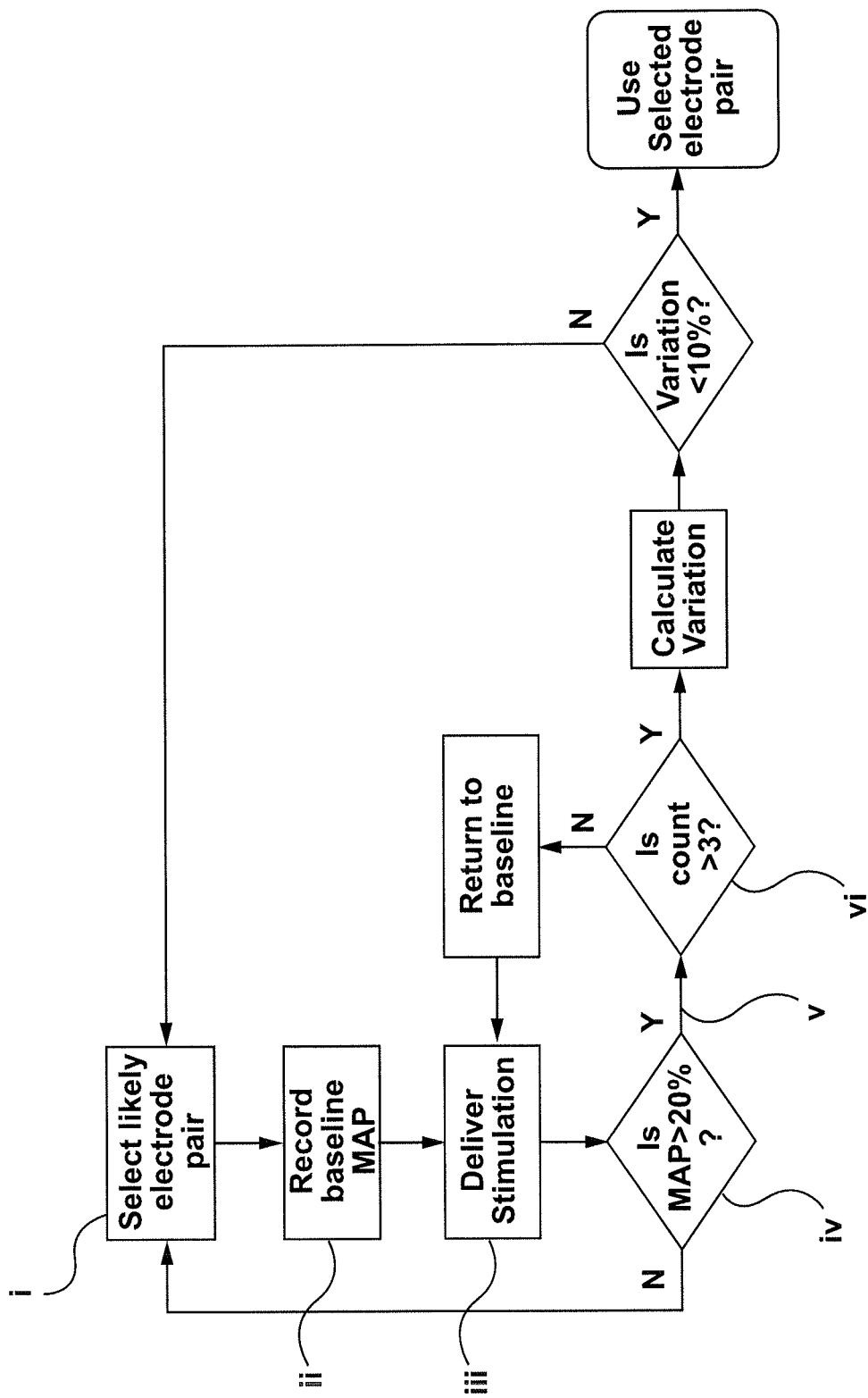
FIG. 16 is a mapping algorithm used to determine an optimal electrode pair that is based on in Mean Arterial Pressure (MAP) levels recorded after a stimulus is delivered.
Figure 17A:
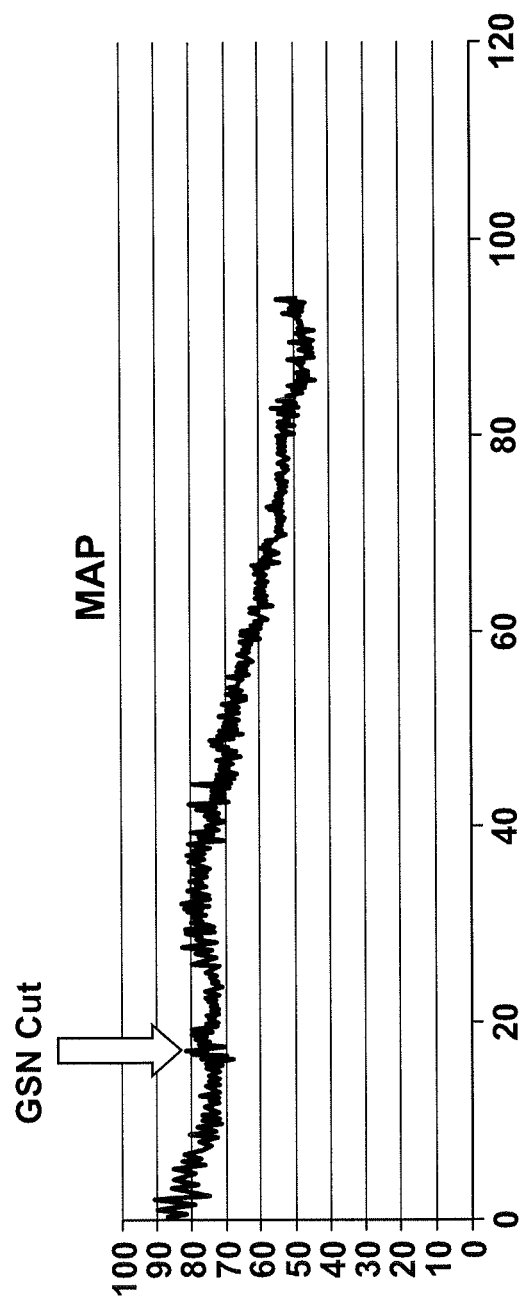
FIGS. 17A, 17B, 17C and 17D are graphs illustrating responses of the patient to the blocking of a nerve.
Figure 17B:
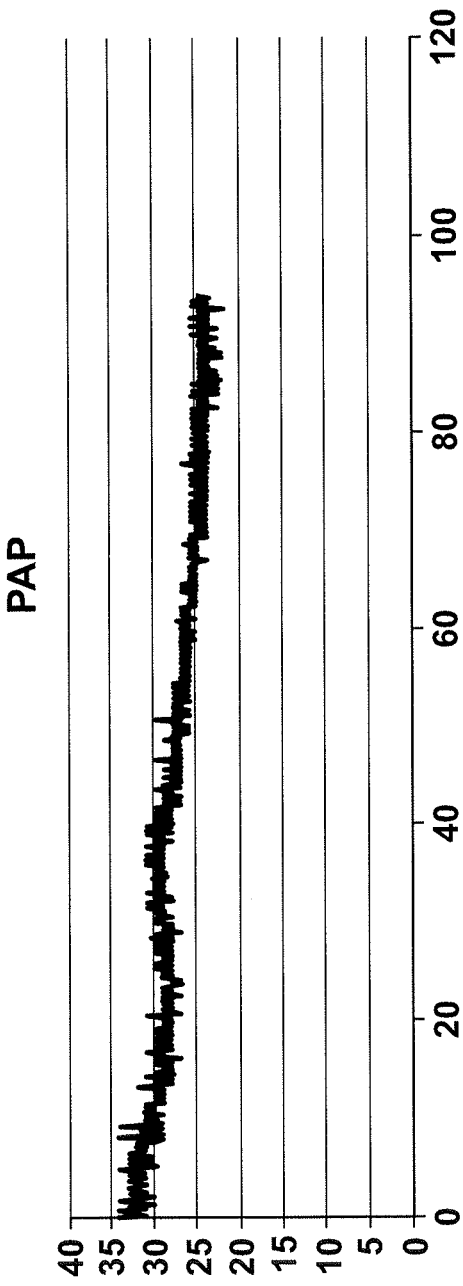
Figure 17C:
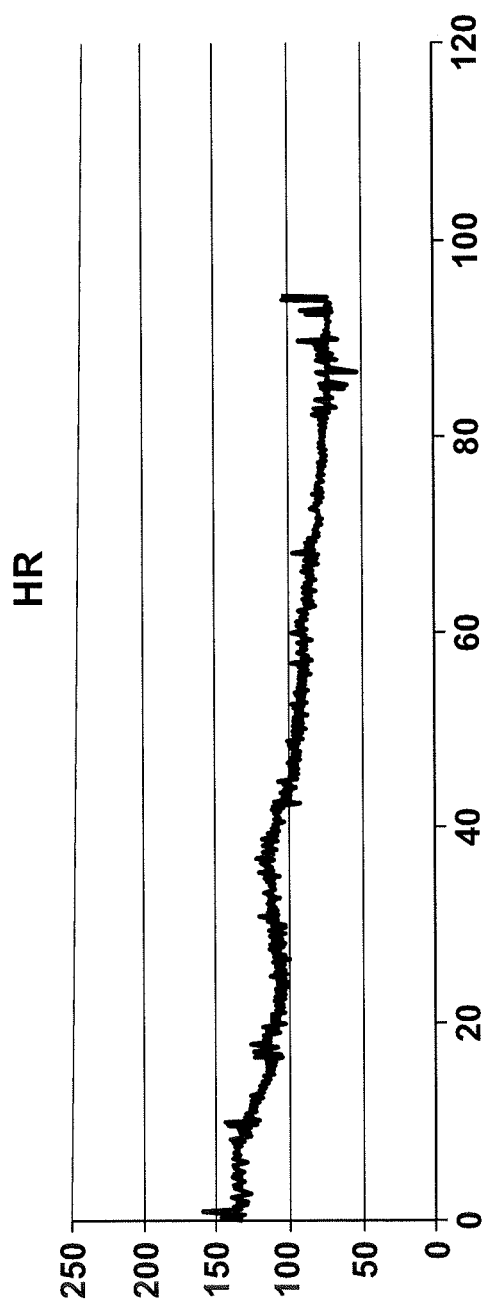
Figure 17D:
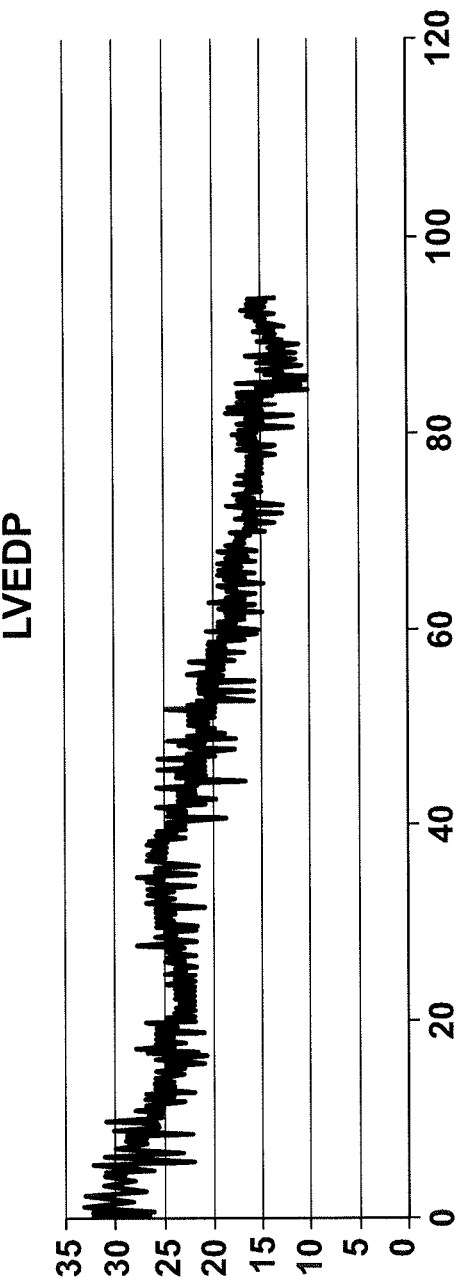

An exemplary mapping algorithm, shown in FIG. 16, comprises the following steps:

(i) Select electrode pairs (e.g., within 2 or 3 vertebral levels above the diaphragm or along a selected intercostal vein at these levels and within 0 to 5 cm from azygos or hemiazygos branching, within 0 to 3 cm from azygos or hemiazygos branching, between the costovertebal joint and the ostium at the azygos or hemiazygos branching). It is understood that electrode pairs refer to bipolar stimulation and ablation and one electrode may be selected if ablation or stimulation is monopolar.

(ii) Record a selected hemodynamic parameter (e.g., MAP, CVP, PAP, RAP) to establish the baseline. See, e.g., FIGS. 17A to 17D before "GSN cut".

(iii) Deliver Stimulation pulse with Current (I), pulse width (pw), frequency (F) and duty cycle (D) in about I=0 to 10 mA, pw=100 to 1000 us, F=20 to 40 Hz, D=50% for 20 to 60 s. On and at least 20 to 60 s OFF. (See FIG. 18).

(iv) Record a selected hemodynamic parameter or parameters (e.g., HR, MAP, CVP, PAP, RAP) such as shown in FIGS. 17A to 17D after GSN cut.

(v) If the selected hemodynamic parameter >20% from baseline allow to return to baseline and possibly repeat.

(vi) Average measurements for 3 stimulations, for example, and if standard error is within +/−10%, the change in the selected hemodynamic parameter may be considered to be relevant.

Another method of confirming a suitable location for the ablation and stimulation elements prior to delivering ablation energy comprises a stimulation test in which a specific current, frequency and pulse width are selected (e.g., manually or automatically by a computerized algorithm) and stimulation is performed between pairs of electrodes that are in contact with the wall of the vessel (e.g., vein, azygos vein, hemiazygos vein). When the electric field is sufficient to activate the TSN, a rapid rise in Mean Arterial Pressure (MAP) or CVP or PAP and other hemodynamic changes occurs within a few seconds and can be graphically recorded and compared to assess ablation element placement.

A method of confirming technical success following delivery of ablation energy, in other words confirming that a target nerve has successfully been ablated, may comprise the same or similar electrical stimulation parameters delivered from the same stimulation electrodes following ablation. Alternatively or additionally, electrical stimulation may be delivered from stimulation electrodes positioned proximal to the location of an ablation (closer to the brain or sympathetic chain) where a physiologic response was elicited prior to ablating. Absence of responses or significant attenuation of responses will indicate technical success of the ablation.

Figure 18:
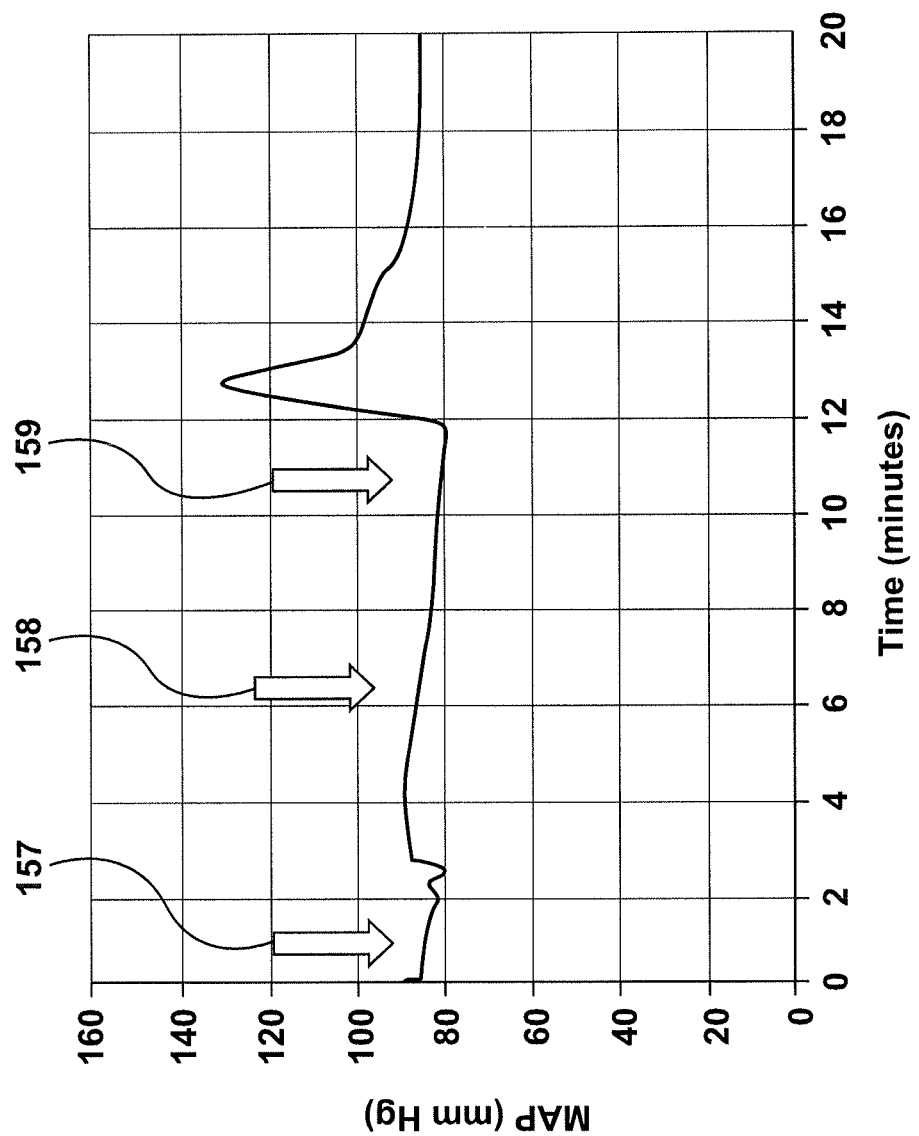
FIG. 18 is a plot of mean arterial pressure over time showing response to stimulation of an ablated nerve.

To confirm this concept, FIG. 18 illustrates an experiment where the hemodynamic response to a greater splanchnic nerve stimulation and block with locally injected lidocaine, a nerve blocking agent, was tested in an animal. Time on the X-axis is in minutes. The Y-axis represents mean arterial blood pressure in mmHg. The first arrow 157 from the left indicates the time of injection of lidocaine. The second arrow 158 indicates the time of application of electrical stimulation to the greater splanchnic nerve proximal to the blocked area of the nerve. The term "proximal" as used herein with reference to a relative position on a nerve denotes a location nearer to a point of origin, such as brain, spinal cord, sympathetic chain or a midline of the body and where the term "distal" is used to denote a location further away from the point of origin and closer to the innervated peripheral organ such as splanchnic vascular beds, liver and spleen. Following the first stimulation 158 proximal to the nerve block 157, no or very little physiologic response is observed on arterial blood pressure, or other physiologic parameters that are omitted on this graph for simplicity. The third arrow 159 illustrates electrical stimulation of the greater splanchnic nerve for 30 seconds applied distal to the lidocaine blocked area. The physiologic response manifests by increase of mean arterial blood pressure and other hemodynamic parameters as described in this application. This experiment, performed using surgery, can be replicated using endovascular ablation with the use of appropriate tools and advanced imaging. Moving the stimulation electrode along an azygos or intercostal vein, for example, to points distal and proximal the ablation lesion can confirm the effectiveness of ablation.

Alternatively switching between multiple electrodes spaced along the length of a catheter (See FIG. 14 for example) can be used. A simple automation device can be envisioned to test different electrode pairs and measure responses then creating a report on the user interface.

Alternatively, multiple catheters may be positioned in intercostal veins (e.g., at T9, T10, and T11) to stimulate along different positions of the length of the TSN.

Fluoroscopic imaging using body landmarks such as vertebrae, heart, veins and the diaphragm can be used to facilitate positioning of an ablation element or stimulation elements of a catheter. If the nerve were unsuccessfully ablated, which may be indicated by a positive hemodynamic change in response to stimulation of the greater splanchnic nerve proximal the ablation, then recourse may comprise ablation repeated at a higher energy level, ablation repeated at a different location, or improved electrode apposition.

It is noted that MAP monitoring as mentioned above is an example and hemodynamic monitoring does not necessarily need to be invasive monitoring and may be accomplished with a less invasive monitoring of blood pressure, for example using a Nexfin or ClearSight device (Edwards) for continuous monitoring of hemodynamics commonly used in hospitals. The ClearSight system quickly connects to the patient by wrapping an inflatable cuff around the finger. The ClearSight system provides noninvasive access to automatic, up-to-the-minute hemodynamic information including: SV, CO, SVR, or Continuous Blood Pressure (cBP). Such a monitoring device may be hooked up to a computerized console to communicate physiologic response to the computer, which may determine stimulation or ablation parameters based on the physiologic responses.

An embodiment of a system may comprise an ablation catheter having at least one ablation element (e.g., RF electrode) and at least one associated stimulation element (e.g., stimulation electrode), a computerized console configured to generate and control delivery of a stimulation signal to the stimulation element, and a computerized console configured to generate and control delivery of an ablation signal (e.g., RF electrical current) to the ablation element. The stimulation console and the ablation console may be separate machines or integrated into one machine and may communicate to one another. The system may further comprise components necessary to support the type of ablation energy for example, if the ablation energy is RF electrical current the system may further comprise a dispersive grounding pad; if the ablation energy is a chemical agent the system may further be configured to inject the agent such as a manually operated syringe or automatically controlled pump. The system may further comprise a hemodynamic monitoring device that is in communication with the stimulation console or ablation console to provide feedback of hemodynamic response to stimulation or ablation. The computerized consoles may comprise one or more algorithms stored in memory and executable by a processor that facilitate analysis of stimulation and hemodynamic response. For example, an algorithm may compute if a hemodynamic response to a stimulation event is significant based on time of response, repeatability, difference from baseline.

In embodiments wherein an ablation catheter comprises multiple ablation elements and associated stimulation elements, see FIGS. 14 and 18, an algorithm may facilitate selection of an optimal ablation element or elements for example, based on strongest or quickest response to stimulation, and then deliver ablation energy to the selected ablation element or selected ablation elements. A console may comprise a graphical user interface that provides intuitive graphics or messages that help a user understand analysis of a stimulation response.

Figure 19:
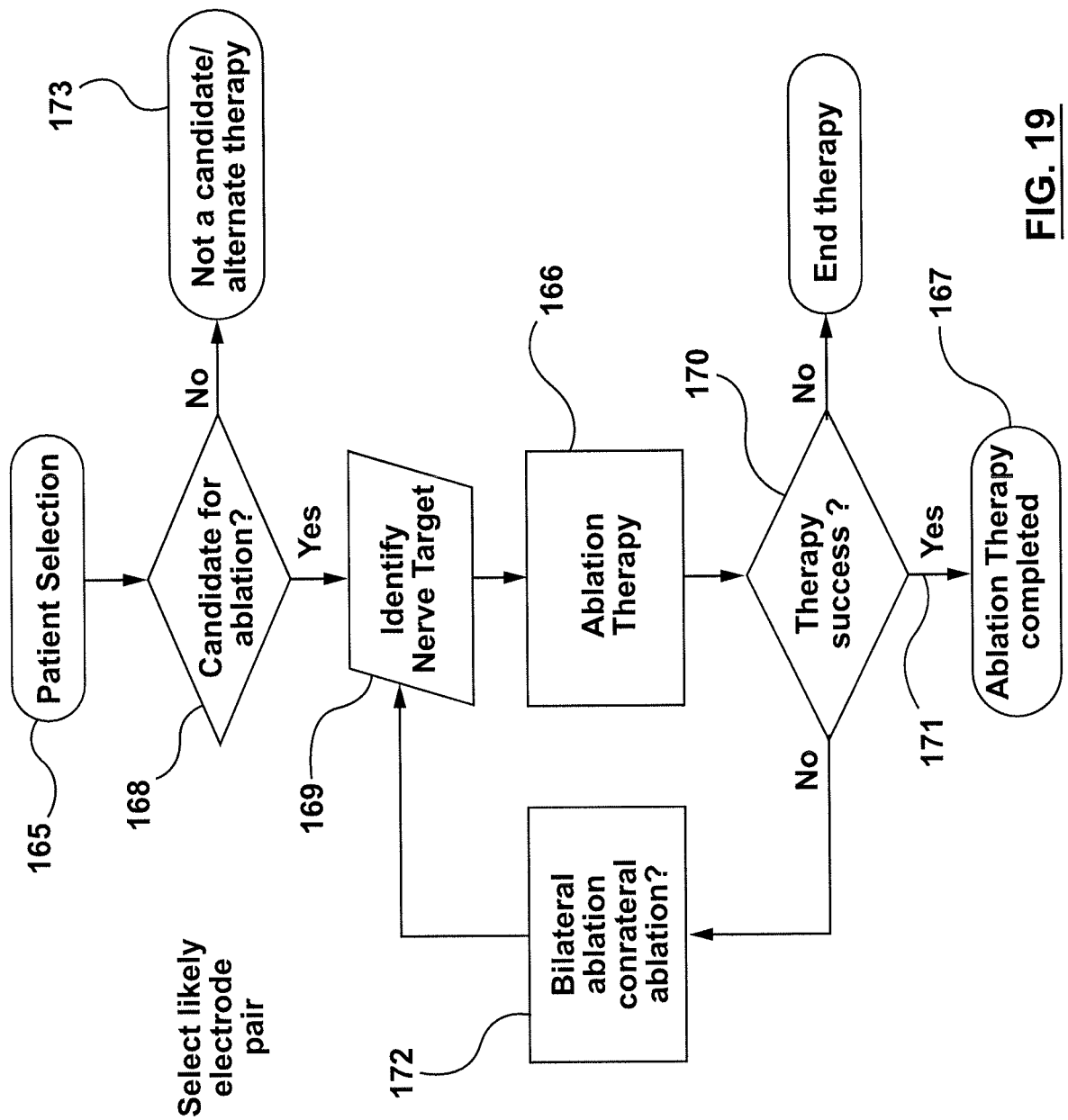
FIG. 19 is a flowchart illustrating the steps from patient selection to ablation therapy.

FIG. 19 is a flowchart that illustrates an example of patient flow from patient selection 165 to the execution of ablation of the TSN 166 to the completion of a successful therapy 167 to treat heart failure. The selection 168 of patients suitable for TSN ablation may comprise evaluation of splanchnic vascular capacitance. An orthostatic stress test (tilt table test), fluid challenge, exercise test or an appropriate drug challenge can help distinguish low vascular compliance from normal. Alternative tests include exercising on a bicycle or a treadmill or even a simple hand-grip exercise. Orthostatic stress causes blood shifts from the stressed volume to the unstressed volume. In healthy patients, to compensate for the volume shift, local sympathetic tone increases resulting in splanchnic vasoconstriction and rapid mobilization of blood from the unstressed compartment to the active circulation. Similarly exercise causes a release of blood from the unstressed volume into circulation. The hemodynamic response to tilt or exercise in chronic CHF is atypical, as there is not significant peripheral pooling in the upright posture indicating diminished splanchnic vascular capacitance. Acute oral or intravenous fluid challenge is another test to assess splanchnic vascular capacitance. A fluid challenge could test the capacitance by measuring the effects of a fluid bolus on cardiac filling and pulmonary pressures. Patients with low capacitance of the splanchnic venous reservoir will be unable to compensate for the hemodynamic effect of the fluid bolus. Patients with HF, HFPEF and patients with increased SNA will be more likely to respond to the fluid challenge with a disproportional rise in cardiac filing pressure and other related and measurable physiologic parameters. This response would indicate that the patient might be a candidate for TSN ablation therapy or may not be a candidate 173. After patient identification as a candidate for ablation therapy, the process of identifying the appropriate nerve target 169 is implemented as the first step in the ablation procedure. Proper identification of the target nerve as well as non-target nerves or structures within the range of the ablative energy (mapping) is important to confirm the safety and efficacy of the ablation procedure.

FIGS. 15A and 15B illustrate a use of differences in physiological responses to electrical stimulation to identify a target nerve (e.g., GSN) or different target nerve (for example, sympathetic chain) or a nearby non-target nerve. The choices of therapy can be made selectively by the physician based on the mapping information and the patient's individual responses and needs. For example an HFpEF patient with high chronic HR or BP (hypertension) may require different targeting than one with low blood pressure. After nerve target identification 169 and selection, one optional example of confirmation of procedural efficacy 170 is to temporarily block the nerve target and evaluate whether the physiological response is consistent with the desired clinical effect. After nerve target identification has been confirmed, the non-target nerves or other structures have been deemed outside of the range of ablation energy, and procedural efficacy has been confirmed; ablation therapy 166 may be initiated.

Confirmation of the technical efficacy or success 170 of the ablation procedure may be accomplished by delivering electrical stimulation proximal to the location of an ablation where a physiological response was elicited prior to ablation. Absence or attenuation of responses will indicate technical success of the ablation procedure (see FIG. 18). Another example of confirming technical efficacy 170 may be evaluating splanchnic vascular capacitance (e.g., tilt table and/or fluid challenge) and compare to results before the procedure. If the ablation procedure is a success 171, no further action is needed and the ablation therapy is completed 167. If the procedure is not successful, the clinician may opt to provide additional ablation therapy 172 at the same site and/or repeat the procedure of identifying additional nerve targets 160 (e.g., bilateral ablation) and providing ablation therapy 166 as described previously.

The stimulation waveform may be tuned to optimize a physiological response to TSN stimulation while minimizing response of pain receptors. Table 1 below shows rheobase (124 V/m) and time constant (1 ms) for C-fibers, which usually resemble the behavior of pain fibers. By comparison, the time constant of the TSN is closer to that of A-type fibers, in the 0.12 ms range. Correspondingly, the rheobase of the TSN is much lower than that for pain fibers. Consequently, a waveform with fast slew rates and low amplitudes would be more likely to capture the TSN but not cause pain to the patient.

TABLE 1 parameters for obtaining A-fiber and C-fiber excitation thresholds with a constant electric field.

| Parameter | A-Fiber | C-Fiber |
|---|---|---|
| SENN-equivalent fiber diameter (μm) | 20 | 1 |
| Rheobase (V/m) | 6.15 | 124 |
| $\tau_e$ (μs), uniform field | 120.7 | 1000 |
| SENN temporal scaling factor | 1 | 8.29 |

Per the strength-duration formula, the amplitude I of a stimulating pulse of duration d, which is sufficiently strong to capture a nerve, is given by:

$$I = I_{rh} * (1 + \tau/d)$$

where $I_{rh}$ is the rheobase and $\tau$ is the time constant or the chronaxie. In one embodiment, the current used to stimulate a target nerve (e.g., TSN) would have a short duration, in a range about the respective chronaxie, and generate an electric field of a minimum intensity equal to:

$$E_{TSN} = 6.15 \text{ V/m} * (1 + 0.12 \text{ ms}/0.12 \text{ ms}) = 12.3 \text{ V/m}$$

To generate such field, a 3 F to 8 F catheter carrying electrodes configured in a monopolar or bipolar stimulation configuration may be used. The electrodes may have a length of 0.5 to 4 mm. If configured for bipolar stimulation, the electrodes may be separated by a 0.5 to 20 mm distance. For a typical stimulating impedance of 200 to 1000Ω, the resulting stimulating currents may be in a range of 0.1 mA to 5 mA as demonstrated by the following example equation:

$$I_{GSN} = \frac{12.3 \frac{V}{m} \times 4 \text{ mm}}{200 \text{ } \Omega} = 0.246 \text{ mA}$$

Correspondingly, stimulating voltages may be in the range of 0.05-5 V. Note that stimulating currents with parameters such as those presented above are insufficiently strong to capture pain fibers. Indeed, for a stimulating pulse duration of 0.12 ms, as used without any implied limitation in the above example, the electric field intensity required to stimulate pain fibers is:

$$E_{PAIN} = 124 \text{ V/m} * (1 + 1 \text{ ms}/0.12 \text{ ms}) = 1157.3 \text{ V/m}$$

Figures 15C, 15D:
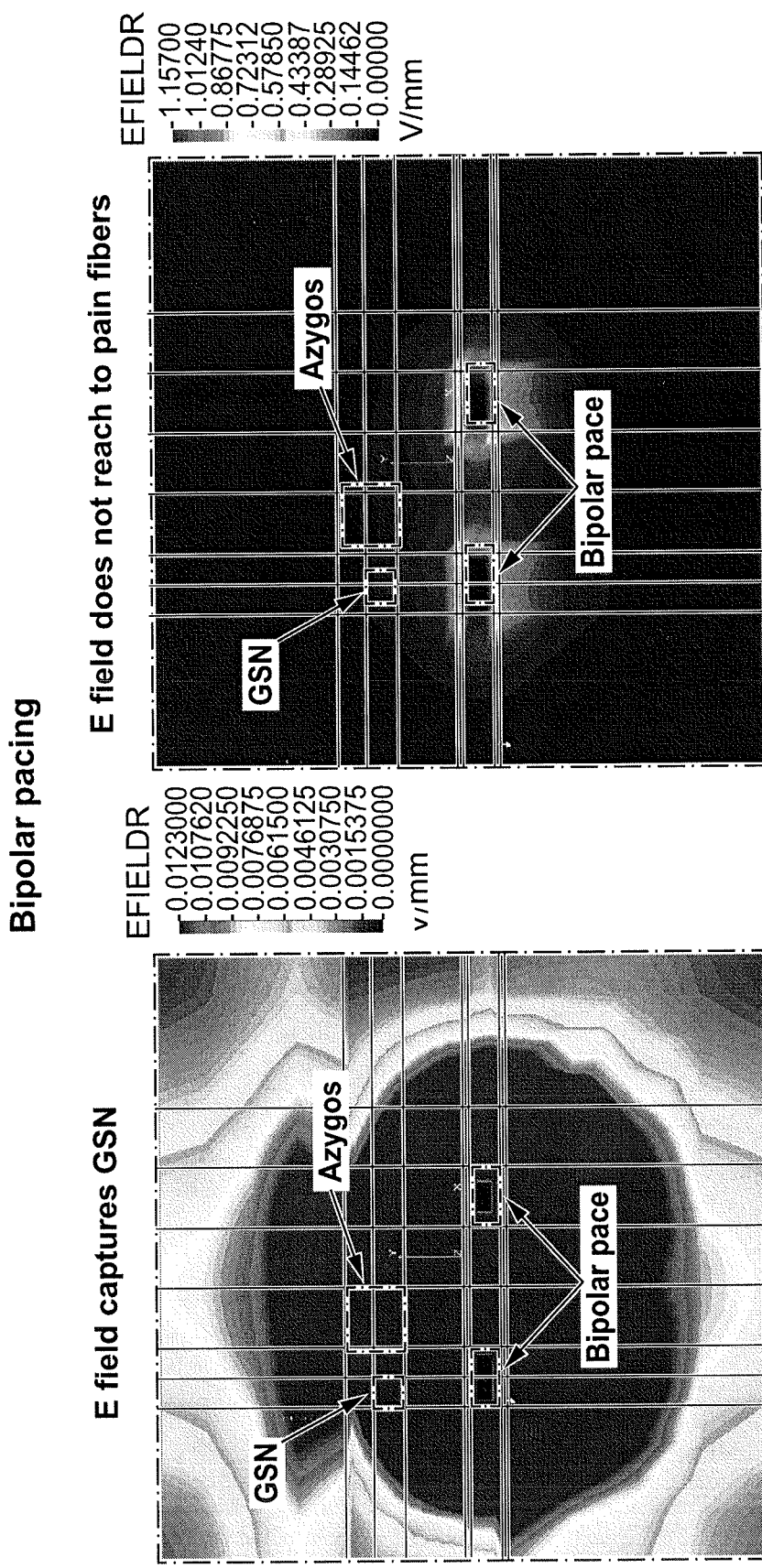
FIGS. 15C and 15D illustrate finite element models of electric field intensity showing a stimulation signal capable of stimulating a target nerve while avoiding stimulation of pain fibers.

This value offers a safety margin 94 times greater than the intensity needed to stimulate the TSN. As such, electric field intensities for example in the range of 30 to 500 V/m, at pulse durations of 0.12 ms, can be safely used to stimulate the target TSN without causing pain to patients. Such fields can be generated with catheters such as those described above and connected to standard stimulating equipment, such as external pacemaker or TENS devices with their output stage adapted for connectivity to intravascular electrodes. FIGS. 15C and 15D are illustrations of finite element models comprising bipolar electrodes (e.g., 4 mm long, 2 mm diameter) spaced 8 mm apart in an intercostal vein with a target TSN 4 mm away from the intercostal vein, supporting this concept. As shown in FIG. 15C, at a stimulating current of 9.6 mA, corresponding to a voltage of 1.5 V, the extent of the 0.0123 V/mm (equal to 12.3 V/m) iso-electric-field contour, sufficient to capture the target TSN. For the same stimulating current parameters, FIG. 15D shows the extent of the iso-electric-field contour of 1.157 V/mm (equal to 1157 V/m), needed to stimulate pain fibers. Assuming that the pain fibers are located nearby the target TSN, FIG. 15D indicates that the intensity of the electric field, produced by the bipolar stimulation configuration described above, is insufficient to elicit pain. In fact, an electric field intensity of about 0.6 V/mm, half the intensity required to elicit a pain response, barely reaches beyond the intercostal vein wall.

Ablation Catheter Embodiments

Any of the following methods, systems, and devices related to ablation can be incorporated or used with any of the methods, systems, and devices set forth with respect to Stimulation Confirmation above.

Figure 20A:
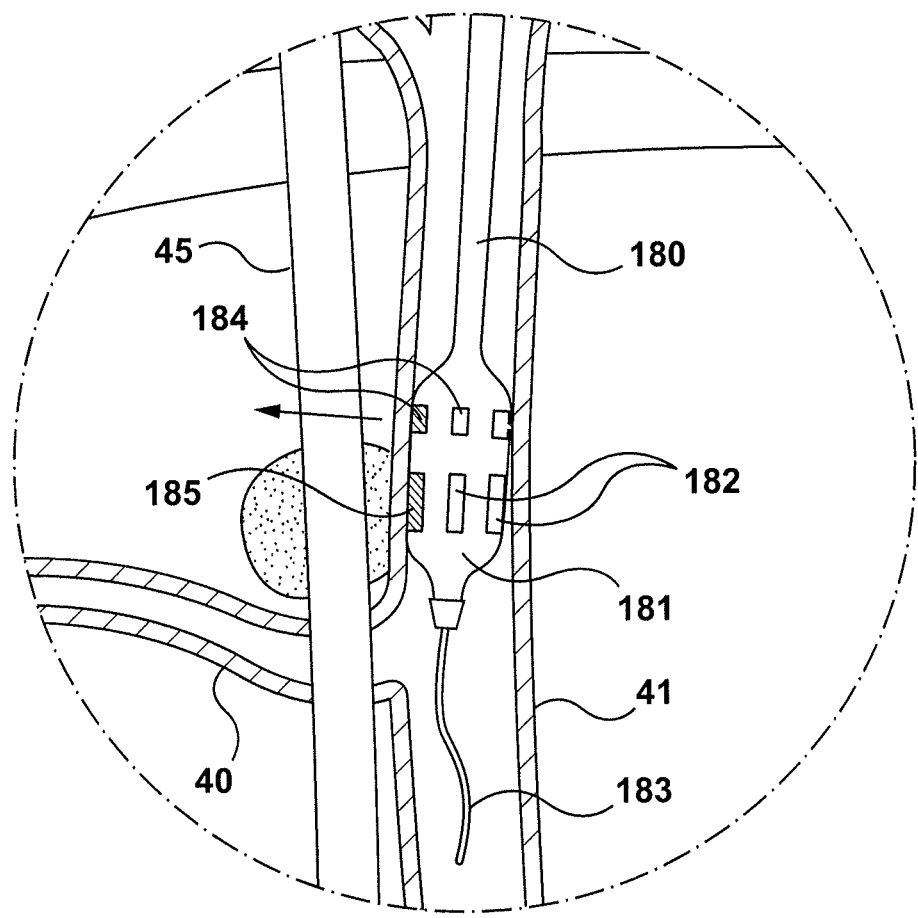
FIGS. 20A and 20B are schematic illustrations of a distal end of an ablation catheter.
Figure 20B:
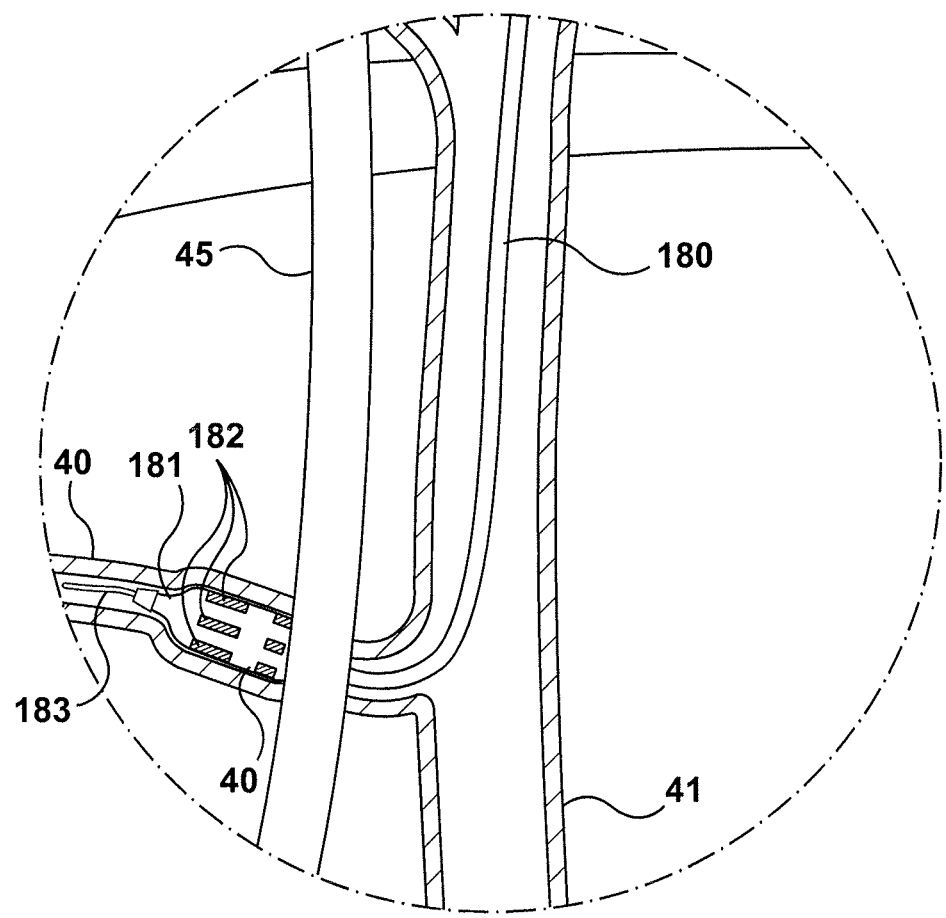

FIG. 20A schematically illustrates a distal end of a catheter 180 comprising a deployable balloon 181 (or other deployable structure) comprising a plurality of surface electrodes 182 capable of transvenous stimulation and RF ablation of a nerve (e.g., GSN 45) from within a blood vessel (e.g., Azygos vein 41 as shown in FIG. 20A or intercostal vein 40 as shown in FIG. 20B). This device can be used in conjunction with hemodynamic monitoring to locate the greater splanchnic nerve, confirm a suitably safe and effective placement of ablation electrodes 182, ablate the greater splanchnic nerve 45, and confirm technical success of the ablation prior to withdrawing the device from the body and closing the venous puncture. In this embodiment the catheter shaft 180 connects to or facilitates the delivery of a deployable structure such as a balloon 181, which is shown placed in an azygos vein 41 or intercostal vein 40 and possibly distending the walls of the vein to bring ablation electrodes 182 and stimulation electrodes 184 in apposition with the walls of the vein. If the vein is occluded and distended less energy is required to ablate the nerve. Application of a stimulation level current (energy) systematically from stimulation electrodes 184 positioned around the balloon and in contact with the vein wall around its inner circumference while observing physiologic response may be done to identify where the greater splanchnic nerve is located along the circumference of the vein. If the electric field generated by the stimulation current from the electrode elicits the expected hemodynamic response, the radially corresponding ablation electrode 185 can be used to apply an ablation level of energy to create a lesion.

Application of stimulation current to the electrode 184 following delivery of ablation energy while observing physiologic response can be used to confirm technical success, wherein absence or decrease of a physiologic response compared to the response observed prior to ablation may indicate that the nerve was successfully ablated.

In one embodiment, the catheter may be delivered transvenously through the cardiovascular system, specifically to the azygos vein or intercostal vein via femoral, radial, or internal jugular vein (IJV) access. It is envisioned that the ablation element may be positioned with or without the aid of a guide wire 183. When desired, a hollow, multi-pole catheter can be used to maintain natural flow levels within a blood vessel.

Stimulation elements used for confirmation of an ablation element's position or confirmation of technical or clinical success are envisioned to contain one, two or more electrodes arranged in series or arrays, distributed and spaced circumferentially or longitudinally, which are chosen selectively to provide a sufficient, optimal, or a situational amount of electrical signaling. In these embodiments, the stimulation element may also have a plurality of electrodes that may be used initially to map a suitable location in an azygos vein, intercostal vein or other suitable vein where the greater splanchnic nerve runs within close proximity for the length of 1 to 5 cm at a distance of about 1 to 5 millimeters, or crosses the vein (e.g., about 1 to 3 millimeters from the vein wall), through detecting a specific hemodynamic response to stimulation.

By way of example, in some embodiments, a catheter and console system may comprise a catheter having multiple electrodes spaced along a flexible shaft having a distal end region configured to be placed in an intercostal vein of a patient (for example as shown in FIG. 14). The console can be configured to generate and control delivery of ablation signals (e.g., high energy RF electrical pulses) and electrical stimulation signals (e.g., low energy low frequency electrical pulses). The low energy signals may include frequencies in the range of 5-50 Hz and high-energy signals include frequencies in the range of 350-500 kHz. The low energy signal is selected to stimulate nerves proximate to the active electrode and the high-energy signal is configured to ablate the nerves proximate to the active electrode. The signals are applied to the electrodes on the distal end region of the catheter. The console is capable of selectively applying low and high levels of energy to each the electrodes, such as by sequentially applying low energy pulses to all of the electrodes and applying high energy pulses to selected electrodes determined to be within ablating distance of the target nerve(s) as identified by the low energy stimulation signals and elicitation of physiologic response. The console may be configured with a controller configured, e.g., programmed with one or more algorithms, to select and thereby activate an electrode and or group of electrodes (monopolar and/or bipolar) and; to select delivery of high or low energy. A configuration for selecting ablation electrode(s) and delivery may include a switch or program logic. The console may include physiologic monitoring device or devices in communication with the console, where the physiological monitoring device may include sensors located on the catheter device, elsewhere within the patient vasculature, and/or non-invasively.

A computer controller in the console may execute software and logic that include algorithms that facilitate analysis of, for example, hemodynamic and physiologic values recorded from patient monitoring device or devices in communication with the console. Examples of hemodynamic and physiological parameters are pupil dilation, increased sweating, increased heart rate, increased blood pressure, increased mean arterial pressure and any combination thereof.

The one or more algorithms may confirm the positioning of the electrodes along the catheter in the intercostal vein with respect to the target nerve by automatically detecting a change in at least one selected hemodynamic or physiological parameter, which occurs in response to the activation of an electrode on the catheter by a stimulation pulse. The algorithm may initially include the recording of a baseline value of the hemodynamic parameter. Thereafter, algorithm causes stimulation pulse to be applied to the intercostal vein by one or more of the electrodes on the catheter. The stimulation pulse may have a current (I), a pulse width (pw), a frequency (F) and a duty cycle (D) wherein I=0 to 10 mA, pw=100 to 1000 us, F=20 to 40 Hz, and D=50% pulsing between 20 to 60 s. As each stimulation pulse is applied, the algorithm records the value of the selected hemodynamic or physiological parameter. The application of a stimulation pulse and recording the parameter value resulting from the pulse may proceed in a sequence for each of the electrodes on the catheter.

The recorded parameter values are used to select the electrodes to receive ablation energy pulses. The selection may be the electrode(s) corresponding to the largest change in the parameter value from the baseline value. Further, the selection may be to identify electrodes, which while applying the stimulation pulse, caused the parameter value to exceed a certain threshold, such as for example a twenty percent change (20%) from the baseline value.

To ensure a reliable parameter value, the stimulation pulse may be applied several times, such as three by each of the electrodes. The parameter value is recorded during each stimulation pulse. The average of the parameter values for each of the stimulation pulse applied to a specific electrode may be used as the parameter value to select an electrode for the ablation pulse. Also, a check may be made to the parameter values to conform that are within a certain range, such as within ten percent of each other. If any of the values are outside of the range, additional stimulation pulses may be applied to determine the average value or an alert may be generated by the console that is given to the health care provider.

The algorithm followed by the computer controller may be used to confirm a patient will experience the desired physiological effect of ablation before delivering ablation therapy is performed by an automated algorithmic process. Such an algorithm may include: temporarily blocking the target nerve with a stimulation signal, recording the physiologic response while the nerve is blocked, and evaluating the physiologic response to determine if the patient should undergo ablation of nerve by ablating the intercostal vein near the nerve. Clinical effectiveness is determined by comparing the recorded response to the desired physiologic response. The desired response may be progressive reductions in pressures (e.g., MAP, PAP, and LVEDP). The target nerve may also be temporarily blocked pharmacologically or cryogenically. If temporary blocking does not achieve the desired effect, the physician may decide not to proceed with ablation, select a different electrode configuration on the catheter to apply a stimulation signal and thereafter an ablation signal, or move rotationally or laterally the catheter and its electrodes in the intercostal vein.

An algorithm executed by the computer controller may also confirm the technical efficacy or success of the ablation procedure. The confirmation steps would be after (post) the ablation of the nerve via the intercostal vein. The conformation steps may include electrical stimulation by the catheter to a region of the intercostal vein the same as or proximal to the location of the ablation. The patient's response (physiological or hemodynamic) to the electrical stimulation is recorded and compared to the response prior to ablation. If the comparison indicates an attenuation or absence of a response, the algorithm will indicate technical success of the ablation procedure.

If the comparison indicates an unsuccessful ablation procedure, the physician or other health care provider may repeat the ablation therapy at the same site and/or repeat the therapy procedure for other nerve targets. Additional nerve targets could include additional intercostal veins or bilateral ablation.

The console may include a graphical user interface configured to present information from the physiological signals where the information is the physiological response following (e.g., 5-60 seconds) the delivery of low and/or high energy and; algorithms that compare the physiologic signals to data from memory stored baseline values providing automated selection of appropriate electrode configurations and/or the appropriate energy delivery.

While certain forms of electrodes, or arrays/series of electrodes have been illustrated and described herein, it is not to be limited to the specific forms or arrangement of parts described and shown.

Figure 21:
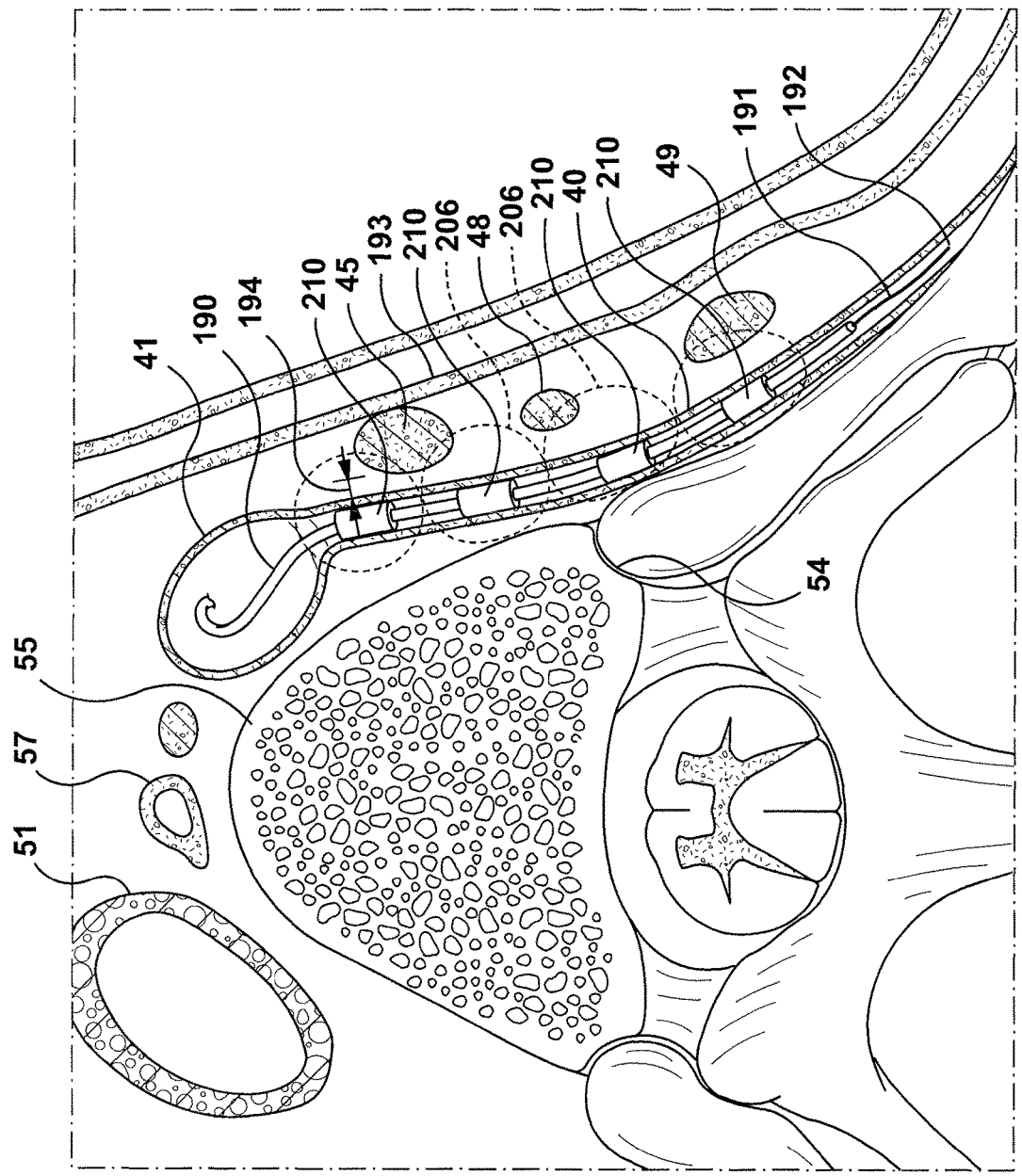
FIGS. 21, 22A, and 22B are schematic illustrations of a transverse view of a patient showing an ablation catheter delivered to an intercostal vein for ablation of a target nerve.

FIG. 21 is a transverse sectional view of placement of an ablation catheter 190 in an intercostal vein 40 of a patient, which is shown in a frontal coronal view in FIG. 11B and FIG. 14. In this embodiment the ablation catheter 190 is introduced over a guidewire 191 that is threaded through a lumen in the catheter. An ablation catheter that is configured to be delivered over a guidewire is referred to as an Over The Wire (OTW) ablation catheter. Use of guidewires to deliver ablation catheters is known and cardiologists are familiar with their use. The appropriate intercostal vein 40 may be found where it branches from the azygos vein 41 using fluoroscopy with or without contrast dye and the guidewire 191 can be threaded into the selected intercostal vein 40 as deep as desired for secured operation of the catheter 190. A guidewire may be equipped with an atraumatic tip 192 to avoid injury to the vessel.

An ablation catheter 190 can therefore slide along the guidewire 191 inside the desired intercostal vein 40 in order to locate and ablate the target nerve (e.g., GSN 45) that crosses the intercostal vein 40 and is positioned tightly between the parietal pleura 193 and the intercostal vein 40. The distance 194 between the vein 40 and the nerve 45 at the point where they cross each other can be approximately 1 to 3 mm, which is advantageous for ablation via ablation modalities generating an ablation zone in a range of about 5 mm such as RF ablation.

FIG. 21 illustrates positioning of an OTW ablation catheter 190 in a selected intercostal vein 40. The selected vein may be selected superior to and as close to the diaphragm as possible and yet from veins suitable for insertion of the catheter based on a venogram and possible explorations with a guidewire 191. Based on the authors' experience with patients, the intercostal veins at the T8 through T10 vertebrae levels are likely candidates for the placement of the ablation catheter, but contributing nerves can be found as high as T6. The target nerve may be the TSN or the nerves contributing to the TSN (e.g., roots) or the sympathetic chain trunk where they intercept the selected intercostal vein. More than one nerve may be targeted and ablated (e.g., GSN 45, GSN roots 48, Sympathetic trunk 49).

As illustrated in FIGS. 20B and 21B, methods of ablating nerves from within an intercostal vein can comprise ablating nerve tissue in a nerve that is not innervating the vein, and the nerve generally extends in a non-parallel relationship with the intercostal vein lumen.

An exemplary embodiment of a method of ablating a target nerve (e.g., TSN, TSN root) and a method of using embodiments of catheters described herein (e.g., as illustrated in FIG. 21) can comprise the following steps: access the venous system of a patient suffering from heart failure (e.g., via a femoral vein, radial vein, brachial vein, subclavian vein, jugular vein); advance a guidewire 191 to the inferior or superior vena cava 42 and engage with the azygos vein 41 just below the bifurcation of the left and right innominate vein; if treating the right side, advance the guidewire 191 down the azygos vein 41 to the level of diaphragm 52, which is approximately at the level of T10 to T11 vertebrae 55, or as far caudal as possible that is superior to the diaphragm, and into an adjacent intercostal vein 40; advance the ablation catheter over a guidewire into the intercostal vein to deliver ablation energy; using the guidewire as a lead, engage with adjacent intercostal veins in order to advance the ablation catheter to the correct position; if treating the left side, use the guidewire to engage the hemiazygos vein 43, which is approximately at the level of the T8 vertebra and use the guidewire to engage intercostal veins 40 for ablation. In addition, the TSN may cross the hemiazygos vein as it crosses the spine. Optionally, one may consider ablation along the hemiazygos vein in this area, but care must be taken to not injure the thoracic duct 57 or descending aorta 51, which crosses the hemiazygos as well. Significant variability in azygos and hemiazygos vein anatomy should be considered with respect the procedural steps. Consideration of anatomic variability is more critical for left-sided treatment than for right-sided treatment.

Figure 22A:
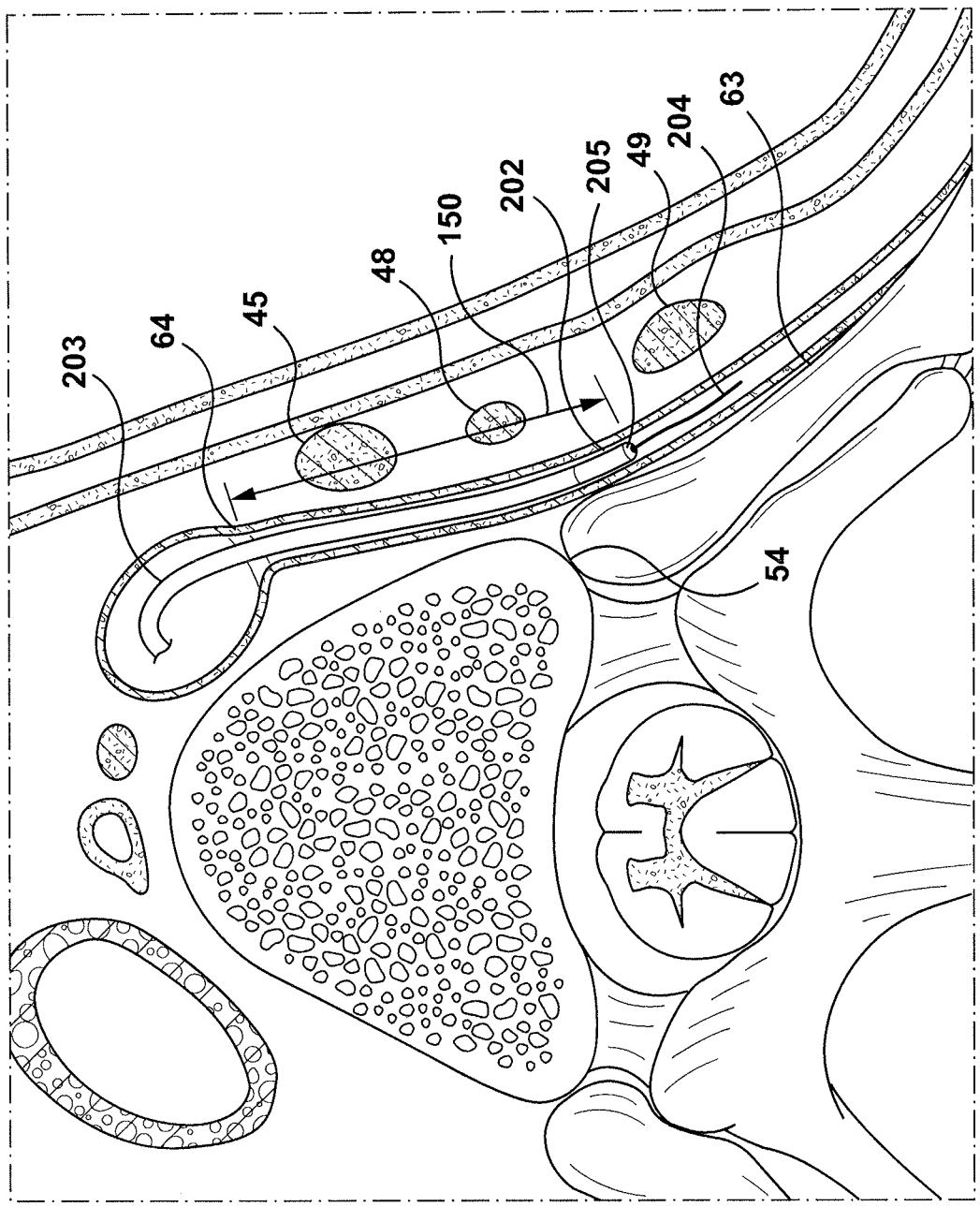
Figure 22B:
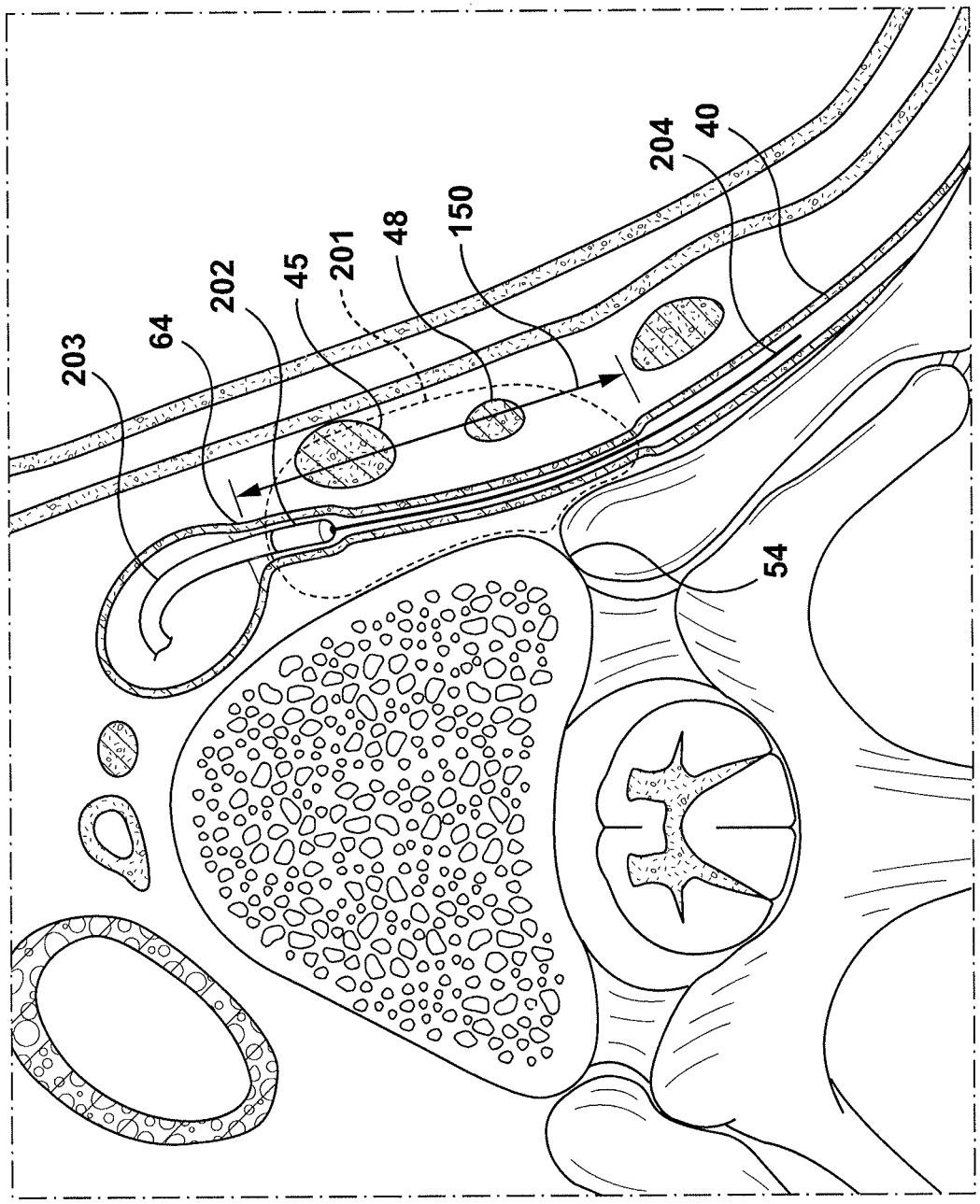

As described herein, in some embodiments the exact location of the intersection of the intercostal vein and a target nerve may be mapped by stimulation with electric current. Alternatively, as shown in FIGS. 22A and 22B a long lesion 201 may be created following a track formed by a portion 150 of an intercostal vein 40. If this lesion is 3 to 5 cm long and extends distally from the ostium 64 of the intercostal vein 40 at the point where it braches from the azygos vein 41, such lesion is very likely to include the targeted nerve or several targeted nerves (e.g., GSN 45 and GSN roots 48) that can be expected to be intercepted by the track made along the intercostal vein 40 by the energy delivery element 202 of the catheter, which may be an RF electrode. In this embodiment an OTW ablation catheter 203 may be advanced distally over a guidewire 204 and then slowly retracted while energy is applied and the track is ablated. Since the TSN forms from preganglionic fibers emerging from the sympathetic trunk, which relay to the celiac ganglion, the long lesion only needs to extend distally as far as the sympathetic trunk in order to ablate the TSN or the TSN roots. The sympathetic chain 49 runs parallel to the spine and lies at the neck of the ribs 63 at the costovertebral joint 54 or junction, just lateral to the radiate ligament at the head of the rib. This anatomical landmark can be used as a distal boundary while the ostium 64 of the intercostal vein 40 where it braches from the azygos vein 40 may be used as a proximal boundary, the lesion extending between the distal and proximal boundaries. Imaging of this landmark via X-Ray, computerized tomography (CT) or magnetic resonance imaging (MRI), for example, can be fused with fluoroscopy or techniques and software for tracking a device position in space (e.g., EnSiteNavX, CARTO) to guide the ablation.

With the device 203 inserted to a known or desired depth 150 as shown in FIG. 22A (before ablation energy is delivered), retraction can be done automatically with a motorized unit at a constant rate or at rate dependent on feedback from the device to ensure sufficient energy is applied to the tissue in order to ablate the targeted nerve. The desired depth 150 may comprise a depth in the intercostal vein starting at the ostium 64 to the azygos vein and extending to a depth that aligns with the costovertebral joint 54. Alternatively, the desired depth 150 may be a predetermined depth that is determined by the probable range of where a thoracic splanchnic nerve passes the targeted intercostal vein. For example in most humans the thoracic splanchnic nerves reside within about 5 cm on the right side or about 3 cm on the left side at the T6 to T8 levels, or within about 2 cm at the T9 level, or within 1 cm at the T10 level, or within about 0.5 mm at the T11 level. Alternatively, a manual mechanical device can be used to retract the catheter at a constant speed using a ratchet or a lead screwdriver. A control system may include feedback based on temperature measured by a temperature sensor 205 or impedance changes measured between electrode 202 and a dispersive electrode positioned on the patient's skin (not shown) during ablation. This information may be used to speed up or slow down ablation and also to stop it. Delivering ablation energy may cause the vein 40 to be deformed as shown in FIG. 22B, for example become constricted, sealed, coagulated or closed. This is not a big risk for the patient since venous drainage typically has several redundant pathways and collateral veins open eventually to sustain perfusion of intercostal muscles. The impedance and temperature changes that occur in conjunction with vein constriction may indicate successful ablation at that particular spot. Such a feedback signal may induce automatic motorized pull back, or act as an indicator for an operator to move the ablation element to a new location.

Retraction of an ablation catheter may also be done manually by the operator. For example, an operator may physically withdraw or advance the ablation catheter and serially ablate. Another way would be to have an actuator on the handle of the ablation catheter that retracts the device a fixed distance to ensure better ablative coverage. For example, the retraction steps may be 50% of the electrode length.

In an alternative embodiment, the ablation element may be moved within a target range 150 (e.g., in an intercostal vein between the ostium of the azygos vein and within about 0 to 5 mm of a costovertebral joint or within about 1.5 to 5 cm into the intercostal vein from the ostium of the azygos vein) and ablation repeated. For example, the catheter can be advanced or different electrodes selected on the catheter placed along the target range 150 crossing or traversing the target nerve(s) (e.g., GSN 45, GSN roots 48, lesser splanchnic nerve 46 or sympathetic chain 49). Alternatively, a catheter may comprise multiple ablation elements 210 positioned along a length (e.g., about 1 to 5 cm) of a distal segment of the catheter and ablation energy may be delivered to each of the ablation elements consecutively or simultaneously to create a long lesion spanning the target range 150 as shown in FIG. 21.

Catheter Embodiments for Mitigating Variability Due to Blood Flow and Uncontrolled Vein Closure Any of the methods, systems, and devices in this section can be incorporated with any of the Stimulation Confirmation and Ablation methods, devices, and systems herein.

As described herein an endovascular approach to ablating thoracic splanchnic nerves may comprise delivering at least one ablation element on a catheter or other medical device through the patient's vasculature to a placement region within a blood vessel, which may be defined as a region of a blood vessel within a suitable proximity and orientation to the target nerve where ablation energy may be delivered to a target region. Intercostal veins in particular are relatively narrow (e.g., having an inner diameter most of the time of about 2 to 3.5 mm) and can shrink in diameter when heated during delivery of ablation energy, which may create variable electrical and thermal properties, which in turn can cause erratic behavior of an energy delivery control system that can impede precise formation of a lesion directed toward a target nerve, which may reduce efficacy or safety. Blood flow in the placement region within a blood vessel may also interact with delivery of ablation energy creating variable electrical and thermal properties during the duration of ablation energy delivery, which may impede precise formation of a lesion directed toward a target nerve. The blood flow through the placement region within a vessel (e.g., intercostal vein) may result in convective cooling of the ablation elements and of the vein wall and some tissue beyond the wall possibly including targeted regions. Depending on the volumetric flow rate of the blood flow, the level of convective cooling may result in lesions that may be insufficiently deep to ablate the target nerve effectively.

A system that incorporates an energy delivery algorithm having one or more feedbacks based on parameters such as impedance and temperature that takes into account changing conditions due to a vein closing around an energy delivery element is one exemplary method of mitigating such an imprecise lesion formation.

Alternative embodiments of devices and methods of use to mitigate this effect and improve the efficacy of nerve ablation described herein include without limitation reducing or eliminating blood flow through the placement region within the blood vessel while ablation energy is delivered, controlled irrigation in the placement region within the blood vessel while ablation energy is delivered, controlled closed-loop irrigation of an energy delivery electrode, and a deployable balloon catheter configured to be deployed in the placement region within the blood vessel to occlude blood flow (e.g., reduce or eliminate blood flow) and position ablation delivery elements within the placement region. Reducing or eliminating blood flow over an ablation element may also improve safety of the nerve ablation procedure. For example, an ablation element such as radiofrequency electrode may comprise a temperature sensor that measures temperature within or on the surface of the electrode. In a blood-cooled environment the hottest spot of tissue in an ablation zone around the electrode may be a distance away from the electrode and thus the temperature sensor associated with the electrode may indicate a temperature lower than the hottest spot. Conversely, in an environment that is not cooled by blood flow or irrigation fluid the temperature sensor associated with the electrode may indicate the hottest temperature in the ablation zone or at least a much closer representation of the hottest temperature. Ablation energy may be delivered in a temperature-controlled mode or temperature-limited mode in which an accurate representation of the hottest temperature may facilitate creation of a lesion that is an appropriate size. If the hottest temperature is unknown there may be a risk of creating a lesion that is too large which may cause undesired injury to nearby tissue such as lung parenchyma or visceral pleura.

Intentional Closure of Vessel Followed by TSN Ablation

An exemplary method to reduce electrical and thermal variability due to the blood flow and contraction of the placement region of the blood vessel (e.g., intercostal vein) is to intentionally close the vein prior to delivering ablation energy to ablate the target nerve. A few intercostal veins may be occluded or closed, even permanently, without harm to the patient, due to redundant venous drainage pathways. A portion of a vessel may be intentionally closed for example by heating the vessel wall, applying an electric signal or other form of irritation that induces smooth muscle contraction of the vessel wall, applying vacuum within the vessel, or delivering a vasoconstrictor drug to the vessel.

Methods of transvascular ablation of a thoracic splanchnic nerve herein may comprise intentionally closing a portion of an intercostal vein, optionally occluding a portion of the adjacent azygos system vein, then delivering ablative energy to the target nerve(s). For example, closing a portion of the intercostal vein may comprise closing the intercostal vein upstream to a placement region of the intercostal vein; optionally occluding a portion of the adjacent azygos vein may comprise occluding the azygos-intercostal vein ostium adjacent to the placement region of the intercostal vein (e.g., following the step of closing the intercostal vein) or occluding the vein up to or near (e.g., 1-5 mm from) the ostium; and delivering ablation energy to the target nerve may be performed following the step of occluding the ostium. In these methods, blood flow is blocked from the placement region of the intercostal vein from both the upstream and downstream directions and blood flow through the azygos is prevented from flowing over the ostium that contributes or drains into the azygos. In some patients a target splanchnic nerve may be sufficiently close to the ostium such that blood flow in the azygos vein may cool the extravascular tissue within about 5 mm and impede a thermal ablation of the target nerve. Preventing blood flow over the ostium zone may facilitate a more effective ablation of the target nerve proximate the ostium. With blood flow blocked from the placement region of the intercostal vein, possibly including the ostium region, ablation energy may be delivered in a less variable environment. Optionally, the placement region of the intercostal vein may be left patent, irrigated or also be closed around an ablation element. Optionally, the ablation energy may comprise radiofrequency electrical current (e.g., monopolar configuration, bipolar configuration). Optionally, the ablation energy may comprise relatively lower power for relatively longer duration.

Any of the devices and system below related to vein closure or occlusion (full or partial) can be used according to any of the methods herein related to vein closure or occlusion (full or partial)

TSN Ablation Catheter Configured to Close a Vein Distal to an Ablation Region of the Vein Without limitation, one modality to reduce blood flow in a placement region is to deliver sufficient thermal energy into the vein wall to cause it to close, for example by denaturing collagen fibers in the vein wall or stimulating smooth muscle contraction of the vein wall. Systems and methods that can be used to close veins for a different purpose have previously been disclosed. For example, U.S. Pat. No. 3,301,258 describes a system for treating varicose veins. The disclosed system passes an electric current through tissue adjacent to a section of vein between two electrodes of a probe deployed in the vein, the current being such as to generate sufficient heat in the vein section to close the vein section. However, the system was never intended to and is not described as being adapted to treat nerves, ablate tissue or to provide neuromodulation therapy. In fact, the '258 patent teaches that impairment of the function of the nearby nerves due to application of heat should be only temporary, which is specifically contrary to and teaches away from the methods of use and therapies herein. Hence, treatments described in the '258 patent specifically allow the nerve function to recover after the treatment.

Figure 38A:
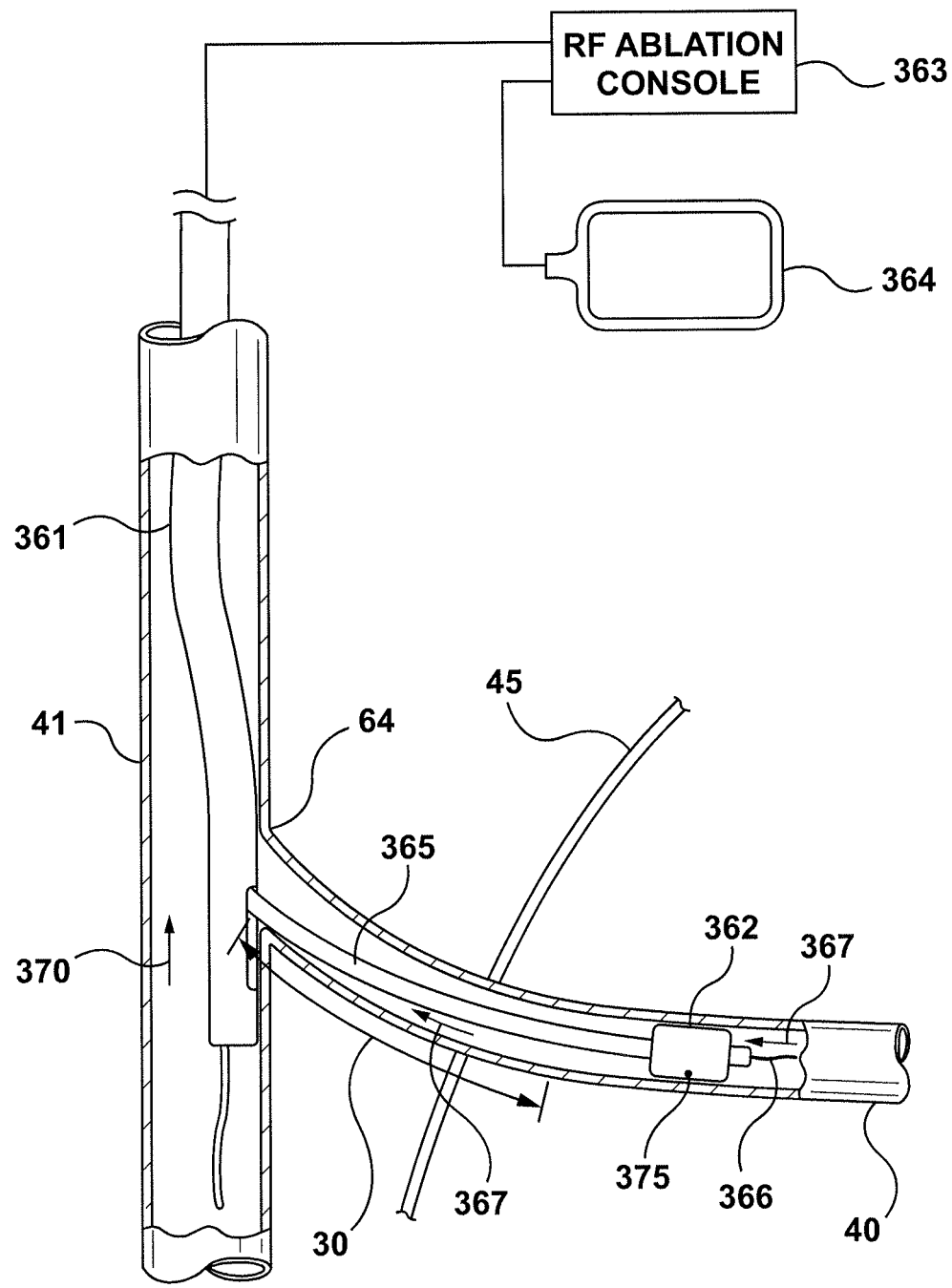
FIGS. 38A to 38E are schematic illustrations of a TSN ablation catheter closing an intercostal vein distal to an ablation region followed by transvascular ablation of a target nerve.
Figure 38B:
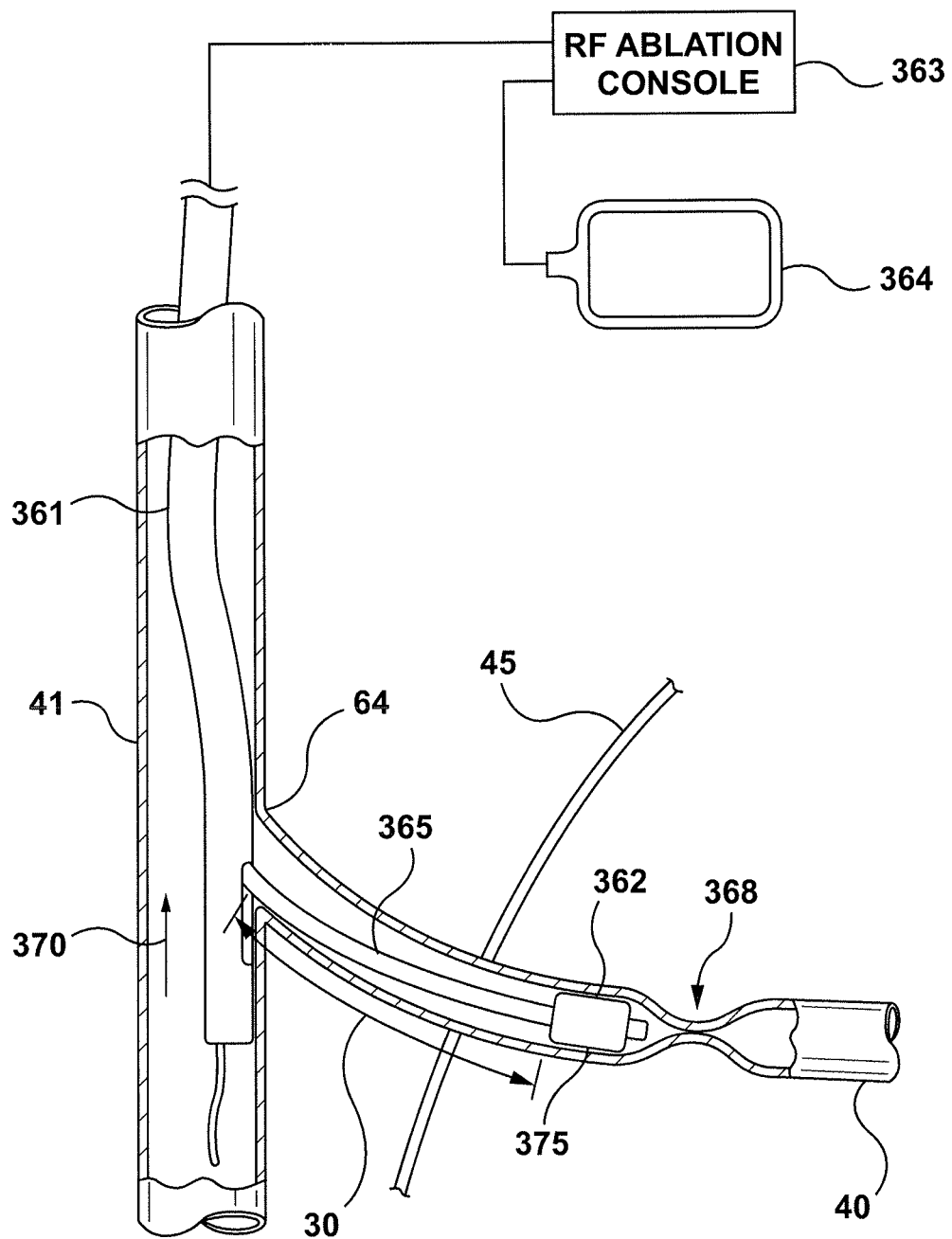
Figure 38C:
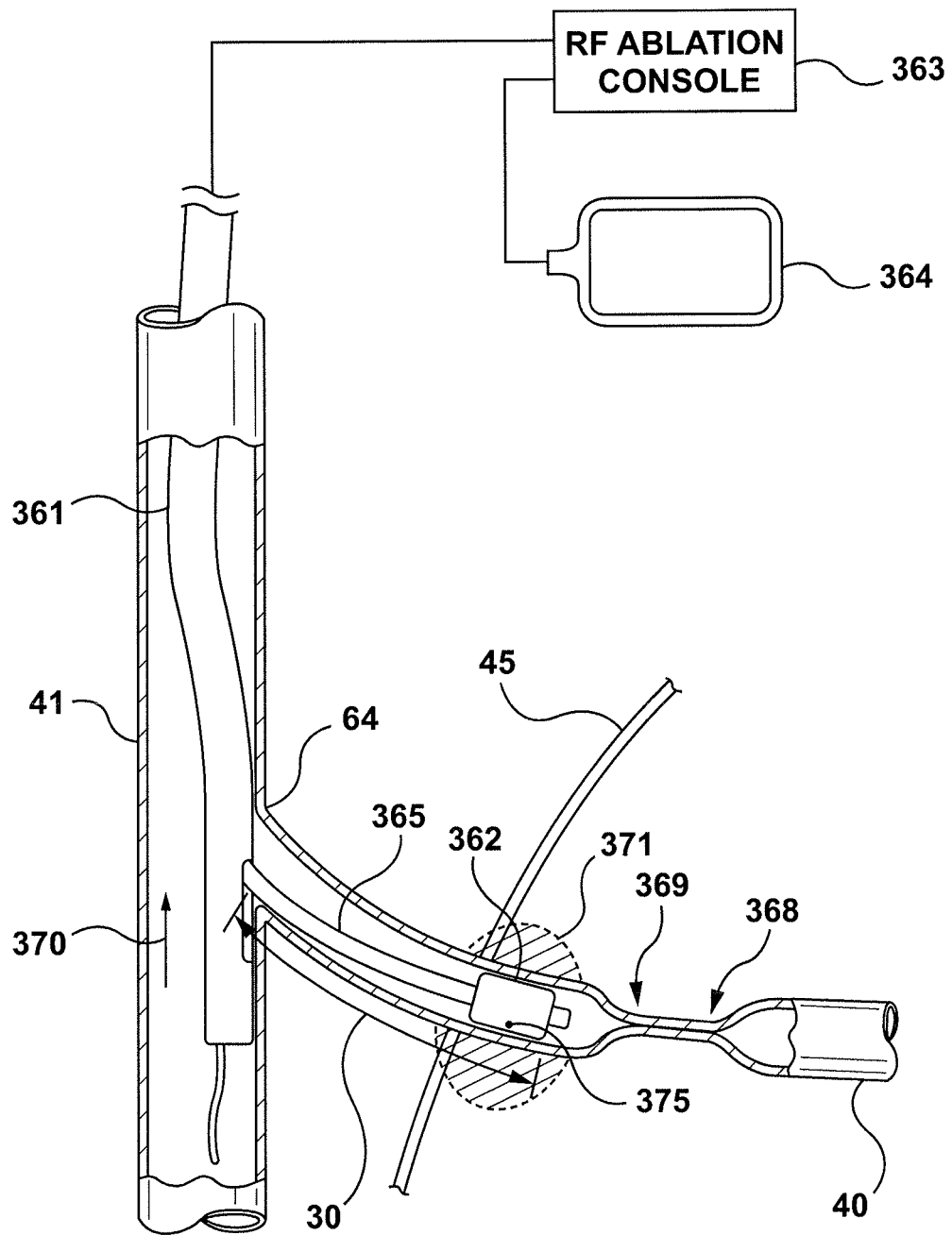
Figure 38D:
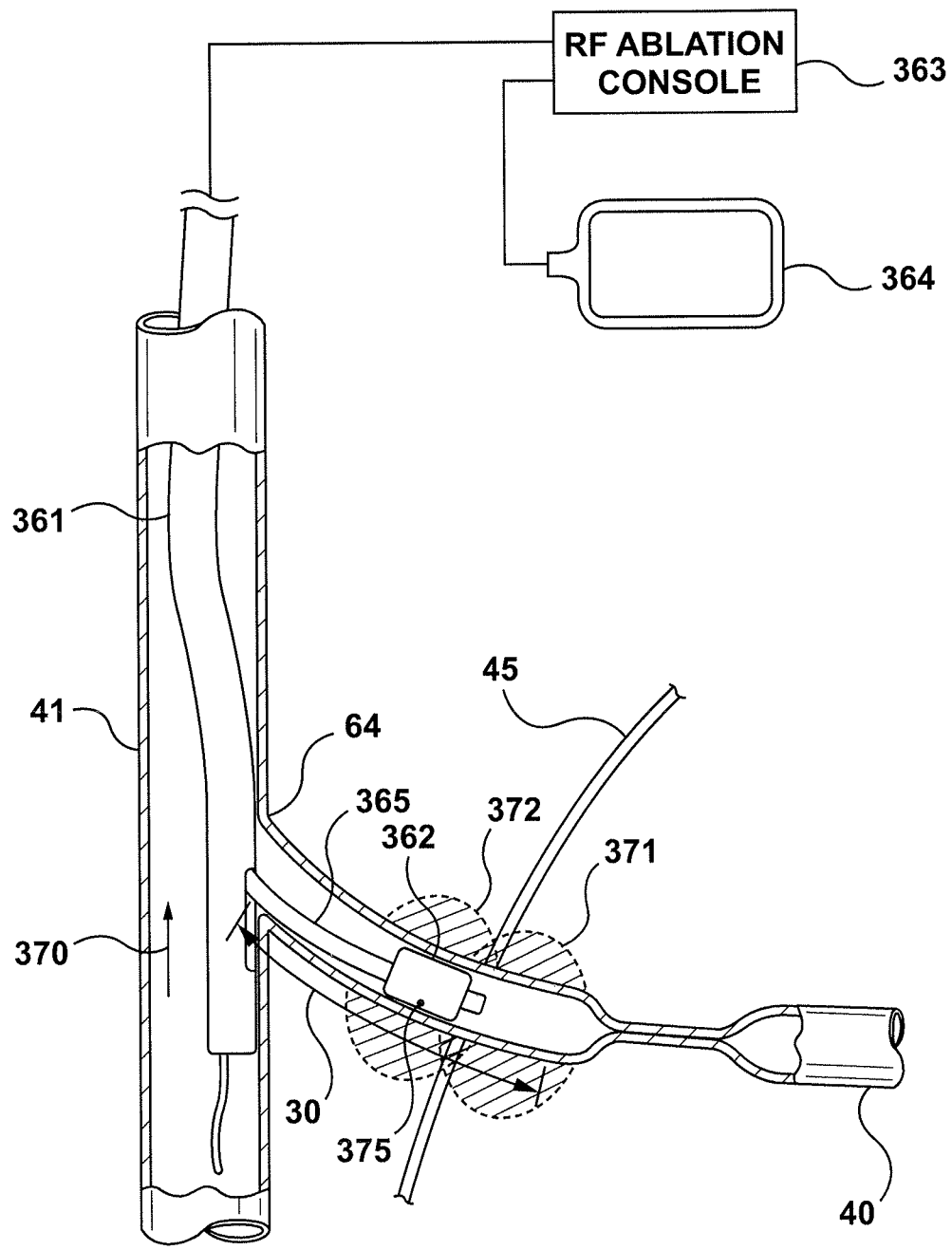
Figure 38E:
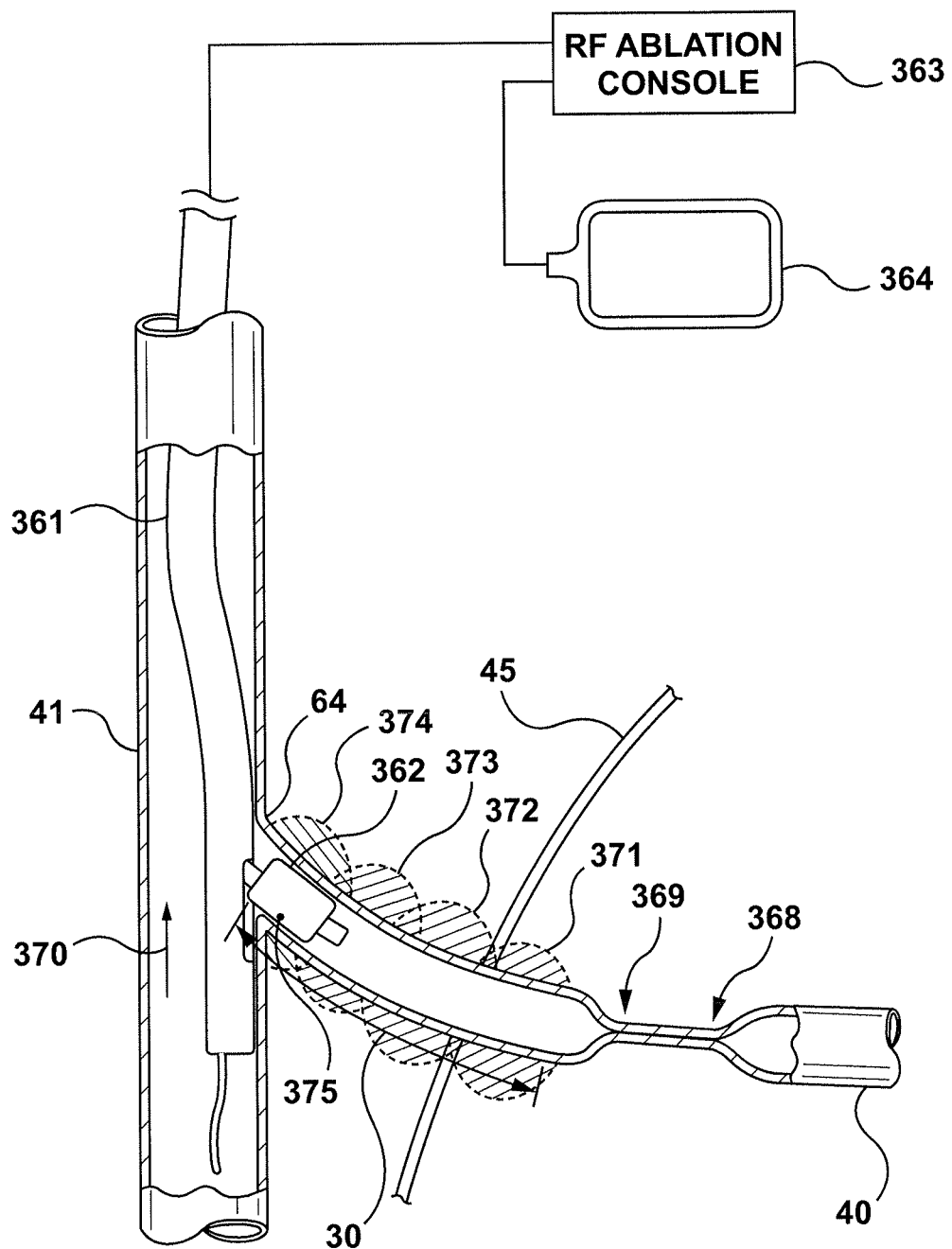

FIGS. 38A to 38E are illustrations of a merely exemplary method and device. In FIGS. 38A and 38E, endovascular catheter 361 includes an energy delivery element 362, and wherein the energy delivery element may function as and be used as an ablation element and a vein closure element. Optionally, the energy delivery element 362 may also function as a nerve stimulation element. Optionally, an endovascular catheter may comprise a separate nerve stimulation element. Optionally, the energy delivery element 362 may comprise multiple ablation elements, for example the energy delivery element(s) 362, may be on the surface of the catheter shaft and positioned at increments (e.g., regular increments, increments with spacing of about 4 to 6 mm between electrodes) along a length of a distal end region of the catheter.

Figure 38F:
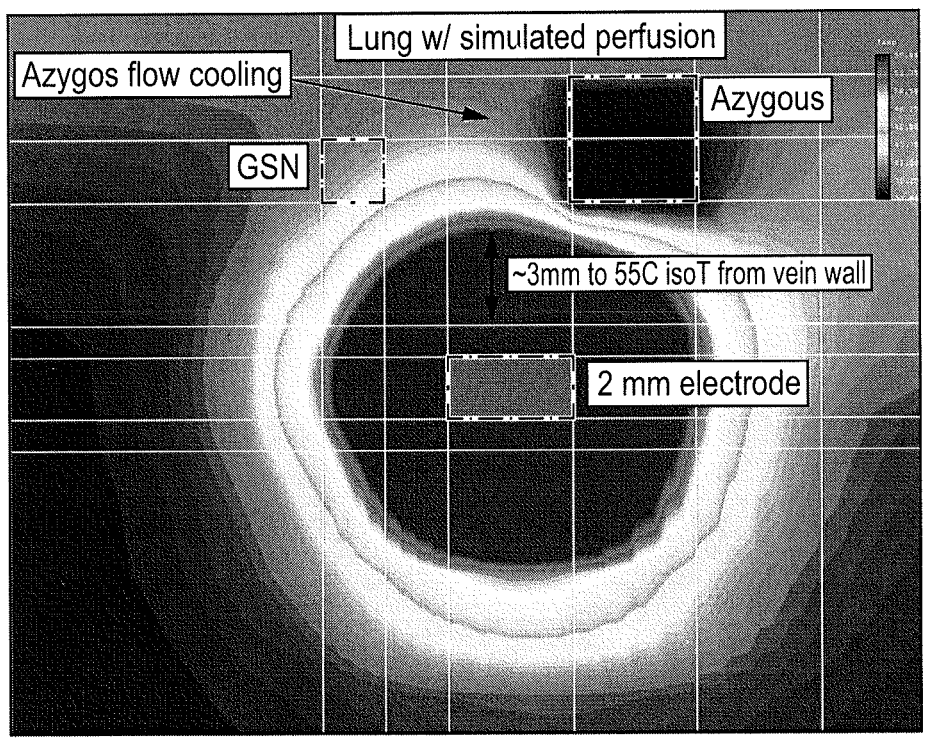
FIG. 38F is an illustration of a finite element model showing an effect of azygos vein blood flow near an ablation zone.
Figure 38G:
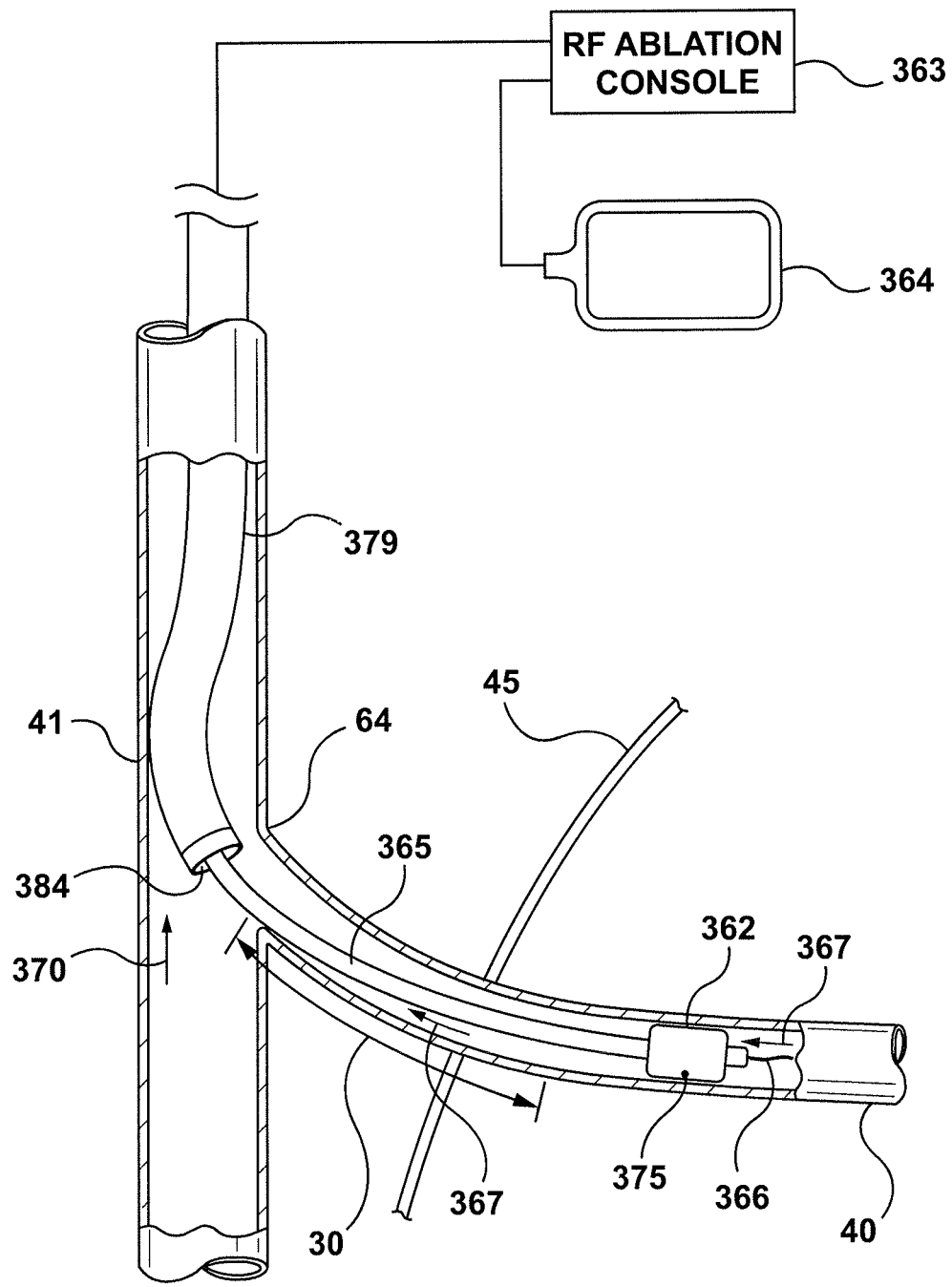
FIG. 38G is a schematic illustration of a TSN ablation catheter delivered through a sheath.

In an alternative embodiment shown in FIG. 38G the energy delivery element 362 may be delivered on a catheter 365 that is delivered through a sheath 379 for example through a lumen of the sheath exiting a port 384 on the sheath's distal end.

In FIGS. 38A-38E, the distal region of the catheter 361 can be navigated into an azygos vein 41 and intercostal vein (e.g., an intercostal vein of thoracic vertebrae T5 to T11) as illustrated by FIG. 38A wherein the energy delivery element(s) of the catheter is in sufficient proximity to the targeted nerve to effectively deliver ablation energy to the targeted nerve(s). The diameter of the electrodes can be 2-6 mm and almost occluding and even possibly distending the intercostal vein. The targeted nerve can be identified by using electrical stimulation of the nerves along the catheter using selected electrodes as cathodes and anodes and monitoring physiological responses to nerve stimulation. An ablation console 363 may be a computer controlled radiofrequency (RF) ablation generator. Optionally, the ablation console 363 may also function to deliver a nerve stimulation signal.

Figure 42A:
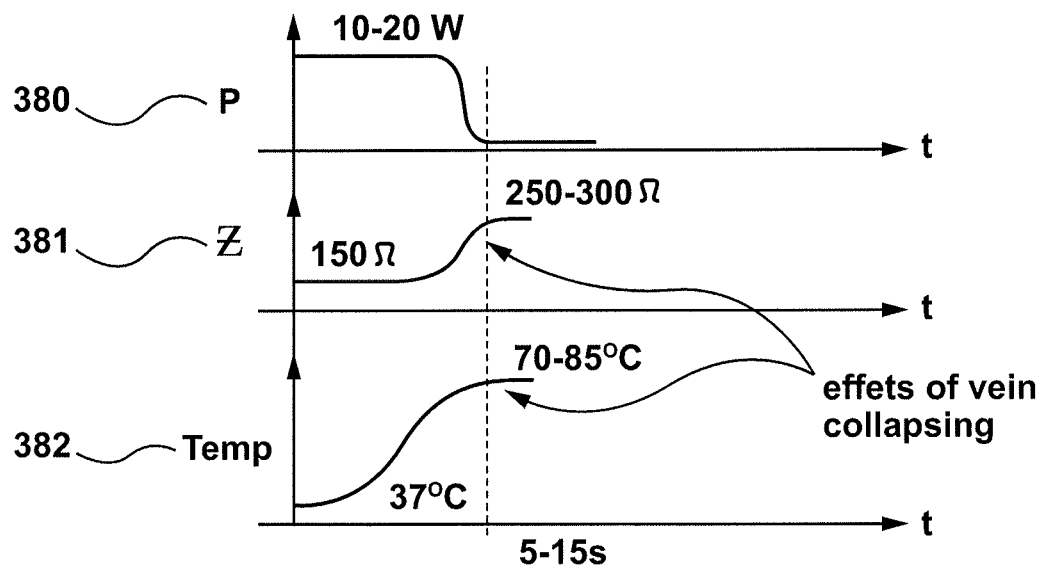
FIGS. 42A and 42B are plots of power, tissue impedance and monitored temperature with respect to time during a vein closure procedure and subsequent nerve ablation procedure.
Figure 42B:
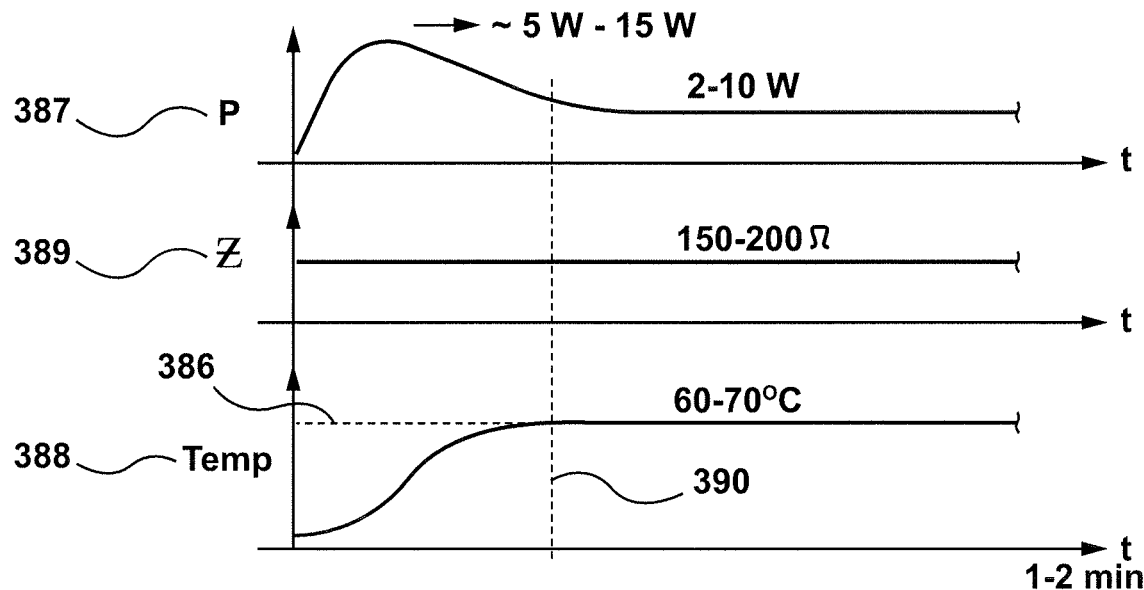

The catheter 361 delivers vein closing energy to the vein wall distal (e.g., upstream) to the ablation element placement region 30 in order to heat it and cause its lumen to close or reduce in diameter sufficiently to reduce its respective blood flow to levels that support effective ablation of the target nerve when ablative energy is delivered with a control algorithm configured for a low-flow environment (e.g., an energy delivery control algorithm illustrated by FIG. 42B). Without limitation, the vein closing energy or ablation energy delivered by catheter 361 can be of radiofrequency (RF) form, microwave, ultrasound, direct thermal heating, optical (e.g., laser), or other forms of energy that instigate vein closure, for example by heating the vein wall. FIGS. 38A to 38E illustrate an embodiment whereby the vein closing energy comprises RF energy delivered in monopolar modality, wherein an RF electrical circuit is created from an RF ablation console 363 to the energy delivery element 362 and through the patient's body to a dispersive electrode 364. The energy delivery element 362 carried on catheter 361 may have a length of 2 to 10 mm and a diameter of 4 to 10 French Size (F). Alternatively, bipolar RF modalities can be used as effectively for this purpose. Alternatively, multi-electrode catheter constructions may be utilized as effectively. For example, without limitation, a flexible body (e.g. catheter, guidewire, sheath, etc.) may carry one, two or more electrode elements configured to deliver ablative or stimulating energy. They can be arranged in a spaced apart relationship at the distal region of the flexible body. The flexible body may be made of an electrically insulating material, such as, but not limited to, polyurethane and PEBAX® plastic material. The flexible body may carry electrodes of different diameters, or of same diameters, distributed along its length. Such electrodes are made of electrically conductive material (e.g., Pt, PtIr, Stainless-Steel, Au, etc.). Alternatively, such electrodes may be made of balloon-type materials having electrically conductive walls. The flexible body may be steerable, or have a lumen that allows over-the-wire deployment. The heating of the vein wall may need to be performed at several locations to effectively reduce the blood flow. FIGS. 38A to 38E illustrate a step-by-step approach, with heating energy delivered at two locations distal to the placement region 30, where ablation energy is delivered towards the targeted nerve 45. The energy delivered to close or reduce the vein lumen may be of higher amount but shorter durations, so that to achieve the desired vein closure quickly. Furthermore, the vein closure energy may be configured to generate heat in the vein wall (e.g., above 63° C., in a range of about 60° C. to 80° C., in a range of about 63° C. to 75° C.) while avoiding generation or conduction of heat to surrounding tissue beyond 1 mm from the outer surface of the vein and while avoiding excessive heat in blood that causes boiling or production of steam. Alternatively, vein closure energy may be configured to thermally close or reduce a portion of the vein lumen while avoiding thermal injury to tissue external to and in proximity to the vein such as lung parenchyma or visceral pleura.

FIG. 38A shows a first step of the overall exemplary method wherein catheter 361 is delivered to an azygos vein 41 (e.g., a vein of the azygos system that connects to an intercostal vein such as an azygos, hemiazygos or accessory hemiazygos vein) and an ablation portion 365 of the catheter comprising the energy delivery element 362 is delivered into an intercostal vein 40 distal to a placement region 30 that is proximate a target nerve 45. For example, the ablation portion 365 may optionally be delivered over a guidewire 366. Prior to closing the vein, blood flow 367 passes through the intercostal vein 40 toward the azygos vein 41. Vein closure energy is then delivered from the energy delivery element 362 to the vessel to close or reduce the vein lumen.

Optionally, vein closure energy may be delivered to multiple locations of the intercostal vein distal to the placement region, which may facilitate sufficient reduction of blood flow. FIG. 38B shows a second optional step wherein the energy delivery element 362 has been retracted proximally from the portion of the vein 368 (FIG. 38B) that was closed from the electrode placement of FIG. 38A, yet still distal to the placement region 30. Vein closure energy may be delivered from this position to cause additional vein closure.

Optionally, blood flow 370 through an azygos vein may also be occluded prior to ablation of a target nerve. Mitigating effects of azygos blood flow and embodiments for doing so are described in more detail, and can be incorporated into any of the methods herein. FIG. 38C shows a segment 369 and 368 of the intercostal vein 40 closed distal to the region 30 and azygos blood flow 370 diverted away from the ostium 64. The energy delivery element 362 has been retracted into the placement range 30 and ablation energy is delivered to create a lesion 371 through the vessel wall to tissue around the vessel (e.g., up to about 5 mm from the vessel wall). Optionally, a nerve stimulation signal may be delivered prior to delivering ablation energy to confirm proximity to the target nerve, examples of which provided herein.

It may be desired to ablate a portion of the range 30 that corresponds to location(s) where nerve stimulation mapping indicated proximity to one or more target nerves. Alternatively, it may be desired to create lesions along the entire range 30 to increase the likelihood of ablating all target nerves possibly if nerve stimulation (also called nerve mapping) was not performed. Multiple ablations may be created, in this embodiment sequentially, by retracting the electrode and delivering ablation energy again. FIG. 38D shows creation of a second lesion 372 proximal to the first lesion 371, wherein the second lesion partially overlaps the first, for example by about 20% by retracting the energy delivery element 362 an amount approximately equal to the length of the electrode (e.g., about 4 mm). FIG. 38E shows multiple lesions 371, 372, 373, and 374 covering the full placement range 30. More than 4 lesions may be required to cover the range 30, and in other embodiments ablation energy may be delivered from a portion of the range 30.

FIG. 38F shows a finite element model demonstrating generation of heat from the application of RF energy wherein the azygos blood flow can have sufficient convective cooling effects so to impact the ability of effective ablation of a targeted nerve. This is of particular concern when the distance between the azygos vein and the targeted nerve is short, between 0-5 mm. The finite element model comprises a 2 mm RF electrode in a lumen of a vein, an azygos vein assumed to be cooled to body temperature by blood flowing in the azygos within 5 mm of the electrode, and a 55° C. isotherm extending from the vein into tissue about 4 mm. The model represents a scenario in which RF energy is delivered with a power of 11.7 W in monopolar configuration for 120 seconds with tissue having an impedance of 187Ω.

Optionally, in any of the methods herein, blood flow 370 in the azygos vein 41 may be temporarily diverted away from the ostium 64 of where the intercostal vein 40 connects to the azygos vein 41. Temporarily diverting blood flow 370 from the ostium 64 may comprise for example occluding the azygos vein distal (e.g., upstream) to the intercostal vein that is being targeted, distal and proximal (e.g., both upstream and downstream) to the intercostal vein that is being targeted, at the ostium 64, or a combination of these. Alternatively, blood flow 370 in the azygos vein may be allowed to flow through the azygos vein but not over the ostium or within a region of the azygos vein that is about 5 mm proximal or distal to the ostium 65.

Figure 43A:
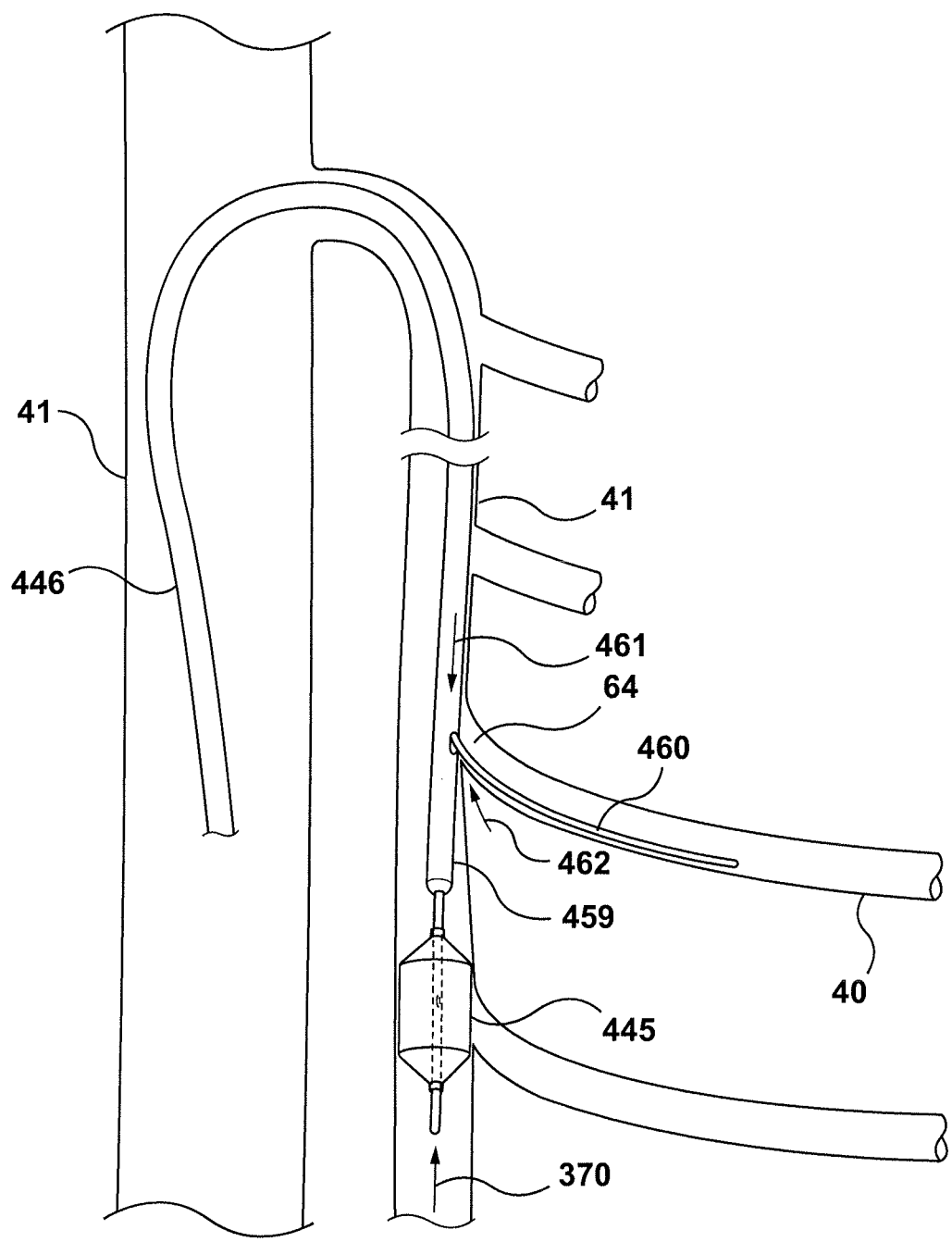
FIG. 43A is a schematic illustration of a catheter configured to couple to an azygos vein to intercostal vein ostium of a targeted intercostal vein.

An embodiment of a catheter 446 adapted for occluding azygos vein blood flow 370 distal to the intercostal vein 40 that is being targeted is shown in FIG. 43A, wherein a balloon 445 is deployed in the azygos vein 41 to at least partially occlude blood flow 370. Several balloon, stent, catheter or guidewire-based concepts may be used to achieve this goal. For example, without limitation, U.S. Pat. No. 6,165,172 describes expandable elements, such as balloon structures, which can be used to obstruct, or occlude, blood flow through veins. Such expandable structures may be used in partial achievement of the goals of the present invention. For example, a flexible introducer device may be deployed through the superior vena cava into the azygos vein, just distal of the ostium of the targeted intercostal vein.

The obstructing member of the flexible device can then be expanded to block the blood flow through the azygos vein. An ablation catheter, which delivers energy for closing or reducing a portion of a lumen of the intercostal vein and for ablating the targeted nerve(s), can then be inserted separately, for example as shown in FIGS. 43A and 43B, or any of the other ablation catheters described herein. Alternatively, the ablation catheter and the occluding member may be combined into one single device.

For this particular application, and in any of the methods herein, it may be desired to block or occlude the blood flow through the azygos vein at a location proximal from the ostium of the targeted intercostal vein, possibly including the ostium, for example in addition to occluding blood flow distal to the ostium. Even with distal occlusion, blood back flow from intercostal veins located superior with respect to the targeted ostium (e.g., downstream) may still provide sufficient convective cooling to impact the effectiveness of the nerve ablation. Occluding blood flow both proximally and distally from the targeted ostium may be achieved with a longer expandable member, such as the one shown in FIG. 43A, but longer. Alternatively, flexible devices carrying dual expandable members, such as dual balloon structures, may be used as effectively.

An exemplary embodiment of methods and catheters for diverting azygos vein blood flow away from the ostium without occluding it is shown in FIGS. 43A and 43B, and 38A to 38E. These methods and catheter can be used with any other methods and devices herein. In these embodiments, a catheter or other elongate medical device comprises a bifurcation that may be coupled to the ostium 64 with a gentle forward force to the catheter, which pushes a portion of the catheter shaft against the ostium. Blood may continue to flow through the azygos vein but not across the ostium. The portion of the catheter that is pushed up against the ostium may be large enough to cover an ostium having a diameter between 2 to 3.5 mm yet narrow enough to be delivered through an azygos vein having a diameter of about 9 mm. For example the portion of the catheter pushed up against the intercostal vein ostium may have a diameter in a range of about 4 mm to 8 mm. This embodiment may occlude flow or reduce it sufficiently to allow thermal ablation of a target nerve positioned within 0 to 5 mm of the ostium 64.

Figure 39A:
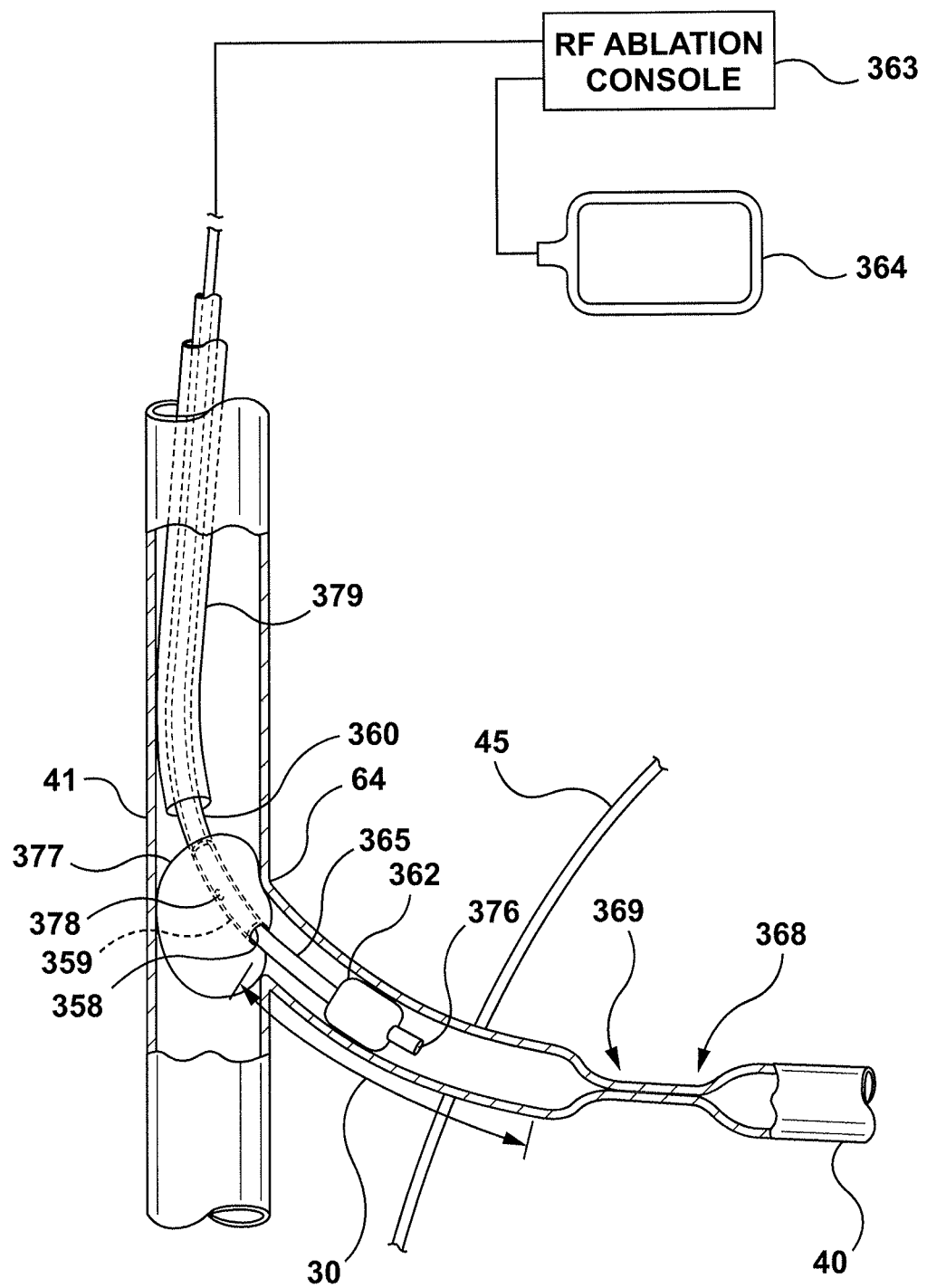
FIG. 39A is a schematic illustration of an energy delivery catheter configured to reduce blood flow across an azygos vein to an intercostal vein ostium.

FIG. 39A shows an alternative embodiment of a method of, and an exemplary device configured for use in the method, occluding azygos blood flow from ostium 64. A delivery sheath 379 may be inserted through a patient's vasculature to an azygos vein 41, for example over a guidewire. A catheter 360 may be delivered through the sheath 379 and may comprise a compliant balloon 377 mounted to or otherwise carried by an elongate tubular structure 359 of the catheter 360. An inflation port 378 may be positioned on the tubular structure 359 within the balloon 377 and be in fluid communication with an inflation port such as a luer lock hub on a proximal region of the catheter. Air or fluid such as sterile water or saline may be injected through the inflation port 378 and into the balloon to inflate it. The tubular structure may comprise a lumen 358 that extends through the balloon and through which a shaft 356 may slidably engage. An energy delivery element 362 may be connected to or carried by the shaft 365 and function as at least one of a nerve stimulation electrode, a vein closure electrode, and a transvascular ablation electrode as described herein with regards to FIGS. 38A to 38E. The energy delivery element 362 may be moved while the balloon 377 remains in place. For example, energy delivery element 362 may be moved to a section distal to ablation region 30 to close or reduce the vein 368 and 369, then retracted to within the region 30 to optionally deliver nerve stimulation signals or ablate tissue to target the nerve(s) 45. Optionally, shaft 365 may comprise a lumen 376 in communication with the distal end of the shaft 365 and the proximal end of the catheter. Lumen 376 may be used to deliver the device over a guidewire or to inject radiopaque contrast agent to assess how well the vein is occluded. To remove the catheter 360 the balloon 377 may be deflated by removing the air or fluid from the balloon through the injection port 378 and the catheter 360 along with the energy delivery element(s) 362 may be removed through the delivery sheath 379.

Figure 39B:
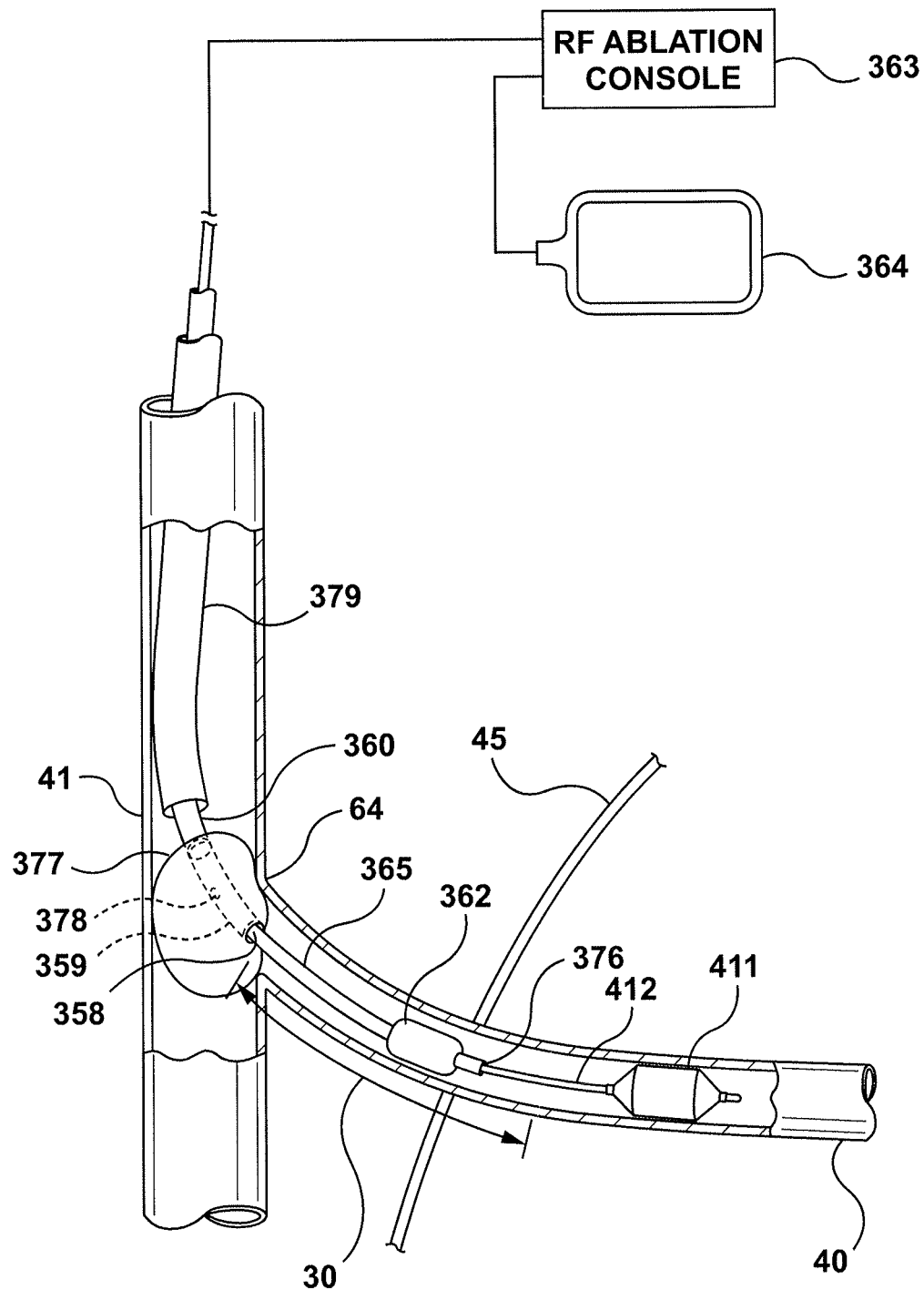
FIG. 39B is a schematic illustration of an energy delivery catheter configured to temporarily occlude a section of a targeted intercostal vein, reduce blood flow across an azygos vein to intercostal vein ostium, and deliver energy to stimulate or ablate a target nerve.

FIG. 39B shows a similar embodiment as the one shown in FIG. 39A, which may be incorporated into any other embodiment herein, however instead of occluding the vein 40 by applying thermal energy to the vein wall to close or reduce the vein lumen, an occlusion balloon 411 mounted to a shaft 412 is delivered through lumen 376 and inflated in the vein. The energy delivery element 362 may slide within region 30 while the balloon 411 and balloon 377 remain in place. Occlusion 411 is shown expanded in place, to at least partially occlude the vein 40.

Figure 40:
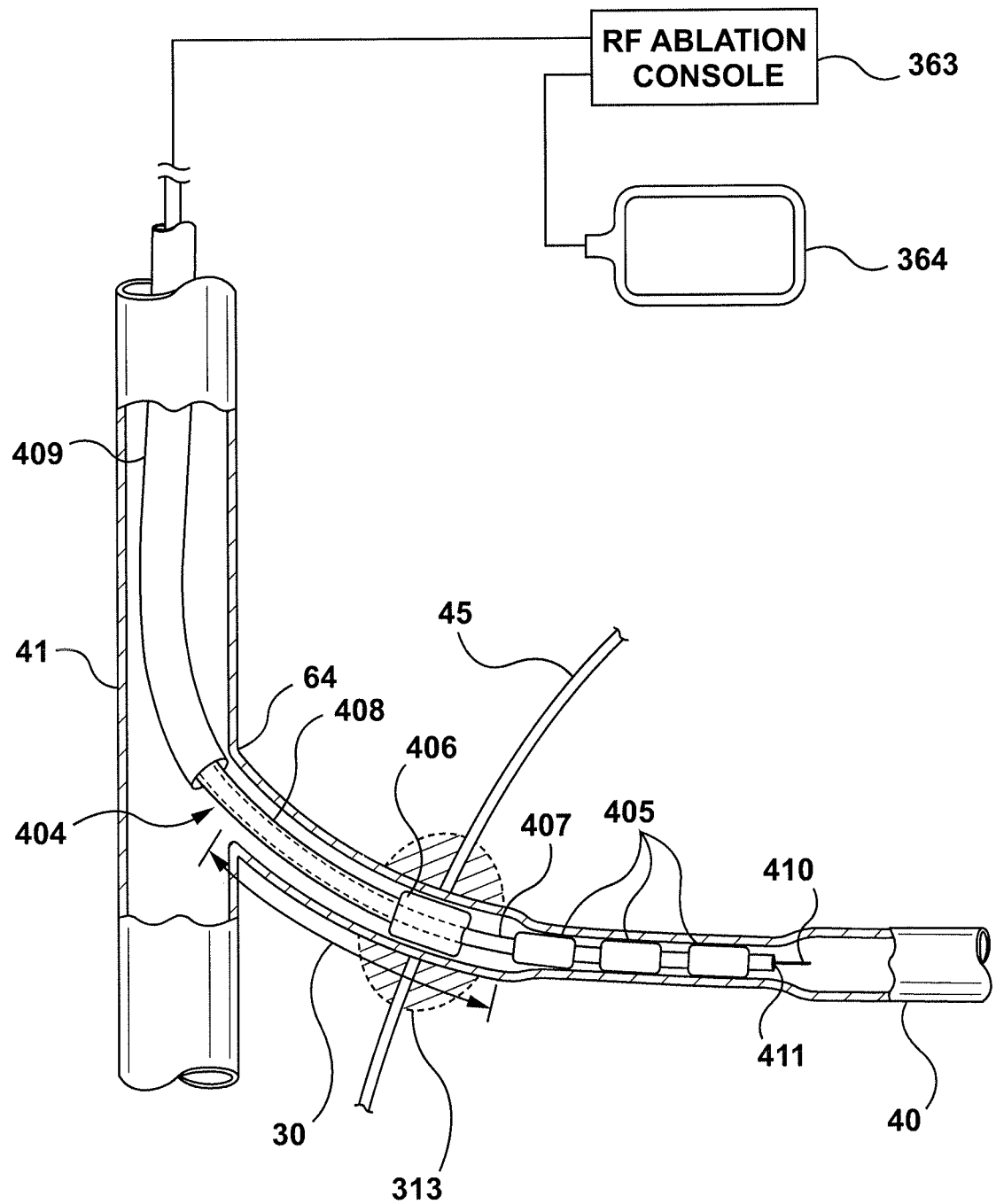
FIG. 40 is a schematic illustration of an energy delivery catheter comprising a vein closure section and a stimulation or ablation section.

TSN Ablation Catheter Comprising a Separate Vein Closure Element and Ablation Element FIG. 40 illustrates an exemplary embodiment of a catheter that includes one or more vein closure electrodes and one or more separate ablation elements. Catheter 404 comprises one or more vein closure electrodes 405, axially spaced, and one or more separate transvascular ablation electrodes 406. The vein closure electrodes may be positioned in a targeted vessel such as an intercostal vein 40 as shown and distal to region 30. Energy (e.g., RF) may be delivered from the vein closure electrodes 405 to generate thermal energy in the vessel wall for example using an energy delivery profile as shown in FIG. 42A to close or reduce the vessel lumen down snug around the vein closure electrodes 405 as shown. The electrodes 405 may be left in place in the closed vein while an ablation is performed, which may help to occlude the vessel. The ablation electrode 406 may also function as a nerve stimulation electrode to map a location of a target nerve(s) within the range 30. The vein closure electrode(s) may be connected to or otherwise carried by a shaft 407 and the ablation electrode(s) 406 may be connected to or otherwise carried by a shaft 408 such that the ablation electrode(s) 406 can slide within range 30 while the vein closure electrode(s) remain in place. For example, as shown the shaft 407 may pass through a lumen in ablation electrode 406 and shaft 408. The ablation electrode 406 may be moved by pulling or pushing the shaft 408 from a proximal end of the catheter. For example, the shaft 408 may be connected to an actuator on a handle (not shown) that may move the shaft 408 and thus the electrode 406 in increments approximately equal to the length of the ablation electrode 406, which may facilitate coverage of range 30 during steps of nerve stimulation mapping or creating multiple ablations. Following ablation the catheter may be removed from the vessel removing the vein closure electrodes from the partially closed vein, which may allow blood to flow through the vein even though it is partially closed. Optionally, the catheter 404 may comprise a guidewire lumen 411 and be delivered over a guidewire 410. Radiopaque contrast agent may be injected to the intercostal vein distal (upstream) to the occluded section, for example, through the guidewire lumen 411 to confirm that the vein 40 is sufficiently occluded. Optionally, the catheter 404 may be delivered through a delivery sheath 409 as shown. Optionally, blood flow in the azygos vein 41 may be occluded or diverted away from the ostium 64 as described herein. Optionally, the catheter 404 may be delivered from a side port 441 of a catheter 440 as shown in FIG. 43A to create a catheter bifurcation that may be coupled to the ostium 64.

Figure 41A:
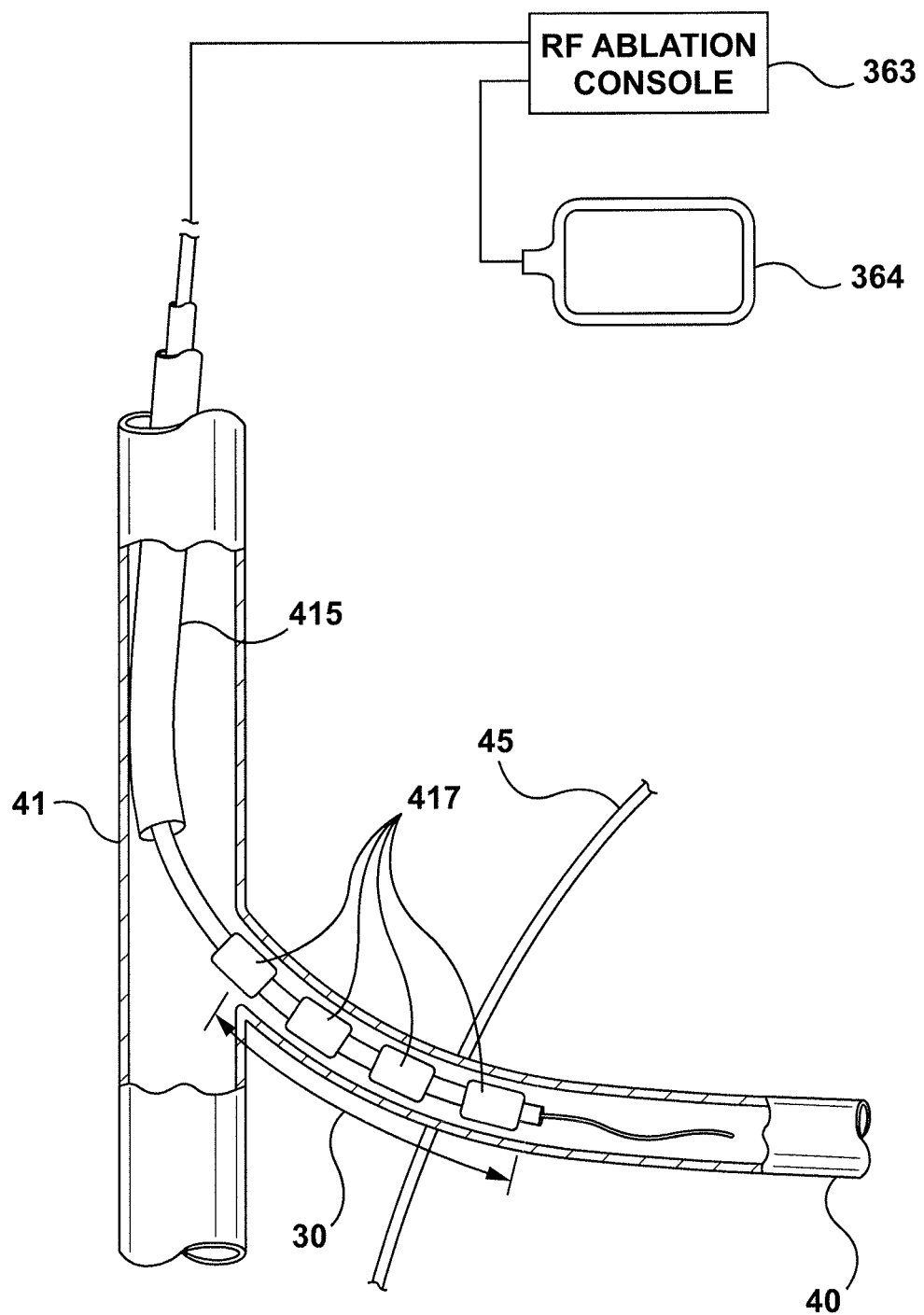
FIGS. 41A and 41B is a schematic illustrations of a catheter having multiple energy delivery elements and a method of use wherein a targeted intercostal vein is closed around the energy delivery elements before ablation energy is delivered to a target nerve.
Figure 41B:
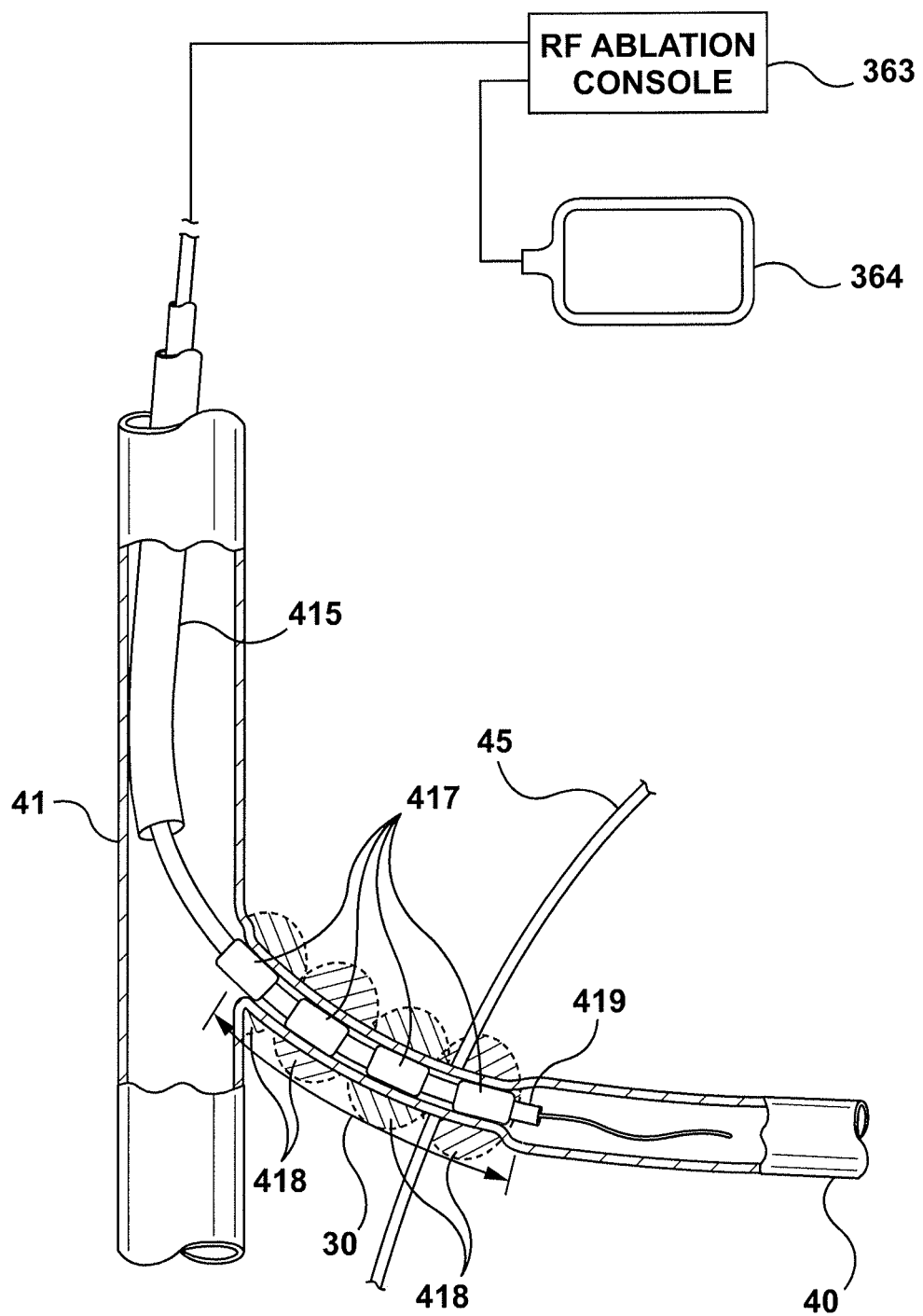

TSN Ablation Catheter Configured to Close a Vein Around Energy Delivery Elements within an Ablation Region of the Vein In an alternative embodiment shown in FIGS. 41A and 41B a TSN ablation procedure may comprise positioning an energy delivery element 417 in the range where a target nerve is expected to cross 30 (FIG. 41A), delivering energy to generate thermal energy in a vein wall in the range 30 to first close the vein over the energy delivery element 417, then deliver ablation energy from the energy delivery element to tissue surrounding or proximate to the range 30 (FIG. 41B) to create multiple lesions 418 to cover the length of the region 30 to ablate the target nerve 45. Closing the vein 40 within the ablation range 30 may reduce or eliminate blood flow over the electrode(s) to facilitate the safe and effective creation of lesions to ablate the target nerve(s) 45. Closing the vein within the ablation range prior to delivering energy for ablating the target nerve may also provide circumferential apposition between the energy delivery elements 417 and the vein wall, which may facilitate a consistent circumferential ablation around the vein, which in turn may improve efficacy. A catheter configured for this method may comprise an energy delivery element that is approximately the length of the region 30 (e.g., about 3 to 4 cm, about 3 cm, about 1.5 cm, about 1 cm to 3 cm). As shown the energy delivery element 417 comprises multiple RF electrodes mounted to and axially spaced on a shaft 419. The multiple electrodes may be configured for monopolar or bipolar modes. In monopolar mode RF energy may be delivered from the multiple electrodes sequentially, for example, using energy delivery profiles for vein closure followed by ablation as illustrated by FIGS. 42A and 42B. RF electrodes may also function as nerve stimulation electrodes to assess technical success of an ablation procedure. The energy delivery element may be flexible to negotiate tortuous vasculature. Alternatively, the energy delivery element may comprise a single long flexible electrode such as a metal coil or laser cut metal tube. Alternatively, an energy delivery element may be configured to deliver other energy modalities that generate thermal energy such as direct heat, microwave, or optical energies.

RF Delivery Profiles for Closing a Vein and Transvascular Nerve Ablation

Figure 42C:
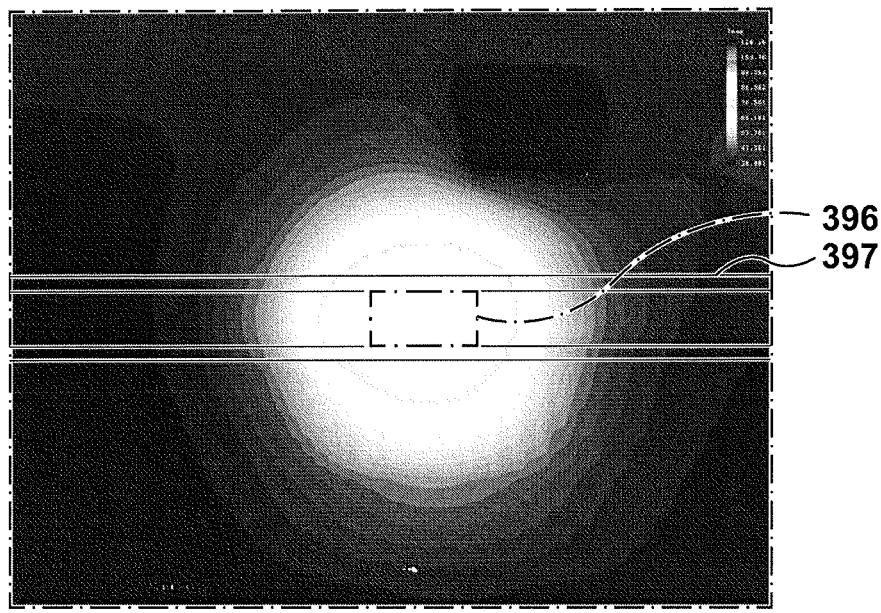
FIGS. 42C and 42D are illustrations of finite element models showing an effect of increased duration of energy delivery.
Figure 42D:
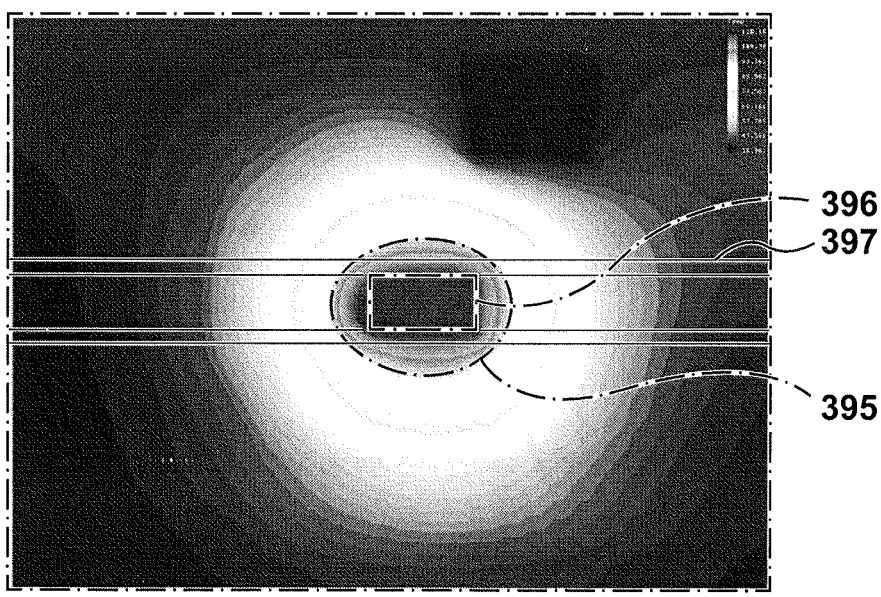

With the blood flow over the adjacent azygos to intercostal vein ostium (optionally) and the targeted intercostal veins reduced, or eliminated, the procedure may proceed with the step of ablating the targeted vein structure. FIGS. 42A and 42B illustrate embodiments of controlling the power of energy delivery based on sensed temperature and impedance for the purposes of closing a portion of an intercostal vein (FIG. 42A) and transvascular ablation of a target nerve (FIG. 42B). For example as shown in FIG. 42A along with FIGS. 38A to 38E, RF energy power 380 may be applied in the form of constant power (e.g., in a range of 10 to 20 W) until the corresponding impedance 381 increases (e.g., from about 150Ω to a higher impedance in a range of about 250 to 300Ω), as a sign that the intercostal vein 40 has closed 383, or shrunk, sufficiently around the ablation electrode 362. Correspondingly, if the ablation catheter 361 is equipped with an optional temperature sensor 375, the sensed temperature 382 will increase (e.g., from body temperature to a higher temperature in a range of about 70 to 85° C.) as the convective cooling provided by the blood flow 367 through the intercostal vein 40 is reduced, or eliminated. As discussed above and shown in FIGS. 38A, 38B and 38C, this step may be repeated until a sufficiently long segment (e.g., a range 30 from the ostium 64 to about 3 cm into the intercostal vein, a range 30 from the ostium 64 to position in the intercostal vein aligned with an adjacent costovertebral joint) of the targeted intercostal vein has been closed or shrunk. Ablation of the targeted nerve may be then achieved by applying energy in temperature-controlled modality, as shown in FIG. 42B along with FIGS. 38A to 38E. Until the target temperature 386 is reached, the ablation console 363 may deliver an increased level of power 387 (e.g., power in a range of about 5 W to 15 W). However, as the sensed temperature 388 reaches or approaches target 386, the power may drop to lower levels (e.g., about 2 W to 10 W) as indicated by time event 390. Ablation may continue for a longer period of time to allow the lesion to expand and reach out to the location of the targeted nerve 45. FIGS. 42C and 42D show finite element analysis (FEA) results that demonstrate that the lesion depth may continue to grow as ablation duration increases. FIG. 42C is an FEM at 60 seconds while FIG. 42D is an FEM of the same energy delivery parameters but continued until 120 seconds showing a 55° C. isotherm 395 extending from an electrode 396 beyond an intercostal vein wall 397.

Alternatively, a constant power energy delivery modality approach may be employed. In an embodiment, the energy delivery is guided by temperature sensing. Alternatively, if the thermodynamic conditions at the specific ablation location are well controlled (e.g., blood flow is occluded) then application of low power levels (e.g., 2 to 20 W) for longer durations (e.g., 30 to 240 s) may also achieve the desired clinical effect. Low power long duration delivery of ablation energy may be configured to sufficiently heat a target TSN through joule heating to ablate the nerve while other tissues proximate the electrode(s) such as the intercostal vein or lung tissue may heat less due to metabolic cooling because they are more perfused than the target nerve or fat surrounding the nerve, and thus contralateral injury may be avoided.

Irrigation Catheter to Cool Vessel Wall

In some instances, sufficient reduction in blood flow through the targeted intercostal vein or through the azygos vein may not be achievable, or desired. For example, in order to allow for a repeated ablation procedure at a later time, it may be desired that the targeted intercostal vein be only partially, or reversibly, closed or reduced in lumen diameter. In other cases, the vein may be sufficiently large that attempting its complete closure may not be a desired goal. In such cases, in order to overcome the cooling provided by the blood flow, higher power levels may be used. However, in order to avoid char or coagulum build-up on the ablation electrode, irrigation may be used. The irrigation comprises injecting physiologically compatible and sterile fluid, such as 0.9% physiological saline, either in an open-loop or closed-loop approach. In an open-loop approach, the irrigating fluid cools the energy-delivering element and is then infused into the patient's blood circulation. With a closed-loop approach, the irrigating agent is circulated inside the energy delivery element. With the open-loop approach, attention may need to be paid to the volumetric flow rate of irrigating agent infused into the patient. Depending on their condition, some patients may not be able to undertake large amounts of additional fluid into their circulatory system. As such, it is preferable to operate the open-loop irrigated ablation system at low flow rates, such as 2 to 10 ml/min.

Figure 42E:
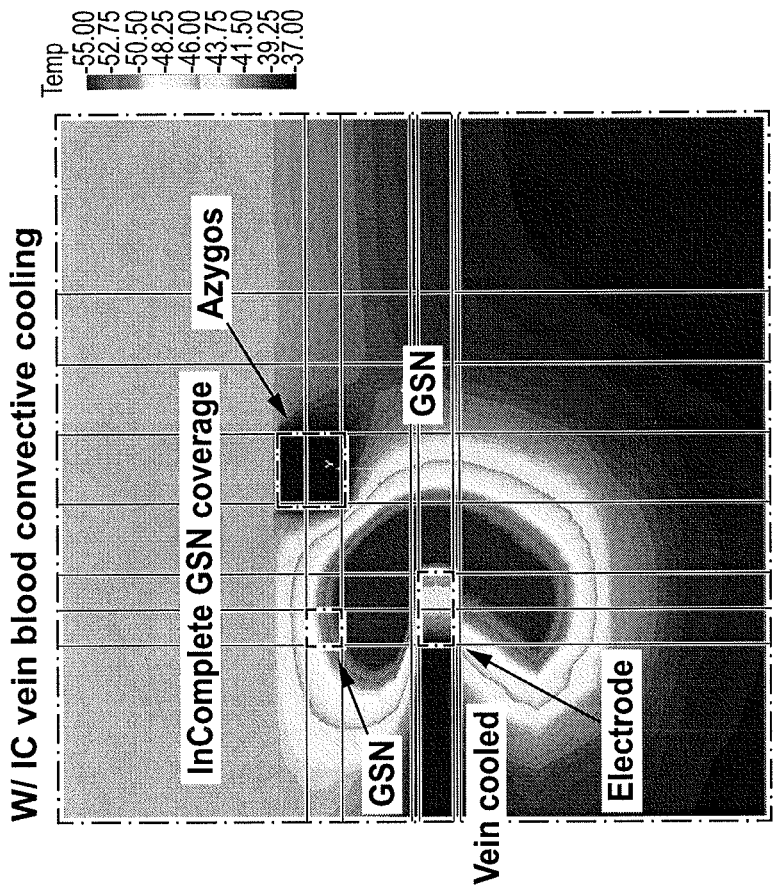
FIG. 42E is an illustration of a finite element model showing an effect of creating an ablation from an occluded vein compared to a non-occluded vein.
Figure 42E:
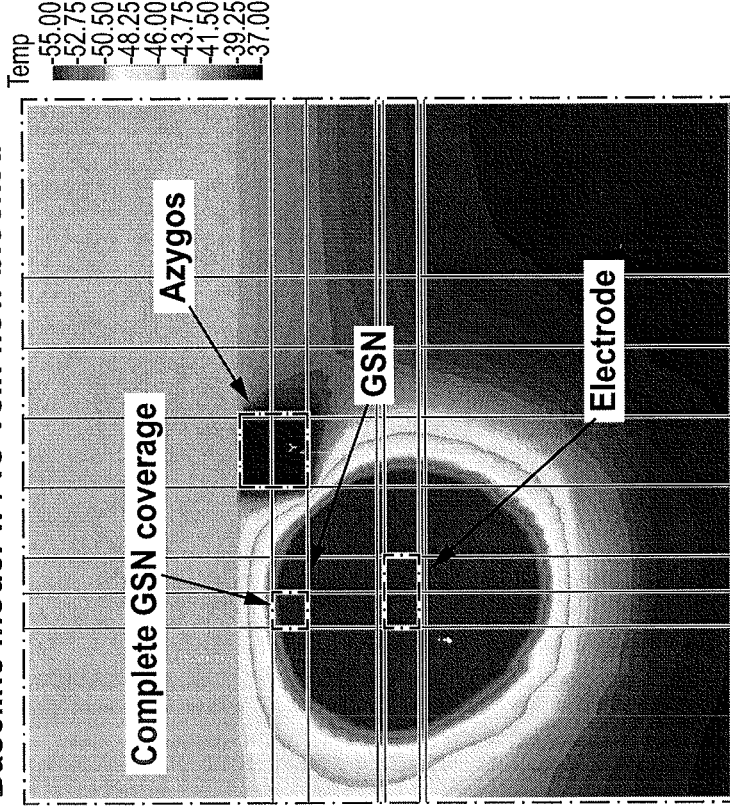
Figure 42F:
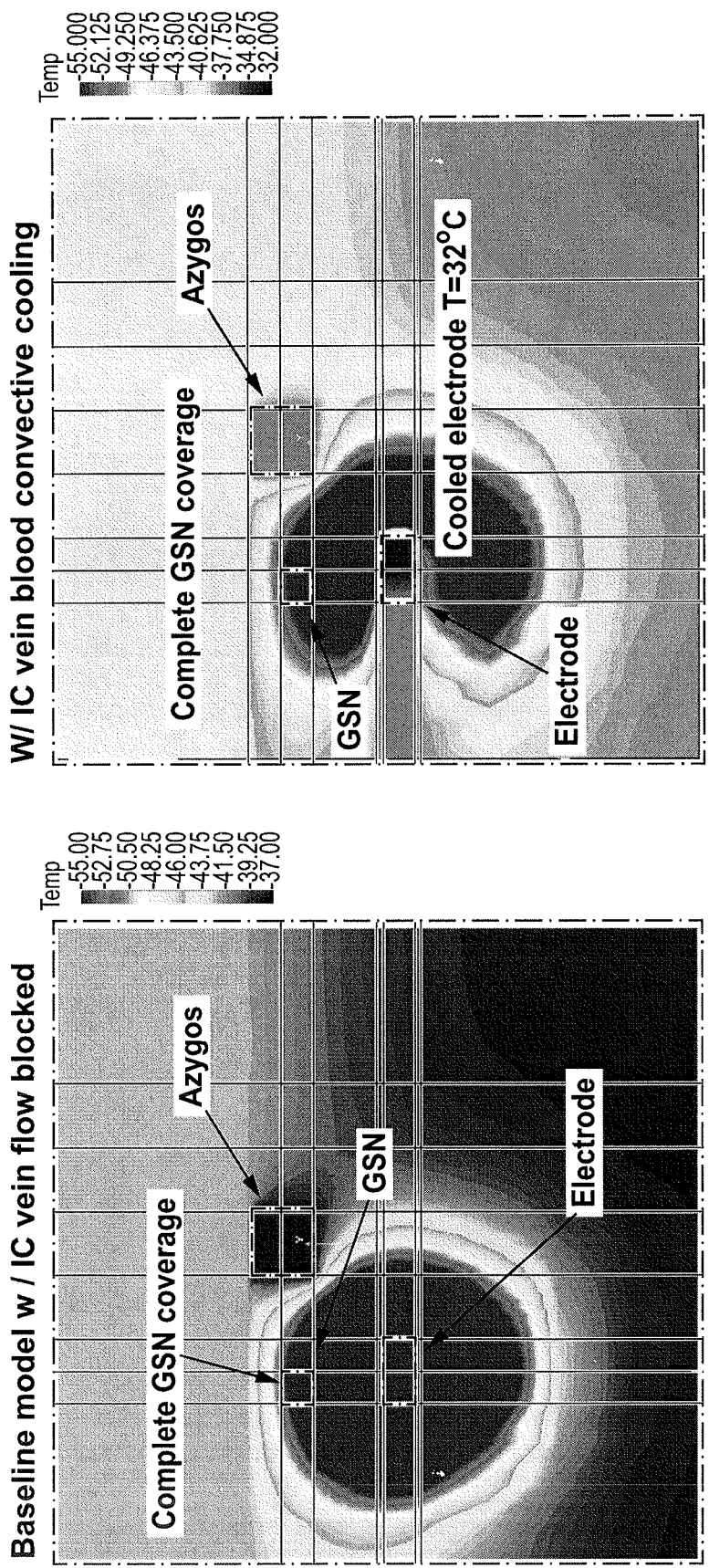
FIG. 42F is an illustration of a finite element model showing an effect of creating an ablation from an occluded vein compared to an irrigated electrode in a non-occluded vein.

To demonstrate this concept finite element models are shown in FIGS. 42E and 42F. FIG. 42E shows two finite element models that compare a scenario shown on the left in which blood flow in an intercostal vein is blocked to a scenario shown on the right in which blood flows up to an electrode inhibiting thermal rise in the electrode and some of the surrounding tissue. In both scenarios the same power (10.5 W), tissue impedance (167Ω), and duration (120 s) were applied. A target TSN located 4 mm from the electrode is heated above 55° C. indicating effective ablation on the left scenario. In the scenario on the right the target TSN is not warmed as much possibly indicating a less effective ablation. FIG. 42F shows two finite element models that compare a scenario on the left in which blood flow in an intercostal vein is blocked to a scenario shown on the right in which blood flows up to the electrode and additionally the electrode is irrigated with a fluid such as saline having a temperature of 32° C. in a closed-loop mode. For example the irrigating fluid may have an initial temperature equal to room temperature and as the fluid travels through the catheter in the patient's vasculature, it warms up slightly. Therefore, the resulting temperature of the RF electrode is somewhat higher than the room temperature, but lower than the body temperature justifying a temperature of about 32° C. An irrigating fluid temperature range of 4 to 35° C. may result in equivalent effects. Both scenarios apply the same tissue impedance (167Ω) and duration (120 s) however the left scenario applies a power of 10.5 W while the irrigated scenario on the right applies a higher power of 16.3 W. The target TSN in the irrigated scenario is warmed above 55° C. indicating ablation. Additionally, the vein wall that is in contact with the irrigated electrode is maintained at a lower temperature, which may prevent vein closure during delivery of ablation energy.

Balloon Catheter to Hold Vessel Open and Occlude Blood Flow

Figure 43C:
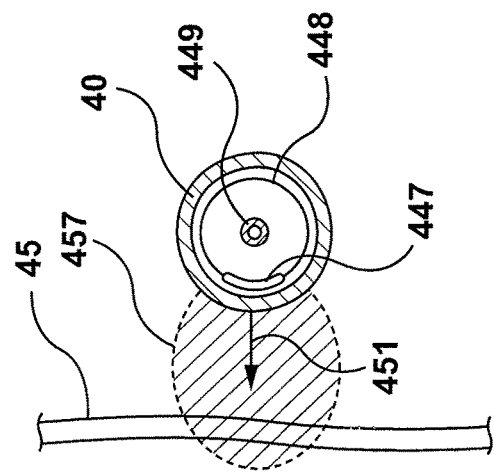
FIG. 43B to 43F are schematic illustrations of a TSN ablation catheter configured to orient ablation elements in a direction of a target nerve when the catheter is couple to the ostium.
Figure 43B:
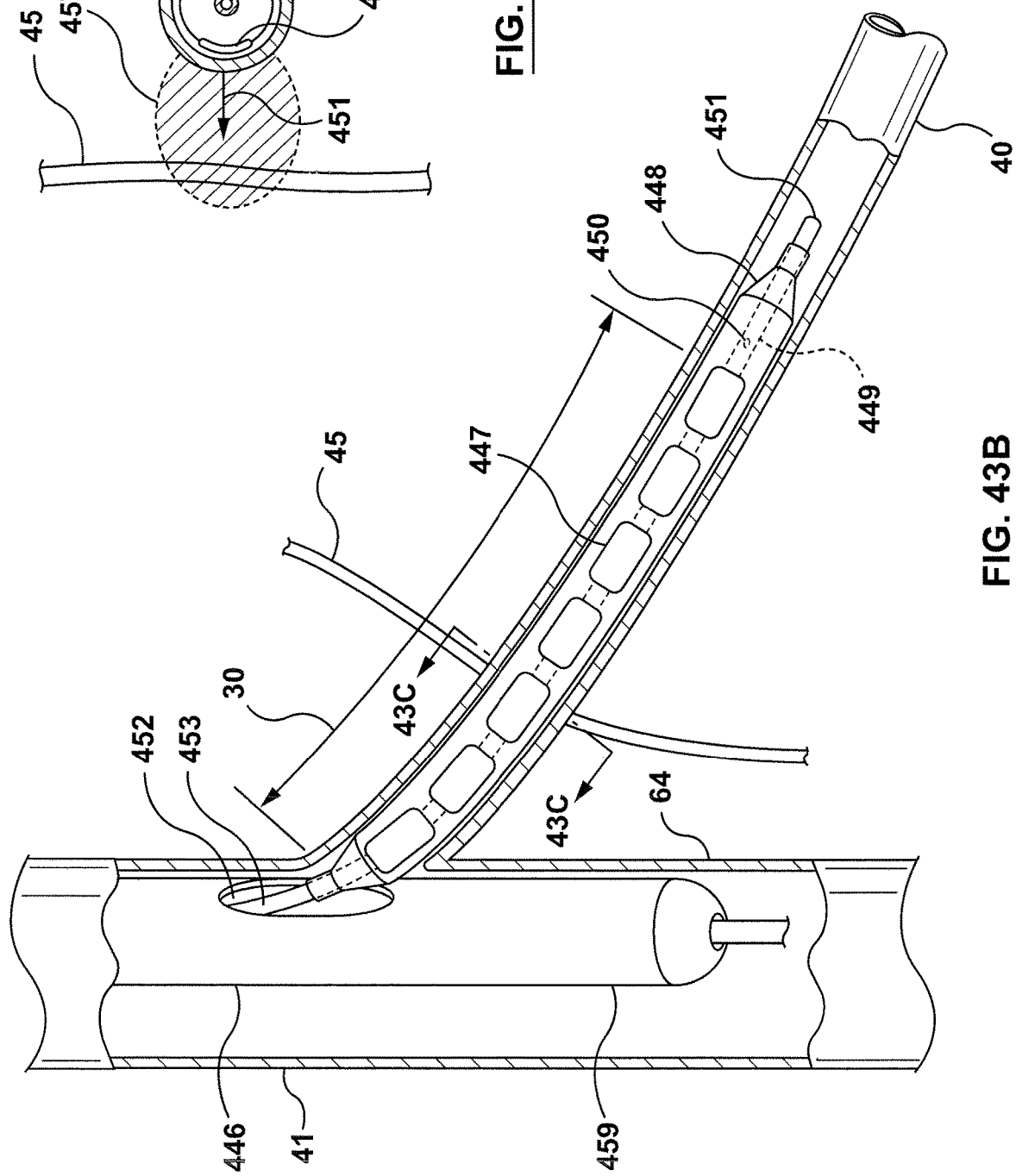

An alternative embodiment of a TSN ablation catheter is shown in FIG. 43A to 43F. FIG. 43B shows an energy delivery element(s) 447 in the form of multiple electrodes mounted on the surface of a deployable balloon 448. The balloon 448 may have a diameter about equal to the inner diameter of a targeted region 30 of an intercostal vein 40 (e.g., 2 mm, 2.5 mm, 3 mm, 3.5 mm) and when inflated the balloon may fill or slightly distend the vein, which prevents blood from flowing over the energy delivery element(s) 447, positions the energy delivery element(s) into firm apposition with the vessel wall, may prevent the vessel from collapsing, and may position energy delivery elements slightly closer to the target nerve. These features may mitigate the effect of variable thermal and electrical properties during energy delivery, which may facilitate a more precise, safe and effective nerve ablation procedure. Furthermore, by maintaining vessel patency, blood may flow through the vessel after the device is removed and if it is necessary to repeat the nerve ablation procedure at a later time a device may be delivered to the patent vein. As shown, the balloon 448 is relatively long and slender and configured to position energy delivery element(s) 447 within the range 30 where the target nerve may cross. For example, the balloon 448 may have a length in a range of 2.5 cm to 4 cm (e.g., about 3 cm). Materials and methods of manufacturing balloons for catheters are known in the art. The balloon 448 may be mounted to or carried by a shaft 449 having an inflation port 450 located in the balloon and in fluid communication with a lumen to a proximal region of the catheter to inject or remove air or fluid such as saline to inflate or deflate the balloon. Optionally, the shaft 449 may comprise a lumen 451 for delivering over a guidewire. The lumen 451 may also be used to inject a radiopaque contrast agent into the intercostal vein 40 to assess if the balloon 448 is sufficiently occluding the vein. As shown, the energy delivery element(s) 447 may comprise multiple electrodes mounted to the surface of the balloon 448 (e.g., manufactured as a flex circuit). The electrodes may be oriented on a side of the balloon 448 so they aim in a direction 451 (e.g., the same direction, or a radial direction in a range of 0 to 45 degrees of one another) toward the target nerve 45 as shown in FIG. 43C, which is a cross section taken along the line 43C-43C on FIG. 43B. Optionally, the energy delivery element comprises multiple energy delivery elements configured for bipolar or multipolar or multiphasic RF delivery. Alternatively, the energy delivery element may comprise a single, long, flexible electrode. Alternatively, electrodes may be oriented around the balloon to generate a circumferential ablation. Energy delivery element(s) 447 may be electrically connected to conductors that pass through the catheter to the proximal region of the catheter where they may be connected to a computerized ablation console, which may also function to deliver a nerve stimulation signal to the energy delivery element(s) 447.

Optionally, the balloon 448 may be inflated with circulating fluid that removes heat from the electrode(s) 447 and a small region of tissue such as the vein wall allowing a greater amount of power to be delivered so an ablation zone is increased in depth, which may be particularly advantageous in patients having a greater distance between a targeted intercostal vein 40 and target nerve(s) 45.

The balloon catheter may be delivered to an intercostal vein 40 through a delivery sheath positioned in a vein 41 of the azygos vein system and optionally over a guidewire.

Alternatively as shown in FIG. 43B the balloon catheter may be delivered into an intercostal vein 40 from a parent catheter 446 configured to couple with ostium 64. The parent catheter 446 is configured to deploy the balloon catheter from a side port 452 with the electrodes 447 always in the same orientation with respect to the parent catheter 446, which allows a configuration with electrodes aiming toward target nerves. For example, in FIGS. 43A, 43B and 43D the parent catheter 446 comprises a side port 452 directed to the right; the balloon catheter 453 is always oriented in the parent catheter with its electrodes facing forward (out of the page) because it comprises at least a portion of a shaft 454 that is square or another shape that is rotationally constrained in a mating lumen 455 of the patent catheter's shaft 456 as shown in FIG. 43E. When the balloon catheter is advanced from the side port 452 the electrodes 447 maintain a forward facing (out of the page) orientation. When positioned in a patient's right side intercostal vein 40, the electrodes 447 aim anteriorly, which is toward the target nerve. An embodiment in which energy delivery element(s) are oriented toward a target nerve only may use less power to make an effective ablation, may cause less collateral injury (e.g., be less painful or heal quicker), may be safer by minimizing the ablation zone 457. The tortuous vascular pathway to access the targeted intercostal vein may make it difficult to precisely transmit torque along a catheter to a distal region to orient an energy delivery element in a direction toward a target nerve. However, it may be easier to transmit torque along a catheter 446 to a distal region 458 to orient the side port 452 toward an intercostal vein 40 because the catheter 446 may have a larger diameter (e.g., 15 to 18 Fr), more wiggle room in the azygos, and less tortuosity compared to a catheter that fits in an intercostal vein.

Figure 43D:
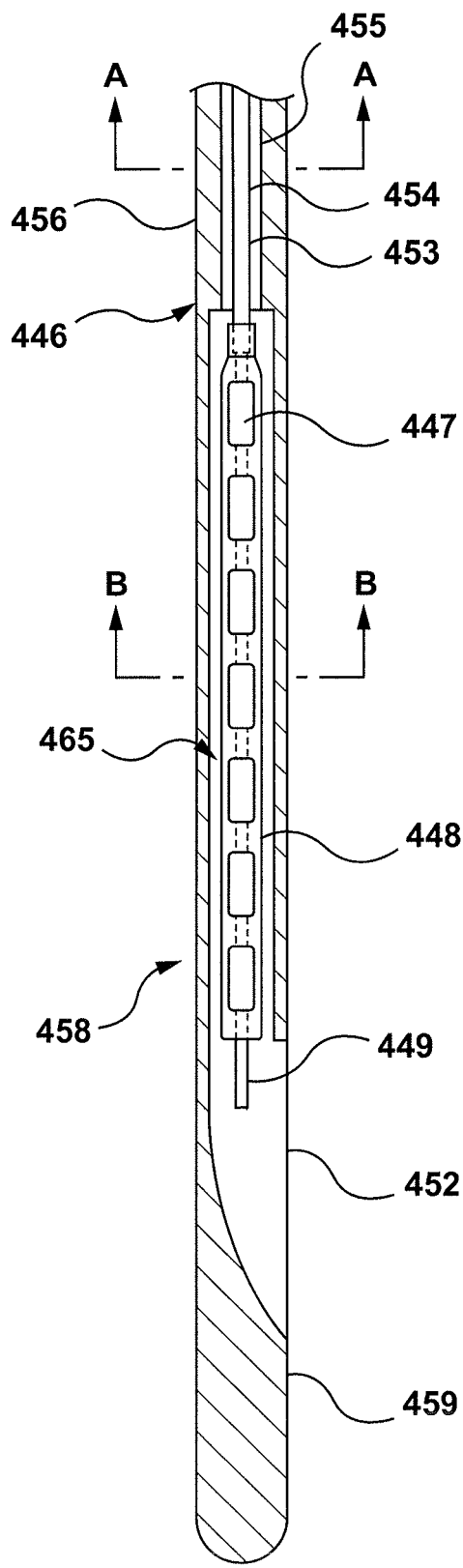
Figure 43E:
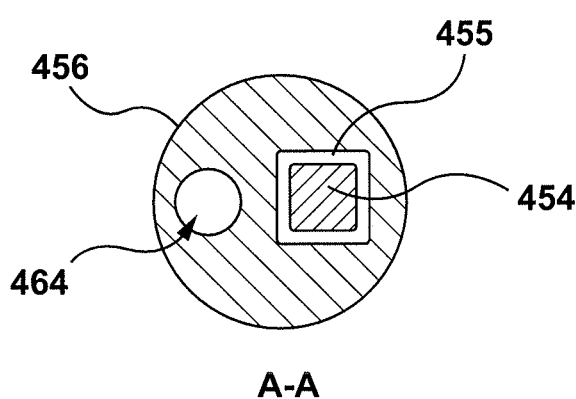
Figure 43F:
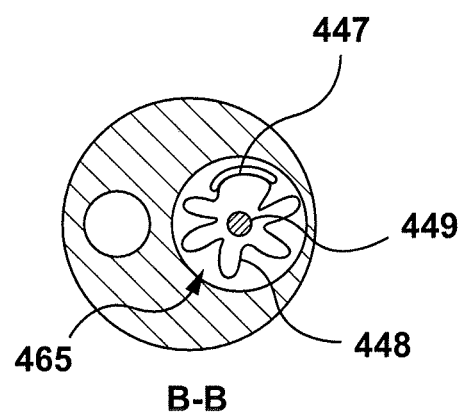

The catheter 446 may further comprise a portion of shaft 459 that extends beyond the side port (e.g., by a length of about 1 to 2 cm) as shown in FIGS. 43A, 43C, and 43D. When the balloon catheter 453 or in other embodiments a guidewire or other ablation catheter is deployed from the side port 452 into an intercostal vein 40 and gentle forward force 461 is applied to the catheter 446 the portion of shaft 459 and side-extending catheter (e.g., 453 in FIG. 43B or guidewire 460 in FIG. 43A) form a bifurcation that couples and pushes against the inferior edge 462 of ostium 64 (FIG. 43A). This configuration provides an anchoring force to maintain a fixed position during energy delivery. Furthermore, this configuration pushes the shaft of catheter 446 against the ostium 64 diverting blood flow in the azygos vein away from the ostium.

Optionally, as shown in FIG. 43A, catheter 446 may comprise a lumen through which a balloon catheter 445 may be delivered to occlude the azygos vein 41 upstream of the targeted intercostal vein 40.

Consoles and Controllers for Different Energy Delivery Modes

The disclosure herein describes methods and devices that can, in some embodiments, reduce the blood flow in a vein prior to delivering ablation energy. In any of these embodiments, there may be a console or other apparatus disposed outside of the patient in communication with an intravascular device. The console may include a computer executable method (e.g., an algorithm) stored on a memory and executable by a processor, the computer executable method comprising a lumen reducing energy mode and an ablation energy mode, wherein the lumen reducing energy mode is, when initiated, adapted to cause a first type of energy to be generated and delivered from an energy delivery element on a medical device, and wherein the ablation energy mode is, when initiated, adapted to cause a second type of energy to be generated and delivered from a second energy delivery element on the medical device, the second type different than the first type, and wherein the energy delivery element and the second energy delivery element can be the same element or different elements on the medical device. The different types of energy can be adapted for lumen reducing steps and ablation steps, respectively.

An external device such as a console can be in or put into communication with the intravascular device (e.g., any of the catheters herein), the intravascular device carrying one or more energy delivery elements, wherein the computer executable method is adapted to cause energy delivery to the one or more energy delivery elements.

The ablation energy mode may comprise a lower power energy and may be for a longer duration than the lumen reducing energy mode. For example, the lumen reducing mode can cause the delivery of RF energy with a power in a range of 10 to 20 W for a duration in a range of 5 to 15 seconds, and the ablation energy mode can cause the delivery of RF energy with a power in a range of 2 to 10 W for a duration in a range of 1 to 2 minutes. The ablation energy mode can further comprise an initial delivery of RF energy with power in a range of 5 W to 15 W until a target temperature is reached.

The lumen reducing energy mode can be adapted to stop or initiate a stop in energy delivery in response to a rise in tissue impedance, optionally from about 150 ohms to 250-300 ohms.

The computer executable method can be adapted to, upon receiving an input, initiate the ablation energy mode. The computer executable method can also be further adapted to, upon receipt of the input, stop the lumen reducing energy mode, and optionally automatically initiate the ablation energy mode.

Figure 44:
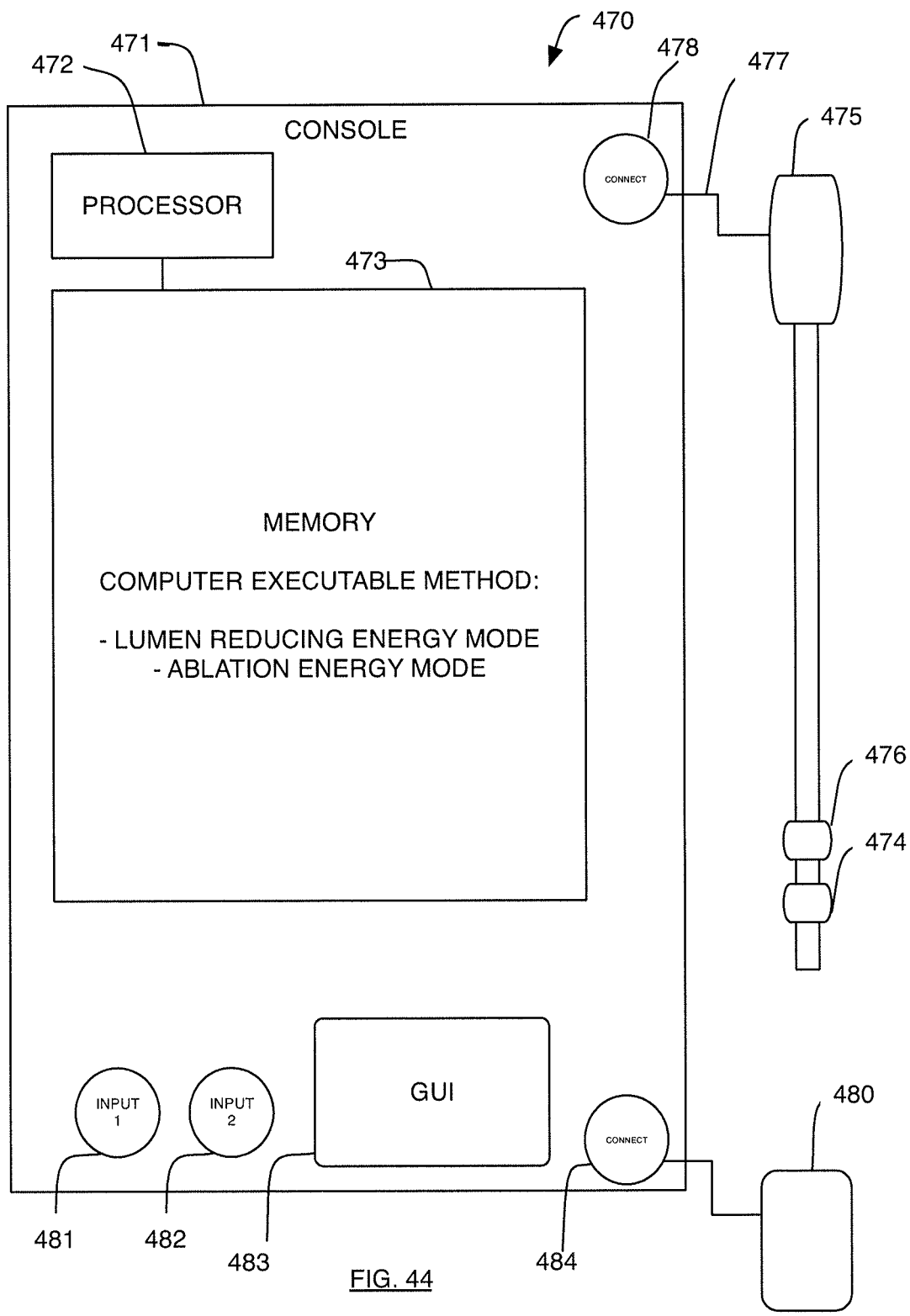
FIGS. 44, 45 and 46 are schematic illustrations of a system for reducing a lumen of a blood vessel and ablating a nerve.

In one embodiment, as shown in FIG. 44 a system 470 comprises a computerized console 471 comprising a processor 472, a memory device 473 comprising a computer executable method. The computer executable method comprises a lumen reducing energy mode and an ablation energy mode, wherein the lumen reducing energy mode is, when initiated, adapted to cause a first type of energy to be generated and delivered from an energy delivery element 474 on a medical device 475, and wherein the ablation energy mode is, when initiated, adapted to cause a second type of energy to be generated and delivered from a second energy delivery element 476 on the medical device, the second type different than the first type, and wherein the energy delivery element and the second energy delivery element can be the same element or different elements on the medical device. The medical device and console are adapted to be connected together for example with an electrical connector cable 477 having a connector 479 that mates with a connector input 478 on the console. The connection between the medical device and console may provide transfer of both lumen reducing energy and ablation energy, as well as feedback signals from sensors on the medical device such as temperature or impedance, and optionally delivery of a nerve stimulation signal. The console may further be adapted to connect to a dispersive ground pad 480 used to complete an electrical circuit for nerve stimulation or RF energy delivery. The console may further comprise user input actuators 481 and 482 such as buttons, dials, touch screen, or foot pedal, which may be used to instigate energy delivery in either lumen reducing mode or ablation mode. The console may further comprise a graphical user interface 483 that displays information to the user such as state of the computer executable method, feedback signals, errors or messages.

Figure 45:
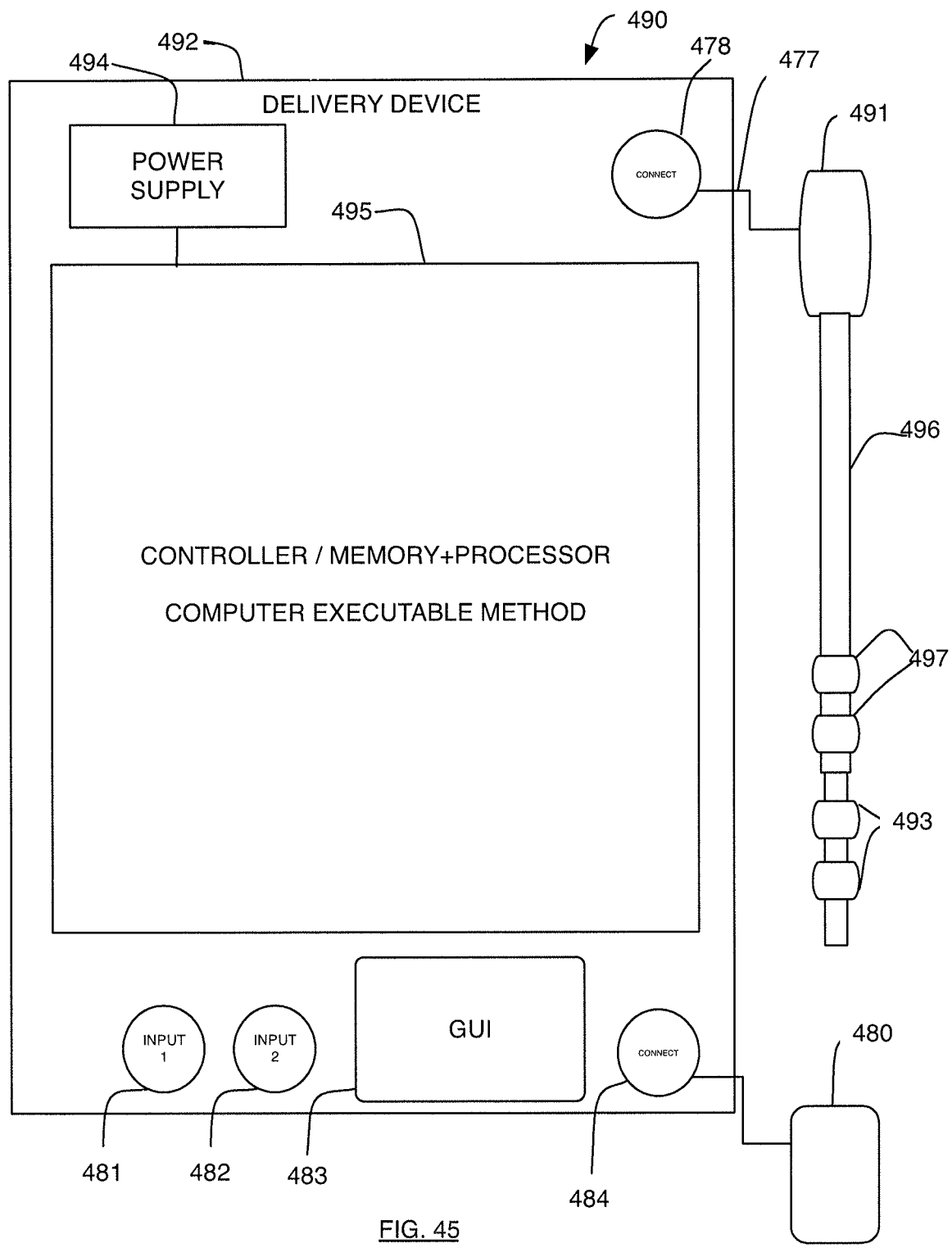

An alternative embodiment of a system 490 is shown in FIG. 45. The system comprises a medical device such as a catheter or elongated shaft 491 having one or more electrodes 493 and a console or delivery device 492. The delivery device may comprise a power supply 494 configured to supply energy to said number of electrodes; a controller 495 connected to the power supply, wherein the controller is configured to execute the following controller steps: when the delivery device is in the lumen reducing energy mode, control the power supply to deliver to one of said number of electrodes the first energy configured to cause a reduction in the size of the vessel lumen, and when the delivery device is in the ablation energy mode, control the power supply to deliver to one or more of said number of electrodes the second energy configured to cause ablation of said target nerve. The medical device 491 may comprise a further elongated shaft 496 with a further number of electrodes 497 carried by a portion of the further elongated shaft; and the delivery device may comprise a power supply configured to supply energy to said number of electrodes and to said further number of electrodes; a controller connected to the power supply, wherein the controller is configured to execute the following controller steps: when the delivery device is in the lumen reducing energy mode, control the power supply to deliver to one of said number of electrodes the first energy configured to cause a reduction in the size of the vessel lumen; and when the delivery device is in the ablation energy mode, control the power supply to deliver to one or more of said further number of electrodes the second energy configured to cause ablation of said target nerve. The first energy configured to cause a reduction in the size of the vessel lumen may comprise delivering an electric signal to said number of electrodes causing one or more of: heating of the vessel wall predetermined temperature, which may conduct heat back to the electrode surface (e.g., an electrical signal that is RF energy); and causing emission from the electrode of a stimulating signal causing contraction of the blood vessel. The second energy configured to cause ablation of said target nerve may comprise delivering ablative radiofrequency electrical current.

Figure 46:
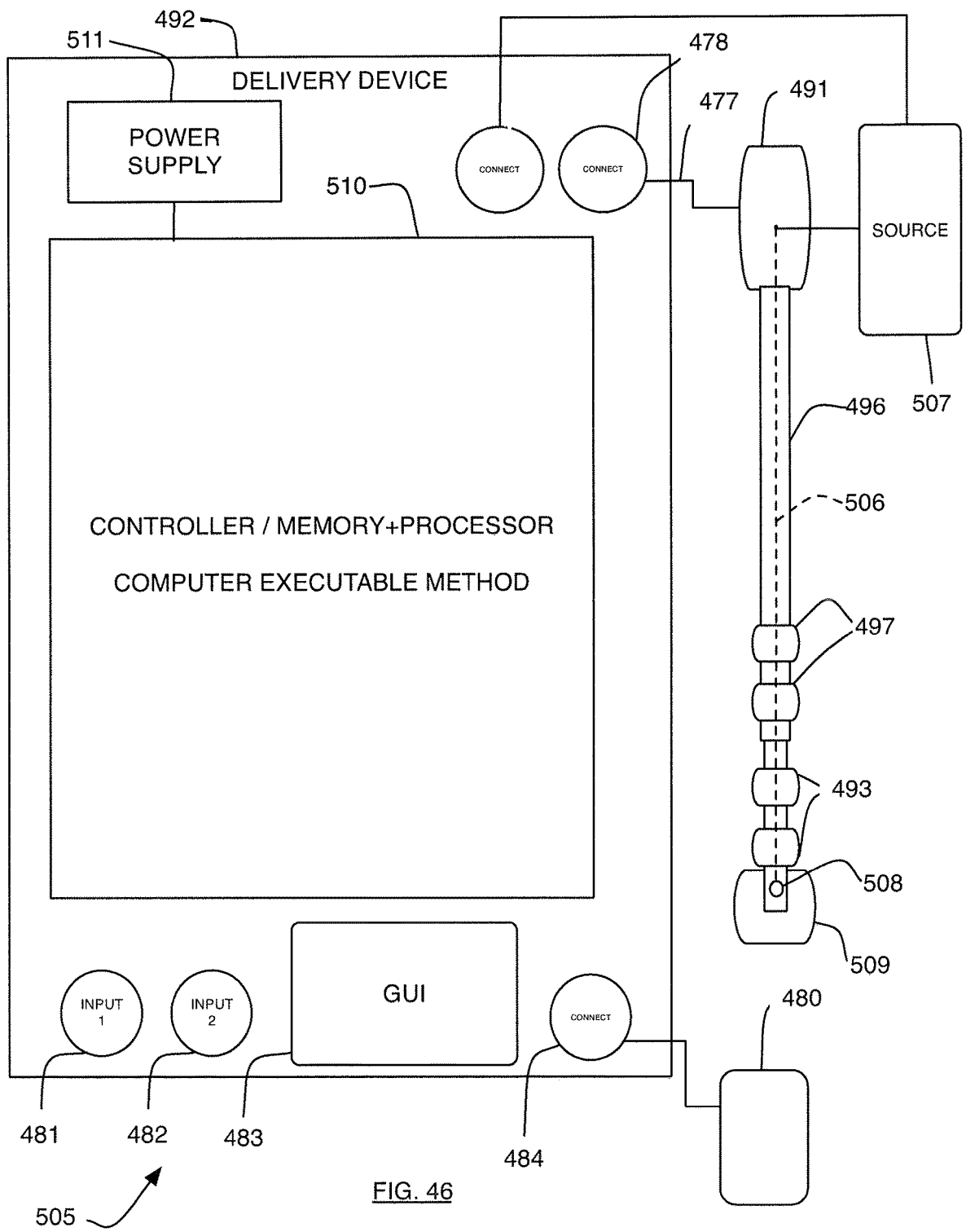

Optionally or alternatively, a system as shown in FIG. 46 may be configured to shrink or occlude the targeted blood vessel with a drug, suction or an occluding balloon. The medical device or elongate shaft may comprise a conduit 506 fluidly connectable to a source 507, including at least one of: a vacuum source or a vasoconstrictor drug source, or a source of balloon inflation fluid. The source may be part of or connectable to the console and the controller of the console may control the source. The conduit may have an aperture 508 located in proximity of the number of electrodes or the conduit supplies a balloon 509 located in proximity of the number of electrodes. The system 505 may comprise a controller 510 connected to the power supply 511 and connectable to the source, said controller being configured to execute the following controller steps: when the delivery device is in the lumen reducing energy mode, control the source to respectively cause one of: suction of fluid through said aperture to cause a reduction in size of the vessel lumen, or delivery of said vasoconstrictor drug through said aperture to cause a reduction in size of the vessel lumen, or supply of the balloon inflation fluid to inflate the balloon and occlude the vessel lumen; when the delivery device is in the ablation energy mode, control the power supply to deliver to one or more of said number of electrodes an energy configured to cause ablation of said target nerve. The controller may be configured to sequentially control said source and then the power supply to first cause one of said suction of fluid or delivery of said vasoconstrictor drug or supply of balloon inflation fluid and, then, delivery of said energy to the number of electrodes, thereby first causing occlusion or partial occlusion of said vessel lumen and then determining ablation of said target nerve. The ablative energy may be for example radiofrequency, ultrasound, or microwave energy.

Protection of the Lung and Visceral Pleura

One reason to choose an intercostal vein closest to the diaphragm as a target vein is to minimize potential injury to the lung from the ablative energy (e.g., thermal energy). Taking reference to FIG. 6B, the target nerves are surrounded by several organs and tissues. Some of them, such as the spine bones, skeletal muscles, diaphragm, and parietal pleura 60 are inherently protected from heat by high blood flow or can sustain scarring without risks to health and life. However, the lung tissue can be perfused relatively poorly and cannot disperse or conduct heat efficiently. The lung is enclosed in a thin membrane called visceral pleura 61. If visceral pleura is damaged and perforated by heat from ablation air can escape into the pleural space 62 and pneumothorax may occur. In the clinical practice a pneumothorax can be mediated by placement of chest tubes but it is preferable to avoid pneumothorax altogether.

In one embodiment the lung may be protected from accidental injury by ablating a target nerve (e.g., TSN or TSN roots) where the lung is retracted and pleural recess is formed. A recess is a pseudo space or potential space in the thoracic cavity where the lung is retracted by inspiration and the parietal pleura 60 is folded upon itself.

There are four recesses of the pleural cavity 62, one behind the sternum and costal cartilages called the costomediastinal recess, one between the diaphragm and chest wall called the costodiaphragmatic recess, one between the diaphragm and mediastinum called the phrenicomediastinal recess, and one between the vertebral bodies and mediastinum called the vertebromediastinal recess. The latter two recesses are of particular interest since they can be used to protect the lung from the accidental ablation by thermal energy during ablation of a target nerve (e.g., TSN or TSN roots).

Figure 23:
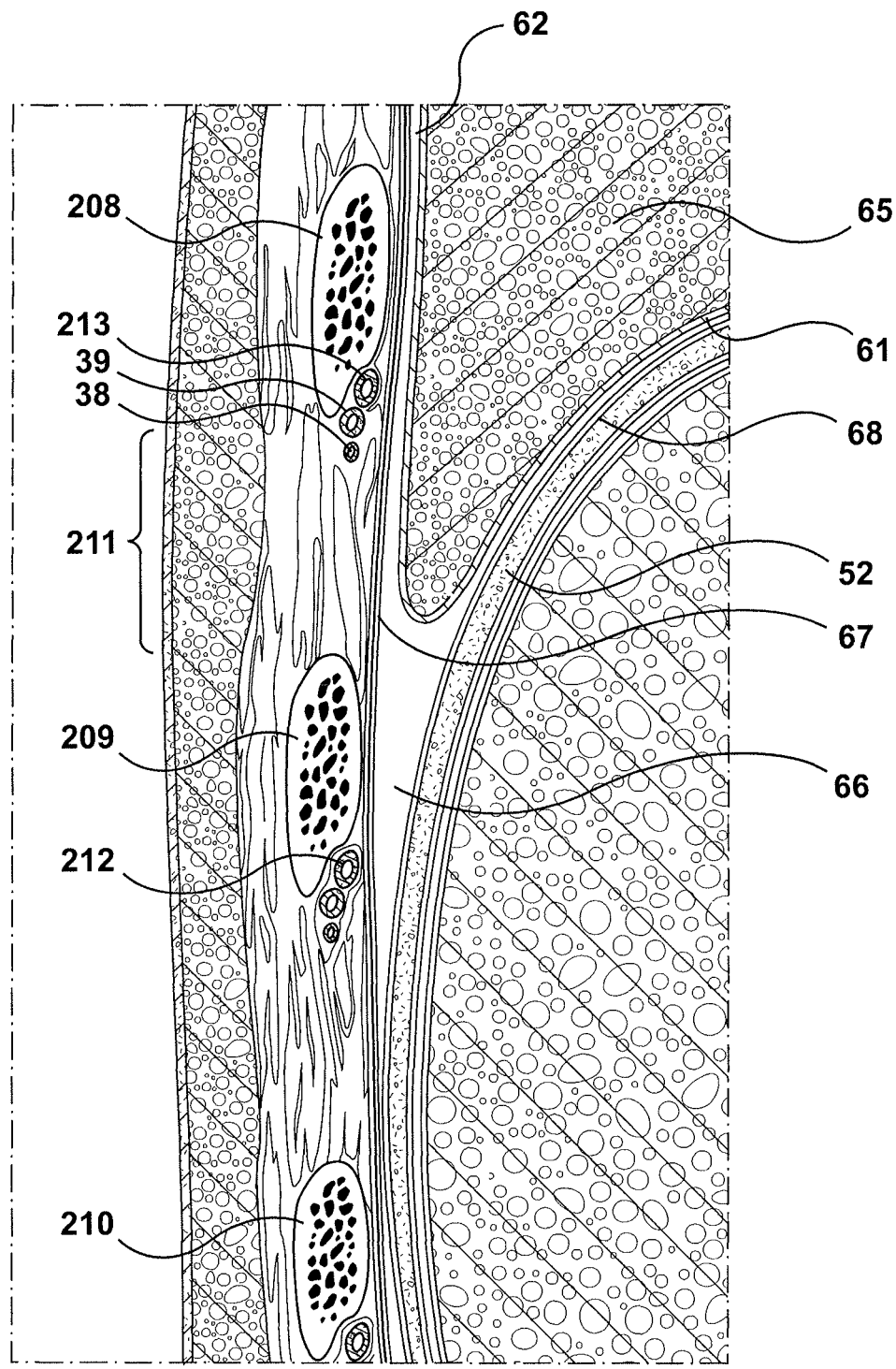
FIG. 23 is a schematic illustration of a frontal cross section of a portion of a patient's chest showing potential target intercostal veins next to an $8^{th}$ rib and a $9^{th}$ rib.

As shown in FIG. 23 the costodiaphragmatic recess 66, also called the costophrenic recess or phrenicocostal sinus, is a potential space in the pleural cavity 62, at the posteriormost tips of the cavity, located at the junction of the costal part 67 of the parietal pleura and diaphragmatic part 68 of the parietal pleura, which is in the costophrenic angle. It measures approximately 5 cm vertically and extends from the eighth rib 208 to the tenth rib 210 along the mid-axillary line. Pleural effusions collect in the costodiaphragmatic recess 66 when in standing position.

During deep inspiration, the lungs fill the pleural cavities, but during quiet ventilation, the lungs do not occupy parts of these cavities. When the lungs are not fully occupying parts of the pleural cavities, portions of the parietal pleura come in contact in the pleural recesses. During forced expiration these recesses extend further. A thoracentesis (pleural tap) is often performed while a patient is in full expiration because of less risk of puncturing the lungs and thereby causing pneumothorax. Similarly, ablation can be performed with the lung moved out of the way enlarging pleural recesses by expiration of air.

Diaphragmatic excursion during normal ventilation is 1 to 2 cm, but can be as high as 5 to 8 cm when a patient exhales forcefully and holds their breath. This will force the lungs above the level of T10. One could ask patient to hold their breath prior to or during ablation. The effectiveness of this approach may be limited in patients with asthma or COPD, and in women.

The costodiaphragmatic recesses 66 are slit-like intervals between the costal 67 and diaphragmatic 68 parts of the parietal pleurae on each side. They become alternatingly smaller and larger as the lungs move in and out of them during inspiration and expiration. The costomediastinal recesses are potential spaces that lie along the anterior margin of the pleura. Here, the costal and mediastinal parts of the parietal pleura come into contact. The left recess is larger because of the presence of a semicircular deficiency, the cardiac notch, in the left lung anterior to the pericardium. The costomediastinal recesses lie at the anterior ends of the 4th and 5th intercostal spaces. During inspiration and expiration, a thin tongue-like edge of the left lung, called the lingula slides in and out of the left costomediastinal recess.

FIG. 23 further illustrates how an embodiment of a therapy can take advantage of a pleural recess during the respiratory cycle to protect the lung 65 or visceral pleurae 61 from damage. The lung is shown retracted by expiration or quiet breathing to the level of the eighth intercostal space 211. Ablation of nerves from the intercostal vein 212 next to the ninth rib 209 is safe since the costodiaphragmic recess 66 at this level does not contain lung tissue. The intercostal vein 213 next to the eighth rib 208 is in close proximity to the lung 65 and visceral pleura 61 and ablating a target nerve from this intercostal vein 213 may carry additional risk of iatrogenic injury causing pneumothorax. A TSN ablation catheter configured to detect if lung tissue is within an ablation zone or safely beyond the ablation zone (e.g., such as catheters disclosed herein) may be positioned in a vessel (e.g., intercostal vein) next to a pleural recess as shown in FIG. 23 to facilitate assessment of a safe location, or to detect motion of the lung to control ablation in concordance with safety.

Figure 24A:
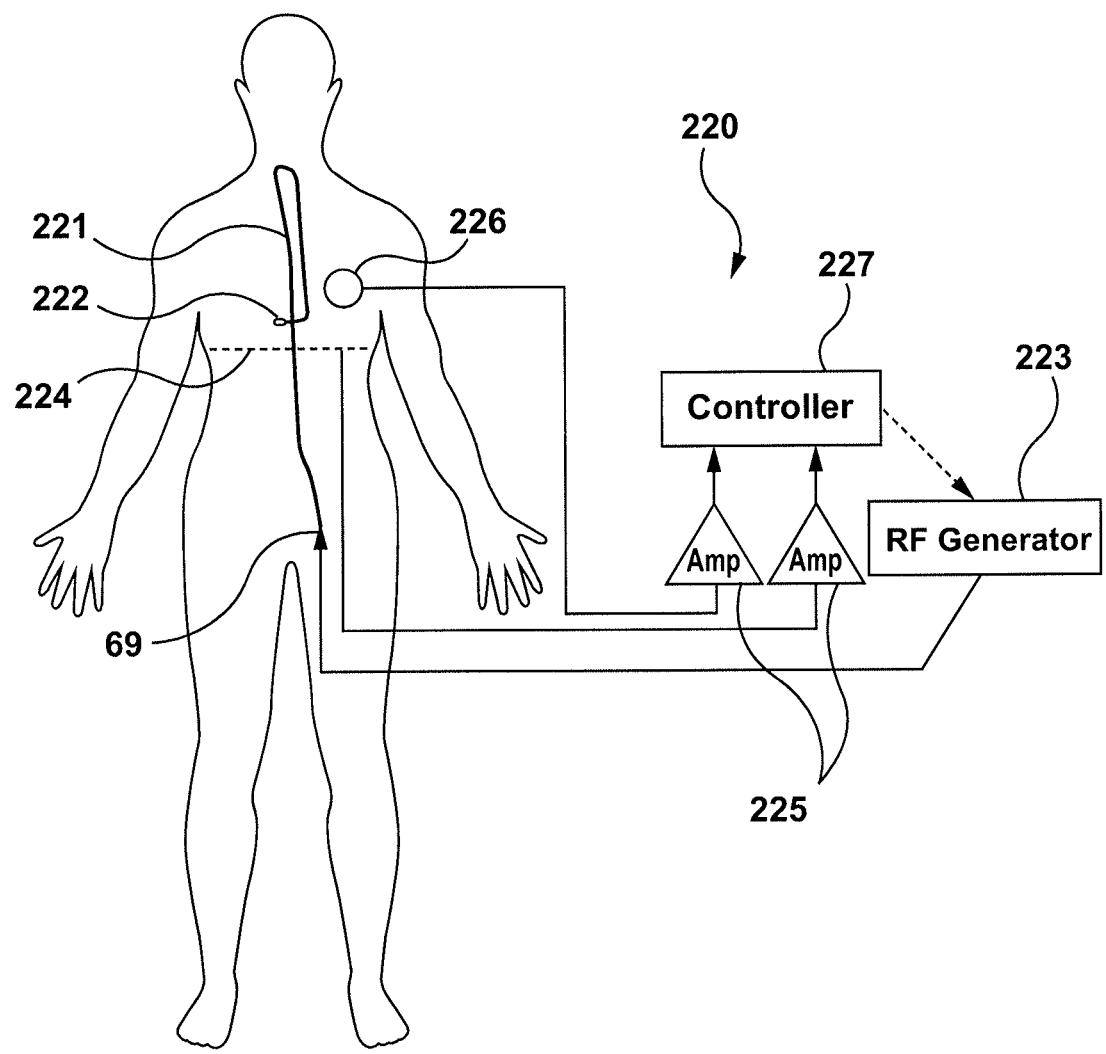
FIG. 24A is a schematic illustration of a TSN ablation system comprising respiratory feedback and control.

FIG. 24A is a schematic illustration showing a system 220 that takes advantage of the retraction of the lung during expiration to increase safety of TSN ablation. An ablation catheter 221 is shown inserted into a femoral vein 69 via an incision in the groin of the patient, threaded through the inferior vena cava into the azygos vein and further into the elected intercostal vein. The catheter is equipped with an energy delivery element 222 that can be an electrode for delivery of RF energy in monopolar or bipolar configuration connected to an external RF generator 223. Respiratory sensors, for example a respiratory belt 224, accelerometers 226 or other, such as impedance-based or ultrasound-based, are connected to amplifiers 225 and to a computer controller 227 that can process and analyze them in real time and determine when the patient exhales or starts inhaling. The delivery of energy can be synchronized or gated to only occur during expiration, or time intervals correlated to expiration. The system may also instruct the patient to preform maximal forced expiration during the ablation to improve safety. In gating to ventilation, which may vary in frequency, the ablation system may adjust power or ablation time in order to maintain total energy delivery.

Figure 24B:
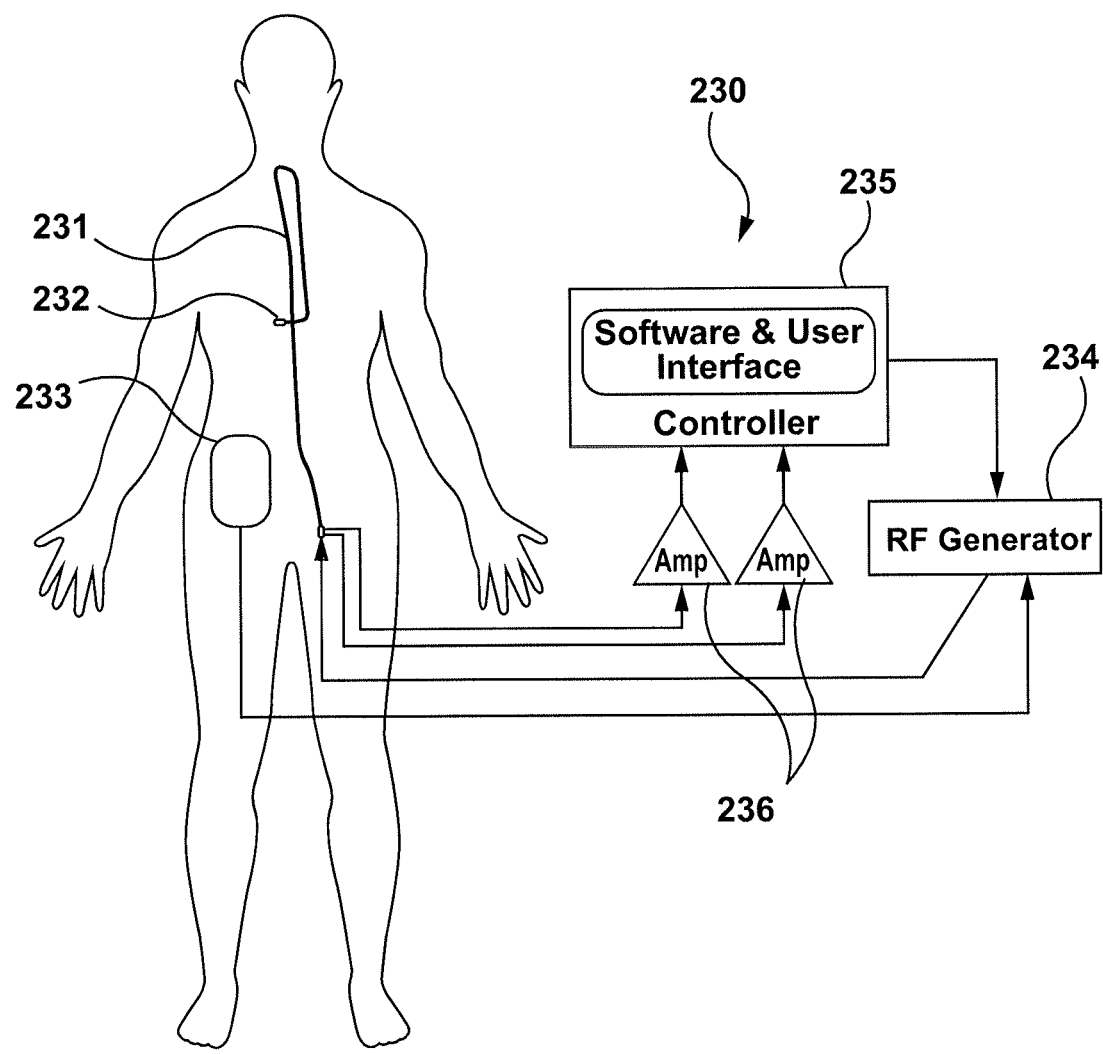
FIG. 24B is a schematic illustration of a TSN ablation system comprising tissue impedance and temperature feedback and control.

As shown in a schematic illustration of FIG. 24B a system 230 may be configured to identify proximity of lung tissue by sensing the impedance measured by an ablation catheter 231 (e.g., configured as monopolar, bipolar, or between an ablation catheter electrode and an external element). Electrical impedance, or impedance-associated parameters such as phase or frequency characteristics, between the catheter electrode 232 and dispersive electrode 233 or between a first electrode and a second electrode may be used to predict presence of the lung in the ablation zone.

Impedance (Z) is a measure of the total opposition to current flow in an alternating current (AC) circuit and is defined in terms of its three individual components: resistance (R), inductance (L), and capacitance (C), and represented by the equation $Z=R+j(\Omega L-1/\Omega C)$. The angular frequency of the current is represented by $\Omega$, and j is the square root of (−1). Impedance can best be understood as the AC correlate of resistance (R) in direct current (DC) circuits (R=V/I), and is likewise expressed in Ohm.

Impedance measurement or "bioimpedance" is a complex variable that reflects resistance and capacitance of tissues in the path of alternating current. It is a function of the excitation frequency at which impedance is measured. Measurement of impedance across several frequencies or frequency ranges is called impedance spectrum or impedance spectroscopy. Resistivity is a measure of any material specific resistance and it is frequently used in relevant literature. It may be adjusted by an electrode calibration constant to correct for small physical differences between electrodes.

Both individual cells and biologic tissue can be ideally modeled with a simple equivalent circuit in which extracellular resistance (Re), intracellular fluid resistance (Ri), and cell membrane capacitance (Cm) are represented. Individual real time measurements of electric current and voltage allow determination of resistance and capacitance at different frequencies. Such circuits and algorithms are well described in literature and the term "impedance" used herein incudes such measurements.

Tissues and physiological fluids have characteristic ranges of impedance values. This principle has been used in select applications to distinguish tissues and confirm anatomic localization of probes and needles.

In prior art many devices used impedance sensing to guide penetration of a surgical probe or to activate the probe (e.g., to apply ablative heat or inject a drug) when the probe tip applicator is in the desired type of tissue. Most common examples include application of heat to tumors that often have impedance different from surrounding liver, kidney, or lung tissue. In such applications the needle or probe is gradually advanced to the desired location whilst impedance is monitored for an expected range. When the targeted location is reached, the probe is immobilized and ablation is performed.

Continuous monitoring of tissue impedance was previously used to guide tissue ablation with RF energy. For example, U.S. Pat. No. 5,447,529 issued Sep. 5, 1995 "Method of using endocardial impedance for determining electrode-tissue contact, appropriate sites for arrhythmia ablation and tissue heating during ablation" used the fact that impedance of tissues decreases with heating.

U.S. Pat. No. 6,569,160 issued May 27, 2003 "System and method for detecting electrode-tissue contact" discloses a system employing closed circuit impedance to monitor electrode contact with tissue including the use of a reference electrode. The system for detecting electrode-tissue contact comprises a catheter having a location sensor and a distal tip electrode. The catheter comprises a reference electrode that is protected from making contact with tissue. The system further comprises a signal generator to transmit test signals to the distal tip and reference electrodes. Tissue contact is detected by comparing a signal across the tip electrode to a return electrode versus a signal across the reference electrode to a return electrode. Ablation energy may be delivered to the distal tip electrode if contact of the electrode with tissue is detected.

Automatic termination of tissue ablation has been proposed in response to impedance changes. U.S. Pat. No. 7,367,972 Francischelli, et al. May 6, 2008 "Ablation system" discloses a system for creating lesions and assessing their completeness or transmurality. Assessment of transmurality of a lesion is accomplished by monitoring the impedance of the tissue to be ablated. Rather than attempting to detect a desired drop or a desired increase impedance, completeness of a lesion is detected in response to the measured impedance remaining at a stable level for a desired period of time, referred to as an impedance plateau.

Automatic monitoring and action (power change) based on impedance signals was also proposed to safely ablate nerves transvenously while protecting non-targeted tissues. For example U.S. Pat. No. 9,345,530 Ballakur, et al. May 24, 2016 "Devices, systems and methods for evaluation and feedback of neuromodulation treatment", and U.S. Pat. No. 9,345,900 Wu, et al. May 24, 2016 "Methods and systems for thermally-induced renal neuromodulation".

"Application of electrical impedance analysis for diagnosis of a pulmonary mass" by Kimura in Chest. 1994 Jun.; 105(6):1679-82, describes differential measurements or resistance and capacitance of lung tissue compared to other tissues and blood. Measured at a frequency of 10 kHz healthy lung tissue had impedance of 6,581 ohms and capacitance of 893 pF while muscle had resistance of 2,252 ohms and capacitance of 2,366 pF. Other sources measured resistivity of lung at 100 kHz at 1,400 ohm×cm and resistivity of muscle at 225 ohm×cm. Since the sensitivity zone for the TSN ablation can include muscle, membranes (e.g., pleurae), blood vessels, fat and lung parenchyma, the system may be calibrated for patients using data collected during natural or controlled breathing.

Figure 25A:
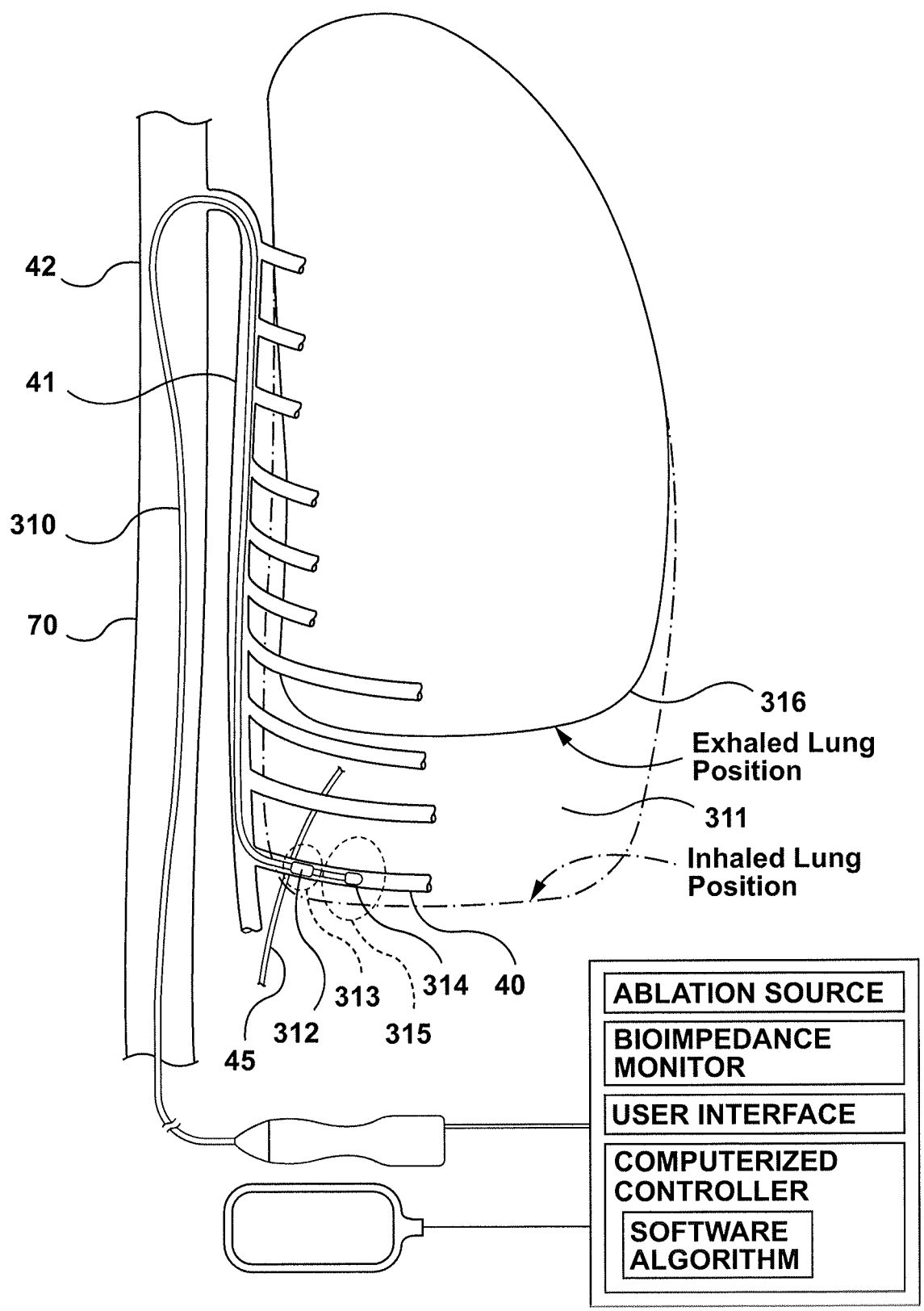
FIGS. 25A and 25B are schematic illustrations of a TSN ablation catheter positioned in an intercostal vein configured to detect proximity of lung tissue to an ablation zone.
Figure 25B:
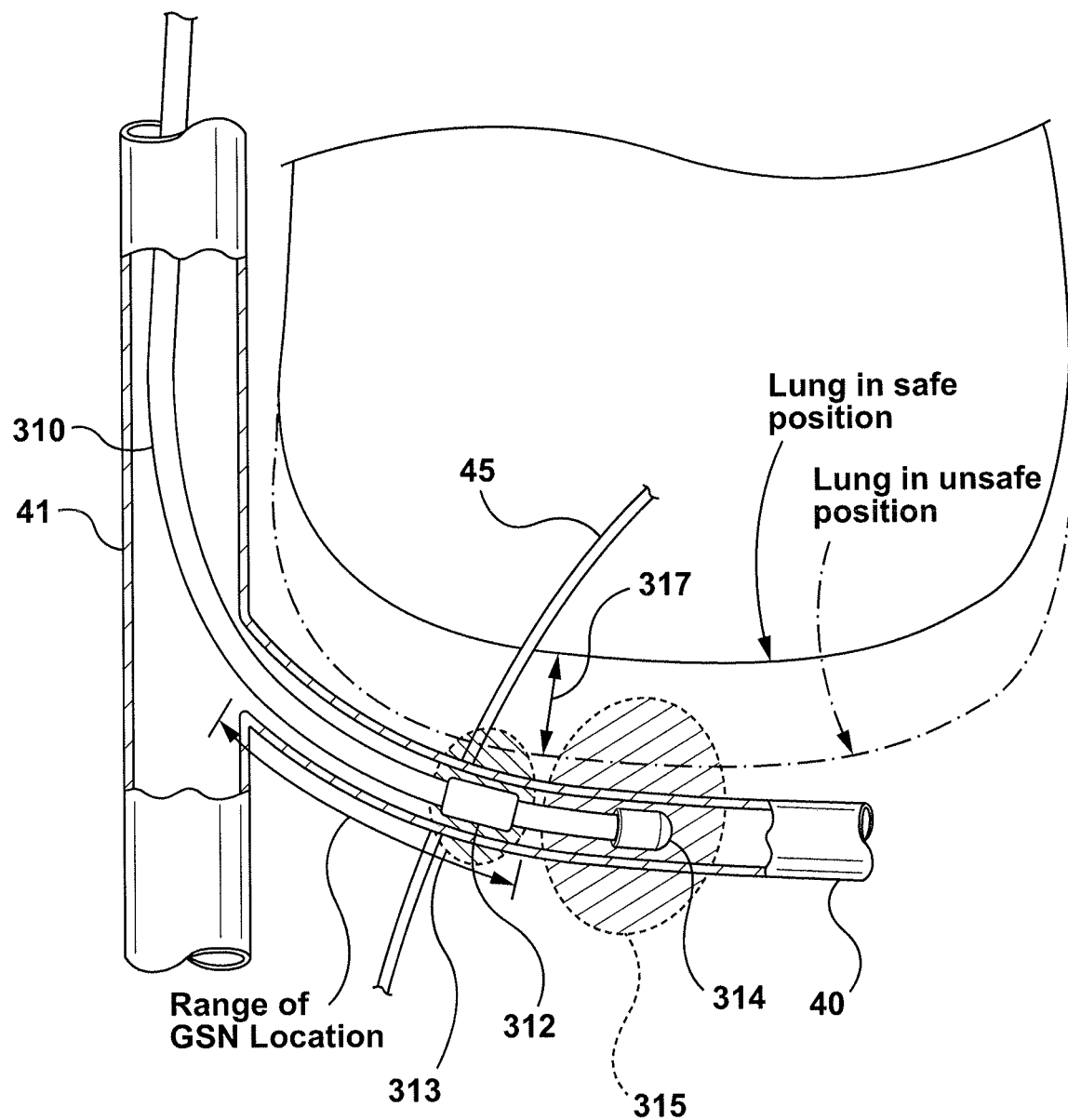

The authors propose a novel use of the bioimpedance measurement during a transvascular nerve ablation procedure to detect if lung tissue is within an ablation zone and control delivery of ablation energy based in part on the detection to avoid collateral injury of the lung tissue, which may move in and out of the ablation zone as the patient breathes. In an embodiment as shown in FIG. 25A an ablation catheter is advanced through the venous system (e.g., introduced to a femoral vein and delivered through a vena cava 70 to a superior vena cava 42 into an azygos vein 41 or azygos vein system) to a location proximate the ablation target (e.g., GSN 45). Said location may be in a posterior intercostal vein 40 next to a pleural recess 311. The ablation catheter 310 may comprise an ablation element 312 such as a radiofrequency electrode having an ablation zone 313 of about 5 mm radius around the electrode. The non-target lung tissue 316 or visceral pleura bordering the lung tissue may be within the ablation zone 313 or may move in and out of the ablation zone. The catheter 310 comprises an impedance-monitoring electrode 314 that is sensitive to tissue within a bioimpedance sensitivity zone 315 around the impedance-monitoring electrode 314. Ablation energy is only applied when lung is not present in the ablation zone. The impedance monitoring electrode 314 may be positioned on the catheter relative to the ablation element 312 such that when the distal region of the catheter is positioned in vessel for ablation of a target nerve detection of lung tissue in the bioimpedance sensitivity zone 315 will provide an accurate indication of lung tissue 316 within the ablation zone 313 or within a safe distance from the ablation zone 313. For example, the bioimpedance sensitivity zone 315 may be adjacent to the ablation zone 313, overlapping the ablation zone, or not overlapping the ablation zone. As shown in FIG. 25B a catheter 310 may be configured with an impedance-monitoring electrode 314 distal to an ablation element 312 such that the bioimpedance sensitivity zone 315 and ablation zone 313 are adjacent but not overlap and when positioned in an intercostal vein the motion of the lung 317 is somewhat perpendicular to the intercostal vein and the lung tissue present in the bioimpedance sensitivity zone 314 coordinates with presence in the ablation zone 312. For example, a catheter configured to have an ablation zone radius of 5 mm and a sensitivity zone radius of about 10 mm, may comprise a distance between the ablation electrode and impedance-monitoring electrode of at least 15 mm (e.g., between about 15 and 20 mm). Since tissue impedance changes as it is heated or becomes desiccated, this configuration may provide an impedance measurement that is not influenced by the heating tissue in the ablation zone, which may provide a more accurate detection of lung tissue in the sensitivity zone. In this configuration, although the ablation zone and sensitivity zone do not overlap, the detection of lung tissue in the sensitivity zone may infer that it is not safe to deliver ablation energy when the catheter is placed in an intercostal vein that runs approximately perpendicular to the direction of lung movement. Alternatively, the bioimpedance sensitivity zone may be measured along a vector which transverses the ablation zone, such that information is acquired related to the likelihood of lung tissue extending into the ablation zone.

Since breathing is periodic and the lung may move in and out of the ablation zone, application of energy can be repeated until the targeted tissue is effectively ablated while critical non-target tissue (e.g., the lung or visceral pleura) is protected. This application of bioimpedance monitoring and ablation control may be particularly advantageous to detect proximity of lung tissue since it is mostly full of air and has a relatively high impedance compared to fibrous tissue, muscle, interstitial fluid, and blood.

In general, the volume sensitivity of an impedance measurement is a function of the square of the current density in a given tissue volume. A unipolar measurement will have an electrode configuration wherein the highest current density is in tissue adjacent to the active electrode surface. In this way, the measured impedance will be dominated by tissue in the vicinity of the active electrode, and dependent on the area and geometry of the electrode. The impedance data will reflect averaging over the tissue in the dominant sensitivity volume. The smaller the active electrode area, the higher the obtained spatial resolution. For example, for a hemispheric electrode in a homogenous medium, 90% of the measured resistance is expected to be due to the volume within a radius ten times the radius of the electrode. An impedance-monitoring electrode in monopolar configuration (e.g., the electrical circuit is through tissue to a dispersive electrode on the patient's skin) of embodiments disclosed herein may have a diameter in a range of 1.5 to 2.5 mm. In this configuration measured impedance will predominantly reflect impedance of tissue in a radius of approximately 10 mm around the electrode. This zone is herein referred to as a "sensitivity zone". An ablation zone, or radius within which temperature is sufficiently high to cause permanent tissue damage, for embodiments of RF ablation of the TSN is expected to be within 5 mm of the ablation electrode surface. Thus, the sensitivity zone is greater than the ablation zone and the impedance monitoring should be able to detect the presence of lung tissue within the sensitivity zone as it approaches the ablation zone and stop delivering ablation energy before the lung tissue enters the ablation zone.

Figure 34:
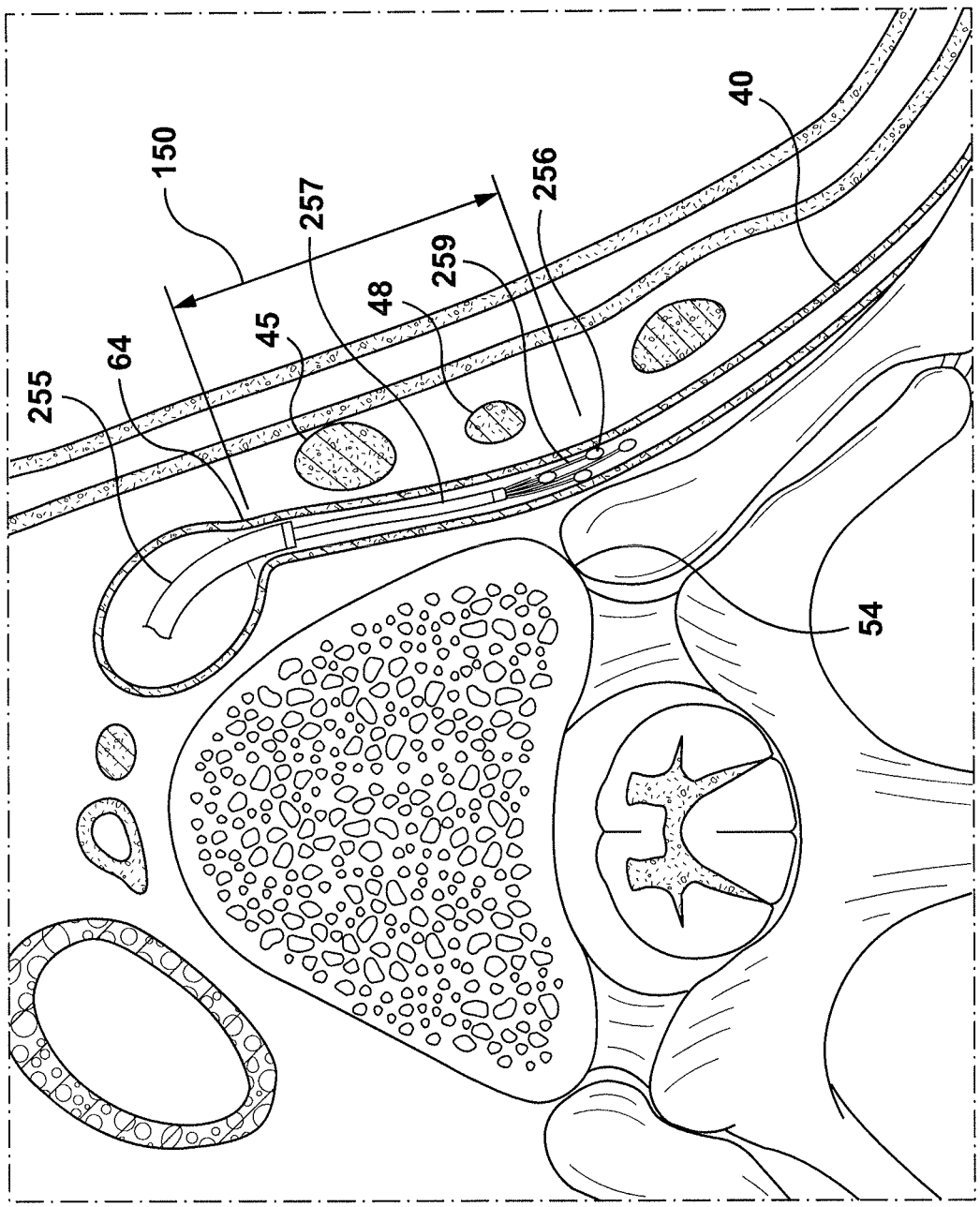
FIGS. 34 and 35 are schematic illustrations showing use of a TSN ablation catheter comprising multiple ablation elements.
Figure 35:
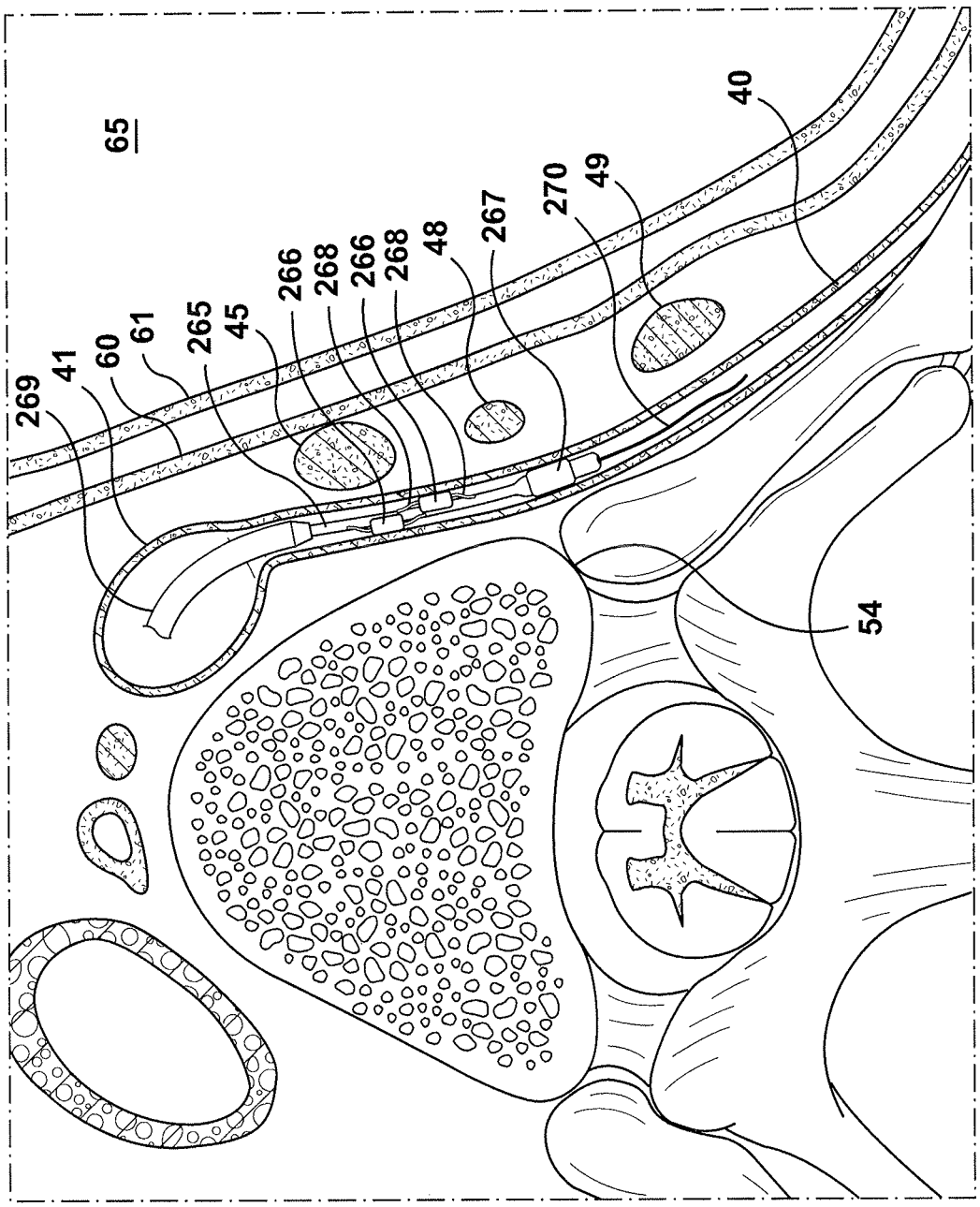
Figure 36:
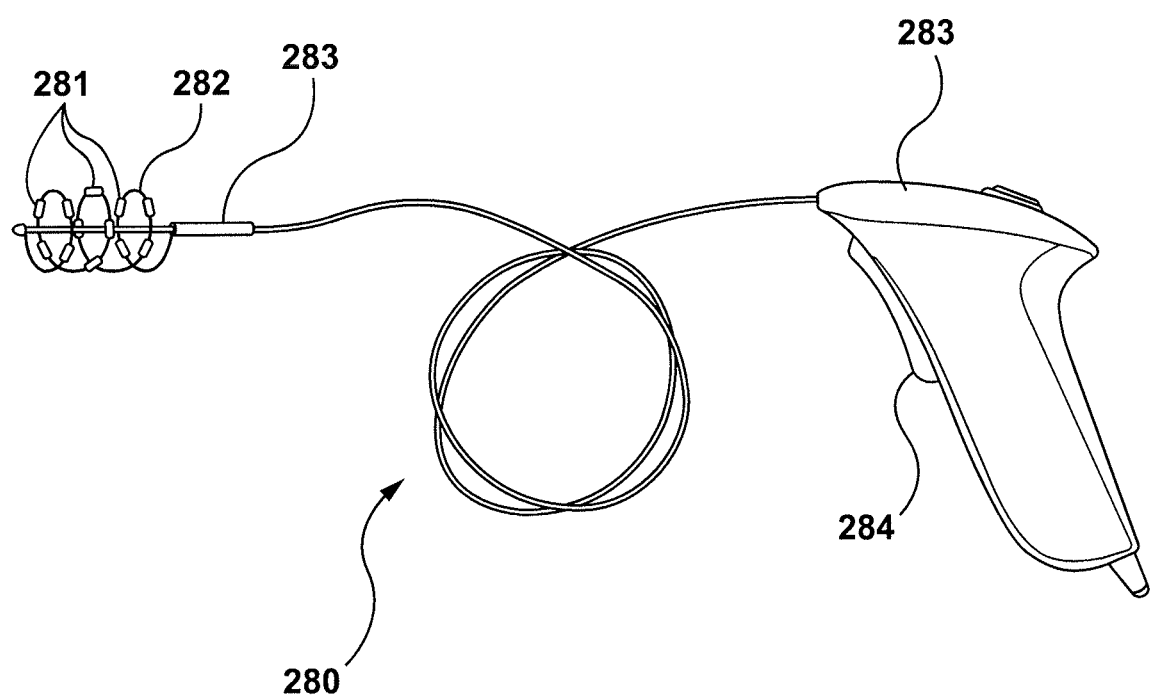
FIG. 36 is a schematic illustration showing a TSN ablation catheter comprising multiple ablation elements positioned on a deployable helical structure.

The catheter shown in FIGS. 25A and 25B comprises one ablation element 312. However, the ablation element may be an RF electrode in monopolar mode, a pair of RF electrodes in bipolar mode, multiple RF electrodes in monopolar or bipolar configuration positioned within the range of TSN location 313, a sliding RF electrode that slides along the catheter shaft within the range of TSN Location while the bioimpedance measuring electrode 314 remains in a stationary position, one or more RF electrodes positioned on a deployable structure such as splines, a balloon, helix or struts as shown in FIGS. 34, 35 and 36 or another form of ablation element such as an ultrasound transducer, cryogenic applicator, or chemical injection needle.

Figure 26:
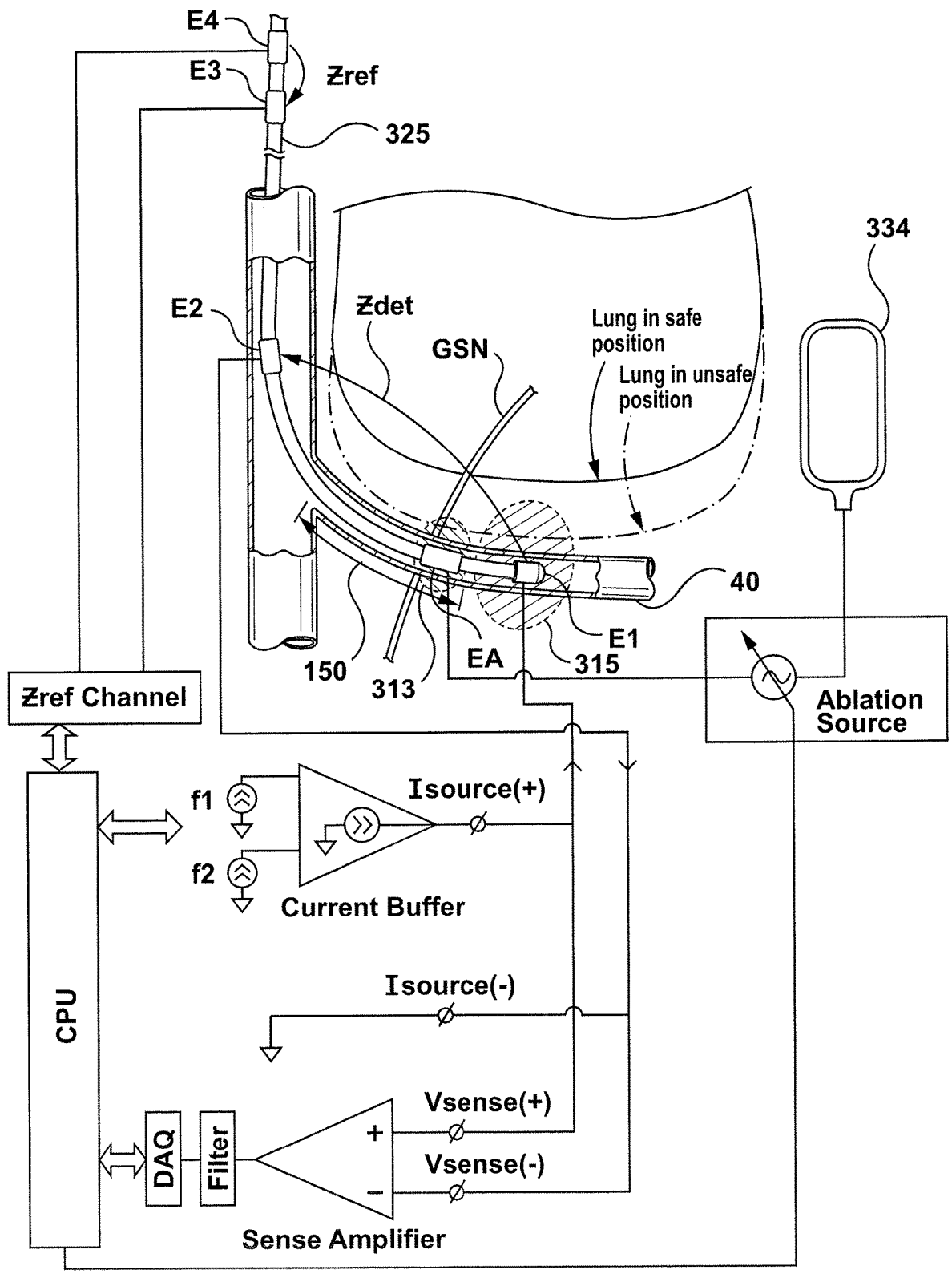
FIG. 26 is a schematic illustration of a system for transvenous TSN ablation configured to ablate a target nerve while safely avoiding injury to lung tissue.

FIG. 26 illustrates an embodiment of a system for transvascular TSN ablation configured to detect safe or unsafe proximity to lung tissue as the lung moves and to deliver ablation energy when the lung tissue is a safe distance from the ablation zone. Catheter 325 is fed into the intercostal vein 40 according to previously described procedures. Catheter 325 carries several electrodes: bioimpedance electrodes E1 and E2, bioimpedance reference-channel electrodes E3 and E4 and ablation element (e.g., RF ablation electrode EA completing a circuit through the patient's body to a dispersive electrode 334). For the purpose of describing the concept of regulating ablation energy based on lung-related bioimpedance feedback, this paragraph presents a bipolar impedance measurement subsystem, which controls a unipolar ablation source. One of skill in the art would know how to apply the invention, without deviating from its essence, by applying equivalent concepts to measure unipolar impedances or to drive bipolar ablation energy sources or configurations. Also, while we illustrate a two-electrode impedance measuring technique, three- or four-electrode impedance measuring techniques may be used. Furthermore, the ablation element EA alternatively may be for example, an RF electrode in monopolar mode, a pair of RF electrodes in bipolar mode, multiple RF electrodes in monopolar or bipolar configuration positioned within the range of TSN location 313, a sliding RF electrode that slides along the catheter shaft within the range of TSN Location while the bioimpedance measuring electrode 314 remains in a stationary position, one or more RF electrodes positioned on a deployable structure such as splines, a balloon, helix or struts as shown in FIGS. 34, 35 and 36 or another form of ablation element such as an ultrasound transducer, cryogenic applicator, or chemical injection needle.

Figure 27:
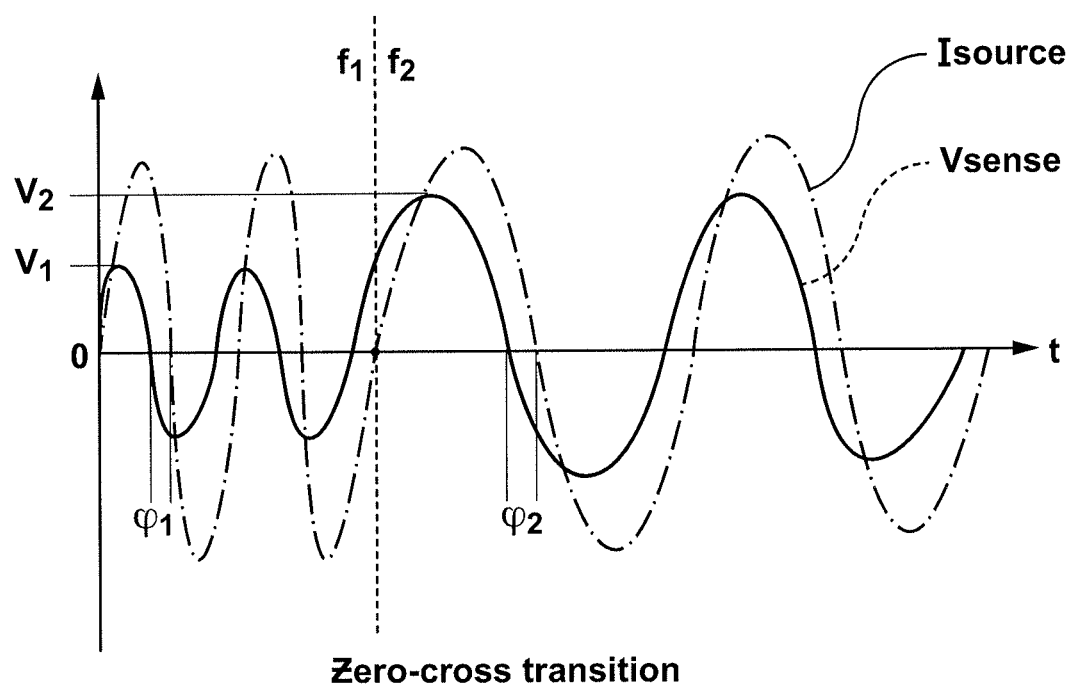
FIG. 27 is a plot showing two frequencies used to identify complex impedance parameters of a bioimpedance sensitivity zone.

Electrodes E1 and E2 are driven by a constant current travelling between Isource(+) and Isource(−). Preferably, this current source applies current waveforms of at least two different frequencies, f1 and f2. For example, f1 and f2 may be between 500-1000 kHz and between 10-100 kHz, respectively. Other ranges may be used. For example, results equivalent to those achieved by the present embodiment may be obtained with f1 and f2 in the range of 5 kHz-5 MHz. Current waveforms f1 and f2 may be applied sequentially (e.g., frequency f1 precedes waveform of frequency f2), or simultaneously. If applied sequentially, as shown in FIG. 27, it is important to ensure that the waveform transition from f1 to f2 and back to f1 occurs at zero-crossings. This helps preserve an average value of zero for the overall current waveform, even over short time intervals. In turn, this minimizes the chances of inadvertent tissue or cardiac stimulation at the waveform transition points.

Alternatively, rather than applying waveforms of discrete frequency values, the current source Isource on FIG. 26 (Isourse− and Isourse+ from FIG. 26) may sweep its operating frequency within a range of values, such as those described above. To comply with patient safety, it is important to limit the applied current magnitude to levels stipulated by international medical safety standards, such as IEC 60601-1. For example, if f1=1000 kHz the corresponding current magnitude may be 10 mA. For f2=100 kHz, its corresponding magnitude may be 1 mA.

Figure 28:
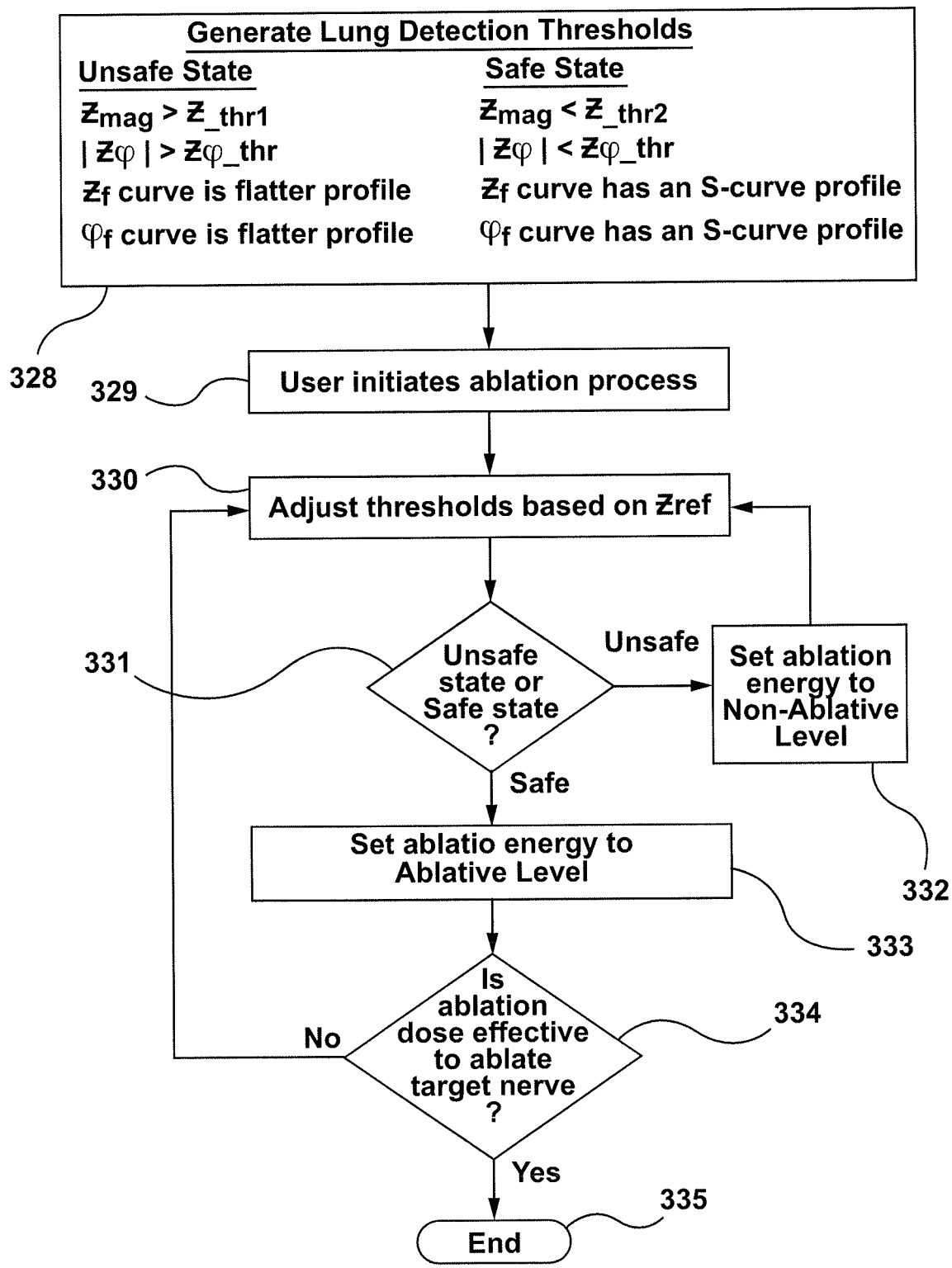
FIG. 28 is a flowchart of a computerized algorithm for ablation and lung detection.

The resulting voltage across E1 and E2 (FIG. 26) is then sensed by the sensing module Vsense (see FIGS. 26 and 27). Vsense is the sensed voltage on the bioimpedance electrodes E1 and E2 passed to a data acquisition system (DAQ) and to the CPU. The sensed voltage is amplified and conditioned accordingly. For example, a bandpass filter with two bands, one centered on f1 and one on f2, respectively, may be used. The filters may be implemented as analog filters, connecting at the output of the Vsense amplifier. Alternatively, just one wider band analog filter may be placed at the output of the Vsense amplifier, allowing both f1 and f2 to pass through but filtering out higher and lower frequencies. In such case, digital filters may be employed to extract the information carried by frequencies f1 and f2. Other filtering techniques may be used, such as phase-locked loops, FFT-based filters, etc. Of course, any such digital filtering element would reside after the data acquisition (DAQ) element, which serves the function of digitizing the conditioned Vsense. The data are then passed to a control unit (CPU), which processes the information further and implements any of the detection algorithms described herein. For example, the CPU extracts the magnitude, Zmag, and phase, $\varphi$, of the complex impedance between electrode E1 and E2. The variations in Zmag and $\varphi$ are then evaluated at f1 and f2. In case more than two frequencies are used, the technique is performed at all, or at a subset, of the applied frequencies. If swept frequencies are used, Zmag and $\varphi$ are computed over the range of the frequency sweep. Control unit CPU uses the information to compare it against known detection thresholds 331, as shown in FIG. 28.

Optionally, an equivalent impedance measurement module may be employed to extract Zref, the complex impedance between reference electrodes E3 and E4. Similarly, the magnitude and phase of complex impedance Zref is processed and computed by control unit CPU. Electrode E3 and E4 are mostly exposed to blood flowing through the azygos vein or another neighboring vein, such as, for example, another intercostal vein. It is expected that, during the course of the procedure, Zref would display changes, which correlate with the fluid intake experienced by the patient. Additionally, Zref may be affected by anesthetics used during the procedure. Relative changes determined in the magnitude and phase of Zref may be used to adjust accordingly the detection thresholds 330 (see FIG. 28). For example, if the magnitude of Zref decreases 10% due to infused fluid intake, the threshold corresponding to Zmag may be reduced by 10%.

Figure 29A:
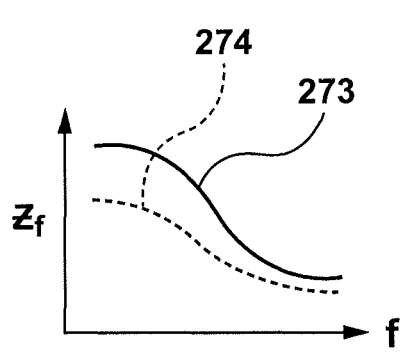
FIGS. 29A, 29B, 29C, and 29D are frequency profiles of impedance and phase showing differences in the presence or absence of lung tissue in a bioimpedance sensitivity zone.
Figure 29B:
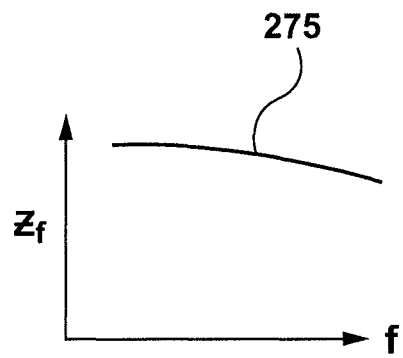
Figure 29C:
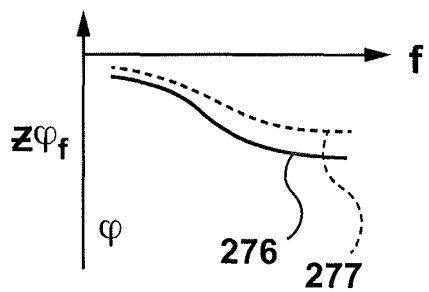
Figure 29D:
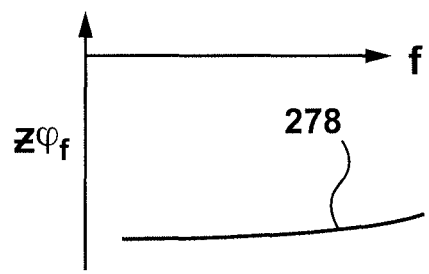

In order to differentiate between a state when lungs are deflated (i.e., less air) and one when lungs are inflated (e.g., more air), several thresholds, or combination thereof, may be employed. To determine thresholds 328 (FIG. 28) a catheter may be positioned in a vein to target a TSN (e.g., in the range 150 of an intercostal vein 40) and impedance measurements may be recorded while a patient is asked to inhale and exhale deeply, in order to determine impedance changes during ventilation and use impedance measurements to discern between the presence of lung tissue and lack of lung tissue within the sensitivity zone. Optionally, medical imaging may confirm that threshold values coordinate with lung proximity. For example, radiopaque contrast agent may be injected into the pleural cavity in the region of the sensitivity zone or ablation zone (e.g., using a needle inserted percutaneously or with a deployable needle from an ablation catheter) allowing fluoroscopic imaging of lung movement to confirm that it moves safely away from the ablation zone or to confirm that impedance measurements correspond to presence or lack of lung tissue in the sensitivity zone Lung detection thresholds may comprise Impedance thresholds Z_thr1 and Z_thr2, which may be the same or equal, or Impedance Phase threshold Z$\varphi$_thr. For example, since air is less electrically conductive than biological living tissue, if Zmag exceeds Z_thr1 a decision may be reached that the lung is entering an inhale phase. Conversely, if Zmag drops below Z_thr2 the lung may enter an exhale phase. Z_thr1 may be equal or greater than Z_thr2. Z_thr1 and Z_thr2 depend on the electrode geometry, separation distance, and the values used for f1 and f2, and are expected to be in the 500-2000Ω range. Alternatively, or in addition to, Z$\varphi$ may be compared against corresponding thresholds. For example, Z$\varphi$ during exhale is expected to negative and lower in absolute magnitude than Z$\varphi$ during inhale. For example, with less air in the lungs (i.e., ablation safe state) Z$\varphi$ may be in the range −5° to −25°, whereas with more air in the lungs (i.e., ablation unsafe state) Z$\varphi$ may lie in the interval −30° to −50°. Yet alternatively, or additionally, the frequency profile of Zmag (labeled Zf in FIGS. 29A and 29B and shown as solid lines) would have an S-curve shape 273, as shown in FIG. 29A, when less air is present in the lungs (i.e., ablation safe state). The profile would become flatter 275, as shown in FIG. 29B, when more air is present in the lungs (i.e., ablation unsafe state). As shown in FIG. 29A, Zmag may also be used to assess the extent and effects of ablation in embodiments where bioimpedance is measured from an ablation electrode to compare profiles before, during or after ablation energy is delivered, or in embodiments wherein the bioimpedance sensitivity zone overlaps with the ablation zone. The Zmag frequency characteristic of ablated tissue (dotted line 274) vs. that of normal tissue (solid line 273) would be flatter, although not as flat as that of lungs filled with air as shown by line 275 of FIG. 29B. In general, ablated tissue presents lower Zmag values than normal, healthy, or unablated tissue. Yet alternatively, or additionally, the frequency profile of impedance phase, $Z\varphi$, of normal tissue (labeled $Z\varphi f$ in FIGS. 29C and 29D and shown as solid lines) would be curved 276, as shown in FIG. 29C when less air is present in the lungs (i.e., ablation safe). The profile would become flatter 278, as shown in FIG. 29D, when more air is present in the lungs (i.e., ablation unsafe). As shown in FIG. 29C, $Z\varphi$ may also be used to assess the extent and effects of ablation. The $Z\varphi$ frequency characteristic of ablated tissue (dotted line 277) vs. that of normal tissue (solid line 276) would be flatter, although not as flat as that of lungs filled with air. Both ablated and unablated or normal tissues would still present negative values for impedance phase, $Z\varphi$, given the capacitive characteristic of cell membrane. However, in general, because of the thermal injury caused by ablation at cellular level, ablated tissue presents lower phase absolute values than normal, healthy, or unablated tissue. These effects are captured by the dotted lines of FIGS. 29A and 29C.

Figure 30:
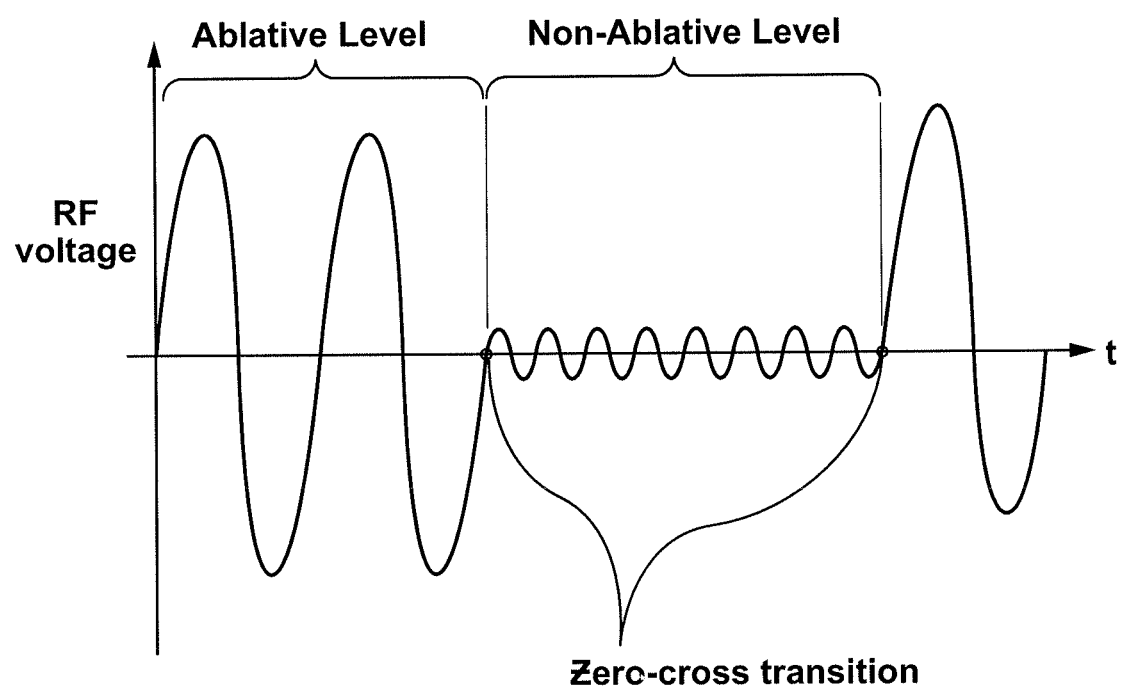
FIG. 30 is a plot showing change of amplitude of RF voltage from an ablative level to a non-ablative level.

Depending on the exact bioimpedance electrode configuration employed, the frequency profiles of Zmag and $Z\varphi$ may vary, but they are expected to be significantly different between states when the lungs have more vs. those with less air. The exact profiles may be determined empirically or experimentally. Once determined, the exact profiles are programmed into the control unit CPU. The CPU uses one or more of the detection criteria described above, or a combination thereof, to determine whether the lungs are in a safe-to-ablate state 333 or unsafe-to-ablate state 332 (FIG. 28). Based on such decision, the CPU drives the ablation source to deliver ablative or non-ablative energy levels, respectively, to the ablation electrode EA. As shown in FIG. 30, to minimize inadvertent tissue or cardiac stimulation, it is important to transition the ablation waveform, from one state to the next, at its zero crossings.

FIG. 28 is a flowchart of a computerized algorithm for ablation of a TSN configured for detection of lung tissue within an ablation zone and control of ablation energy to ablate the target nerve while safely avoiding injury of the lung tissue. The CPU may generate lung detection thresholds 328 or states as described herein by calculating parameters of complex impedance from multiple frequencies delivered through bioimpedance electrodes. This may be done while the patient is instructed to inhale and exhale deeply or with controlled ventilation with the catheter 325 (FIG. 26) positioned for TSN ablation. The lung detection thresholds or states 328 may comprise multiple decision factors, which may improve safely particularly if there are artifacts or noise from other tissues or energy sources. The physician may initiate an ablation process 329 by pressing a button on a user interface of the control unit. The controller may continuously or periodically check the decision states and modify them based on information from the impedance reference channel 330. The reference channel may show the blood impedance measured by the Zref electrodes and if that changes during the course of the procedure (e.g., such as because of infused fluid loading or because of anesthetics effects) then the detection thresholds may be adjusted accordingly. Bioimpedance parameters are calculated and compared to the lung detection thresholds or states 331. If an unsafe state is determined ablation energy may be set to a non-ablative level 332, which may be zero amplitude or a very small amplitude and the algorithm may continue monitoring Zref and bioimpedance until a safe state is determined. For example, if ablation energy is being delivered at an ablative level during a safe state and the algorithm determines that an unsafe state has been entered, setting ablation energy to a non-ablative level 332 may comprise decreasing power but not terminating the power, and the change in amplitude may comprise a zero-cross transition as shown in FIG. 30. If a safe state is determined ablation energy may be set to an ablative level 333, which may comprise turning on ablative energy or ramping up power of ablative energy from a non-ablative level to an ablative level. In this context, a non-ablative level of ablation energy may be defined as incapable of causing thermal injury to lung tissue or visceral pleura if within the ablation zone for a predefined period of time (e.g., about 3 seconds). Optionally or alternatively, if an unsafe state is detected to continue for more than a predefined period of time (e.g., about 3 seconds) the ablation energy may be decreased further or turned off or a message may be displayed to alert the user. As discussed transition from a non-ablative level to an ablative level may comprise a zero-cross transition as shown in FIG. 30. The algorithm may calculate if a cumulative ablation dose is sufficient to ablate the target nerve 334, which may be a function of time and temperature and previous periods of ablative energy delivery. If the ablation dose is sufficient to ablate the target nerve the ablation process may be ended 335. If the ablation dose is not sufficient to ablate the target nerve the algorithm may continue to monitor Zref and bioimpedance to detect lung presence and deliver ablative energy when it is safe to do so. Bioimpedance may be used to assess whether sufficient ablation effect has been achieved. For example, Zmag and $Z\varphi$, as measured when there is less air in the lungs, may show different characteristics in unablated vs. ablated tissues. For example, although Zmag may still exceed Z_thr1, with less air in the lungs, Zmag might be less than Z_thr3 (Zmag<Z_thr3) if the ablation dose was sufficient. Similarly, $Z\varphi$ may show a flatter frequency profile when the ablation dose was sufficient, but in a range of values consistent with absence of air from the lungs. Alternatively, or additionally, a decision that a sufficient ablation dose was achieved may be made based on the temperature profile measured by the temperature sensors carried by the catheter. If the measured temperature reached a therapeutically-effective set-point (e.g. 55-75° C.) for a sufficiently-long duration (10 to 60 s) ablation effects may be considered sufficient and energy application discontinued.

Alternatively, an algorithm may be configured to detect if the lung is moving with respect to the ablation zone deliver ablation energy only when the lung is moving or not present within an ablation zone. Delivery of ablation energy to moving lung tissue may safely avoid injury to the lung if ablation energy is sufficiently deposited over a larger volume of tissue and sufficient time allows thermal energy to dissipate.

Impedance measurements may be influenced by electrode polarization impedance (EPI). This is especially true for small electrodes. EPI can be reduced by increasing the excitation frequency of impedance measurement. For example frequencies of above 10 and more so 50 kHz are much less influenced by EPI.

Figure 31A:
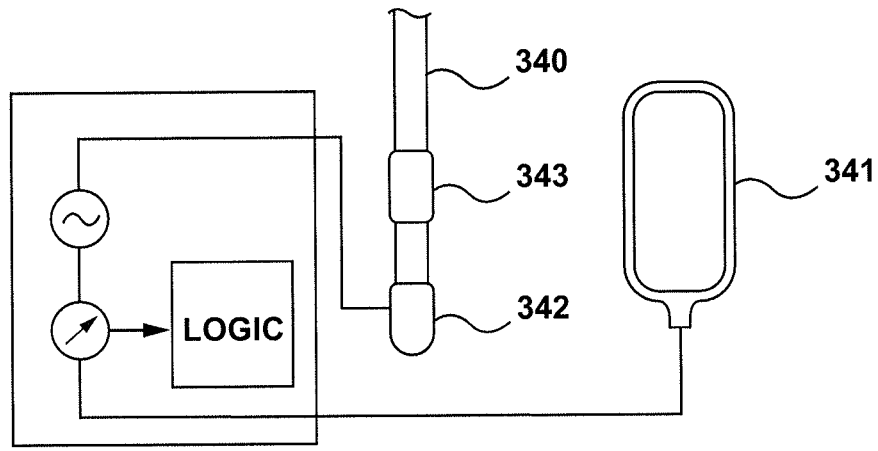
FIGS. 31A and 31B are schematic illustrations of a two electrode and three electrode impedance measuring configuration.
Figure 31B:
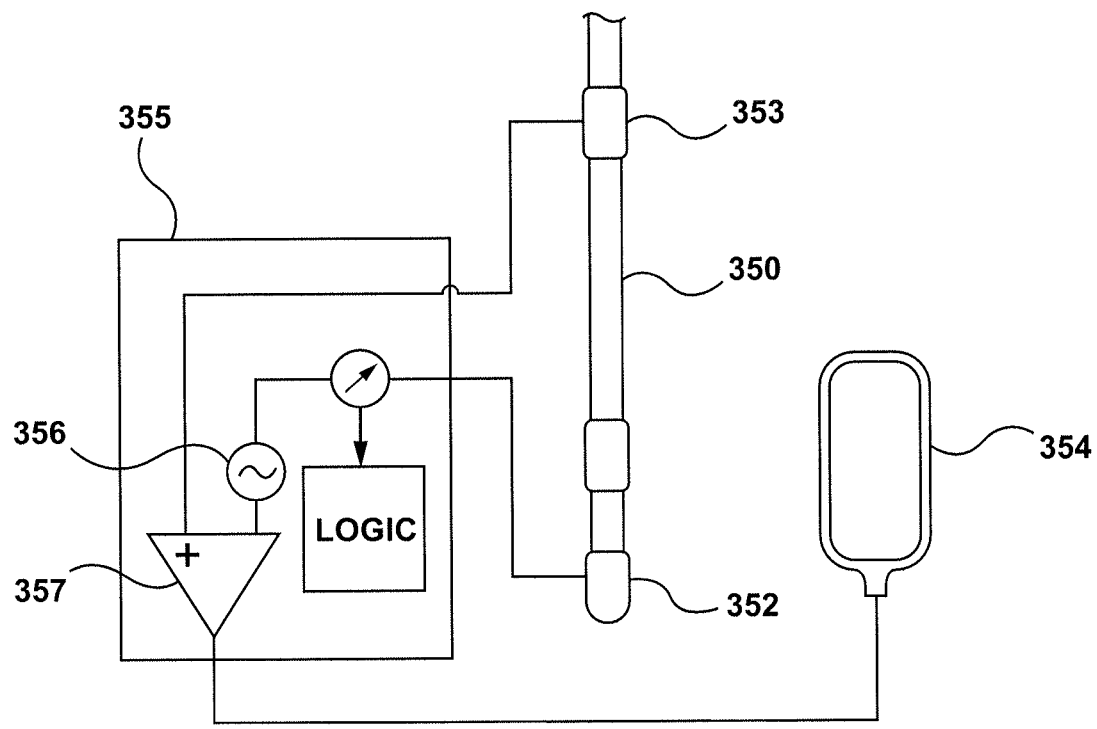

Embodiments of impedance measurement electrode configurations are shown in FIGS. 31A and 31B. FIG. 31A shows a schematic illustration of a two-electrode unipolar impedance measurement setup with a small active impedance measuring electrode 342 mounted on a catheter 340 and a large neutral electrode 341 that can be a skin adhesive patch dispersive electrode. A separate ablation electrode 343 is also shown. In such case, the current is applied and the sensed voltage is measured using the said two electrodes 342 and 341. The LOGIC element then computes the impedance based on the applied current and on the measured sensed voltage. In certain situations, this technique may be more prone to EPI artifacts. In comparison, FIG. 31B shows a schematic illustration of the principle of a three-electrode unipolar measurement configuration. Similarly to the configuration shown in FIG. 31A, the current still flows between the active impedance measurement electrode 352 and a dispersive electrode 354. However, in this configuration, the sensed voltage is measured between electrodes 353 and 354. By doing so, effects of EPI, or other artifacts, associated with small electrode 352 are reduced. The impedance-monitoring channel 355 of the system is indicated by the box. A block diagram shows a signal source 356 and an active operational amplifier 357. Element 357 measures the sensed voltage between 353 and 354. Since no current is passing through the catheter electrode 353, the EPI and other noise is eliminated from the measurements, and the measurements are consequently dominated by the properties of the active electrode 352 and its surrounding tissue. A system for transvascular TSN ablation and bioimpedance monitoring may optionally comprise a two-electrode unipolar configuration as shown in FIG. 31A, or a three-electrode unipolar configuration as shown in FIG. 31B. Other configurations, known to those of skill in the art, can be employed with equivalent results. For example, four-electrode impedance measurements may be used in a similar fashion. The electrodes involved may reside on the same catheter or on different catheters. Combinations of the above configurations may be used with equivalent results.

A system may comprise a computerized controller having software-based logic that can integrate various algorithms for respiratory signal gating of ablation. A respiratory cycle consists of inspiration, expiration and respiratory pause. During inspiration the lung gradually fills recesses and may enter an ablation zone of and ablation catheter, in which case delivery of ablation energy may be unsafe. During expiration the lung is retracted and may move out of the ablation zone wherein it may be safe to deliver ablation energy. There are known ways to measure lung volume in real time that can be applied to this disclosure: transthoracic impedance, respiratory belt distention, accelerometers, pneumo-tachometers and others. Initial calibration of the measurement may involve asking the patient to perform respiratory maneuvers such as inspiration, expiration and breath hold.

A computerized controller that gates delivery of ablation energy to motion of lung tissue may further be configured to calculate an effective thermal treatment for ablation of the target nerve. A thermal treatment using RF as ablation energy may be a function of power, rate of power increase, duration of power delivery, duration of rest when power is not delivered or reduced to avoid injury to the lung. For example, it may be desired to achieve a predefined thermal dose, which is a function of tissue temperature and duration or an integral of a temperature time plot for temperature above resting body temperature. Thermal dose is a concept used in research to understand the effect of varying thermal applications on biological tissue. This concept has limitations dependent on conditions during heating and rate of heating. Calculations may be derived from bench models and animal studies that replicate a range of energy delivery profiles that comprise rest periods to reflect respiration cycles. For example, energy may be delivered for periods of 0.5 s to 10 s with rest periods of 0.5 s to 10 s to simulate respiration cycles in models to understand the effect of heating with rest periods and how to achieve tissue necrosis and formulate equations that the computerized controller can use while delivering ablation energy corresponding to varying respiration.

Figure 32:
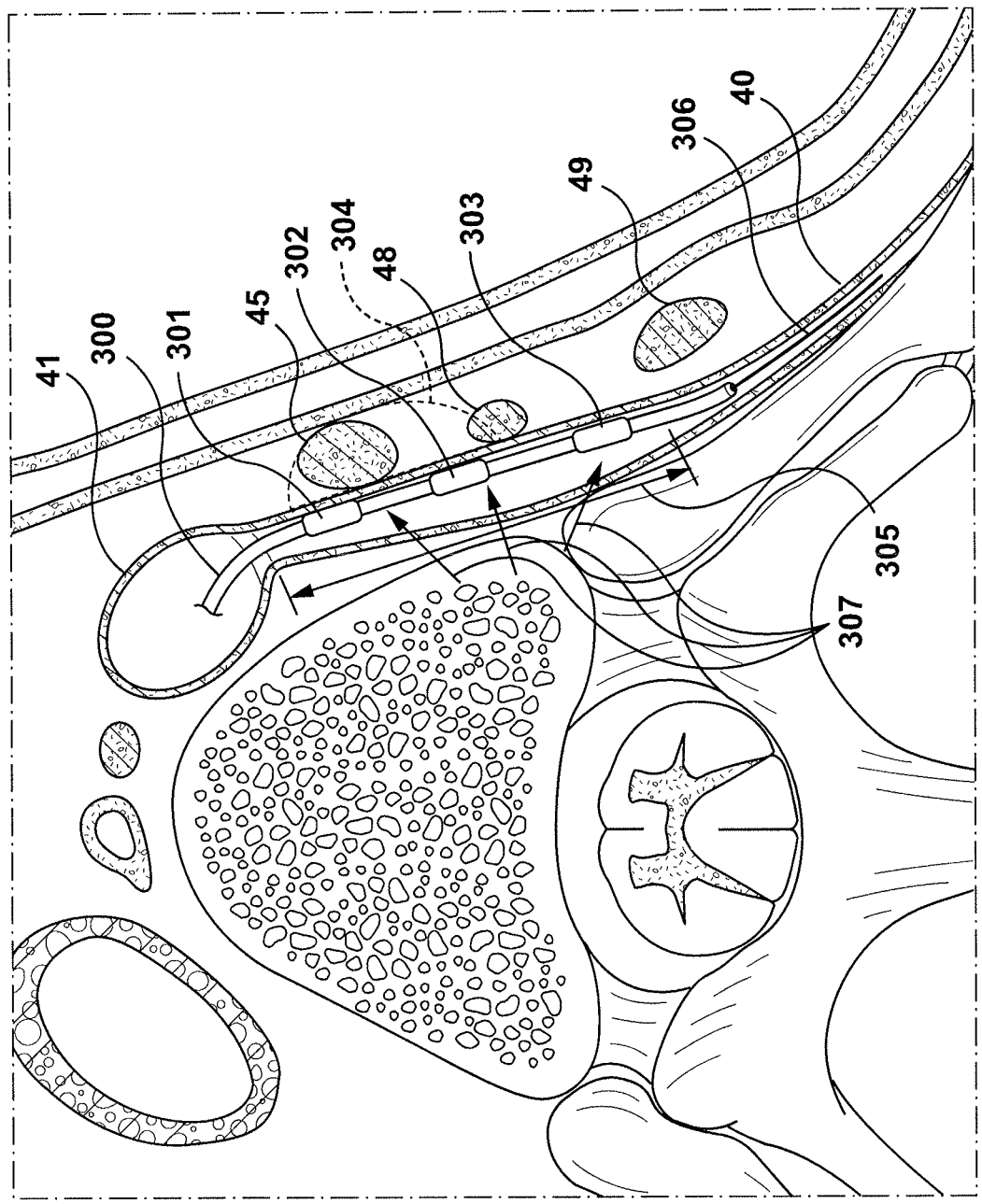
FIG. 32 is a schematic illustration of a transverse view of a patient showing an ablation catheter delivered to an intercostal vein for ablation of a target nerve.

An embodiment shown in FIGS. 22A and 22B may be used to monitor tissue impedance to assess proximity of lung tissue or visceral pleura and optionally control delivery of ablation energy in concordance with safety. The electrode 202 may be used to delivery ablative RF energy and also to monitor tissue impedance. In an alternative embodiment as shown in FIG. 32 a TSN ablation catheter 300 comprises a pair of ablation electrodes 301 and 302 configured to deliver ablative RF energy in a bipolar modality, and a separate impedance monitoring electrode 303 positioned beyond a thermal ablation zone 304 of the bipolar RF electrodes, which may provide a more accurate impedance measurement suitable for lung detection since tissue impedance changes as the tissue heats or dehydrates during ablation. The impedance-monitoring electrode 303 may complete an electrical circuit with a dispersive electrode placed on the patient's skin. As shown the catheter 300 may be configured to be delivered over a guidewire 306. To ensure consistent apposition between ablation electrodes 301 and 302 and impedance monitoring electrode 303, the electrodes may be sized to fit snugly within an intercostal vein 40. For example they may have diameter of about 3 mm. Alternatively, as shown in FIG. 30, the electrodes may be sized to be smaller than the inner diameter of an intercostal vein (e.g., 1.5 mm to 2 mm) and the distal region of the catheter 300 may comprise a deflectable region 305 which when deflected imposes a gentle curve to the deflectable region that places electrodes 301, 302, and 303 in apposition with the vessel wall. The deflectable region 305 may be about 3 to 5 cm long and the maximum deflected state may comprise a gentle bend having a large radius of curvature deflecting the distal end of the deflectable region by approximately 1 cm. When constrained in a vessel (e.g., intercostal vein 40) and by a guidewire 306 the deflection may move the deflectable region 305 in a direction 307 applying contact pressure between ablation and impedance electrodes 301, 302 and 303 and the vessel wall. The deflection may be implemented by integrating a pull wire operable from outside of the body at the catheter handle into the internal lumen of the catheter.

Alternatively a catheter having a distally positioned impedance monitoring electrode may be configured for monopolar RF ablation with one RF electrode as shown in FIG. 22A or multiple RF electrodes as shown in FIG. 20.

FIGS. 33A and 33B show an embodiment where a form of intravascular imaging is used to determine distance 241 from the intercostal vein 40 to the lung 65. An ablation catheter 242 in this embodiment has an integrated ultrasound imaging transducer 243 or array of transducers that is used to view soft tissue. An ultrasound image of a lung is a recognizable dark mass since air does not absorb ultrasound energy and is located adjacent to the vein (e.g., intercostal vein 40) in the direction of the target nerve (e.g., GSN 45). The ultrasound imaging transducer or array of transducers 243 may be in electrical communication (e.g., via electrical conductors running through the catheter shaft or an electrical cable) with an ultrasound imaging computerized console and display 250, which may be integrated with an computerized ablation console 251 to automatically control delivery of ablation energy when an imaging analysis algorithm identifies that the lung or visceral pleura is a safe distance 246 from the ablation elements 245. Alternatively, a user may view the imaging console display 250 to identify a suitable vessel proximal to a pleural recess as illustrated by FIG. 23, or to assess lung proximity and deliver ablation energy only when the lung or visceral pleura is a safe distance 246 to avoid iatrogenic injury from ablation. An array of ultrasound imaging transducers positioned around the circumference of the catheter shaft may be configured to generate an image of tissue within a plane 244 at a radial distance (e.g., about 1 to 3 cm) around the transducer array 243, which may facilitate placement of the catheter by eliminating the need to torque the catheter to orient a particular side toward a particular direction. Optionally, a system illustrated by FIG. 24A or 24B can use this imaging information in combination with impedance measurement to detect lung proximity or ventilation analysis and prediction to determine when the lung is sufficiently far from the ablative element(s) 245 to safely deliver ablation energy without injuring the lungs. For example, as shown in FIG. 33A the imaging plane 244 generated by the transducer array 243 may show the border of the lung 65, which is covered by the visceral pleura 61, being a first distance 241 from the transducer array 243 that is within an ablation zone 247 of ablation element(s) 245, indicating that it is unsafe to deliver ablation energy. If the border of the lung 65 moves away from the ablation zone (e.g., when the patient exhales, holds their breath out, or when a mechanical respirator pulls air from the lungs) as shown by the dashed outline of the visceral pleura 248 and the visceral pleura is a greater distance 246 from the transducer array 243, which is beyond the ablation zone 247 then the image generated by the transducer array may indicate that it is safe to deliver ablation energy.

In another embodiment, the system measures the distance 65 between the vein and the lung and titrates the ablative energy to create a lesion that reduces injury to the lung. For example, the distance 65 or 246 may be measured using an image formed from the ultrasound transducer automatically with image processing or computerized analysis of the image. Scale of the image may be determined by referencing a known dimension of the catheter, for example. Wherein the ablative element is RF, the titration may involve changes in the magnitude or energy, ramp, and time. Wherein the ablative element is configured for focused or unfocused high frequency or low frequency ultrasound, the titration may involve changes in magnitude of energy, time, focal depth, or frequency. In another embodiment, the system may guide the physician to instruct the patient in forced expiration maneuvers. Intravascular imaging from an ultrasound imaging transducer associated with the ablation catheter may be used to ensure that ablation energy is directed away from other sensitive collateral structures like the spine 55, thoracic duct 57, esophagus 56, aorta 51, or diaphragm 52.

The lung on the side of treatment can be selectively intubated and deflated, thus eliminating the risk of pneumothorax, but this is a complex procedure involving multiple disciplines and carries other risks to health of the patient. Pleural carbon dioxide insufflation is a known technique used in thoracoscopic procedures to aid in the compression of lung parenchyma and the effacement of subpleural lesions, and to act as a retractor when combined with changes in patient position. Traditional insufflation may be used in conjunction with the vascular-based ablation therapy to protect the lungs, but again this introduces a lot of complexity to the procedure and carries health risks to the patient.

FIG. 34 illustrates an embodiment where a substantial length of tissue around an intercostal vein 40 in which an ablation catheter 257 is placed is ablated, possibly contracting or sealing the heated portion of the vein, in order to ablate the target nerves 45 and 48 that cross the track of the vein in a location that is not precisely known but with a range 150 between the ostium 64 and costovertebral joint 54. In this example an electrode system of four electrodes 256 is deployed from a guide catheter sheath 255 and advanced distally 3 to 10 cm into the intercostal vein. The sheath 255 can be inserted and positioned over a guidewire (not shown), as described previously and once the sheath is positioned in the desired vessel (e.g., intercostal vein 40) the guidewire may be replaced with the ablation catheter 257. Alternatively catheter 257 may be configured to be delivered over a guidewire as well as through a delivery sheath. The electrodes 256 are mounted on splines 259 that press the electrodes against the wall of the vein 40 further improving efficiency of energy delivery and decreasing distance to the target nerve. The energy may be applied continuously or in pulses and the catheter electrode system is slowly retracted whilst energy is applied along the walls of the vein. Optionally the catheter can be slowly rotated in a spiral pattern as it is retracted. The electrodes 256 can be monopolar electrodes connected in parallel or in series or bipolar electrodes intended to localize the lesion more than monopolar electrodes. As the ablation track is made target nerves (e.g., 45 and 48) that cross the track are ablated. The intercostal vein 40 may be closed or reduced in diameter by heat and sealed in the process. This and other similar designs can be combined with imaging and impedance monitoring to ensure that the lung is not close to the track. Mechanical retraction systems such as ratchets and motor actuated retractors can be used to remove the inconsistency of manual retraction. The sheath 255 stays in place and its inner surface is lubricious and smooth to further facilitate continuous and consistent retraction of electrodes. It is understood that while retraction is used as an illustration alternatively the electrode system can be advanced distally and retraction is not to be construed as a limitation. Although in the illustration four electrodes 256 on splines 259 are shown it is understood that one electrode may be sufficient or alternatively other combinations can be used such as two, three or more electrodes. For example, an embodiment of a device may have four splines 259 with ball electrodes 256 at the tips of the splines as shown in FIG. 27. The electrodes make contact with the vessel wall to deliver ablative energy through the wall to the target nerve. The splines of the device are configured to have sufficient flexibility so that the electrodes can make contact with the wall of a vein that is 3 to 6 mm in diameter and is very distensible. The sheath 255 can be moved independently back and forth to collapse the splines, collect them into the sheath for safe removal or repositioning, which is important to facilitate navigation of the electrode assembly system through the venous system of the patient.

Alternatively, electrodes can be mounted on the surface of a balloon (e.g., as shown in FIG. 12) to assure good apposition to the walls of the vein and the balloon can be mounted on the distal region of an OTW type catheter to simplify placement and retraction.

An embodiment of a method of use of the device shown in FIG. 34 comprises: delivering the ablation catheter 257 through a sheath 255 to an intercostal vein 40 near a distal boundary of an ablation track 150 as indicated by an anatomical landmark (e.g., costovertebral joint 54); retracting the sheath 255 to deploy the splines 259 comprising ablation electrodes 256; confirming contact between the ablation electrodes and the vessel wall with impedance measurement; and pulling the electrode assembly back slowly at a constant rate, for example about 1 mm per second while delivering ablation energy to create an elongated lesion, or alternatively making multiple stationary lesions by delivering ablation energy in short increments, for example making multiple 5 mm lesions that overlap. While delivering ablation energy a change of temperature or impedance can indicate that the lesion is completed and it is time to retract a step. The splines may be made of superelastic material such as Nitinol and may have the ability to conform to the contours of the vessel wall. Each electrode may have a separate temperature sensor mounted on the electrode surface. The system may also be deployed, retracted, moved, and redeployed in a different vein. Alternatively, electrodes may be hemispherical to enable better folding into smaller sheath. Splines can be different lengths in order for them to be packed into smaller device when collected into the sheath.

FIG. 35 shows a schematic illustration of an ablation catheter 265 having ablation electrodes 266 that are configured to contact different circumferential segments of the vessel (e.g., intercostal vein 40) and a separate electrode 267 used to measure tissue impedance to detect proximity to the lung. As shown two electrodes 266 are configured to contact opposing sides of the inner wall of the vessel at a first longitudinal location and a second longitudinal location. Alternatively, more than two electrodes may be configured to contact different segments of the circumference of the inner wall of the vessel (e.g., three electrodes configured to contact 110° to 130° of the circumference of the 2 to 4 mm diameter vessel, four electrodes configured to contact 80° to 100° of the circumference), or even one electrode may be sized to contact all of or a majority (e.g., at least 60%) of the circumference, which may even distend the vessel wall. The impedance monitoring electrode 267 positioned away from the ablation electrode(s) (e.g., beyond an ablation zone, beyond 5 mm from the ablation electrodes, about 10 mm distal to the ablation electrodes) may be monitor impedance more precisely or with less noise caused by delivery of ablation energy (e.g., RF) or caused by heating tissue. This may provide a more accurate impedance reading used to detect lung proximity. As shown in FIG. 28 the ablation electrodes 266 are configured to deploy from the sides of the catheter shaft, for example, they may be connected to the shaft with elastic members 268 such as preformed Nitinol wires shaped to press the electrodes 266 radially outward from the catheter shaft when not constrained by a delivery sheath 269. Optionally, the catheter 265 may be delivered over a guidewire 270.

FIG. 36 illustrates an alternative embodiment of an ablation catheter 280 in which electrodes 281 are mounted on a resilient spring 282 in the shape of the helix. The helix can be extended and retracted into a guide catheter sheath or sliding mechanism 283 and deployed in the intercostal vein 40 by use of the actuation mechanism 284 located in the handle 285 of the catheter 280. Electric current can be applied to multiple electrodes simultaneously in monopolar or multi-polar configurations or sequentially in monopolar configuration in order to ablate a length of the intercostal vein. The catheter can be quickly repositioned several times, if needed, to create denser lesions.

Figure 37:
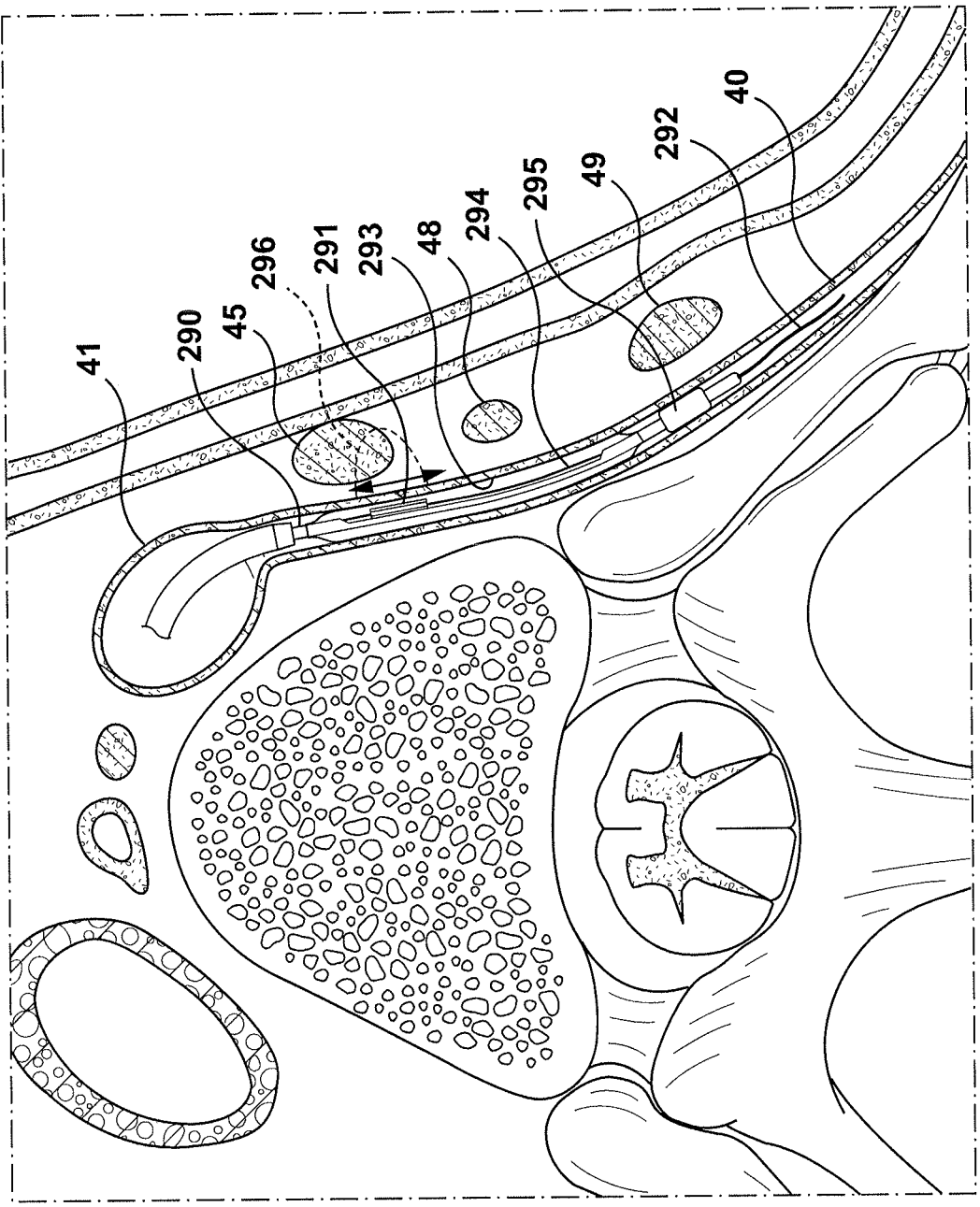
FIG. 37 is a schematic illustration of a TSN ablation catheter comprising an ultrasound ablation transducer.

FIG. 37 illustrates an embodiment of an ablation catheter 290 that enables ablation over a long length (e.g., in a range of about 2.5 to 5 cm, in a range of about 3 to 5 cm, in a range of about 3 to 4 cm, about 3 cm) of a target ablation range 150 in a vein when the exact nerve position is not known using comprising a therapeutic ultrasound ablation element 291. The distal region of the catheter 290 may be delivered over a guidewire 292 to a desired vessel (e.g., intercostal vein 40) and advanced distally into the vessel. A balloon 293 is then inflated with fluid (e.g., sterile water, saline). The balloon 293 containing fluid maintains a functioning temperature of the therapeutic element and also provides a fixed medium for transmission of ultrasound energy from the ultrasound ablation element 291 to the vessel wall and target tissue beyond the vessel wall. The therapeutic ultrasound transducer 291, which may be high frequency, low frequency, flat shaped, concave or convex, sits on an independent rail 294 that enables it to slide up and down the length of the balloon 293 allowing for easier and quicker ablation of the entire range 150 without having to otherwise move the entire catheter, which could also require deflating and inflating the balloon for repositioning. The ultrasound transducer can be retracted by the physician via an actuator in a handle or automatically via a system-controlled motorized sled. Optionally, the catheter 291 may be configured to detect proximity to lung tissue with an impedance monitor 295 as described herein.

While at least one exemplary embodiment is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein, wherein decreasing the size of the lumen comprises at least one of mechanically irritating at least a portion of the intercostal vein, applying a vacuum to at least a portion of intercostal vein, and delivering a vasoconstrictor to at least a portion of the intercostal vein;

after the decreasing step, delivering ablation energy from the ablation element towards the thoracic splanchnic nerve; and ablating at least a portion of the thoracic splanchnic nerve with the ablation energy, to treat at least hypertension.

2. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein, wherein decreasing the size of the lumen comprises contracting smooth muscle of the intercostal vein;

after the decreasing step, delivering ablation energy from the ablation element towards the thoracic splanchnic nerve; and ablating at least a portion of the thoracic splanchnic nerve with the ablation energy, to treat at least hypertension.

3. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein, wherein decreasing the size of the lumen comprises denaturing collagen fibers in the intercostal vein wall;

after the decreasing step, delivering ablation energy from the ablation element towards the thoracic splanchnic nerve; and ablating at least a portion of the thoracic splanchnic nerve with the ablation energy, to treat at least hypertension.

4. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein;

after the decreasing step, delivering ablation energy from the ablation element towards the thoracic splanchnic nerve; and ablating at least a portion of the thoracic splanchnic nerve with the ablation energy, to treat at least hypertension, further comprising, before commencing delivering ablation energy, diverting blood flow away from or at least partially occluding a portion of an adjacent azygos system vein.

5. A method of claim 4 diverting blood flow away from or at least partially occluding a portion of an adjacent azygos system vein comprises occluding an ostium where the intercostal vein meets the azygos system vein.

6. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein;

after the decreasing step, delivering ablation energy from the ablation element towards the thoracic splanchnic nerve; and ablating at least a portion of the thoracic splanchnic nerve with the ablation energy, to treat at least hypertension, wherein the location is upstream to a location where the ablation element is positioned in the intercostal vein when delivering ablation energy from the ablation element towards the thoracic splanchnic nerve.

7. The method of claim 6, wherein decreasing the size of the lumen comprises delivering energy from the ablation element.

8. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein;

after the decreasing step, delivering ablation energy from the ablation element towards the thoracic splanchnic nerve; and ablating at least a portion of the thoracic splanchnic nerve with the ablation energy, to treat at least hypertension, wherein delivering ablation energy comprises delivering ablative radiofrequency electrical current, and wherein decreasing the size of the lumen comprises delivering radiofrequency electrical current to the intercostal vein, and wherein the ablative radiofrequency electrical current is delivered at a lower power and for a longer duration than the radiofrequency electrical current delivered when decreasing the size of the lumen.

9. A method of transvascular ablation of a thoracic splanchnic nerve to treat at least heart failure or symptoms of heart failure, comprising:

advancing an elongate shaft carrying an ablation element into an intercostal vein proximate to a thoracic splanchnic nerve, the intercostal vein having a lumen;

decreasing the size of the lumen at a location along the intercostal vein;

after the decreasing step, delivering ablation energy from the ablation element towards the thoracic splanchnic nerve;

ablating at least a portion of the thoracic splanchnic nerve with the ablation energy, to treat at least hypertension; and determining proximity to the thoracic splanchnic nerve by delivering a nerve stimulation signal towards the thoracic splanchnic nerve and measuring a physiological response to the stimulation signal.

10. The method of claim 9, wherein decreasing the size of the lumen comprises fully occluding the lumen at the location.

11. The method of claim 9, wherein decreasing the size of the lumen comprises delivering energy to the intercostal vein.

12. The method of claim 11, wherein delivering energy to the intercostal vein comprises at least one of heating at least a portion of the intercostal vein, applying an electric signal to at least a portion of the intercostal vein.

13. A method of claim 9 configured to electrically stimulate a target thoracic splanchnic nerve without electrically stimulating pain fibers.

14. A method of claim 13 wherein an energy delivery electrode is positioned in the intercostal vein that is within 0 to 5 mm from the target thoracic splanchnic nerve, a stimulation signal is delivered from the energy delivery electrode, wherein the stimulation signal comprises a voltage in a range of 0.05 V to 5 V and a pulse duration in a range of 0.12 ms to 0.9 ms.

15. A method of claim 13 wherein the stimulation element has a caliber of 3 French to 8 French and a length of 0.5 mm to 4 mm and the waveform is configured to generate an electric field intensity in a range of 30 to 500 V/m with a pulse duration of 0.12 ms.

16. The method of claim 9, wherein the location at least partially overlaps with a location where the ablation element is positioned in the intercostal vein when delivering ablation energy from the ablation element towards the thoracic splanchnic nerve.

17. The method of claim 9 further comprising decreasing the size of the lumen at a plurality of locations.

18. A method of transvascular ablation of a thoracic splanchnic nerve to treat at least heart failure or symptoms of heart failure, comprising:
   advancing an elongate shaft carrying an ablation element into an intercostal vein proximate to a thoracic splanchnic nerve, the intercostal vein having a lumen;
   decreasing the size of the lumen at a location along the intercostal vein;
   after the decreasing step, delivering ablation energy from the ablation element towards the thoracic splanchnic nerve;
   ablating at least a portion of the thoracic splanchnic nerve with the ablation energy, to treat at least hypertension; and
   after delivering ablation energy, moving the ablation element within the intercostal vein to a different location, and again delivering ablation energy from the ablation element towards the thoracic splanchnic nerve.

19. A method of transvascular ablation of a thoracic splanchnic nerve to treat at least heart failure or symptoms of heart failure, comprising:
   advancing an elongate shaft carrying an ablation element into an intercostal vein proximate to a thoracic splanchnic nerve, the intercostal vein having a lumen;
   decreasing the size of the lumen at a location along the intercostal vein;
   after the decreasing step, delivering ablation energy from the ablation element towards the thoracic splanchnic nerve;
   ablating at least a portion of the thoracic splanchnic nerve with the ablation energy, to treat at least hypertension; and
   positioning a second elongate shaft into an azygos vein, and wherein advancing the elongate shaft carrying an ablation element into an intercostal vein comprises extending the elongate shaft away from the second elongate shaft and into the intercostal vein.

20. A method of transvascular ablation of a thoracic splanchnic nerve to treat at least heart failure or symptoms of heart failure, comprising:
   advancing an elongate shaft carrying an ablation element into an intercostal vein proximate to a thoracic splanchnic nerve, the intercostal vein having a lumen;
   decreasing the size of the lumen at a location along the intercostal vein;
   after the decreasing step, delivering ablation energy from the ablation element towards the thoracic splanchnic nerve;
   ablating at least a portion of the thoracic splanchnic nerve with the ablation energy, to treat at least hypertension; and
   diverting blood away from an ostium where the intercostal vein meets an azygos system vein.

\* \* \* \* \*